US011554097B2

(12) United States Patent
Chilkoti et al.

(10) Patent No.: US 11,554,097 B2
(45) Date of Patent: Jan. 17, 2023

(54) RECOMBINANT PRODUCTION OF HYBRID LIPID-BIOPOLYMER MATERIALS THAT SELF-ASSEMBLE AND ENCAPSULATE AGENTS

(71) Applicant: Duke University, Durham, NC (US)

(72) Inventors: Ashutosh Chilkoti, Durham, NC (US); Kelli Luginbuhl, Durham, NC (US); Davoud Mozhdehi, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/614,282

(22) PCT Filed: May 15, 2018

(86) PCT No.: PCT/US2018/032785

§ 371 (c)(1),
(2) Date: Nov. 15, 2019

(87) PCT Pub. No.: WO2018/213320

PCT Pub. Date: Nov. 22, 2018

(65) Prior Publication Data

US 2021/0154143 A1 May 27, 2021

Related U.S. Application Data

(60) Provisional application No. 62/506,593, filed on May 15, 2017, provisional application No. 62/534,442, filed on Jul. 19, 2017, provisional application No. 62/544,720, filed on Aug. 11, 2017, provisional application No. 62/545,313, filed on Aug. 14, 2017.

(51) Int. Cl.

| | |
|---|---|
| ***A61K 9/00*** | (2006.01) |
| ***A61K 9/127*** | (2006.01) |
| ***A61K 9/107*** | (2006.01) |
| ***A61K 31/337*** | (2006.01) |
| ***A61K 31/704*** | (2006.01) |
| ***A61K 47/42*** | (2017.01) |
| ***A61K 38/02*** | (2006.01) |

(52) U.S. Cl.
CPC .......... *A61K 9/1275* (2013.01); *A61K 9/1075* (2013.01); *A61K 31/337* (2013.01); *A61K 31/704* (2013.01); *A61K 38/02* (2013.01); *A61K 47/42* (2013.01)

(58) Field of Classification Search
CPC .... A61K 9/1275; A61K 31/357; A61K 47/42; A61K 38/02
See application file for complete search history.

(56) References Cited

U.S. PATENT DOCUMENTS 4,415,732 A 11/1983 Caruthers et al.
4,458,066 A 7/1984 Caruthers et al.
4,500,707 A 2/1985 Caruthers et al.
4,554,101 A 11/1985 Hopp
4,668,777 A 5/1987 Caruthers et al.
4,973,679 A 11/1990 Caruthers et al.
4,976,734 A 12/1990 Urry et al.
5,153,319 A 10/1992 Caruthers et al.
5,250,516 A 10/1993 Urry
5,278,302 A 1/1994 Caruthers et al.
5,336,256 A 8/1994 Urry
5,453,496 A 9/1995 Caruthers et al.
5,534,408 A 7/1996 Green et al.
5,578,577 A 11/1996 Ching et al.
5,580,859 A 12/1996 Felgner et al.
5,602,244 A 2/1997 Caruthers et al.
5,676,646 A 10/1997 Hofmann et al.
5,679,647 A 10/1997 Carson et al.
5,702,359 A 12/1997 Hofmann et al.
5,703,055 A 12/1997 Felgner et al.
5,935,776 A 8/1999 Green et al.
6,068,650 A 5/2000 Hofmann et al.
6,096,020 A 8/2000 Hofmann
6,120,493 A 9/2000 Hofmann
6,150,148 A 11/2000 Nanda et al.
6,181,964 B1 1/2001 Hofmann et al.
6,192,270 B1 2/2001 Hofmann et al.
6,207,749 B1 3/2001 Mayes et al.
6,208,893 B1 3/2001 Hofmann
6,216,034 B1 4/2001 Hofmann et al.
6,233,482 B1 5/2001 Hofmann et al.
6,241,701 B1 6/2001 Hofmann
6,245,515 B1 6/2001 Vogelstein et al.
6,296,831 B1 10/2001 Weller et al.
6,302,874 B1 10/2001 Zhang et al.
(Continued)

FOREIGN PATENT DOCUMENTS

AU 2007265628 B2 12/2012
CA 2327325 A1 11/1999
(Continued)

OTHER PUBLICATIONS

Resh (Curr Biol. May 20, 2013; 23(10): R431-R435).*
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
U.S. Appl. No. 62/622,249, filed Jan. 26, 2018.
PCT/US2019/015176, Jan. 25, 2019, WO2019/147954, Aug. 1, 2019.
U.S. Appl. No. 16/964,832, filed Jul. 24, 2020.
U.S. Appl. No. 62/647,199, filed Mar. 23, 2018.
PCT/US2019/023583, Mar. 22, 2019, WO2019/183476, Sep. 26, 2019.
(Continued)

*Primary Examiner* — Jeanette M Lieb
(74) *Attorney, Agent, or Firm* — Michael Best & Friedrich LLP

(57) ABSTRACT

Disclosed herein are conjugates including a fatty acid, a self-assembly domain, and a polypeptide having phase transition behavior. Further disclosed are methods of using the conjugates to treat disease, methods of delivering an agent, and methods of preparing the conjugates.

28 Claims, 65 Drawing Sheets

Specification includes a Sequence Listing.

(56) References Cited

U.S. PATENT DOCUMENTS 6,413,587 B1 7/2002 Hawker et al.
6,512,060 B1 1/2003 Matyjaszewski et al.
6,541,580 B1 4/2003 Matyjaszewski et al.
6,623,950 B1 9/2003 Osten et al.
6,649,138 B2 11/2003 Adams et al.
6,660,247 B1 12/2003 Gutowska et al.
6,841,617 B2 1/2005 Jeong et al.
6,852,834 B2 2/2005 Chilkoti
6,869,588 B2 3/2005 Weller et al.
7,033,571 B2 4/2006 Gutowska et al.
7,087,244 B2 8/2006 Jeong et al.
7,300,922 B2 11/2007 Sullenger et al.
7,429,458 B2 9/2008 Chilkoti
7,531,524 B2 5/2009 Rusconi
7,664,545 B2 2/2010 Westersten et al.
7,674,882 B2 3/2010 Kaplan et al.
8,129,330 B2 3/2012 Martinez et al.
8,283,125 B2 10/2012 Cebolla Ramirez et al.
8,470,967 B2 6/2013 Chilkoti et al.
8,497,356 B2 7/2013 Chilkoti et al.
8,506,963 B2 8/2013 Li et al.
8,586,347 B2 11/2013 Lochhead et al.
8,841,414 B1 9/2014 Raucher et al.
8,912,310 B2 12/2014 Chilkoti et al.
8,937,153 B2 1/2015 Abrahmsén et al.
9,127,047 B2 9/2015 Chilkoti
9,132,178 B2 9/2015 Philip
9,138,743 B2 9/2015 Yager et al.
9,482,664 B2 11/2016 Chilkoti et al.
9,592,303 B2 3/2017 Chilkoti et al.
9,771,396 B2 9/2017 Chilkoti et al.
9,804,170 B2 10/2017 Krishna et al.
9,890,420 B2 2/2018 Chilkoti et al.
10,064,954 B2 9/2018 Wu
10,131,690 B2 11/2018 Bonny et al.
10,302,636 B2 5/2019 Chilkoti et al.
10,364,451 B2 7/2019 Chilkoti et al.
10,385,115 B2 8/2019 Chilkoti et al.
10,434,182 B2 10/2019 Weng et al.
2001/0034050 A1 10/2001 Chilkoti
2002/0052443 A1 5/2002 Greenwald et al.
2002/0146794 A1 10/2002 Tomycz
2003/0008308 A1 1/2003 Enzelberger et al.
2003/0138829 A1 1/2003 Unger et al.
2003/0175290 A1 9/2003 Renner et al.
2003/0185741 A1 10/2003 Matyjaszewski et al.
2003/0225251 A1 12/2003 Sallberg et al.
2003/0233675 A1 12/2003 Cao et al.
2004/0053976 A1 3/2004 Martinez et al.
2004/0101852 A1 5/2004 Bennett et al.
2004/0192072 A1 9/2004 Snow et al.
2005/0186214 A1 8/2005 Liu et al.
2005/0255554 A1 11/2005 Chilkoti
2005/0288229 A1 12/2005 Sindrey et al.
2006/0025524 A1 2/2006 Schneider et al.
2006/0034796 A1 2/2006 Ashwell et al.
2006/0051798 A1 3/2006 Mirkin et al.
2007/0087114 A1 4/2007 Chilkoti et al.
2007/0117173 A1 5/2007 Levison et al.
2008/0181861 A1 7/2008 Jiang et al.
2009/0098652 A1 4/2009 Stupp et al.
2009/0215194 A1 8/2009 Magni et al.
2010/0015070 A1 1/2010 Bollschweiler et al.
2010/0022455 A1 1/2010 Chilkoti
2010/0048473 A1 2/2010 Chaikof et al.
2010/0120018 A1 5/2010 Quake et al.
2010/0241054 A1 9/2010 Dacey et al.
2010/0311059 A1 12/2010 Didion et al.
2010/0311669 A1 12/2010 Greene et al.
2010/0325765 P1 12/2010 Pait et al.
2011/0082283 A1 4/2011 Dagher
2011/0119778 A1 5/2011 Liss
2011/0165557 A1 7/2011 Ah et al.
2011/0207673 A1 8/2011 Chilkoti et al.
2011/0248698 A1 10/2011 Kikuchi et al.
2011/0294189 A1 12/2011 Chilkoti et al.
2011/0303303 A1 12/2011 Proper et al.
2011/0305718 A1 12/2011 Mugica et al.
2012/0121709 A1 5/2012 Chilkoti et al.
2012/0172298 A1 7/2012 Andersen et al.
2012/0208742 A1 8/2012 Primiano et al.
2013/0039927 A1 2/2013 Dewhurst et al.
2013/0079277 A1 3/2013 Chilkoti
2013/0079280 A1 3/2013 Baca et al.
2013/0096058 A1 4/2013 Baca et al.
2013/0102993 A1 4/2013 Kim et al.
2013/0130384 A1 5/2013 Okamoto et al.
2013/0157889 A1 6/2013 Chilkoti et al.
2013/0165389 A1 6/2013 Schellenberger et al.
2013/0172274 A1 7/2013 Chilkoti
2013/0197359 A1 8/2013 Park et al.
2013/0281624 A1 10/2013 Chilkoti et al.
2013/0315823 A1 11/2013 Trieu
2013/0330335 A1 12/2013 Bremel et al.
2014/0024600 A1 1/2014 Chilkoti et al.
2014/0163201 A1 6/2014 Winter et al.
2014/0275227 A1 9/2014 Hoge et al.
2014/0294932 A1 10/2014 Kim et al.
2015/0094270 A1 4/2015 Harris et al.
2015/0099707 A1 4/2015 Pastan et al.
2015/0112022 A1 4/2015 Chilkoti et al.
2016/0017278 A1 1/2016 Montclare et al.
2016/0114053 A1 4/2016 Chilkoti
2016/0120952 A1 5/2016 Chilkoti
2016/0200787 A1 7/2016 Matem et al.
2016/0209356 A1 7/2016 Herget et al.
2016/0220727 A1 8/2016 Lu et al.
2016/0250165 A1 9/2016 Sullenger et al.
2016/0271262 A1 9/2016 Lopez et al.
2016/0303091 A1 10/2016 Wang
2016/0348147 A1 12/2016 Lopez et al.
2016/0355802 A1 12/2016 Isaacs et al.
2017/0088670 A1 3/2017 Rowan et al.
2017/0102357 A1 4/2017 Liang et al.
2017/0166621 A1 6/2017 Boettcher et al.
2017/0170142 A1 6/2017 Edelstein et al.
2017/0189545 A1 7/2017 Lee et al.
2017/0233714 A1 8/2017 Chilkoti et al.
2017/0239363 A1 8/2017 Chilkoti et al.
2017/0369651 A1 12/2017 Cheng et al.
2018/0135060 A1 5/2018 Romero Ramos et al.
2018/0161772 A1 6/2018 Rammohan et al.
2018/0171337 A1 6/2018 O'Neill et al.
2018/0200196 A1 7/2018 Fahmy et al.
2018/0217136 A1 8/2018 Chilkoti et al.
2018/0231469 A1 8/2018 Gibbons et al.
2018/0238864 A1 8/2018 Burd et al.
2018/0258157 A1 9/2018 Chilkoti et al.
2018/0326044 A1 11/2018 Carter
2018/0327752 A1 11/2018 Pillay et al.
2019/0016763 A1 1/2019 Kitazawa et al.
2019/0204309 A1 7/2019 Gibbs
2019/0285623 A1 9/2019 Chilkoti et al.
2019/0292549 A1 9/2019 Zhang et al.
2019/0345228 A1 11/2019 Chilkoti et al.
2020/0078313 A1 3/2020 Roy et al.
2020/0121809 A1 4/2020 Hope et al.
2020/0163878 A1 5/2020 Baumhof et al.
2020/0181555 A1 6/2020 Hinojosa et al.
2021/0154143 A1 5/2021 Chilkoti et al.

FOREIGN PATENT DOCUMENTS

CA 2423488 A1 4/2002
CN 104725628 B 4/2018
EP 1670315 B1 4/2017
EP 2664340 B1 2/2020
JP 2014-156428 A 8/2014
JP 2014-534265 A 12/2014
WO WO1991/019813 A1 12/1991
WO WO 2003/040165 A2 10/2002
WO WO 2004/096124 A2 11/2004
WO WO 2006/004778 A2 1/2006
WO 2006/110292 A2 10/2006

(56) References Cited

FOREIGN PATENT DOCUMENTS

| | | | |
|---|---|---|---|
| WO | WO 2007/073486 | A2 | 6/2007 |
| WO | WO 2007/108013 | A2 | 9/2007 |
| WO | WO 2007/134245 | A2 | 11/2007 |
| WO | 2008/012543 | A1 | 1/2008 |
| WO | 2008/030968 | A2 | 3/2008 |
| WO | WO 2009/067584 | A1 | 5/2009 |
| WO | WO 2010/054699 | A1 | 5/2010 |
| WO | WO 2010/057154 | A1 | 5/2010 |
| WO | WO 2010/096422 | A1 | 8/2010 |
| WO | 2011/025572 | A1 | 3/2011 |
| WO | WO 2011/123813 | A2 | 10/2011 |
| WO | 2012/162426 | A1 | 11/2012 |
| WO | WO2013/049234 | A2 | 4/2013 |
| WO | WO 2013/065009 | A1 | 5/2013 |
| WO | 2013/106715 | A1 | 7/2013 |
| WO | WO2014/037373 | A1 | 3/2014 |
| WO | WO 2014/194244 | A1 | 12/2014 |
| WO | 2015/011231 | A1 | 1/2015 |
| WO | WO 2015/130846 | A2 | 9/2015 |
| WO | 2016/065300 | A1 | 4/2016 |
| WO | WO 2016/065273 | A1 | 4/2016 |
| WO | WO 2016/090103 | A1 | 6/2016 |
| WO | WO 2016/154530 | A1 | 9/2016 |
| WO | WO 2017/015132 | A1 | 1/2017 |
| WO | WO 2017/024182 | A1 | 2/2017 |
| WO | WO 2017/112825 | A2 | 6/2017 |
| WO | WO 2017/112826 | A2 | 6/2017 |
| WO | WO 2017/192449 | A1 | 11/2017 |
| WO | WO2018/115401 | A1 | 6/2018 |
| WO | WO 2018/144854 | A1 | 8/2018 |
| WO | 2019/103744 | A1 | 5/2019 |
| WO | WO 2019/147954 | A1 | 8/2019 |
| WO | 2020/037214 | A1 | 2/2020 |
| WO | 2020/160472 | A1 | 8/2020 |

OTHER PUBLICATIONS

U.S. Appl. No. 62/664,512, filed Apr. 30, 2018.
PCT/US2019/030022, Apr. 30, 2019, WO2019/213150, Nov. 7, 2019.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020.
U.S. Appl. No. 62/713,752, filed Aug. 2, 2018.
PCT/US2019/044911, Aug. 2, 2019, WO2020/028806, Feb. 6, 2020.
U.S. Appl. No. 62/985,174, filed Mar. 4, 2020.
U.S. Appl. No. 62/985,179, filed Mar. 4, 2020.
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Agarwal et al., "One-step microfluidic generation of pre-hatching embryo-like core-shell microcapsules for miniaturized 3D culture of pluripotent stem cells," Lab Chip, 2013, 13:4525-4533.
Amiram et al., "Evolution of translation machinery in recoded bacteria enables multi-site incorporation of nonstandard amino acids," Nat Biotechnol, 2015, 33: 1272-1279.
Appleyard et al., "Multiplexed protein quantification with barcoded hydrogel microparticles," Anal Chem, 2011, 83: 193-199.
Bain et al., "Formation of monolayer films by the spontaneous assembly of organic thiols from solution onto gold," Journal of the American Chemical Society, 1989, 111: 321-335.
Boeynaems et al., "Spontaneous driving forces give rise to protein-RNA condensates with coexisting phases and complex material properties," Proc Natl Acad Sci U S A, 2019, 116: 7889-7898.
Cha et al., "Microfluidics-assisted fabrication of gelatin-silica core-shell microgels for injectable tissue constructs," Biomacromolecules, 2014, 15:283-290.
Chapin et al., "Rapid microRNA profiling on encoded gel microparticles," Angew Chem Int Ed Engl, 2011, 50: 2289-2293.
Chin et al., "Addition of p-azido-l-phenylalanine to the genetic code of *Escherichia coli*," Journal of the American Chemical Society, 2002, 124: 9026-9027.
Choi et al., "Multiplexed detection of mRNA using porosity-tuned hydrogel microparticles," Anal Chem, 2012, 84: 9370-9378.
Choi et al., "Recent advances in engineering microparticles and their nascent utilization in biomedical delivery and diagnostic applications," Lab Chip, 2017, 17: 591-613.
Chu et al., "Controllable monodisperse multiple emulsions," Angew Chem Int Ed Engl, 2007, 46: 8970-8974.
Costa et al., "Photo-crosslinkable unnatural amino acids enable facile synthesis of thermoresponsive nano- to microgels of intrinsically disordered polypeptides," Adv Mater, 2018, 30(5): 1704878.
Darling et al., "Viscoelastic properties of zonal articular chondrocytes measured by atomic force microscopy," Osteoarthritis Cartilage, 2006, 14: 571-579.
Griffin et al., "Accelerated wound healing by injectable microporous gel scaffolds assembled from annealed building blocks," Nat Mater, 2015, 14: 737-744.
Hutter et al., "Calibration of atomic-force microscope tips," Review of Scientific Instruments, 1993, 64: 1868-1873.
Hwang et al., "Differentially degradable janus particles for controlled release applications," Macromol Rapid Commun, 2012, 33: 1178-1183.
Jang et al., "Engineering Globular Protein Vesicles through Tunable Self-Assembly of Recombinant Fusion Proteins," Small, 2017, 13(36): 1700399.
Khademhosseini et al., "Micromolding of photocrosslinkable hyaluronic acid for cell encapsulation and entrapment," J Biomed Mater Res A, 2006, 79: 522-532.
Kim et al., "Generation of core-shell microcapsules with three-dimensional focusing device for efficient formation of cell spheroid," Lab Chip, 2011, 11: 246-252.
Liu, L. et al., "Monodisperse core-shell chitosan microcapsules for pH-responsive burst release of hydrophobic drugs," Soft Matter, 2011, 7: 4821-4827.
Ma et al., "Core-shell hydrogel microcapsules for improved islets encapsulation," Adv Healthc Mater, 2013, 2: 667-672.
Matsunaga et al., "Molding cell beads for rapid construction of macroscopic 3D tissue architecture," Adv Mater, 2011, 23: H90-94.
Oh et al., "The development of microgels/nanogels for drug delivery applications," Progress in Polymer Science, 2008, 33(4): 448-477.
Panda et al., "Stop-flow lithography to generate cell-laden microgel particles," Lab Chip, 2008, 8: 1056-1061.
Paulsen et al., "Optofluidic fabrication for 3D-shaped particles," Nat Commun, 2015, 6: 6976.
Roberts et al., "Injectable tissue integrating networks from recombinant polypeptides with tunable order," Nature Materials, 2018, 17(12): 1154-1163.
Rodriguez-Cabello et al., "Elastin-like polypeptides in drug delivery," Adv Drug Deliv Rev, 2016, 97: 85-100.
Song et al., "Budding-like division of all-aqueous emulsion droplets modulated by networks of protein nanofibrils," Nat Commun, 2018, 9: 2110.
Srinivas et al., "Aptamer-functionalized microgel particles for protein detection," Anal Chem, 2011, 83: 9138-9145.
Tsuda et al., "Monodisperse cell-encapsulating peptide microgel beads for 3D cell culture," Langmuir, 2010, 26: 2645-2649.
Utada et al., "Monodisperse double emulsions generated from a microcapillary device," Science, 2005, 308: 537-541.
Uversky, "Protein intrinsic disorder-based liquid-liquid phase transitions in biological systems: Complex coacervates and membrane-less organelles," Adv Colloid Interface Sci, 2017, 239: 97-114.
Volodkin et al., "One-Step Formulation of Protein Microparticles with Tailored Properties: Hard Templating at Soft Conditions," Advanced Functional Materials, 2012, 22: 1914-1922.
Wang et al., "Functional polymeric microparticles engineered from controllable microfluidic emulsions," Acc Chem Res, 2014, 47: 373-384.
Yeh et al., "Micromolding of shape-controlled, harvestable cell-laden hydrogels," Biomaterials, 2006, 27: 5391-5398.

(56) References Cited

OTHER PUBLICATIONS

United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
Resh, "Covalent Lipid Modifications of Proteins," Curr Biol., May 2013, 23(10): R431-R435.
United States Patent Office Action for Application No. 16/477,229 dated Apr. 12, 2021 (14 pages).
U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, Mar. 25, 2016, WO2016/154530, Sep. 26, 2016.
U.S. Appl. No. 15/561,799, filed Sep. 26, 2017, U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, Mar. 13, 2019.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018.
U.S. Appl. No. 62/728,582, filed Sep. 7, 2018.
PCT/US2019/050077, Sep. 6, 2019.
U.S. Appl. No. 62/767,736, filed Nov. 15, 2018.
PCT/US2019/061144, Nov. 13, 2019.
PCT/US2019/044911, filed Aug. 2, 2019.
AACR, "AACR Cancer Progress Report 2016," Clin Cancer Res, Oct. 2016, vol. 22, Issue 19, 143 pages.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, Jul. 2009, vol. 90B, Issue 1, pp. 67-74.
Adamska et al., "Pancreatic ductal adenocarcinoma: Current and evolving therapies," J Mol Sci, Jun. 2017, vol. 18, Issue 7, pp. 1338-1380.
Adiseshaiah et al., "Nanomedicine strategies to overcome the pathophysiological barriers of pancreatic cancer," Nat Rev Clin Oncol, Dec. 2016, vol. 13, Issue 12, pp. 750-765.
Aladini et al., "Chemical Synthesis and Characterization of Elastin-Like Polypeptides (ELPs) With Variable Guest Residues," J Pept Sci, May 2016, vol. 22, Issue 5, pp. 334-342.
Alarcon et al., "Exendin 4 controls insulin production in rat islet beta cells predominantly by potentiation of glucose-stimulated proinsulin biosynthesis at the translational level," Diabetologia, 2006, 49(12):2920-2929.
Albanese et al., "The effect of nanoparticle size, shape, and surface chemistry on biological systems," Annu. Rev. Biomed. Eng., Aug. 2012, vol. 14, pp. 1-16.
Alconcel et al., "FDA-approved poly(ethylene glycol)—protein conjugate drugs," Polym. Chem., vol. 2, Apr. 2011, Issue 7, pp. 1442-1448.
Alley et al., "Feasibility of drug screening with panels of human tumor cell lines using a microculture tetrazolium assay," Cancer Res., 1988, 48, 589-601.
Ahiri et al., "Elastin-like peptide amphiphiles Form nanofibers with tunable length," Biomacromolecules, Sep. 2012, vol. 13, Issue 9, pp. 2645-2654.
American Diabetes Association, Standards of medical care in diabetes—2018. Diabetes Care, Jan. 2018, vol. 41, Supplement 1, pp. S1-S159.
Amiram et al., "A depot-forming glucagon-like peptide-1 fusion protein reduces blood glucose for five days with a single injection," J. Control. Release, Nov. 2013, vol. 172, Issue, pp. 144-151.
Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.
Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.
Antos et al., "Lipid Modification of Proteins through Sortase-Catalyzed Transpeptidation," J. Am. Chem. Soc., Dec. 2008, vol. 130, Issue 48, pp. 16338-16343.
Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.
Arias et al., "Superior preclinical efficacy of gemcitabine developed as chitosan nanoparticulate system," Biomacromolecules, Jan. 2011, vol. 12, Issue 1, pp. 97-104.
Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.
Armstrong et al., "The Hydrodynamic Radii of Macromolecules and Their Effect on Red Blood Cell Aggregation," Biophys. J., 2004, 87, 4259-4270.
Amer et al., "FGF21 attenuates lipolysis in human adipocytes—a possible link to improved insulin sensitivity," FEBS Lett, May 2008, vol. 582, Issue 12, pp. 1725-1730.

(56) References Cited

OTHER PUBLICATIONS

Arnida et al., "Geometry and surface characteristics of gold nanoparticles influence their biodistribution and uptake by macrophages," Eur J Pharm Biopharm, Apr. 2011, vol. 77, Issue 3, pp. 417-423.
Asai et al., "Protein polymer hydrogels by in situ, rapid and reversible self-gelation," Biomaterials, Jul. 2012, vol. 33, Issue 21, pp. 5451-5458.
Atun et al., "Expanding global access to radiotherapy," Lancet Oncol, Sep. 2015, vol. 16, Issue 10, pp. 1153-1186.
Averick et al., "ATRP under biologically relevant conditions: grafting from a protein," ACS Macro. Lett., Jan. 2012, vol. 1, Issue 1, pp. 6-10.
Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, Feb. 2012, vol. 109, Issue 40, pp. 16101-16106.
Azhdarinia et al., "Regional radiochemotherapy using in situ hydrogel," PharmRes., 2005, 22, 776-783.
Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.
Badi, "Non-linear PEG-based thermoresponsive polymer systems," Progress in Polymer Science, Mar. 2017, vol. 66, pp. 54-79.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Baggio et al., "Biology of Incretins: GLP-1 and GIP," Gastroenterology, May 2007, vol. 132, Issue 6, pp. 2131-2157.
Bailey et al., "Genomic analyses identify molecular subtypes of pancreatic cancer," Nature, Mar. 2016, vol. 531, Issue 7592, pp. 47-52.
Bamford et al., "The COSMIC (Catalogue of Somatic Mutations in Cancer) database and website," British Journal of Cancer, 2004, 91, 355-358.
Banga et al., "Parenteral controlled delivery and parmacokinetics of therapeutic peptides and proteins," (CRC Press, Boca Raton, FL, 2005).
Bansal et al., "PEGylation improves pharmacokinetic profile, liver uptake and efficacy of Interferon gamma in liver fibrosis," J. Control. Release, Sep. 2011, vol. 154, Issue 3, pp. 233-240.
Barbuti et al., "Paclitaxel through the ages of anticancer therapy: Exploring its role in chemoresistance and radiation therapy," Cancers, Dec. 2015, vol. 7, Issue 4, pp. 2360-2371.
Barnett et al., "Normal tissue reactions to radiotherapy: towards tailoring treatment dose by genotype," Nat Rev Cancer, Feb. 2009, vol. 9, Issue 2, pp. 134-142.
Barton et al., "Estimating the demand for radiotherapy form the evidence: A review of changes from 2003 to 2012," Radiother Oncol, Jul. 2014, vol. 112, Issue 1, pp. 140-144.
Baskar et al., "Cancer and Radiation Therapy: Current Advances and Future Directions," Int. J. Med. Sci., Feb. 2012, vol. 9, Issue 3, pp. 193-199.
Bedford et al., "WW domain-mediated interactions reveal a spliceosome-associated protein that binds a third class of proline-rich motif: The proline glycine and methionine-rich motif," PNAS, 1998, 95: 10602-10607.
Beenken et al., "The FGF family: biology, pathophysiology and therapy," Nat Rev Drug Discov, Mar. 2009, vol. 8, Issue 3, pp. 235-253.
Begg et al., "Strategies to improve radiotherapy with targeted drugs," Nat Rev Cancer, Apr. 2011, vol. 11, Issue 4, pp. 239-253.
Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.
Bellucci et al., "Three-in-One Chromatography-Free Purification, Tag Removal, and Site-Specific Modification of Recombinant Fusion Proteins Using Sortase a and Elastin-like Polypeptides," Angewandte Chemie International Edition, Mar. 2013, vol. 52, Issue 13, pp. 3703-3708.
Bender et al., "Synthesis, Crystallization, and Biological Evaluation of an Orally Active Prodrug of Gemcitabine," J. Med. Chem., Nov. 2009, vol. 52, Issue 22, pp. 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, Sep. 2011, vol. 50, Issue 43, pp. 9200-9211.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, Mar. 2010, vol. 142, Issue 3, pp. 312-318.
Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.
Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.
Bidwell et al., "Development of elastin-like polypeptide for thermally targeted delivery of doxorubicin," Biochemical Pharmacology, Mar. 2007, vol. 73, Issue 5, pp. 620-631.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation: Multiple exploitable mechanisms for combined treatment," Eur J Cancer, Jan. 2013, vol. 49, Issue 1, pp. 245-253.
Bobo et al., "Nanoparticle-based medicines: a review of FDA-approved materials and clinical trials to date." Pharmaceutical research, Oct. 2016, vol. 33, Issue 10, pp. 2373-2387.
Bocci et al., "The pharmacological bases of the antiangiogenic activity of paclitaxel," Angiogenesis, Jul. 2013, vol. 16, Issue 3, pp. 481-492.
Bochicchio et al., "Investigating by CD the molecular mechanism of elasticity of elastomeric proteins," Chirality, Sep. 2008, vol. 20, Issue 9, pp. 985-994.
Boekhorst et al., "Genome-wide detection and analysis of cell wall-bound proteins with LPxTG-like sorting motifs," J. Bacteriol. 187, 2005, 4928-4934.
Boldt, "Use of albumin: an update," Br J. Anaesth, Mar. 2010, vol. 104, Issue 3, pp. 276-284.
Bond, "Exenatide (Byetta) as a novel treatment option for type 2 diabetes mellitus," Proc. (Bayl. Univ. Med. Cent.), Jul. 2006, vol. 19, Issue 3, pp. 281-284.
Bontempo et al., "Streptavidin as a macroinitiator for polymerization: in situ protein-polymer conjugate formation," J. Am. Chem. Soc., 2005, 6508-6509.

(56) References Cited

OTHER PUBLICATIONS

Boyer et al., "Well-Defined Protein-Polymer Conjugates via in Situ RAFT Polymerization," J. Am. Chem. Soc., Jun. 2007, vol. 129, Issue 22, pp. 7145-7154.
Branco et al., "Self-assembling materials for therapeutic delivery," Acta Biomaterialia, Mar. 2009, vol. 5, Issue 3, pp. 817-831.
Broyer et al., "Emerging synthetic approaches for protein-polymer conjugations," Chem. Commun., Feb. 2011, vol. 47, Issue 8, pp. 2212-2226.
Brusa et al., "Antitumor activity and pharmacokinetics of liposomes containing lipophilic gemcitabine prodrugs," Anticancer Res., Jan. 2007, vol. 27, Issue 1A, pp. 195-199.
Burchard, "Light Scattering Techniques," Physical techniques for the study of food biopolymers, 1994, 151-213.
Burnouf, "Modern plasma fractionation," Transfus. Med. Rev., Apr. 2007, vol. 21, Issue 2, pp. 101-117.
Buteau et al., "Glucagon-like peptide-1 prevents beta cell glucolipotoxicity," Diabetologia, 2004, 47(5):806-815.
Butler et al., "β-Cell Deficit and Increased β-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechnology, Oct. 2011, vol. 6, Issue 12, pp. 815-823.
Cabrera et al., "Automated, High-Throughput Assays for Evaluation of Human Pancreatic Islet Function," Cell Transplant, First published Nov. 2007, vol. 16, Issue 10, pp. 1039-1048.
Cabrera et al., "Glutamate is a Positive Autocrine Signal for Glucagon Release," Cell Metab, Jun. 2008, vol. 7, Issue 6, pp. 545-554.
Cai et al., "Long-acting preparations of exenatide," Drug Des. Devel. Ther., Sep. 2013, vol. 7, pp. 963-970.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, Mar. 2012, vol. 12, Issue 4, pp. 2165-2170.
Camilloni et al., "Determination of secondary structure populations in disordered states of proteins using nuclear magnetic resonance chemical shifts," Biochemistry, Feb. 2012, vol. 51, Issue 11, pp. 2224-2231.
Campbell et al., "Pegylated peptides V. Carboxy-terminal PEGlyted analogs of growth hormone-releasing factor (GRF) display enhanced duration of biological activity invivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, Feb. 2014, vol. 88, Issue 2, pp. 412-418.
Cardenes et al., "Locally advanced pancreatic cancer: Current therapeutic approach," The Oncologist, Jun. 2006, vol. 11, Issue 6, pp. 612-623.
Carrico et al., "Introducing genetically encoded aldehydes into proteins," Nat Chem Biol, Jun. 2007, vol. 3, Issue 6, pp. 321-322.
Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.
Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.
Ceska et al., "A new and rapid method for the clinical determination of a-amylase activities in human serum and urine. Optimal conditions," Clinica Chimica Acta, 1969, 26, 437-444.
Chakrabartty et al., "Stability of α-Helices," Adv Protein Chem, 1995, 46, 141-176.
Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.
Chatterjee et al., "Type 2 diabetes," The Lancet, Jun. 2017, vol. 389, Issue 10085, pp. 2239-2251.
Chaudhury et al., "The major histocompatibility complex-related Fc receptor for IgG (FcRn) binds albumin and prolongs its lifespan," J Exp Med, 2003, 197(3): p. 315-22.
Chen et al., "Anisotropic hydrogels fabricated with directional freezing and radiation-induced polymerization and crosslinking method," Materials Letters, Dec. 2012, vol. 89, pp. 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers to Probe the Mechanism of Elastin Elasticity," J. Am. Chem. Soc., Mar. 2010, vol. 132, Issue 13, pp. 4577-4579.
Chen et al., "Rheology of Soft Materials," Annual Review of Condensed Matter Physics, May 2010, vol. 1, pp. 301-322.
Chen et al., "Site-specific labeling of cell surface proteins with biophysical probes using biotin ligase," Nat Methods, 2005, 2(2):99-104.
Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.
Chilkoti et al., "Design of thermally responsive, recombinant polypeptide carriers for targeted drug delivery," Advance Drug Delivery Reviews, 2002, 54:1093-1111.
Chilkoti et al., "Stimulus responsive elastinbiopolymers: applications in medicine and biotechnology," Curr Opin Chem Biol, Dec. 2006, vol. 10, Issue 6, pp. 652-657.
Chilkoti et al., "Targeted drug delivery by thermally responsive polymers," Advanced Drug Delivery Reviews, 2002, 54:613-630.
Chithrani et al., "Determining the size and shape dependence of gold nanoparticle uptake into mammalian cells," Nano Lett, Apr. 2006, vol. 6, Issue 4, pp. 662-668.
Chitkara et al., "Self-Assembling, Amphiphilic Polymer—Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.
Cho et al., "Effects of hofmeister anions on the phase transition temperature of elastin-like polypeptides," J. Phys. Chem. B., Nov. 2008, vol. 112, Issue 44, pp. 13765-13771.
Cho et al., "Hydrogen bonding of β-turn structure is stabilized in D(2)O," J Am Chem Soc, Oct. 2009, vol. 131, Issue 42, pp. 15188-15193.
Cho et al., "Therapeutic nanoparticles for drug delivery in cancer," Clin. Cancer Res., Mar. 2008, vol. 14, Issue 5, pp. 1310-1316.
Chockalingam et al., "Design and application of stimulus-responsive peptide systems," Protein Engineering, Design & Selection, Apr. 2007, 20(4):155-161.
Choi et al., "Renal Clearance of Nanoparticles," Nature biotechnology, Oct. 2007, vol. 25, Issue 10, pp. 1165-1170.
Chow et al., "Peptide-based biopolymers in biomedicine and biotechnology," Mater. Sci. Eng. R Reports, Jan. 2008, vol. 62, Issue 4, pp. 125-155.
Chow et al., "Ultra-High Expression of a Thermally Responsive Recombinant Fusion Protein in *E. coli*," Biotechnology Progress, Sep. 2006, vol. 22, Issue 3, pp. 638-646.
Choy et al., "Investigation of taxol as a potential radiation sensitizer," Cancer, 1993, 71, 3774-3778.
Christensen et al., "Fusion order controls expression level and activity of elastin-like polypeptide fusion proteins," Protein Science, Jul. 2009, vol. 18, Issue 7, pp. 1377-1387.
Christensen et al., "Predicting Transition Temperatures of Elastin-Like Polypeptide Fusion Proteins," Biomacromolecules, Mar. 2013, vol. 14, Issue 5, pp. 1514-1519.
Cid-Arregui et al., "Perspectives in the treatment of pancreatic adenocarcinoma," World Journal of Gastroenterology, Aug. 2015, vol. 21, Issue 31, pp. 9297-9316.
Ciezki et al., "Brachytherapy or surgery? A composite view," Oncology, Oct. 2009, vol. 23, Issue 11, pp. 960-964.
Cima, "AVMA Guidelines for the Euthanasia of Animal: 2013 Edition," Journal of the American Veterinary Medical Association, Jan. 2013, vol. 242, 102 pages.

(56) References Cited

OTHER PUBLICATIONS

Cirulis et al., "Viscoelastic properties and gelation of an elastin-like polypeptide," Journal of Rheology, Sep. 2009, vol. 53, Issue 5, pp. 1215-1228.
Clarke et al., "Tropoelastin massively associates during coacervation to form quantized protein spheres," Biochemistry, Jul. 2006, vol. 45, Issue 33, pp. 9989-9996.
Clavé et al., "Amylase, lipase, pancreatic isoamylase, and phospholipase A in diagnosis of acute pancreatitis," Clinical Chemistry, 1995, 41, 1129-1134.
Coin et al., "Solid-phase peptide synthesis: from standard procedures to the synthesis of difficult sequences," Nat. Protoc., Dec. 2007, vol. 2, Issue 12, 3247-3256.
Colomb et al., "Radiation-Convertible Polymers from Norbornenyl Derivatives. Crosslinking with Ionizing Radiation," Journal of Applied Polymer Science, 1970, 14, 1659-1670.
Conrad et al., "ELPylated anti-human TNF therapeutic single-domain antibodies for prevention of lethal septic shock," Plant Biotechnology Journal, Jan. 2011, vol. 9, Issue 1, pp. 22-31.
Coskun et al., "Fibroblast Growth Factor 21 Corrects Obesity in Mice," Endocrinology, Dec. 2008, vol. 149, Issue 12, pp. 6018-6027.
Craik et al., "The future of peptide-based drugs," Chemical biology & drug design 81, Dec. 2013, vol. 81, Issue 1, pp. 136-147.
Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.
Cui et al., "Self-assembly of peptide amphiphiles: from molecules to nanostructures to biomaterials," Biopolymers, Jan. 2010, vol. 94, Issue 1, pp. 1-18.
Dalla Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.
Darzynkiewicz et al., "DNA content measurement for DNA ploidy and cell cycle analysis," Current Protocols in Cytometry, 2001, 7.5.1-7.5.24.
Dasgupta et al., "Isopeptide Ligation Catalyzed by Quintessential Sortase A: Mechanistic Cues From Cyclic and Branched Oligomers of Indolicidin," The Journal of Biological Chemistry, May 2011, vol. 286, No. 27, pp. 23996-24006, Supplemental Information.
Day et al., "A new glucagon and GLP-1 co-agonist eliminates obesity in rodents," Nat Chem Biol, Oct. 2009, 5:749.
De et al., "Temperature-Regulated Activity of Responsive Polymer-Protein Conjugates Prepared by Grafting—from via RAFT Polymerization," J. Am. Chem. Soc. Jul. 2008, 130, 11288-11289.
De Simone et al., "Accurate random coil chemical shifts from an analysis of loop regions in native states of proteins," J Am Chem Soc, Nov. 2009, 131, 16332-16333.
Deer et al., "Phenotype and genotype of pancreatic cancer cell lines," Pancreas, May 2010, 39, 425-435.
Dejana et al., "The role of adherens junctions and VE-cadherin in the control of vascular permeability," J Cell Sci, Jul. 2008, 121, 2115-2122.
Delaglio et al., "NMRPipe: A multidimensional spectral processing system based on UNIX pipes," Journal of Biomolecular NMR 6, 1995, 277-293.
DeLisser et al., "Vascular endothelial platelet endothelial cell adhesion molecule 1(PECAM-1) regulates advanced metastatic progression," PNAS, Oct. 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated Atrp: a viable and potentially superior alternative to PEGylation for stabilizing biologics," Acta Biomater. Feb. 2009, 5, 560-569.
Deshayes et al., "Radium 223 dichloride for prostate cancer treatment," Drug Des Devel Ther, Sep. 2017, 11, 2643-2651.
DeYoung et al.,"Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.
Diana et al., "Prognostic role and correlation of CA9, CD31, CD68 and CD20 with the desmoplastic stroma in pancreatic ductal adenocarcinoma," Oncotarget, Nov. 2016, 7, 72819-72832.
Diehl et al., "A Good Practice Guide to the Administration of Substances and Removal of Blood Including Routes and Volumes," J Appl Toxicol, 2001, 21, 15-23.
Ding et al., "Mechanism for the alpha-helix to beta-hairpin transition," Proteins, 2003, 53, 220-228.
Ding et al., "βKlotho is Required for Fibroblast Growth Factor 21 Effects on Growth and Metabolism," Cell Metab, Sep. 2012, 16(3):387-393.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. Jan. 2008, 130, 687-694.
Dreher et al., "Thermal cycling enhances the accumulation of a temperature-sensitive biopolymer in solid tumors," Cancer Res, May 2007, 67, 4418-4424.
Dreher, M. R. PhD. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., Aug. 2007, 341, 207-214.
Drucker "Mechanisms of Action and Therapeutic Application of Glucagon-like Peptide-1," Cell Metab, Apr. 2018, 27(4):740-756.
Drucker et al., "The incretin system: glucagon-like peptide-1 receptor agonists and dipeptidyl peptidase-4 inhibitors in type 2 diabetes," Lancet 368, Nov. 2006, 1696-1705.
Drucker, "Glucagon-like peptides," Diabetes 47, 1998, 159-169.
Drucker, "Incretin action in the pancreas: potential promise, possible perils, and pathological pitfalls," Diabetes, Oct. 2013, 62, 3316-3323.
Du et al., "Endoscope-assisted brachytherapy for pancreatic cancer: From tumor killing to pain relief and drainage," Journal of interventional gastroenterology, Jan. 2011, 1, 23-27.
Du et al., "Tailor-made dual pH-sensitive polymer-doxorubicin nanoparticles for efficient anticancer drug delivery," J. Am. Chem. Soc., Oct. 2011, 133, 17560-17563.
Duan et al., "Fibronectin type III domain based monobody with high activity," Biochemistry, Oct. 2007 46(44):12656-12664.
Dubey et al., "Development and evaluation of folate functionalized albumin nanoparticles for targeted delivery of gemcitabine," Int J Pharm., Aug. 2015, 492(1-2):80-91.
Ducreux et al., "Radiation plus docetaxel and cisplatin in locally advanced pancreatic carcinoma: A non-comparative randomized phase II trial," Digestive and Liver Disease, Oct. 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer, Sep. 2006, 6, 688-701.
Duronio et al., "Protein N-myristoylation in *Escherichia coli*: Reconstitution of a eukaryotic protein modification in bacteria," Proc. Nail. Acad. Sci. USA, 1990, vol. 87, pp. 1506-1510.
Dyrberg et al., "Peptide as Atigens," J. Exp. Med., 1986, 164:1344-1349.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.

(56) References Cited

OTHER PUBLICATIONS

Eisenhaber et al., "Prediction of lipid posttranslational modifications and localization signals from protein sequences: Big-II, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, Jan. 2009, 45(2):228-247.
El-Assaad et al., "Saturated Fatty Acids Synergize with Elevated Glucose to Cause Pancreatic β-Cell Death," Endocrinology, 2003, 144(9):4154-4163.
Ellis, "Macromolecular crowding: obvious but underappreciated," Trends Biochem. Sci., 2001, 26 (10), 597-604.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) invitro," Cancer Chemother. Pharmacol., 1997, 39 (5), 467-472.
Etrych et al., "Hpma Copolymer Conjugates of Paclitaxe; and Docetaxel with pH-Controlled Drug Release," Molecular Pharmaceutics, Jun. 2010, 7(4):1015-1026.
Falk et al., "Hyperthermia in oncology," Int J Hyperthermia, 2001, 17, 1-18.
Farazi et al., "Structures of Saccharomyces cerevisiae N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Feng et al., "Protein resistant surfaces: comparison of acrylate graft polymers bearing oligo-ethylene oxide and phosphorylcholine side chains," Biointerphases, Mar. 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.
Finan et al., "A rationally designed monomeric peptide triagonist corrects obesity and diabetes in rodents," Nat Med, Jan. 2015, 21:27-36.
Finan et al., "Unimolecular Dual Incretins Maximize Metabolic Benefits in Rodents, Monkeys, and Humans," Sci Transl Med, Oct. 2013, 5(209):209ra151.
Fluegel et al., "Chain stiffness of elastin-like polypeptides," Biomacromolecules, Oct. 2010, 11, 3216-3218.
Fosgerau et al., "Peptide therapeutics: current status and future directions," Drug Discovery Today, Jan. 2015, 20, 122-128.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.
Friedman et al., "Directed Evolution to Low Nano molar Affinity of a Tumor-Targeting Epidermal Growth Factor Receptor-Binding Affibody Molecule," J. Mol. Biol., Mar. 2008, 376, 1388-1402.
Frilling et al., "Recommendations for management of patients with neuroendocrine liver metastases," The lancet oncology, Jan. 2014, 15, e8-21.
Fu et al., "Nanoparticle Albumin—Bond (NAB) Technology is a Promising Method for Anti-Cancer Drug Delivery," Recent Patents on Anti-Cancer Drug Discovery, Nov. 2009. 4(3):262-272.
Fujiwara et al., "Modulating effect of the PI3-kinase inhibitor LY294002 on cisplatin in human pancreatic cancer cells," Journal of Experimental & Clinical Cancer Research, Nov. 2008, 27, 76.
Furgeson et al., "Structural optimization of a "smart" doxorubicin-polypeptide conjugate for thermally targeted delivery to solid tumors," Journal of Controlled Release, Jan. 2006, 110:362-369.
Furumoto et al., "Effect of coupling of albumin onto surface of PEG liposome on its in vivo disposition," International Journal of Pharmaceutics, Mar. 2007, 329(1-2): p. 110-116.
Gaberc-Porekar et al., "Obstacles and pitfalls in the PEGylation of therapeutic proteins," Curr. Opin. Drug Discov. Devel. 11, Mar. 2008, 242-250.
Gabizon et al., "Prolonged circulation time and enhanced accumulation in malignant exudates of doxorubicin encapsulated in polyethylene-glycol coated liposomes," Cancer Res., Feb. 1994, 54, 987-992.
Gaich et al., "The Effects of LY2405319, an FGF21 Analog, in Obese Human Subjects with Type 2 Diabetes," Cell Metab, Sep. 2013, 18(3):333-340.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, Feb. 2006, R12-R22.
Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.
Gao et al., "In situ growth of a PEG-like polymer from the C terminus of an intein fusion protein improves pharmacokinetics and tumor accumulation" PNAS Early Edition, Jul. 2010, vol. 107, 1-6.
Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.
Gao et al., "In situ growth of a stoichiometric PEG-like conjugate at a protein's N-terminus with significantly improved pharmacokinetics," Proc. Natl. Acad. Sci., Sep. 2009, 15231-15236.
Gao, "Site-specific and in situ growth of stealth polymer conjugates of proteins with significally improved pharmacology," Journal of Controlled Release, Nov. 2013, 172(1):e116-e117.
Garanger et al., "Structural Evolution of a Stimulus-Responsive Diblock Polypeptide Micelle by Temperature Tunable Compaction of its Core," Macromolecules, Sep. 2015, 48, 6617-6627.
Garay et al., "Antibodies against polyethylene glycol in healthy subjects and inpatients treated with PEG-conjugated agents," Expert Opinion. Drug Deliv. 9, Nov. 2012, 1319-1323.
Gauthier et al., "Peptide/protein-polymer conjugates: synthetic strategies and design concepts," Chem. Commun., Jul. 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (Mar. 2017).
Ghoorchian et al., "Molecular architecture influences the thermally induced aggregation behavior of elastin-like polypeptides," Biomacromolecules, Oct. 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, Oct. 2009, 27, 607-612.
Gibson et al., "Enzymatic assembly of DNA molecules up to several hundred kilobases," Nat Methods, May 2009, 6, 343-345.
Gilroy et al., "Fusion of fibroblast growth factor 21 to a thermally responsive biopolymer forms an injectable depot with sustained anti-diabetic action," J Control Release, May 2018, 277:154-164.
Glassman et al., "Toughening of Thermoresponsive Arrested Networks of Elastin-Like Polypeptides to Engineer Cytocompatible Tissue Scaffolds," Biomacromolecules, Feb. 2016, 17, 415-426.
Gluck et al., "Single Vector System for Efficient N-myristoylation of Recombinant Proteins in *E. coli*," Plos One, Apr. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.

(56) References Cited

OTHER PUBLICATIONS

Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam," Clin. Pharmacol. 22, Dec. 2008, 633-648.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, Aug. 2006, 17, 1263-1268.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin, 2003, 31(3): 529-540.
Greenfield, "Using circular dichroism spectra to estimate protein secondary structure," Nat. Protoc., Dec. 2006, 1(6):2876-90.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Gu et al., "Enzymatic Synthesis of Nucleobase-Modified Single-Stranded DNA Offers Turnable Resistance to Nuclease Degradation," Biomacromolecules, Jul. 2018, 19, 3525-3535.
Gu et al., "Photocontrolled micellar aggregation of amphiphilic DNA-azobenzene conjugates," Colloids Surfaces B: Biointerfaces, Nov. 2015, 135, 126-132.
Güngör et al., "Pancreatic cancer," British Journal of Pharmacology, Jan. 2014, 171, 849-858.
Guo et al., "Nanoparticles escaping RES and endosome: challenges for siRNA delivery for cancer therapy," J. Nanomaterials, Aug. 2011, 2011: 1-12.
Gustafsson, "Nonlinear structured-illumination microscopy: wide-field fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.
Ha et al., "Immunoglobulin Fc Heterodimer Platform Technology: From Design to Applications in Therapeutic Antibodies and Proteins," Front Immunol, Oct. 2016, 7(394) (in English).
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, Nov. 2013, vol. 4, Article 331, 7 pages.
Hamidi et al., "Pharmacokinetic Consequences of Pegylation," Drug Deliv., Dec. 2006, 13, 399-409.
Hamley, "Self-assembly of amphiphilic peptides," Soft Matter, Feb. 2011, 7, 4122.
Hampp et al., "Use of Antidiabetic Drugs in the U.S., 2003-2012," Diabetes Care, May 2014, 37: 1367-1374.
Han et al., "Survival of patients with advanced pancreatic cancer after iodine$^{125}$ seeds implantation brachytherapy: A meta-analysis," Medicine, Feb. 2017, 96, e5719.
Harmon et al., "A Model for Hysteresis Observed in Phase Transitions of Thermally Responsive Intrinsically Disordered Protein Polymers," Biophysical Journal, Feb. 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hart et al., "Attenuation of FGF signalling in mouse β-cells leads to diabetes," Nature, 2000, 408:864.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, Jun. 2015, 48, 4183-4195.
Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.
Hassouneh et al., "Fusions of elastin-like polypeptides to pharmaceutical proteins," Methods Enzymol., Jan. 2012, 502, 215-37.
Hassouneh et al., "Unexpected Multivalent Display of Proteins by Temperature Triggered Self-assembly of Elastin-like Polypeptide Block Copolymers," Biomacromolecules, Apr. 2012, vol. 13, Issue 4, pp. 1598-1605.
Hathout et al., "Analysis of seed loss and pulmonary seed migration inpatients treated with virtual needle guidance and robotic seed delivery," American journal of clinical oncology, Oct. 2011, 34, 449-453.
He et al., "Comparative genomics of elastin: Sequence analysis of a highly repetitive protein," Matrix Biology, Sep. 2007, 26:524-540.
He et al., "Improving protein resistance of α-Al2O3 membranes by modification with POEGMA brushes," Applied Surface Science, Nov. 2011, 258(3):1038-1044.
Heagerty et al., Biometrics, "Time-dependent ROC curves for censored survival data and a diagnostic marker," Jun. 2000, 56(2):337-44.
Heal et al., "N-Myristoyl transferase-mediated protein labelling in vivo," Org. Biomol. Chem., Aug. 2008, 6(13):2308-2315.
Heal et al., "Site-specific N-terminal labelling of proteins in vitro and in vivo using N-myristoyl transferase and bioorthogonal ligation chemistry," Chem. Commun., Jan. 2008, 3, 480-482.
Heredia et al., "In Situ Preparation of Protein-"Smart" Polymer Conjugates with Retention of Bioactivity," J. Am. Chem. Soc. Jan. 2006, 127, 16955-16960.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. 16, Mar. 2014, R63.
Hidalgo, "Pancreatic Cancer," N Engl J Med, Apr. 2010, 362, 1605-1617.
Hingorani et al., "Phase Ib Study of PEGylated Recombinant Human Hyaluronidase and Gemcitabine in Patients with Advanced Pancreatic Cancer," Clinical Cancer Research, Jun. 2016, 22, 2848-2854.
Ho et al., "Chemoenzymatic Labeling of Proteins for Imaging in Bacterial Cells," J. Am. Chem. Soc., Nov. 2016, 138(46):15098-15101.
Ho et al., "Internal radiation therapy for patients with primary or metastatic hepatic cancer: a review," Cancer, 1998, 83, 1894-1907.
Hober et al., "Protein a chromatography for antibody purification," Journal of Chromatography B 848, Mar. 2007, pp. 40-47.
Hochkoeppler, "Expanding the landscape of recombinant protein production in *Escherichia coli*," Biotechnol. Lett., Dec. 2013, 35, 1971-1981.
Holehouse et al., "CIDER: Classification of Intrinsically Disordered Ensemble Regions," Biophysical Journal, Feb. 2015, vol. 108, Issue 2, Supplement 1, p. 228a.
Holm et al., "Transperineal $^{125}$iodine seed implantation in prostatic cancer guided by transrectal ultrasonography," The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, Sep. 2010, 23(11): p. 827-834.

(56) References Cited

OTHER PUBLICATIONS

Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, May 2007, 119, 25-33.
Hruby et al., "Thermoresponsive polymeric radionuclide delivery system—an injectable brachytherapy," Eur J Pharm Sci., Feb. 2011, 42, 484-488.
Hrycushko et al., "Direct intratumoral infusion of liposome encapsulated rhenium radionuclides for cancer therapy: effects of non-uniform intratumoral dose distribution," Med Phys, Mar. 2011, 38, 1339-1347.
Hu et al., "Design of tumor-homing and pH-responsive polypeptide-doxorubicin nanoparticles with enhanced anticancer efficacy and reduced side effects," Chemical Communications, Jun. 2015, 51, 11405-11408.
Hu et al., "Nanografting De Novo Proteins onto Gold Surfaces," Langmuir, 2005, vol. 21:9103-9109.
Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.
Huotari et al., "Endosome maturation," EMBO J, Aug. 2011, 30 (17), 3481-3500.
Hwang et al., "Caprolactonic poloxamer analog: PEG-PCL-PEG," Biomacromolecules, 2005, 6, 885-890.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., Nov. 2015, 7, 1-8.
Ishida et al., "Accelerated blood clearance (ABC) phenomenon upon repeated injection of PEGylated liposomes," International Journal of Pharmaceutics, May 2008, 354(1-2):56-62.
Ito et al., "Impaired negative feedback suppression of bile acid synthesis in mice lacking βKlotho," J Clin Invest, 2005, 115(8):2202-2208.
Ito et al., "Invivo antitumor effect of the mTOR inhibitor CCI-779 and gemcitabine in xenograft models of human pancreatic cancer," International Journal of Cancer, May 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., Jun. 2006, 4482-4486.
Janes et al., "Chitosan nanoparticles as delivery systems for doxorubicin," J. Control Release, 2001, 73, 255-267.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, Feb. 2012, 13, 206-215.
Jia et al., "Preparation, physicochemical characterization and cytotoxicity in vitro of gemcitabine-loaded PEG-PDLLA nanovesicles," World J. Gastroenterol., Feb. 2010, 16(8):1008-1013.
Jiang et al., "The internal structure of self-assembled peptide amphiphiles nanofibers," Soft Matter, Feb. 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Johnson et al., "Fibroblast Growth Factor 21 Reduces the Severity of Cerulein-Induced Pancreatitis in Mice," Gastroenterology, Nov. 2009, 137(5):1795-1804.
Jonsson et al., "Engineering of a fe mto molar affinity binding protein to human serum albumin," Protein Engineering Design and Selection, Aug. 2008, 21(8): 515-527.
Junutula et al., "Site-specific conjugation of a cytotoxic drug to an antibody improves the therapeutic index," Nat Biotechnol, Aug. 2008, 26(8):925-932.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, Feb. 2011, 89, 183-188.
Kamisawa et al., "Pancreatic cancer," Lancet, Jul. 2016, 388, 73-85.
Kanoski et al., "The role of nausea in food intake and body weight suppression by peripheral GLP-1 receptor agonists, exendin-4 and liraglutide," Neuropharmacology 62, Apr. 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karamanolis et al., "Increased expression of VEGF and CD31 in postradiation rectal tissue: implications for radiation proctitis," Mediators Inflamm, May 2013, 515048.
Kaspar et al., "Future directions for peptide therapeutics development," Drug Discovery Today, Sep. 2013, 18, 807-817.
Katakura, "Nuclear Data Sheets for A=125," Nuclear Data Sheets, Mar. 2011, 112, 495-705.
Kato et al., "Acidic extracellular microenvironment and cancer," Cancer Cell Int, Sep. 2013, 13, 89, 8 pages.
Katti et al., "Amino acid repeat patterns in protein sequences: Their diversity and structural-functional implications," Protein Science, 2000, 9: 1203-1209.
Keefe et al., "Poly(zwitterionic)protein conjugates offer increased stability without sacrificing binding affinity or bioactivity," Nat Chem, Jan. 2012, 4(1):59-63.
Keller et al., "Empirical Statistical Model to Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Keten et al., "Nanoconfinement controls stiffness, strength and mechanical toughness of β-sheet crystals in silk," Nat Mater, Mar. 2010, 9, 359-367.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., Sep. 2006, 24, 1065-1066.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, Nov. 2015, 26(11):608-617.

(56) References Cited

OTHER PUBLICATIONS

Kharitonenkov et al., "Fibroblast growth factor 21 night watch: advances and uncertainties in the field," J Intern Med, Nov. 2016, 281(3):233-246.
Kharitonenkov et al., "Inventing new medicines: The FGF21 story," Mol Metab, Jun. 2014, 3(3):221-229.
Khazov et al., "Nuclear Data Sheets for A=131," Nuclear Data Sheets, 2006, 107, 2715-2930.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.
Kim et al., "Recombinant elastin-mimetic biomaterials: Emerging applications in medicine," Adv Drug Deliv Rev, Dec. 2010, 62, 1468-1478.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.
Kim et al., "Ultrasensitive Carbon nanotube-based biosensors using antibody-binding fragments," Analytical Biochemistry, Jul. 2008, 381, 193-198.
Knop et al., "Poly(ethylene glycol) in Drug Delivery: Pros and Cons as Well as Potential Alternatives," Angewandte Chemie International Edition, Aug. 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment of an NMR-Invisible Solubility Enhancement Tag Using a Sortase-Mediated Protein Ligation Method," J Biomol NMR. Mar. 2009, vol. 43, No. 3; pp. 145-150.
Kobayashi et al., "Summary of recombinant human serum albumin development," Biologicals, Mar. 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, Feb. 2012, 41(7):2686-2695.
Koong et al., "Phase II study to assess the efficacy of conventionally fractionated radiotherapy followed by a stereotactic radiosurgery boost inpatients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.
Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, Mar. 2008, 1778, 631- 645.
Krempien et al., "Neoadjuvant chemoradiation in patients with pancreatic adenocarcinoma," HPB (Oxford), Feb. 2006, 8(1):22-28.
Kruger et al., "Analysis of the Substrate Specificity of the Staphylococcus aureus Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., Oct. 2015, 26(10):2153-2160.
Kulkarni et al., "Selective functionalization of the protein N terminus with N-myristoyl transferase for bioconjugation in cell lysate," ChemBioChem, Oct. 2013, 14, 1958-1962.
Kumar et al., "N-Terminal Region of the Catalytic Domain of Human N-Myristoyltransferase 1 Acts as an Inhibitory Module," PLoS One, May 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kurosu et al., "Tissue-specific Expression of βKlotho and Fibroblast Growth Factor (FGF) Receptor Isoforms Determines Metabolic Activity of FGF19 and FGF21," J Biol Chem, Sep. 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling" Cancer Res, Mar. 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Langer et al., "Designing materials for biology and medicine," Nature, 2004, 428, 487-92.
Laybutt et al., "Endoplasmic reticulum stress contributes to beta cell apoptosis in type 2 diabetes," Diabetologia, Apr. 2007, 50(4):752-763.
Le Droumaguet et al., "Recent advances in the design of biocoujugates from controlled/living radical polymerization," Polym. Chem. Jan. 2010, 1, 563-598.
Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. 7, Jan. 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4): 971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.
Lee et al., "Phase transition and elasticity of protein-based hydrogels," J. Biomater. Sci. Polymer Edn, 2001, 12, 229-242.
Lee et al., "Structures of β-klotho reveal a 'zip code'-like mechanism for endocrine FGF signaling," Nature, Jan. 2018, 553:501-505.
Lee et al., "Theranostic nanoparticles with controlled release of gemcitabine for targeted therapy and MRI of pancreatic cancer," ACS Nano, Mar. 2013, 7(3):2078-2089.
Leibowitz et al., "Glucose-Regulated Proinsulin Gene Expression is Required for Adequate Insulin Production during Chronic Glucose Exposure," Endocrinology, 2002, 143(9):3214-3220.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., Nov. 2011, 77(22):8114-28.
Leung et al., "Bio-Click Chemistry: Enzymatic Functionalization of PEGylated Capsules for Targeting Applications**," Angew. Chem. Int. Ed. Jul. 2012, 51, 7132-7136.
Le Vine et al., "Thioflavine T interaction with synthetic Alzheimer's disease beta-amyloid peptides: detection of amyloid aggregation in solution," Protein Sci., 1993, 2, 404-10.

(56) References Cited

OTHER PUBLICATIONS

Levy et al., "Novel Exenatide Analogs with Peptidic Albumin Binding Domains: Potent Anti-Diabetic Agents with Extended Duration of Action," PLoS ONE, Feb. 2014, 9(2): e87704, 9 pages.
Li et al., "Elastin is an essential determinant of arterial morphogenesis," Nature, 1998, 393, 276-280.
Li et al., "FGF21 Is Not a Major Mediator for Bone Homeostasis or Metabolic Actions of PPARα and PPARγ Agonists," J Bone Miner Res, Apr. 2017, 32(4):834-845.
Li et al., "Molecular description of the LCST behavior of an elastin-like polypeptide," Biomacromolecules, Aug. 2014, 15, 3522-3530.
Li et al., "Nanoparticles Evading the Reticuloendothelial System: Role of the Supported Bilayer," Biochim. Biophys. Acta, Oct. 2009, 1788 (10), 2259-2266.
Li et al., "Pancreatic cancer," Lancet, 2004, 363, 1049-1057.
Li et al., "Prediction of solvent-induced morphological changes of polyelectrolyte diblock copolymer micelles," Soft Matter, Nov. 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., Jan. 2015, 36(1):90-95.
Liao et al., "Removal of N-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering, Aug. 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, May 2007, 8(5): 1417-1424.
Lim et al., "In situ cross-linking of elastin-like polypeptide block copolymers for tissue repair," Biomacromolecules, Feb. 2008, 9, 222-230.
Lim et al., "In vivo post-translational modifications of recombinant mussel adhesive protein in insect cells," Biotechnol. Prog., Sep.-Oct. 2011, 27(5):1390-1396.
Lin et al., "Adiponectin Mediates the Metabolic Effects of FGF21 on Glucose Homeostasis and Insulin Sensitivity in Mice," Cell Metab, May 2013, 17(5):779-789.
Lin et al., "Functional expression of a biologically active fragment of soluble gp130 as an ELP-fusion protein in transgenic plants: purification via inverse transition cycling," Biochem J, Sep. 2006, 398(3):577-583.
Lin et al., "Statistical properties of the traditional algorithm-based designs for phase I cancer clinical trials," Biostatistics, 2001, 2(2):203-215.
Lin et al., "Utility of immunohistochemistry in the pancreatobiliary tract," Arch Pathol Lab Med, Jan. 2015, 139, 24-38.
Linder et al., "Lipid Modifications of G Protein Subunits," J. Biol. Chem., 1991, 266(7):4654-4659.
Ling et al., "Protein thioester synthesis enabled by sortase," J. Am Chem Soc, Jul. 2012, 134(26):10749-10752.
Litiere et al., "RECIST—learning from the past to build the future," Nat Rev Clin Oncol, Mar. 2017, 14, 187-192.
Liu et al., "Brachytherapy using injectable seeds that are self-assembled from genetically encoded polypeptides in situ," Cancer Res, Nov. 2012, 72, 5956-5965.
Liu et al., "Hydrophobic modifications of cationic polymers for gene delivery," Prog. In Polym. Sci., Sep. 2010, 35, 1144-1162.
Liu et al., "In Situ Formation of Protein-Polymer Conjugates through Reversible Addition Fragmentation Chain Transfer Polymerization**," Angew. Chem. Int. Ed. Apr. 2007, 46, 3099-3103.
Liu et al., "Injectable intratumoral depot of thermally responsive polypeptide-radionuclide conjugates delays tumor progression in a mouse model," J. Control Release, May 2010, 144(1):2-9.
Liu et al., "Tracking the in vivo fate of recombinant polypeptides by isotopic labeling" Journal of Controlled Release, Sep. 2006, 114, 184-192.
Liu et al., "Tumor accumulation, degradation and pharmacokinetics of elastin-like polypeptides in nude mice," Journal of Controlled Release, Nov. 2006, 116, 170-178.
Livingstone, "Theoretical property predictions. Curr Top Med Chem FIELD Full Journal Title: Current topics in medicinal chemistry," Curr. Top. Med. Chem. 2003, 3, 1171-1192.
Lovshin et al., "Incretin-based therapies for type 2 diabetes mellitus," Nat. Rev. Endocrinol. 5, Jun. 2009, 262-269.
Ludden, "Nonlinear pharmacokinetics: clinical Implications," Clin. Pharmacokinet., 1991, 20 (6), 429-446.
Luginbuhl et al., "One-week glucose control via zero-order release kinetics from an injectable depot of glucagon-like peptide-1 fused to a thermosensitive biopolymer," Nat. Biomed. Eng. 1, Jun. 2017, Article No. 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., Nov. 2017, 56(45):13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lund et al., "Phase II study of gemcitabine (2',2'-difluorodeoxycytidine) in previously treated ovarian cancer patients," J. Natl. Cancer. Inst. 1994, 86(20):1530-1533.
Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, Mar. 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.
Ma et al., "Non-fouling oligo(ethylene glycol)-functionalized polymer brushes synthesized by surface-initiated atom transfer radical polymerization," Advanced Materials 2004, 16 (4), 338.
Ma et al., "Protein-resistant polymer coatings on silicon oxide by surface-initiated atom transfer radical polymerization," Langmuir: the ACS journal of surfaces and colloids, Mar. 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.
MacEwan et al., "Applications of elastin-like polypeptides in drug delivery," Journal of Controlled Release, Sep. 2014, 190: p. 314-330.
MacEwan et al., "Controlled apoptosis by a thermally toggled nanoscale amplifier of cellular uptake," Nano Letters, Apr. 2014, 14, 2058-2064.
MacEwan et al., "Digital switching of local arginine density in a genetically encoded self-assembled polypeptide nanoparticle controls cellular uptake," Nano Lett., Jun. 2012, 12, 3322-3328.
MacEwan et al., "Elastin-like polypeptides: Biomedical applications of tunable biopolymers," Biopolymers, Jan. 2010, 94, 60-77.
MacEwan et al., "Non-chromatographic Purification of Recombinant Elastin-like Polypeptides and their Fusions with Peptides and Proteins from *Escherichia coli*," Jun. 2014, 88, p. e51583.
MacEwan et al., "Phase Behavior and Self-Assembly of Perfectly Sequence-Defined and Monodisperse Multiblock Copolypeptides," Biomacromolecules, Jan. 2017, 18(2):599-609.
Mack et al., "Antiobesity action of peripheral exenatide (exendin-4) in rodents: effects on food intake, body weight, metabolic status and side-effect measures," Int. J. Obes. 30, Sep. 2006, 1332-1340.

(56) References Cited

OTHER PUBLICATIONS

MacKay et al., "Self-assembling chimeric polypeptide-doxorubicin conjugate nanoparticles the abolish tumors after single injection," Nat Mater, Dec. 2009, 8(12):993-999.
Maeda et al., "Tumor vascular permeability and the EPR effect in macro molecular therapeutics: a review," J. Control. Release, Mar. 2000, 65(1-2)271-284.
Magnusson et al., "In Situ Growth of Side-Chain PEG Polymers from Functionalized Human Growth Hormone—A New Technique for Preparation of Enhanced Protein-Polymer Conjugates," Bioconjugate Chem. 21, Mar. 2010, 671-678.
Magnusson et al., "Ion-Sensitive "Isothermal" Responsive Polymers Prepared in Water," Journal of the American Chemical Society, Aug. 2008, 130, 10852-10853.
Maitra et al., "Pancreatic Cancer," Annu Rev Pathol Mech Dis, Feb. 2008, 3, 157-188.
Malik et al., "Recent advances in protein and peptide drug delivery systems," Curr. Drug Deliv. 2, Apr. 2007, 141-151.
Mann et al., "Proteomic analysis of post-translational modifications," Nat. Biotechnol., 2003, 21, 255-61.
Manzoor et al., "Overcoming limitations in nanoparticle drug delivery: triggered, intravascular release to improve drug penetration into tumors," Cancer Res, Nov. 2012, 72, 5566-5575.
Mao et al., "DNA repair by nonhomologous end joining and homologous recombination during cell cycle in human cells," Cell cycle, Sep. 2008, 7, 2902-2906.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram- positive bacteria," Microbiol Mol Biol Rev, Mar. 2006, 70(1):192-221.
Mariam et al., "Albumin corona on nanoparticles—a strategic approach in drug delivery," Drug Deliv., Oct. 2016, 23 (8), 2668-2676.
Marr et al., "Effect of Temperature on the Composition of Fatty Acids in *Escherichia coli*," J Bacteriol., 1962, 84(6):1260-7.
Marten et al., "A randomized multicentre phase II trial comparing adjuvant therapy inpatients with interferon alpha-2b and 5-FU alone or in combination with either external radiation treatment and cisplatin (CapRI) or radiation alone regarding event-free survival—CapRI-2," BMC Cancer, Feb. 2009, 9, 1-8.
Maskarinec et al., "Protein engineering approaches to biomaterials design," Curr. Opin. Biotechnol., 2005, 16, 422-426.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, Jun. 2015, 208:52-8.
Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matsumura, "Cancer stromal targeting (CAST) therapy," Advanced Drug Delivery Reviews, Jun. 2012, 64, 710-719.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, Dec. 2008, 93(12):4810-4817.
Matyjaszewski et al., "Atom transfer radical polymerization," Chem. Rev. 101, Sep. 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the Collagen Type IV Triple Helix:. Cis/Trans Proline-Induced Multiple 1H NMR Conformations and Evidence for a KG/PG Multiple Turn Repeat Motif in the All-Trans proline State," Biochemistry, 1991, 30: 8251-8267.
McConkey et al., "Molecular Characterization of Pancreatic Cancer Cell Lines," Pancreatic Cancer, Jan. 2010, 457-469.
McDaniel et al., "A unified model for de novo design of elastin-like polypeptides with tunable inverse transition temperatures," Biomacromolecules, Aug. 2013, 14(8):2866-2872.
McDaniel et al., "Actively targeting solid tumours with thermoresponsive drug delivery systems that respond to mild hyperthermia," Int J Hyperthermia, Aug. 2013, 29, 501-510.
McDaniel, "Assembly of Highly Asymmetric Genetically-Encoded Amphiphiles for Thermally Targeted Delivery of Therapeutics," Dissertation, 2013, 295 pages.
McDaniel et al., "Doxorubicin-conjugated chimeric polypeptide nanoparticles that respond to mild hyperthermia," Control. Release, May 2012, 159 (3), 362-367.
McDaniel et al., "Drug delivery to solid tumors by elastin-like polypeptides," Adc. Drug Deliver. Rev., Dec. 2010, 62(15):1456-1467.
McDaniel et al., "Noncanonical Self-Assembly of Highly Asymmetric Genetically Encoded Polypeptide Amphiphiles into Cylindrical Micelles," Nano Lett, Sep. 2014, 14(11):6590-6598.
McDaniel et al., "Rational design of "heat seeking" drug loaded polypeptide nanoparticles that thermally target solid tumors," Nano Letters, Apr. 2014, 14, 2890-2895.
McDaniel et al., "Recursive Directional Ligation by Plasmid Reconstruction Allows Rapid and Seamless Cloning of Oligomeric Genes," Biomacromolecules, Feb. 2010, 11(4):944-952.
McDaniel et al., "Self-assembly of thermally responsive nanoparticles of a genetically encoded peptide polymer by drug conjugation," Chem. Int. Ed. Feb. 2013, 52, 1683-1687.
McHale et al., "Synthesis and in vitro evaluation of enzymatically cross-linked elastin-like polypeptide gels for cartilaginous tissue repair," Tissue Eng, 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
Meier et al., "Determination of Optimal Sample Size for Quantification of β-Cell Area, Amyloid Area and β-Cell Apoptosis in Isolated Islets," J Histochem Cytochem, Aug. 2015, 63(8):663-673.
Mejuch et al., "Synthesis of lipidated proteins," Bioconjug. Chem. 27, Jul. 2016, 1771-1783.
Mero et al., "Transglutaminase-mediated PEGylation of proteins: direct identification of the sites protein medificationby mass spectrometry using a novel monodisperse PEG," Bioconjug Chem, Feb. 2009, 20(2):384-389.
Merrick et al., "Seed fixity in the prostate/periprostatic region following brachytherapy," International journal of radiation oncology, biology, physics, 2000, 46, 215-220.
Methods and Welfare Considerations in Behavioral Research with Animal. (Mar. 2002).
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.

(56) References Cited

OTHER PUBLICATIONS

Meyer et al., "Targeting a Genetically Engineered Elastin-Like Polypeptide to Solid Tumors by Local Hyperthermia," Cancer Res., 2001, 61(4):1548-1554.
Miao et al., "Sequence and domain arrangements influence mechanical properties of elastin-like polymeric elastomers," Biopolymers, Jun. 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, Jan. 2013, 62, 317-326.
Micsonai et al. "Accurate secondary structure prediction and fold recognition for circular dichroism spectroscopy," Proc Natl Acad Sci U S A, Jun. 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid α-Helix Propensities," Journal of the American Chemical Society, 2002, 124, 945-962.
Miyata et al., "Polymeric micelles for nano-scale drug delivery," Reaction & Functional Polymers, Mar. 2011, 71, 227-234.
Mjelle et al., "Cell cycle regulation of human DNA repair and chromatin remodeling genes," DNA Repair, Jun. 2015, 30, 53-67.
Morgan et al., "The combination of epidermal growth factor receptor inhibitors with gemcitabine and radiation in pancreatic cancer," Clin Cancer Res, Aug. 2008, 14, 5142-5149.
Mosbach et al., "Formation of proinsulinby immobilized Bacillus subtilis," Nature, 1983, 302, 543-545.
Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.
Muiznieks et al., "Modulated growth, stability and interactions of liquid-like coacervate assemblies of elastin," Matrix Biology 36, Jun. 2014, pp. 39-50.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, Jun. 2006, vol. 3, No. 6, pp. 429-438.
Murphy et al., "A dosimetric model of duodenal toxicity after stereotactic body radiotherapy for pancreatic cancer," Int J Radiation Oncology Biol Phys, Dec. 2010, 78, 1420-1426.
Na et al., "Thermoresponsive pore structure of biopolymer microspheres for a smart drug carrier," Langmuir, Jun. 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials, Aug. 2014, 35(24):6482-6497.
Nairn et al., "A Synthetic Resilin Is Largely Unstructured," Biophysical Journal, Oct. 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Nanoprecision Medical, "Pipeline, Type II Diabetes," <http://www.nanoprecisionmedical.com/pipeline/diabetes>. webpage available as early as Aug. 2018.
Nauck "Glucagon-like Peptide 1 (GLP-1) in the Treatment of Diabetes," Horm Metab Res, 2004, 36(11/12):852-858 (in English).
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, Dec. 2010, 62, 1479-1485.
Nettles et al., "In situ crosslinking elastin-like polypeptide gels for application to articular cartilage repair in a goat osteochondral defect model," Tissue Eng Part A, Jul. 2008, 14, 1133-1140.
Newcomb et al., "Advances in cryogenic transmission electron microscopy for the characterization of dynamic self-assembling nanostructures," Current Opinion in Colloid and Interface Science, Dec. 2012, 17, 350-359.
Newton et al., "Commissioning a small-field biological irradiator using point, 2D, and 3D dosimetry techniques," Medical Physics, Dec. 2011, 38, 6754-6762.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. Jan. 2007, 45, 4697-4699.
Nie, "Understanding and overcoming major barriers in cancer nanomedicine," Nanomedicine (Lond) Jun. 2010, 5(4), 523-528.
Nielsen, "Incretin mimetics and DPP-IV inhibitors for the treatment of type 2 diabetes," Drug Discov. Today 10, 2005, 703-710.
Nies et al., "Fibroblast Growth Factor Signaling in Metabolic Regulation," Front Endocrinol, Jan. 2016, 6(193) (in English).
Nilvebrant et al., "The albumin-binding domain as a scaffold for protein engineering," Computational and Structural Biotechnology Journal, Mar. 2013, 6: e201303009, 8 pages.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, Sep. 2008, 9, 2755-2763.
O'Day et al., "Therapeutic Protein-polymer Conjugates: Advancing beyond PEGylation," J. Am. Chem. Soc., Sep. 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Olafsen et al., "Covalent disulfide-linked anti-Cea diabody allows site-specific conjugation and radiolabeling for tumor targeting applications," Protein Engineering, Design & Selection, 2004, 17(1):21-27.
Ortony et al., "Internal dynamics of a supramolecular nanofibre," Nat. Mater., Aug. 2014, 13, 1-5.
Ozer et al., "Site-Specific and Stoichiometric Stealth Polymer Conjugates of Therapeutic Peptides and Proteins," Bioconjug Chem, Mar. 2017, 28(3):713-723.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, Apr. 2010, 102, 456-463.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, Oct. 2016, 96, S204-S205.
Palva et al., "Secretion of interferon by Bacillus subtilis," Gene, 1983, 22, 229-235.
Pang et al., "A Modular Method for the High-Yield Synthesis of Site-Specific Protein-Polymer Therapeutics," Angew Chem Int Ed Engl, Jul. 2016, 55, 10296-10300.
Paolino et al., "Folate-targeted supramolecular vesicular aggregates as a new frontier for effective anticancer treatment in invivo model," Eur. J. Pharm. Biopharm., Jun. 2012, 82(1):94-102.

(56) References Cited

OTHER PUBLICATIONS

Paolino et al., "Gemcitabine-loaded PEGylated unilamellar liposomes vs Gemzar: biodistribution, pharmacokinetic features and in vivo antitumor activity," J. Control. Release Jun. 2010, 144(2):144-150.
Paoloni et al., "Translation of new cancer treatments from pet dogs to humans," Nat. Rev. Cancer Feb. 2008, 8(2), 147-156.
Papa et al., "PEGylated Liposomal Gemcitabine: Insights Into a Potential Breast Cancer Therapeutic," Cell Oncol. (Dordr), Oct. 2013, 36(6):449-457.
Paramonov et al., "Self-assembly of peptide-amphiphile nanofibers: The roles of hydrogen bonding and amphiphilic packing," J. Am. Chem. Soc., May 2006, 128, 7291-7298.
Park et al., "Exendin-4 and exercise improve hepatic glucose homeostasis by promoting insulin signaling in diabetic rats," Metabolism, Janury 2010, 59, 123-133.
Park et al., "Formulation optimization and in vivo proof-of-concept study of thermosensitive liposomes balanced by phospholipid, elastin-like polypeptide, and cholesterol," PLoS One, Jul. 2014, 9: e103116, 13 pages.
Park et al., "Protein stitchery: Design of a protein for selective binding to a specific DNA sequence," PNAS, 1992, vol. 89:9094-9096.
Parkes et al. "Discovery and development of exenatide: the first antidiabetic agent to leverage the multiple benefits of the incretin hormone, GLP-1," Expert Opinion. Drug Deliv., Feb. 2013, 8(2):219-244.
Parveen et al., "Nanomedicine," Clinical Pharmacokinetics, Oct. 2006, 45(10):965-988.
Patil et al., "Cellular delivery of doxorubicin via pH-controlled hydrazone linkage using multifunctional nano vehicle based on poly(beta-1-malic acid)," Int J Mol Sci, Sep. 2012, 13, 11681-11693.
Peeler et al., "Genetically encoded initiator for polymer growth from proteins," J. Am. Chem. Soc. 132, Oct. 2010, 13575-13577.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., May 2017, 28(5):1403-1412.
Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.
Pinkas et al., "Tunable, post-translational hydroxylation of collagen domains in *Escherichia coli*," ACS Chem. Biol., Apr. 2011, 6(4):320-324.
Pliarchopoulou et al., "Pancreatic cancer: Current and future treatment strategies," Cancer Treatment Reviews, Aug. 2009, 35, 431-436.
Poitout et al., "Glucolipotoxicity: Fuel Excess and β-Cell Dysfunction," Endocr Rev, May 2008, 29(3):351-366.
Pometun et al., "Quantitative observation of backbone disorder in native elastin," J Biol Chem, 2004, 279, 7982-7987.
Popp et al., "Site-specific labeling via sortase-mediated transpeptidation," Curr. Protoc. Protein Sci. 56, Apr. 2009, 15.13.1-15.13.9.
Popp et al., "Sortase-Catalyzed Transformations That Improve the Properties of Cytokines," PNAS, Feb. 2011, vol. 108, No. 8, pp. 3169-3174.
Potters et al., "12-year outcomes following permanent prostate brachytherapy inpatients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Potthoff et al., "Endocrine fibroblast growth factors 15/19 and 21: from feast to famine," Genes Dev, Feb. 2012, 26(4):312-324.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, Mar. 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, Mar. 2012, 21, 418-429.
Provenzano et al., "Hyaluronan, fluid pressure, and stromal resistance in pancreas cancer," Br J Cancer, Jan. 2013, 108, 1-8.
Pulaski et al., "Mouse 4T1 breast tumor model," Curr. Protoc. Immunol., 2001, Chapter 20, Unit 20.2.
Qi et al., "A brush-polymer conjugate of exendin-4 reduces blood glucose for up to five days and eliminates poly(ethylene glycol) antigenicity," Nat Biomed Eng, Nov. 2016, 1:0002.
Qi et al., Dataset for a brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.
Qi et al., "Growing polymers from peptides and proteins: a biomedical perspective," Polym. Chem., Jan. 2014, 5(2):266-276.
Qi et al., "Protein-polymer conjugation—moving beyond PEGylation," Curr. Opin. Chem. Biol. 28, Oct. 2015, 181-193.
Qi et al., "Sortase-catalyzed initiator attachment enables high yield growth of a stealth polymer from the C terminus of a protein," Macromol. Rapid Commun., Aug. 2013, 34(15):1256-1260.
Qiu et al., "Development of Orthotopic Pancreatic Tumor Mouse Models," Methods Mol Biol, Jan. 2013, 980: 215-223.
Qiu et al., "Polymer Architecture and Drug Delivery," Pharmaceutical Research, Feb. 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Sequence heuristics to encode phase behaviour in intrinsically disordered protein polymers," Nat. Mater., Nov. 2015, 14(11):1164-1171.
Rabotyagova et al., "Protein-based block copolymers," Biomacromolecules, Feb. 2011, 12(2): 269-289.
Radivojac et al., "Intrinsic Disorder and Functional Proteomics," Biophysical Journal, Mar. 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.
Rankine et al., "Investigating end-to-end accuracy of image guided radiation treatment delivery using a micro-irradiator," Physics in Medicine and Biology, Nov. 2013, 58(21): 7791-7801.
Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," RegenBiomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.

(56) References Cited

OTHER PUBLICATIONS

Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human avβ3 integrin," J Mol Biol, 2003, 326(5):1475-1488.
Richards et al., "Man's best friend: what can pet dogs teach us about non-Hodgkin lymphoma?" Inmunol Rev., Jan. 2015, 263 (1): 173-191.
Riddles et al., "Ellman's reagent: 5,5'-dithiobis(2-nitrobenzoic acid)—a reexamination," Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., Sep. 2015, 589, 2477-2486.
Robinet et al. "Elastin-derived peptides enhance angiogenesis by promoting endothelial cell migration and tubulogenesis through upregulation of MT1-MMP," J. Cell Science, 2005, 118:343-356.
Rodriguez-Diaz et al., "Alpha cells secrete acetylcholine as a non-neuronal paracrine signal priming beta cell function in humans," Nat Med, Jun. 2011, 17:888-892.
Römer et al., "The elaborate structure of spider silk: structure and function of a natural high performance fiber," Prion, Nov. 2008, 2(4):154-161.
Roopenian et al., "FcRn: the neonatal Fc receptor comes of age," Nat. Rev. Immunol., Sep. 2007, vol. 7, No. 9, 715-725.
Rosenberg et al., "Present and future innovations in radiation oncology," Surg Oncol Clin N Am, Jul. 2013, 22(3):599-618.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, Mar. 2016, 12(5):669-685.
Ryerson et al., "Annual report to the nation on the status of cancer, 1975-2012, featuring the Increasing incidence of liver cancer," Cancer, May 2016, 122(9): 1312-1337.
Saba et al., "A Comparative Oncology Study of Iniparib Defines Its Pharmacokinetic Profile and Biological Activity in a Naturally-Occurring Canine Cancer Model," PLoS One, Feb. 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, Jun. 2009, 131(26): 9304-9310.
Saifer et al., "Selectivity of binding of PEGs and PEG-like oligomers to anti-PEG antibodies induced by methoxyPEG-proteins," Molecular Immunology, Feb. 2014, 57(2):236-246.
Sandler et al., "Gemcitabine: Single-Agent and Combination Therapy in Non-Small Cell Lung Cancer," Oncologist 1999, 4(3)241-251.
Schaal et al., "Injectable polypeptide micelles that form radiation crosslinked hydrogels in situ for intratumoral radiotherapy," Journal of Controlled Release, Apr. 2016, 228, 58-66.
Schellenberg et al., "Gemcitabine chemotherapy and single-fraction stereotactic body radiotherapy for locally advanced pancreatic cancer," Int J Radiation Oncol Biol Phys,Nov. 2008, 72(3): 678-686.
Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.
Schellenberger et al., "A recombinant polypeptide extends the in vivo half-life of peptides and proteins in a tunable manner," Nat. Biotechnol., Dec. 2009, 27(12):1186-1188.
Schlaff et al., "Bringing the heavy: carbon ion therapy in the radiobiological clinical context," Radiation Oncology, Mar. 2014, 9, Article 88, 1-18.
Schneider et al., "NIH Image to ImageJ: 25 years of image analysis," Nature Methods, Jul. 2012, 9(7): 671-675.
Schwendeman et al., "Injectable controlled release depots for large molecules," J Control Release, Sep. 2014, 190, 240-253.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., Oct. 2007, 93(7):2429-2435.
Shadwick, "Mechanical design in arteries," J Exp Biol, 1999, 202, 3305-3313.
Shang et al., "pH-Dependent Protein Conformational Changes in Albumin:Gold Nanoparticle Bioconjugates: A Spectroscopic Study," Langmuir, Feb. 2007, 23 (5), 2714-2721.
Shao et al., "Super-resolution 3D microscopy of live whole cells using structured illumination," Nat Methods, Oct. 2011, 8(12): 1044-1046.
Shen et al., "Conjugation site modulates the in vivo stability and thearpeutic activity of antibody-drug conjugates," Nat Biotechnol, Jan. 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.
Sherman et al., "Next-Generation PEGylation Enables Reduced Immunoreactivity of PEG-Protein Conjugates," Drug and Development & Delivery, Jun. 2012, vol. 12, No. 5, 36-42.
Sherman et al., "Role of the Methoxy Group in Immune Responses to mPEG-Protein Conjugates," Bioconjugate Chemistry, Mar. 2012, 23(3): 485-499.
Shi et al., "Cell adhesion on a POEGMA-modified topographical surface," Langmuir: the ACS journal of surfaces and colloids, Dec. 2012, 28 (49), 17011-8.
Shimoboji et al., "Temperature-Induced Switching of Enzyme Activity with Smart Polymer-Enzyme Conujugates," Bioconjugate Chem. 2003, 14, 517-525.
Shusharina et al., "Micelles of Diblock Copolymers with Charged and Neutral Blocks: Scaling and Mean-Field Lattice Approaches," Macromolecules, 2000, 33(10): 3892-3901.

(56) References Cited

OTHER PUBLICATIONS

Siegel et al., "Absorbed fractions for electrons and beta particles in spheres of various sizes," J Nucl Med, 1994, 35, 152-156.
Siegwart et al., "ATRP in the Design of Functional Materials for Biomedical Applications," Prog Polymer Science, Jan. 2012, vol. 37, No. 1, pp. 18-37.
Silberstein et al., "The Snm Practice Guideline for Therapy of Thyroid Disease with $^{131}$I, 3.0," J Nucl Med, Jul. 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules, Aug. 2012, 45(16):6371-6379.
Simnick et al., "In vivo tumor targeting by a NGR-decorated micelle of a recombinant diblock copolypeptide," J Control Release, Oct. 2011, 155(2): 144-151.
Simnick et al., "Morphing low-affinity ligands into high-avidity nanoparticles by thermally triggered self-assembly of a genetically encoded polymer," ACS Nano, Apr. 2010, 4(4):2217-2227.
Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.
Sisson et al., "Radiation safety in the treatment of patients with thyroid diseases by radioiodine 131I: practice recommendations of the American Thyroid Association," Thyroid, Apr. 2011, 21(4):335-346.
Smith et al., "The Role of Beta Cell Glucagon-like Peptide-1 Signaling in Glucose Regulation and Response to Diabetes Drugs," Cell Metab, Jun. 2014, 19(6):1050-1057.
Sonawane et al., "Hydrazo linkages in pH responsive drug delivery systems," European Journal Pharmaceutical Sciences, Mar. 2017, 99, 45-65.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, Sep. 2016, 234:83-89.
Sriraman et al., "Barriers to drug delivery in solid tumors," Tissue Barriers, Jul. 2014, 2(3): 2-10.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, May 2017, 158(5):1314-1327.
Stefl et al., "RNA sequence-and shape-dependent recognition by proteins in the ribonucleoprotein particle" EMBO reports (2005) 6(1):33-38.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.
Strohmaier et al., "Comparison of $^{60}$Co and $^{192}$Ir sources in HDR brachytherapy," J Contemp Brachyther, Dec. 2011, 3(4): 199-208.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, Apr. 2015, 10, 1-17.
Sumerlin, "Proteins as Initiators of Controlled Radical Polymerization: Grafting-from via ATRP and RAFT," ACS Macro Lett. Jan. 2012, 1(1): 141-145.
Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.
Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, Jan. 2013, 46(1): 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, Jul. 2014, 42(7): 1508-1516.
Swee et al., "Sortase-mediated modification of αDEC205 affords optimization of antigen presentation and immunization against a set of viral epitopes," Proc Natl Acad Sci USA, Jan. 2013, 110(4):1428-1433.
Swers et al., Multivalent Scaffold Proteins as Superagonists of TRAIL Receptor 2-Induced Apoptosis, Mol Cancer Ther, Jul. 2013, 12(7): 1235-1244.
Takalkar et al., "Radium-223 dichloride bone-targeted alpha particle therapy for hormone-refractory breast cancer metastatic to bone," Exp Hematol Oncol, Sep. 2014, 8, Article No. 23.
Tallarida, "Quantitative methods for assessing drug synergism," Genes & Cancer, Nov. 2011, 2(11): 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, Aug. 2006, 45(31): 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., Apr. 2016, 15(4): 419-424.
Tang et al., "Enzymatic Polymerization of High Molecular Weight DNA Amphiphiles That Self-Assemble into Star-Like Micelles," Advanced Materials, Feb. 2014, 26(19): 3050-3054.
Tang et al., "High-Molecular-Weight Polynucleotides by Transferase-Catalyzed Living Chain-Growth Polycondensation," Angew. Chem., Jun. 2017, 56(24): 6778-6782.
Tang et al., "Identification of PECAM-1 in solid tumor cells and its potential involvement in tumor cell adhesion to endothelium," J. Biol. Chem., 1993, 268, 22883-22894.
Tantakitti et al., "Energy landscapes and functions of supramolecular systems," Nat. Mater., Apr. 2016, 15(4): 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, Oct. 2012, 3 (10), 2743-2751.
Teicher, "In vivo/ex vivo and in situ assays used in cancer research: a brief review," Toxicol. Pathol., Jan. 2009, 37 (1), 114-122.
Therasse et al., "New guidelines to evaluate the response to treatment in solid tumors," J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.

(56) References Cited

OTHER PUBLICATIONS

Tomiyama et al., "Relevant use of Klotho in FGF19 subfamily signaling system in vivo," Proc Natl Acad Sci USA, Jan. 2010, 107(4):1666-71.
Tompa et al., "Fuzzy complexes: polymorphism and structural disorder in protein-protein interactions," Trends Biochem Sci, Jan. 2008, 33(1): 2-8.
Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptide that cleaves surface proteins of *Staphylococcus aureus* and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, Apr. 2014, 24(2): 140-147.
Trieu et al., "P0157 Preclinical evaluation of NBN-paclitaxel in pancreatic cancer xenograft models," Eur J Cancer, May 2014, 50(4): e53.
Triola et al., "Chemical biology of lipidated proteins," ACS Chemical Biology, Jan. 2012, 7(1): 87-99.
Troyanskaya et al., "Nonparametric methods for identifying differentially expressed genes in microarray data," Bioinformatics, 2002, 18(11):1454-61.
Tsarevsky et al., "Deactivation efficiency and degree of control over polymerization in ATRP in protic solvents," Macromolecules 37, 2004, 9768-9778.
Tschöp et al., "Unimolecular Polypharmacy for Treatment of Diabetes and Obesity," Cell Metab, Jul. 2016, 24(1):51-62.
Tsume et al., "The development of orally administrable gemcitabine prodrugs with D-enantiomer amino acids: Enhanced membrane permeability and enzymatic stability," Eur. J. Pharm. Biopharm., Apr. 2014, 86(3):514-523.
Tu et al., "Stages in tropoelastin coalescence during synthetic elastin hydrogel formation," Micron, Apr. 2010, 41(3): 268-272.
Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.
Tward et al., "Survival of men with clinically localized prostate cancer treated with prostatectomy, brachytherapy, or no definitive treatment: impact of age at diagnosis," Cancer, Oct. 2006, 107(10): 2392-2400.
Uchida et al., "Potential of adenovirus-mediated REIC/Dkk-3 gene therapy for use in the treatment of pancreatic cancer," Journal of Gastroenterology and Hepatology, Apr. 2014, 29(5): 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Free energy transduction in polypeptides and proteins based on inverse temperature transitions," Prog Biophys Mol Biol, Jan. 1992, 57(1):23-57.
Urry, "Protein elasticity based on conformations of sequential polypeptides: The biological elastic fiber," J Protein Chemistry, 1984, 3, 403-436.
Valkenburg et al., "Targeting the tumour stroma to improve cancer therapy," Nature Reviews Clinical Oncology, Jun. 2018, 15, 366-381.
Van der Lee et al., "Classification of intrinsically disordered regions and proteins," Chem Rev, Jul. 2014, 114(13): 6589-6631.
Van Roey et al., "Short linear motifs: ubiquitous and functionally diverse protein interaction modules directing cell regulation," Chem Rev, Jul. 2014, 114(13): 6733-6778.
Van Roy, "Beyond E-cadherin: roles of other cadherin superfamily members in cancer," Nat Rev Cancer, Feb. 2014, 14(2): 121-134.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., May 2011, 22(5): 976-986.
Vlieghe et al., "Synthetic therapeutic peptides: science and market," Drug Discovery Today, Jan. 2010, 15(1-2): 40-56.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., Nov. 2011, vol. 7, No. 4, pp. 214-220.
Vrhovski et al., "Biochemistry of tropoelastin," Eur J Biochem, 1998, 258, 1-18.
Vrignaud et al., "Strategies for the nanoencapsulation of hydrophilic molecules in polymer-based nanoparticles," Biomaterials, Nov. 2011, 32(33):8593-8604.
Walczak, "Death Receptor—Ligand Systems in Cancer, Cell Death, and Inflammation," Cold Spring Harb. Perspect. Biol., May 2013, 5(5): a008698.
Wali et al., "Measuring Death of Pancreatic Beta Cells in Response to Stress and Cytotoxic T Cells," Methods in Molecular Biology, Mar. 2015, 1292:165-176.

(56) References Cited

OTHER PUBLICATIONS

Walsh et al., "Post-translational modifications in the context of therapeutic proteins," Nat. Biotechnol., Oct. 2006, 24(10): 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteo me diversifications," Angew. Chem. Int. Ed., 2005, 44, 7342-7372.
Wang et al., "Enhanced Tumor Delivery of Gemcitabine via PEG-DSPE/TPGS Mixed Micelles," Mol. Pharm., Apr. 2014, 11(4): 1140-1150.
Wang et al., "Extending Half Life of H-Ferritin Nanoparticle by Fusing Albumin Binding Domain for Doxorubicin Encapsulation," Biomacromolecules, Mar. 2018, 19(3):773-781.
Wang et al., "Quantitative Mapping of the Spatial Distribution of Nanoparticles in Endo-Lysosomes by Local pH," Nano Lett, Feb. 2017, 17(2): 1226-1232.
Wang et al., "Size and dynamics of caveolae studied using nanoparticles in living endothelial cells," ACS nano, Dec. 2009, 3(12): p. 4110-4116.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wei et al., "Anticancer drug nanomicelles formed by self-assembling amphiphilic dendrimer to combat cancer drug resistance," Proceedings of the National Academy of Sciences of the United States of America, Mar. 2015, 112(10): 2978-2983.
Wei et al., "Fibroblast growth factor 21 promotes bone loss by potentiating the effects of peroxisome proliferator-activated receptor γ," Proc Natl Acad Sci USA, Feb. 2012, 109(8):3143-3148.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic β-Cell Function and Survival by Activation of Extracellular Signal—Regulated Kinase 1/2 and Akt Signaling Pathways," Diabetes, Sep. 2006, 55(9):2470-2478.
Werle et al., "Strategies to improve plasma half life time of peptide and protein drugs," Amino Acids 30, Jun. 2006, 30(4):351-367.
Wienkers et al., "Predicting in vivo drug interactions from in vitro drug discovery data," Nat. Rev. Drug. Discov. 2005, 4(10):825-833.
Williams et al., "Targeted radionuclide therapy," Medical Physics, Jul. 2008, 35(7): 3062-3068.
Williamson et al., "Efficient N-terminal labeling of proteins by use of sortase," Angew Chem Int ed Engl, Sep. 2012, 51(37):9377-9380.
Winzell et al., "The high-fat diet-fed mouse: a model for studying mechanisms and treatment of impaired glucose tolerance and type 2 diabetes," Diabetes 53, 2004, S215-S219.
Wold, "Invivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, Mar. 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.
Xia et al., "Tunable self-assembly of genetically engineered silk—elastin-like protein polymers," Biomacromolecules, Nov. 2011, 12(11): 3844-3850.
Xu et al., "A quality by design (QbD) case study on liposomes containing hydrophilic API: II. Screening of critical variables, and establishment of design space at laboratory scale," Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAs) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Poly(carboxybetaine) nano materials enable long circulation and prevent polymer-specific antibody production," Nano Today, Feb. 2014, 9(1):10-16.
Yates et al., "Contemporary management of patients with high-risk non-muscle-invasive bladder cancer who fail intravesical BCG therapy," World journal of urology, May 2011, 29(4): 415-422.
Yeo et al., "Coacervation of tropoelastin," Adv Colloid Interface Sci, Sep. 2011, 167(1-2): 94-103.
Yokoe et al., "Albumin-conjugated PEG liposome enhances tumor distribution of liposomal do xorubicin in rats," International Journal of Pharmaceutics, May 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Do xorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett, Dec. 2018, 18(12): 7784-7793.
Yu et al., "Effectiveness and security of CT-guided percutaneous implantation of (125)I seeds in pancreatic carcinoma," The British journal of radiology, Jul. 2014, 87(1039): 20130642, 7 pages.
Yusta et al., "GLP-1 receptor activation improves β cell function and survival following induction of endoplasmic reticulum stress," Cell Metab, Nov. 2006, 4(5):391-406.
Zhang et al., "A self-assembly pathway to aligned monodomain gels," Nat. Mater., Jul. 2010, 9(7): 594-601.

(56) References Cited

OTHER PUBLICATIONS

Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5):761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Shape Effects of Nanoparticles Conjugated with Cell-Penetrating Peptides (HIV Tat PTD) on CHO Cell Uptake," Bioconjugate Chem, Sep. 2008, 19(9):1880-1887.
Zhao et al., "A new Bliss Independence model to analyze drug combination data," J Biomol Screen, Jun. 2014, 19(5): 817-821.
Zhao et al., "Fluorescence probe techniques used to study micelle formation in water-soluble block copolymers," Langmuir 1990, 6(2):514-516.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.
Zong et al., "Crystal structures of *Staphylococcus aureus* sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting Mar. 2019, 27(3):292-299.
Karperien, A. FracLac for Image J, version 2.5 <http://rsb.info.nih.gov/ij/plugins/fraclac/FLHelp/Introduction.htm> 1999-2012.
Schaal et al., "Biopolymer B-brachytherapy delivered with concomitant paclitaxel outperforms traditional x-ray radiation to include complete regression in multiple pancreatic tumor xenograft models through synergistic modulation of the tumor microenvironment," Poster #5831, 2018.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
United States Patent Office Action for U.S. Appl. No. 16/058,924 dated Nov. 26, 2019 (23 pages).
Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using REVOLVE System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The No. of operations required for completing breast reconstruction," Plast Reconstr Surg Glob Open, 2012, 2: e242.
Frandsen et al., "Recombinant protein-based polymers for advanced drug delivery," Chem Soc Rev, 2012,41: 2696-2706.
Gabriel et al., "Fat grafting and breast reconstruction: tips for ensuring predictability," Gland Surg, 2015, 4: 232-243.
Gylbert, "Applanation tonometry for the evaluation of breast compressibility," Scand J Plast Reconstr Surg Hand Surg, 1989, 23: 223-229.
Hess et al., "Graphene Transistors for Multifunctional Polymer Brushes for Biosensing Applications," Applied Materials & Interfaces, 2014, 6: 9705-9710.
Hsu et al., "Fat grafting's past, present, and future: why adipose tissue is emerging as a critical link to the advancement of regenerative medicine," Aesthet Surg J, 2015, 32: 892-899.
Hwang et al., "Synthesis and Characterization of Polystyrene Brushes for Organic Thin Film Transistors," Journal of Nanoscience and Nanotechnology, 2012, 12: 4137-4141.
Kronowitz et al., "Delayed-Immediate Breast Reconstruction," Plastic and Reconstructive Surgery, 2004, 113: 1617-1628.

(56) References Cited

OTHER PUBLICATIONS

Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co-injections of Autologous Fat with Fillers," International Journal of Surgery & Surgical Techniques, 2016, 2: 7 pages.
Park et al., "Polymer Brush as a Facile Dielectric Surface Treatment for High-Performance, Stable, Soluble Acene-Based Transistors," Chemistry of Materials, 2010, 22: 5377-5382.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg (Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB—P15214 (GST_PROMI) acessed online at <https://www.uniprot.org/uniprot/P152146/> on Jun. 8, 2021, 7 pages.
Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
Zhang et al., "Sensitive and Quantitative Detection of Anti-Poly(ethylene glycol) (PEG) Antibodies by Methoxy-PEG-Coated Surface Plasmon Resonance Sensors," Anal Chern, Aug. 2017, 89(16): 8217-8222.
United States Patent Office Action for U.S. Appl. No. 15/749,797 dated Oct. 20, 2020 (16 pages).
Aaron et al., "Elastin as a Random-Network Elastomer—a Mechanical and Optical Analysis of Single Elastin Fibers," Biopolymers, 1981,20(6):1247-1260.
Allen et al., "Liposomal drug delivery systems: from concept to clinical applications," Adv Drug Deliv Rev, 2013, 65(1):36-48.
Anselmo et al., "Nanoparticles in the clinic, " Bioeng Transl Med, Jun. 2016, 1(1):10-29.
Arami et al., "In vivo delivery, pharmacokinetics, biodistribution and toxicity of iron oxide nanoparticles," Chern Soc Rev, Dec. 2015, 44(23):8576-8607.
Astete et al., "Synthesis and characterization of PLGA nanoparticles," Journal of Biomaterials Science, Polymer Edition 2006, 17(3):247-289.
Babu, "The contribution of intrinsically disordered regions to protein function, cellular complexity, and human disease," Biochem Soc Trans, Oct. 2016, 44(5):1185-1200.
Bae et al., "Targeted drug delivery to tumors: myths, reality and possibility," J Control Release, 2011, 153(3): 198-205.
Balu et al., "An16-resilin: an advanced multi-stimuli-responsive resilin-mimetic protein polymer," Acta Biomater, Nov. 2014, 10:4768-4777.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, 2011, 104:489-507.
Banjade et al., "Phase transitions of multivalent proteins can promote clustering of membrane receptors," Elife, Oct. 2014, 3:e04123.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Bates et al., "Block copolymer thermodynamics: theory and experiment," Annu Rev. Phys. Chem., 1990, 41:525-57.
Best, "Computational and theoretical advances in studies of intrinsically disordered proteins," Curr Opin Struct Biol, Feb. 2017, 42:147-154.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Boeynaems et al., "Protein Phase Separation: A New Phase in Cell Biology," Trends Cell Biol, Jun. 2018, 28(6):420-435.
Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, 2012, 64(11):206-212.
Broome et al., "Expanding the utility of beta-galactosidase complementation: piece by piece," Mol Pharm, 2010, 7(1):60-74.
Burke et al., "Multimodal nanoparticle imaging agents: design and applications," Philos Trans A Math Phys Eng Sci, Nov. 2017, 375:20170261.
Carreiras et al., "Expression and localization of alpha v integrins and their ligand vitronectin in normal ovarian epithelium and in ovarian carcinoma," Gynecol Oncol, 1996, 62(2):260-7.
Champion et al., "Particle shape: a new design parameter for micro- and nanoscale drug delivery carriers," J Control Release, 2007, 121(1-2):3-9.
Champion et al., "Role of particle size in phagocytosis of polymeric microspheres," Pharm Res, 2008, 25(8):1815-21.
Champion et al., "Role of target geometry in phagocytosis," Proc Natl Acad Sci U S A, 2006, 103(13):4930-4.
Champion et al., "Shape induced inhibition of phagocytosis of polymer particles," Pharm Res, 2009, 26(1):244-9.
Chen, "Small-molecule delivery by nanoparticles for anticancer therapy," Trends Mol Med, 2010, 16(12):594-602.
Chithrani et al., "Elucidating the mechanism of cellular uptake and removal of protein-coated gold nanoparticles of different sizes and shapes," Nano letters, 2007, 7(6):1542-1550.
Conner et al., "Regulated portals of entry into the cell," Nature, 2003, 422(6927):37-44.
Costa et al., "Active Targeting of Cancer Cells by Nanobody Decorated Polypeptide Micelle with Bio-orthogonally Conjugated Drug," Nano letters, Dec. 2018, 19(1):247-254.
Dai et al., "Versatile biomanufacturing through stimulus-responsive cell—material feedback," Nature chemical biology, Sep. 2019, 15(10):1017-1024.
Dalhaimer et al., "Single Molecule Visualization of Stable, Stiffness-Tunable, Flow-Conforming Worm Micelles," Macromolecules, 2003, 36(18):6873-6877.
Das et al., "Conformations of intrinsically disordered proteins are influenced by linear sequence distributions of oppositely charged residues," Proc Natl Acad Sci U S A, 2013, 110(33):13392-13397.
Dignon et al., "Relation between single-molecule properties and phase behavior of intrinsically disordered proteins," Proc Natl Acad Sci U S A, Oct. 2018, 115(40):9929-9934.

(56) References Cited

OTHER PUBLICATIONS

Dignon et al., "Sequence determinants of protein phase behavior from a coarse-grained model," PLoS Comput Biol, Jan. 2018, 14(1):e1005941.
Duan et al., "Improving the thermostability and catalytic efficiency of Bacillus deramificans pullulanase by site-directed mutagenesis," Appl Environ Microbiol, 2013, 79(13):4072-4077.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Ehlerding et al., "Biodegradable and Renal Clearable Inorganic Nanoparticles," Adv Sci (Weinh), Feb. 2016, 3(2):1500223.
Elbaum-Garfinkle et al., "The disordered p. granule protein LAF-1 drives phase separation into droplets with tunable viscosity and dynamics," Proc Natl Acad Sci U S A, Jun. 2015, 112(23):7189-7194.
Elsabahy et al., "Design of polymeric nanoparticles for biomedical delivery applications," Chem Soc Rev, 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, 2015, Chapter Six, vol. 98, pp. 169-221.
Farokhzad et al., "Targeted nanoparticle-aptamer bioconjugates for cancer chemotherapy in vivo," Proc Natl Acad Sci U S A, 2006, 103(16):6315-20.
Franzmann et al., "Phase separation of a yeast prion protein promotes cellular fitness," Science, Jan. 2018, 359(6371):eaao5654.
Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D 11972.pdf?sequence=1 &isAllowed=y.
Geng et al., Shape effects of filaments versus spherical particles in flow and drug delivery, Nat Nanotechnol, 2007, 2(4):249-55.
Gilbreth et al., "Structural insights for engineering binding proteins based on non-antibody scaffolds," Curr Opin Struct Biol, 2012, 22(4):413-20.
Gillies et al., "Dendrimers and dendritic polymers in drug delivery," Drug Discovery Today, 2005, 10(1):35-43.
Goldsmith et al., "Enzyme engineering: reaching the maximal catalytic efficiency peak," Curr Opin Struct Biol, Dec. 2017, 47:140-150.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, 2008, 105(33):11613-8.
Gu et al., "Precise engineering of targeted nanoparticles by using self-assembled biointegrated block copolymers," Proc Natl Acad Sci U S A, 2008, 105(7):2586-91.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al.,"Functional Implications of Intracellular Phase Transitions," Biochemistry, May 2018, 57(17):2415-2423.
Huber et al., "Designer amphiphilic proteins as building blocks for the intracellular formation of organelle-like compartments," Nat Mater, Jan. 2015, 14(1):125-132.
Jiang et al., "Nanoparticle-mediated cellular response is size-dependent," Nat Nanotechnol, 2008, 3(3):145-50.
Jokerst et al., "Nanoparticle PEGylation for imaging and therapy," Nanomedicine (Lond), 2011, 6(4):715-28.
Jurney et al., "Unique size and shape-dependent uptake behaviors of non-spherical nanoparticles by endothelial cells due to a shearing flow," J Control Release, Jan. 2017, 245:170-176.
Kamaly et al., "Targeted polymeric therapeutic nanoparticles: design, development and clinical translation," Chem Soc Rev, 2012, 41(7):2971-3010.
Karagoz et al., "Polymerization-Induced Self-Assembly (PISA)—control over the morphology of nanoparticles for drug delivery applications," Polym. Chem., Jan. 2014, 5(2):350-355.
Kataoka et al., "Block copolymer micelles for drug delivery: Design, characterization and biological significance," Advanced Drug Delivery Reviews, 2001, 47:113-131.
Kelly et al., "Shape-specific, monodisperse nano-molding of protein particles," J Am Chem Soc, 2008, 130(16):5438-9.
Kesharwani et al., "Dendrimer as nanocarrier for drug delivery," Progress in Polymer Science, Feb. 2014, 39(2):268-307.
Kulkarni et al., "Design of lipid nanoparticles for in vitro and in vivo delivery of plasmid DNA," Nanomedicine, May 2017, 13(4):1377-1387.
Lee et al., "Polymersomes for drug delivery: design, formation and characterization," J Control Release, 2012, 161(2):473-83.
Lewis et al., "Use of digitized video microscopy with a fluorogenic enzyme substrate to demonstrate cell- and compartment-specific gene expression in *Salmonella enteritidis* and Bacillus subtilis," Molecular microbiology, 1994, 13:655-662.
Li et al., "Phase transitions in the assembly of multivalent signalling proteins," Nature, 2012, 483(7389):336-340.
Li et al., "Tunable Assembly of Protein-Microdomains in Living Vertebrate Embryos," Advanced Biosystems, Oct. 2018, 2(10):1800112.
Lin et al., "Formation and Maturation of Phase-Separated Liquid Droplets by RNA-Binding Proteins," Mol Cell, Oct. 2015, 60(2):208-219.
Lin et al., "Intrinsically disordered sequences enable modulation of protein phase separation through distributed tyrosine motifs," J Biol Chem, Nov. 2017, 292(46):19110-19120.
Lin et al., "Phase Separation and Single-Chain Compactness of Charged Disordered Proteins Are Strongly Correlated," Biophys J, May 2017, 112(10):2043-2046.
Lin et al., "Sequence-Specific Polyampholyte Phase Separation in Membraneless Organelles," Phys Rev Lett, Oct. 2016, 117(17):178101.
Liong et al., "Multifunctional inorganic nanoparticles for imaging, targeting, and drug delivery," ACS Nano, 2008, 2(5):889-96.
Liu et al., "Integrin $\alpha_v\beta_3$-Targeted Cancer Therapy," Drug Dev Res, 2008, 69(6):329-339.
Loh et al., "Utilising inorganic nanocarriers for gene delivery," Biomater Sci, Jan. 2016, 4(1):70-86.
LoPresti et al., "Polymersomes: nature inspired nanometer sized compartments," Journal of Materials Chemistry 2009, 19(22):3576-3590.
Lukyanov et al., "Tumor-targeted liposomes: doxorubicin-loaded long-circulating liposomes modified with anti-cancer antibody," J Control Release, 2004, 100(1):135-44.
Lyons et al., "Comparisons of Recombinant Resilin-like Proteins: Repetitive Domains Are Sufficient to Confer Resilin-like Properties," Biomacromolecules, 2009, 10(11):3009-3014.
Lyons et al., "Design and facile production of recombinant resilin-like polypeptides: Gene construction and a rapid protein purification method," Protein Engineering Design & Selection, 2007, 20(1):25-32.
Maeda et al., "Tumoritropic and lymphotropic principles of macromolecular drugs," Critical reviews in therapeutic drug carrier systems, 1989, 6(3):193-210.
Maeda, "The enhanced permeability and retention (EPR) effect in tumor vasculature: the key role of tumor-selective macromolecular drug targeting," Advances in Enzyme Regulation, 2001, 41(1):189-207.
Malam et al., "Liposomes and nanoparticles: nanosized vehicles for drug delivery in cancer," Trends Pharmacol Sci 2009, 30(11):592-9.
Manders et al., "Dynamics of three-dimensional replication patterns during the S-phase, analysed by double labelling of DNA and confocal microscopy," Journal of cell science, 1992, 103(Pt 3):857-862.
Mao et al., "Net charge per residue modulates conformational ensembles of intrinsically disordered proteins," Proc Natl Acad Sci U S A, 2010, 107(18):8183-8188.

(56) References Cited

OTHER PUBLICATIONS

Masood, "Polymeric nanoparticles for targeted drug delivery system for cancer therapy," Mater Sci Eng C Mater Biol Appl, Mar. 2016, 60:569-578.
Mastria et al., "Nanoparticle formulation improves doxorubicin efficacy by enhancing host antitumor immunity," J Control Release, Jan. 2018, 269:364-373.
McKenzie et al., "Multivalent Binding of a Ligand-Coated Particle: Role of Shape, Size, and Ligand Heterogeneity," Biophys J, Apr. 2018, 114(8):1830-1846.
Meng et al., "Stimuli-responsive polymersomes for programmed drug delivery," Biomacromolecules, 2009, 10(2):197-209.
Merkel et al., "Using mechanobiological mimicry of red blood cells to extend circulation times of hydrogel microparticles," Proc Natl Acad Sci U S A, 2011, 108(2):586-91.
Mitragotri et al., "Physical approaches to biomaterial design," J. Nat Mater, 2009, 8(1):15-23.
Modery et al., "Heteromultivalent liposomal nanoconstructs for enhanced targeting and shear-stable binding to active platelets for site-selective vascular drug delivery," Biomaterials, 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Muiznieks et al., "Proline periodicity modulates the self-assembly properties of elastin-like polypeptides," J Biol Chem, 2010, 285(51):39779-39789.
Muro, "Challenges in design and characterization of ligand-targeted drug delivery systems," J Control Release, 2012, 164(2):125-37.
Napier et al., "Nanoparticle drug delivery platform," Journal of Macromolecular Science, Part C: Polymer Reviews, 2007, 47(3):321-327.
Nayeem et al., "Engineering enzymes for improved catalytic efficiency: a computational study of site mutagenesis in epothilone-B hydroxylase," Protein Eng Des Sel, 2009, 22(4):257-266.
Ni et al., "Engineering of inorganic nanoparticles as magnetic resonance imaging contrast agents," Chem Soc Rev, Nov. 2017, 46(23):7438-7468.
Niu et al., "The role of adhesion molecules, αvβ3, αvβ5 and their ligands in the tumor cell and endothelial cell adhesion," Eur J Cancer Prev, 2007, 16(6):517-27.
Nott et al., "Phase transition of a disordered nuage protein generates environmentally responsive membraneless organelles," Mol Cell, Mar. 2015, 57(5):936-947.
Ortega et al., "Hydrodynamic properties of rodlike and dislike particles in dilute solution," The Journal of Chemical Physics, 2003, 119(18):9914-9919.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Pardridge, "The blood-brain barrier: bottleneck in brain drug development," NeuroRx, 2005, 2(1):3-14.
Parker et al., "Antibody mimics based on human fibronectin type three domain engineered for thermostability and high-affinity binding to vascular endothelial growth factor receptor two," Protein Eng Des Sel, 2005, 18(9):435-44.
Pastuszka et al., "A tunable and reversible platform for the intracellular formation of genetically engineered protein microdomains," Biomacromolecules, 2012, 13(11):3439-3444.
Peng et al., "Length-dependent prediction of protein intrinsic disorder," BMC Bioinformatics, 2006, 7:208.
Petros et al., "Strategies in the design of nanoparticles for therapeutic applications," Nat Rev Drug Discov, 2010, 9(8):615-27.
Qamar et al., "FUS Phase Separation Is Modulated by a Molecular Chaperone and Methylation of Arginine Cation-pi Interactions," Cell, Apr. 2018, 173(3):720-734.e15.
Quiroz et al., "Intrinsically disordered proteins access a range of hysteretic phase separation behaviors," Scientific advances, Oct. 2019, 5(10):eaax5177.
Ravikumar et al., "Mimicking adhesive functionalities of blood platelets using ligand-decorated liposomes," Bioconjugate chemistry, 2012, 23(6):1266-1275.
Rolland et al., "Direct fabrication and harvesting of monodisperse, shape-specific nanobiomaterials," J Am Chem Soc, 2005, 127(28):10096-100.
Rosenholm et al., "Towards multifunctional, targeted drug delivery systems using mesoporous silica nanoparticles—opportunities & challenges," Nanoscale, 2010, 2(10):1870-83.
Rösler et al., "Advanced drug delivery devices via self-assembly of amphiphilic block copolymers," Advanced Drug Delivery Reviews, 2001, 53:95-108.
Ryu et al., "Elastin-like polypeptide for improved drug delivery for anticancer therapy: preclinical studies and future applications," Expert Opinion on Drug Delivery, 2014, 12(4):653-667.
Sanna et al., "Targeted therapy using nanotechnology: focus on cancer," Int J Nanomedicine, Jan. 2014, 9:467-83.
Schnell et al., "Expression of integrin αvβ3 in gliomas correlates with tumor grade and is not restricted to tumor vasculature," Brain Pathol, 2008, 18(3):378-86.
Sharma et al., "Dendrimer nanoarchitectures for cancer diagnosis and anticancer drug delivery," Drug Discov Today, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, 2010, 147(3):408-412.
Shi et al., "Triggered sorting and co-assembly of genetically engineered protein microdomains in the cytoplasm," Adv Mater, 2014, 26(3):449-454.
Shin et al., "Liquid phase condensation in cell physiology and disease," Science, Sep. 2017, 357(6357):eaaf4382.
Sickmeier et al., "DisProt: the Database of Disordered Proteins," Nucleic Acids Res, 2007, 35:D786-793.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.
Skerra, "Alternative non-antibody scaffolds for molecular recognition," Curr Opin Biotechnol, 2007, 18(4):295-304.
Smits et al., "Elastin-Like Polypeptide Based Nanoparticled: Design Rationale Toward Nanomedicine," Macromolecular Bioscience, 2014, 15(1):36-51.
Steichen et al., "A Review of Current Nanoparticle and Targeting Moieties for the Delivery of Cancer Therapeutics," Eur J Pharm Sci, 2013, 48(3):416-27.
Strulson et al., "RNA catalysis through compartmentalization," Nat Chem, 2012, 4(11):941-946.
Suk et al., "PEGylation as a Strategy for Improving Nanoparticle-Based Drug and Gene Delivery ," Adv Drug Deliv Rev, Apr. 2016, 99(Pt A):28-51.
Swider et al., "Customizing Poly(lactic-Co-Glycolic Acid) Particles for Biomedical Applications," Acta Biomater, Jun. 2018, 73:38-51.
Talelli et al., "Core-Crosslinked Polymeric Micelles: Principles, Preparation, Biomedical Applications and Clinical Translation," Nano Today, Feb. 2015, 10(1):93-117.
Thakor et al., "Clinically Approved Nanoparticle Imaging Agents," J Nucl Med, Oct. 2016, 57(12):1833-1837.

(56) References Cited

OTHER PUBLICATIONS

Theillet et al., "The alphabet of intrinsic disorder: I. Act like a Pro: On the abundance and roles of proline residues in intrinsically disordered proteins," Intrinsically Disord Proteins, 2013, 1(1):e24360.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, 2011, 32(33):8462-73.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, 2010, 1804(6):1231-1264.
Vazquez-Lombardi et al., "Challenges and Opportunities for Non-Antibody Scaffold Drugs," Drug Discov Today, Oct. 2015, 20(10):1271-83.
Venkataraman et al., "The Effects of Polymeric Nanostructure Shape on Drug Delivery," Adv Drug Deliv, Rev, 2011, 63(14-15):1228-46.
Verma et al., "Effect of surface properties on nanoparticle-cell interactions," Small, 2010, 6(1):12-21.
Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, 2006, 78(3):620-8.
Vrhovski et al., "Coacervation Characteristics of Recombinant Human Tropoelastin," European Journal of Biochemistry, 1997, 250(1):92-98.
Wang et al., "A Molecular Grammar Governing the Driving Forces for Phase Separation of Prion-like RNA Binding Proteins," Cell, Jul. 2018, 174(3):688-699.e616.
Wang et al., "More effective nanomedicines through particle design," Small, 2011, 7(14):1919-31.
Wang et al., "Nanoparticle delivery of cancer drugs," Annu Rev Med, 2012, 63:185-98.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface to Enhance Cancer Cell Targeting by Polymer Micelles," Nano Lett Oct. 2017, 17(10):5995-6005.
Wechsel et al., "Renal Cell Carcinoma: Immunohistological Investigation of Expression of the Integrin αvβ3," Anticancer research, 1999, 19(2C):1529-1532.
Weis et al., "αV Integrins in Angiogenesis and Cancer," Cold Spring Harb Perspect Med, 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wilkins et al., "Hydrodynamic Radii of Native and Denatured Proteins Measured by Pulse Field Gradient NMR Techniques," Biochemistry, 1999, 38(50):16424-16431.
Wimley et al., "Experimentally determined hydrophobicity scale for proteins at membrane interfaces," Nature Structural & Molecular Biology, 1996, 3(10):842-848.
Wright et al., "Intrinsically disordered proteins in cellular signalling and regulation," Nat Rev Mol Cell Biol, Jan. 2015, 16(1):18-29.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, 2011, 155(2):248-61.
Xu et al., "Inorganic nanoparticles as carriers for efficient cellular delivery," Chemical Engineering Science, 2006, 61(3):1027-1040.
Zhao et al., "Cellular uptake, intracellular trafficking, and cytotoxicity of nanomaterials," Small, 2011, 7(10):1322-37.
Zhao et al., "Tumor αvβ3 Integrin Is a Therapeutic Target for Breast Cancer Bone Metastases," Cancer Res, 2007, 67(12):5821-30.
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
Merriam Webster Dictionary, "Plurality," <https://www.merriam-webster.com/dictionary/plurality> webpage accessed Jun. 25, 2020.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
International Search Report and Written Opinion for Application No. PCT/US2019/061144 dated May 21, 2020 (15 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
International Search Report and Written Opinion for Application No. PCT/US2021/046833 dated Nov. 8, 2021 (12 pages).
International Search Report and Written Opinion for Application No. PCT/US2021/035823 dated Dec. 8, 2021 (16 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.
Amanat et al., "A serological assay to detect SARS-CoV-2 seroconversion in humans," Nat Med, 2020, 26(7): 1033-1036.
American Hospital Association, "AHA Hospital Statistics," 2020 edition. Available at: <https://www.aha.org/statistics/fast-facts-us-hospitals>.
Armbruster et al., "Limit of blank, limit of detection and limit of quantitation," Clin Biochem Rev, 2008, 29 Suppl 1: S49-52.
Arshavsky-Graham et al., "Lab-on-a-Chip Devices for Point-of-Care Medical Diagnostics," Advances in Biochemical Engineering/Biotechnology, 2020, 19 pages.
Atyeo et al., "Distinct Early Serological Signatures Track with SARS-CoV-2 Survival," Immunity, 2020, 53: 524-532.
Baraf et al., "Infusion-related reactions with pegloticase, a recombinant uricase for the treatment of chronic gout refractory to conventional therapy," J Clin Rheumatol, 2014, 20: 427-432.
Benn et al., "Physiology of Hyperuricemia and Urate-Lowering Treatments," Front Med (Lausanne), 2018, 5: 160, 28 pages.
Berry et al., "Development and characterisation of neutralising monoclonal antibody to the SARS-coronavirus," J Virol Methods, 2004, 120: 87-96.
Bryant et al., "Serology for SARS-CoV-2: Apprehensions, opportunities, and the path forward," Sci Immunol, 2020, 5: eabc6347, 4 pages.
Calabrese et al., "Frequency, distribution and immunologic nature of infusion reactions in subjects receiving pegloticase for chronic refractory gout," Arthritis Res Ther, 2017, 19: 191, 7 pages.
Caves et al., "Thermal inactivation of uricase (urate oxidase): mechanism and effects of additives," Biochemistry, 2013, 52: 497-507.
Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.
Chen et al., "Real-world patterns of pegloticase use for treatment of gout: descriptive multidatabase cohort study," BMJ Open, 2020, 10: e041167, 6 pages.

(56) References Cited

OTHER PUBLICATIONS

Chen et al., "The influence of polymer topology on pharmacokinetics: differences between cyclic and linear PEGylated poly(acrylic acid) comb polymers," J Control Release, 2009, 140: 203-209.
Chu et al., "Molecular Diagnosis of a Novel Coronavirus (2019-nCoV) Causing an Outbreak of Pneumonia," Clin Chem, 2020, 66(4): 549-555.
Cong et al., "Nucleocapsid Protein Recruitment to Replication-Transcription Complexes Plays a Crucial Role in Coronaviral Life Cycle," J Virol, 2020, 94: e01925-19, 21 pages.
Crowther, "The ELISA guidebook," Methods Mol Biol, 2000, 149(III-IV): 1-413.
Dincer et al., "Multiplexed Point-of-Care Testing—xPOCT," Trends Biotechnol, 2017, 35(8): 728-742.
Dong et al., "An interactive web-based dashboard to track COVID-19 in real time," Lancet Infect Dis, 2020, 20: 533-534.
Dutta et al., "The Nucleocapsid Protein of SARS-CoV-2: a Target for Vaccine Development," J Virol, 2020, 94(13): e00647-20, 2 pages.
Ekladious et al., "Polymer-drug conjugate therapeutics: advances, insights and prospects," Nature Reviews Drug Discovery, 2019, 18: 273-294.
Fathallah et al., "Immunogenicity of Subcutaneously Administered Therapeutic Proteins—a Mechanistic Perspective," The AAPS Journal, 2013, 15(4): 897-900.
Fox et al., "Soluble polymer carriers for the treatment of cancer: the importance of molecular architecture," Acc Chern Res, 2009, 42(8): 1141-1151.
Garay et al., "Therapeutic perspectives on uricases for gout," Joint Bone Spine, 2012, 79: 237-242.
Harris et al., "Effect of pegylation on pharmaceuticals," Nature Reviews Drug Discovery, 2003, 2: 214-221.
Heggestad et al., "In Pursuit of Zero 2.0: Recent Developments in Nonfouling Polymer Brushes for Immunoassays," Adv Mater, 2020, 32: e1903285.
Hermanson et al., "Peginesatide for the treatment of anemia due to chronic kidney disease—an unfulfilled promise," Expert Opin Drug Saf, 2016, 15(10): 1421-1426.
Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.
Huang et al., "Clinical features of patients infected with 2019 novel coronavirus in Wuhan," China. Lancet, 2020, 395: 497-506.
Hucknall et al., "Simple Fabrication of Antibody Microarrays on Nonfouling Polymer Brushes with Femtomolar Sensitivity for Protein Analytes in Serum and Blood," Adv Mater, 2009, 21 (19): 1968-1971.
Jiang et al., "Neutralizing Antibodies against SARS-CoV-2 and Other Human Coronaviruses," Trends Immunol, 2020, 41(5): 355-359.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.
Joh et al., "Inkjet-printed point-of-care immunoassay on a nanoscale polymer brush enables subpicomolar detection of analytes in blood," Proc Natl Acad Sci USA, 2017, 114: E7054-E7062.
Kang et al., "Crystal structure of SARS-CoV-2 nucleocapsid protein RNA binding domain reveals potential unique drug targeting sites," Acta Pharm Sin B, 2020, 10(7): 1228-1238.
Khailany et al., "Genomic characterization of a novel SARS-CoV-2," Gene Rep, 2020, 9: 100682, 6 pages.
Kozel et al., "Point-of-care testing for infectious diseases: past, present, and future," J Clin Microbiol, 2017, 55: 2313-2320.
Kozma et al., "Anti-PEG antibodies: Properties, formation, testing and role in adverse immune reactions to PEGylated nano-biopharmaceuticals," Adv Drug Deliv Rev, 2020, 154-155, 163-175.
Krammer et al., "Serology assays to manage COVID-19," Science, 2020, 368: 1060-1061.
Kuo et al., "Global epidemiology of gout: prevalence, incidence and risk factors," Nature Reviews Rheumatology, 2015, 11: 649-662.
Laing et al., "A dynamic COVID-19 immune signature includes associations with poor prognosis," Nat Med, 2020, 26:1623-1635.
Lieberman et al., "Comparison of Commercially Available and Laboratory-Developed Assays for In Vitro Detection of SARS-CoV-2 in Clinical Laboratories," J Clin Microbiol, 2020, 58(8):e00821-20.
Lipsitch et al., "Antibody testing will enhance the power and accuracy of COVID-19-prevention trials," Nat Med, 2020, 26: 818-819.
Lipsky et al., "Pegloticase immunogenicity: the relationship between efficacy and antibody development in patients treated for refractory chronic gout," Arthritis Res Ther, 2014, 16: R60.
Lisboa Bastos et al., "Diagnostic accuracy of serological tests for covid-19: systematic review and meta-analysis," BMJ, 2020, 370: m2516.
Liu et al., "High neutralizing antibody titer in intensive care unit patients with COVID-19," Emerg Microbes Infect, 2020, 9: 1664-1670.
Liu et al., "Semi-permeable coatings fabricated from comb-polymers efficiently protect proteins in vivo," Nature Communications, 2014, 5: 5526.
Liu et al., "The experiences of health-care providers during the COVID-19 crisis in China: a qualitative study," Lancet Glob Health, 2020, 8: e790-e798.
Lu et al., "Genomic characterisation and epidemiology of 2019 novel coronavirus: implications for virus origins and receptor binding," Lancet, 2020, 395: 565-574.
McAndrews et al., "Heterogeneous antibodies against SARS-CoV-2 spike receptor binding domain and nucleocapsid with implications for COVID-19 immunity," JCI Insight, 2020, 5(18):e142386, 14 pages.
McElvaney et al., "A linear prognostic score based on the ratio of interleukin-6 to interleukin-10 predicts outcomes in COVID-19," EBioMedicine, 2020, 61: 103026, 8 pages.
Mejía-Salazar et al., "Microfluidic Point-of-Care Devices: New Trends and Future Prospects for eHealth Diagnostics," Sensors, 2020, 20: 1951, 19 pages.
Miller et al., "Disease and healthcare burden of COVID-19 in the United States," Nat Med, 2020, 26: 1212-1217.
Nalla et al., "Comparative Performance of SARS-CoV-2 Detection Assays Using Seven Different Primer-Probe Sets and One Assay Kit," J Clin Microbiol, 2020, 58: e00557-20, 6 pages.
Norman et al., "Ultrasensitive high-resolution profiling of early seroconversion in patients with COVID-19," Nat Biomed Eng, 2020, 11 pages.
Nunn et al., "Crystal Structure of Tobacco Etch Virus Protease Shows the Protein C Terminus Bound within the Active Site," Journal of Molecular Biology, 2005, 350: 145-155.
Nyborg et al., "A Therapeutic Uricase with Reduced Immunogenicity Risk and Improved Development Properties," PLoS One, 2016, 11(12): e0167935, 23 pages.
Okba et al., "Severe Acute Respiratory Syndrome Coronavirus 2-Specific Antibody Responses in Coronavirus Disease Patients," Emerg Infect Dis, 2020, 26: 1478-1488.
Ozer et al., "Effect of Molecular Architecture on Cell Interactions and Stealth Properties of PEG," Biomacromolecules, 2017, 18: 2699-2710.
Pecoraro et al., "A systematic evaluation of immunoassay point-of-care testing to define impact on patients' outcomes," Ann Clin Biochem, 2017, 54(4): 420-431.
Ponti et al., "Biomarkers associated with COVID-19 disease progression," Crit Rev Clin Lab Sci, 2020, 57, 11 pages.
Posthuma-Trumpie et al., "Lateral flow (immuno)assay: its strengths, weaknesses, opportunities and threats. A literature survey," Anal Bioanal Chem, 2009, 393: 569-582.
Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.

(56) References Cited

OTHER PUBLICATIONS

Ravichandran et al., "Antibody signature induced by SARS-CoV-2 spike protein immunogens in rabbits," Sci Transl Med, 2020, 10.1126/scitranslmed.abc3539, 9 pages.
Rogers et al., "Isolation of potent SARS-CoV-2 neutralizing antibodies and protection from disease in a small animal model," Science, 2020, 369: 956-963.
Rosadas et al., "Testing for responses to the wrong SARS-CoV-2 antigen," Lancet, 2020, 396: e23.
Rothe et al., "Transmission of 2019-nCoV Infection from an Asymptomatic Contact in Germany," N Engl J Med, 2020, 382: 10, 2 pages.
Seow et al., "Longitudinal evaluation and decline of antibody responses in SARS-CoV-2 infection," medRxiv, 2020, 24 pages.
Sundy et al., "Efficacy and tolerability of pegloticase for the treatment of chronic gout in patients refractory to conventional treatment: two randomized controlled trials," Jama, 2011, 306(7): 711-720.
Sundy et al., "Pharmacokinetics and pharmacodynamics of intravenous PEGylated recombinant mammalian urate oxidase in patients with refractory gout," Arthritis Rheum, 2007, 56(3): 1021-1028.
Tang et al., "Laboratory Diagnosis of COVID-19: Current Issues and Challenges," J Clin Microbiol, 2020, 58: e00512-20, 9 pages.
Turner et al., "Challenges and Opportunities for the Subcutaneous Delivery of Therapeutic Proteins," Journal of Pharmaceutical Sciences, 2018, 107(5): 1247-1260.
U.S. FDA—Classify your medical devices. Updated as of: Feb 7, 2020. Available at: <https://www.fda.gov/medical-devices/overview-device-regulation/classify-your-medical-device>.
U.S. FDA—In Vitro Diagnostics. Updated as of: Oct 25, 2019. Available at: <https://www.fda.gov/medical-devices/products-and-medical-procedures/vitro-diagnostics>.
Vaninov, "In the eye of the COVID-19 cytokine storm," Nat Rev Immunol, 2020, 20: 277, 1 page.
Vashist et al., "Emerging Technologies for Next-Generation Point-of-Care Testing," Trends Biotechnol, 2015, 33(11): 692-705.
Verhoef et al., "Potential induction of anti-PEG antibodies and complement activation toward PEGylated therapeutics," Drug Discov Today, 2014, 19(12): 1945-1952.
Vugmeyster et al., "Pharmacokinetics and toxicology of therapeutic proteins: Advances and challenges," World J Biol Chem, 2012, 3(4): 73-92.
Waterboer et al., "Suppression of non-specific binding in serological Luminex assays," J Immunol Methods, 2006, 309: 200-204.
Weinhandl et al., "Relative safety of peginesatide and epoetin alfa," Pharmacoepidemiology and Drug Safety, 2014, 23(10): 1003-1011.
Whitman et al., "Evaluation of SARS-CoV-2 serology assays reveals a range of test performance," Nat Biotechnol, 2020, 38: 1174-1183.
Wiersinga et al., "Pathophysiology, Transmission, Diagnosis, and Treatment of Coronavirus Disease 2019 (COVID-19): A Review," JAMA, 2020, 324(8): 782-793.
Winter et al., "The important role of serology for COVID-19 control," Lancet Infect Dis, 2020, 20: 758-759.
Wölfel et al., "Virological assessment of hospitalized patients with COVID-2019," Nature, 2020, 581: 465-469.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Plasma IP-10 and MCP-3 levels are highly associated with disease severity and predict the progression of COVID-19," J Allergy Clin Immunol, 2020, 146: 119-127.
Yang et al., "Uricases as therapeutic agents to treat refractory gout: Current states and future directions," Drug Dev Res, 2012, 73(2): 66-72.
Yong et al., "Connecting clusters of COVID-19: an epidemiological and serological investigation," Lancet Infect Dis, 2020, 20: 809-815.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS ONE, 2012, 7(6): e39659.
Zhao et al., "Antibody responses to SARS-CoV-2 in patients of novel coronavirus disease 2019," Clin Infect Dis, 2020, 22 pages.
International Search Report and Written Opinion for Application No. PCT/US2021/020591 dated Oct. 7, 2021 (14 pages).
United States Patent Office Action for U.S. Appl. No. 15/749,797 dated Nov. 29, 2021 (10 pages).
United States Patent Office Action for U.S. Appl. No. 16/477,229 dated Oct. 26, 2021 (10 pages).
Nikolic et al., "Structural basis for the recognition of LDL-receptor family members by VSV glycoprotein," Nature Communications, 2018, 9: 1029, 12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.
Cohen et al., "First clinical application of an actively reversible direct factor IXa inhibitor as an anticoagulation strategy in patients undergoing percutaneous coronary intervention," Circulation, 2010, 122(6): 614-622.
Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapter 8, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chem. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Gold et al., "Aptamers and the RNA World, Past and Present," Cold Spring Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.

(56) References Cited

OTHER PUBLICATIONS

Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.
Lippard et al., "Platinum complexes: probes of polynucleotide structure and antitumor drugs," Acc. Chern. Res., 1978, 11(5): 211-217.
Maier et al., "From selection hits to clinical leads: progress in aptamer discovery," Mol. Ther. Methods Clin. Dev., 2016, 3: 16014, 10 pages.
McManus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chem Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor Ixa," Nature, 2002, 19(6902): 90-94.
Shu et al., "Gisaid: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 DNA polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
United States Patent Office Action for U.S. Appl. No. 16/477,229 dated Mar. 3, 2022 (10 pages).
United States Patent Office Notice of Allowance for U.S. Appl. No. 15/749,797 dated Mar. 16, 2022 (6 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).
United States Patent Office Action for Application No. 16/477,229 dated Jun. 13, 2022 (11 pages).
United States Patent Office Notice of Allowance for U.S. Appl. No. 15/749,797 dated Jun. 2, 2022 (6 pages).
United States Patent Office Notice of Allowance for U.S. Appl. No. 16/305,696 dated Jun. 10, 2022 (4 pages).
United States Patent Office Action for U.S. Appl. No. 17/265,165 dated Sep. 2, 2022 (5 pages).

* cited by examiner 12 h Post-Treatment $DOX_{Free}$ 12 h Post-Treatment $DOX_{Enc}$, M-$ELP_{90A,80}$ DOX$_{Enc}$
Retentate DOX$_{Free}$
Retentate

SEQUENCE LISTING

<160> NUMBER OF SEQ ID NOS: 37

<210> SEQ ID NO 1
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (2)..(2)
<223> OTHER INFORMATION: any amino acid repeating from 1 to 15 times

<400> SEQUENCE: 1

Pro Xaa Gly
1

<210> SEQ ID NO 2
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (1)..(1)
<223> OTHER INFORMATION: any amino acid independent of Xaa at position 3
and Xaa at position 5 which may repeat 1 to 15 times
<220> FEATURE:
<221> NAME/KEY: Xaa
<222> LOCATION: (3)..(3)
<223> OTHER INFORMATION: any amino acid independent of Xaa at position 1
and Xaa at position 5 which may repeat 1 to 15 times
<220> FEATURE:
<221> NAME/KEY: Xaa
<222> LOCATION: (5)..(5)

```
<223> OTHER INFORMATION: any amino acid independent of Xaa at position 1
      and Xaa at position 3 which may repeat 1 to 15 times

<400> SEQUENCE: 2

Xaa Pro Xaa Gly Xaa
1               5


<210> SEQ ID NO 3
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: may repeat 1 to 200 times

<400> SEQUENCE: 3

Gly Val Gly Val Pro
1               5


<210> SEQ ID NO 4
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: may repeat 1 or more times
<220> FEATURE:
<221> NAME/KEY: Xaa
<222> LOCATION: (3)..(3)
<223> OTHER INFORMATION: a negatively or positively charged amino acid
<220> FEATURE:
<221> NAME/KEY: Xaa
<222> LOCATION: (4)..(4)
<223> OTHER INFORMATION: the other of a negatively or positively charged
      amino acid

<400> SEQUENCE: 4

Val Pro Xaa Xaa Gly
1               5


<210> SEQ ID NO 5
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: may repeat one or more times
<220> FEATURE:
<221> NAME/KEY: Xaa
<222> LOCATION: (3)..(3)
<223> OTHER INFORMATION: a negatively or positively charged amino acid
<220> FEATURE:
<221> NAME/KEY: Xaa
<222> LOCATION: (4)..(4)
<223> OTHER INFORMATION: the other of a negatively or positively charged
      amino acid

<400> SEQUENCE: 5

Val Pro Xaa Xaa Gly
1               5


<210> SEQ ID NO 6
```

<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 6

Pro Xaa Xaa Gly
1

<210> SEQ ID NO 7
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Xaa can be any naturally occurring amino acid

<400> SEQUENCE: 7

Pro Xaa Xaa Xaa Gly
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Xaa can be any naturally occurring amino acid

<400> SEQUENCE: 8

Pro Xaa Xaa Xaa Xaa Gly
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Xaa can be any naturally occurring amino acid

<400> SEQUENCE: 9

Pro Xaa Xaa Xaa Xaa Xaa Gly
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(7)
<223> OTHER INFORMATION: Xaa can be any naturally occurring amino acid

<400> SEQUENCE: 10

Pro Xaa Xaa Xaa Xaa Xaa Xaa Gly
1 5

<210> SEQ ID NO 11
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(8)
<223> OTHER INFORMATION: Xaa can be any naturally occurring amino acid

<400> SEQUENCE: 11

Pro Xaa Xaa Xaa Xaa Xaa Xaa Xaa Gly
1 5

<210> SEQ ID NO 12
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(9)
<223> OTHER INFORMATION: Xaa can be any naturally occurring amino acid

<400> SEQUENCE: 12

Pro Xaa Xaa Xaa Xaa Xaa Xaa Xaa Xaa Gly
1 5 10

<210> SEQ ID NO 13
<211> LENGTH: 11
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(10)
<223> OTHER INFORMATION: Xaa can be any naturally occurring amino acid

<400> SEQUENCE: 13

Pro Xaa Xaa Xaa Xaa Xaa Xaa Xaa Xaa Xaa Gly
1 5 10

<210> SEQ ID NO 14
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(11)
<223> OTHER INFORMATION: Xaa can be any naturally occurring amino acid

<400> SEQUENCE: 14

Pro Xaa Xaa Xaa Xaa Xaa Xaa Xaa Xaa Xaa Xaa Gly
1 5 10

<210> SEQ ID NO 15
<211> LENGTH: 13
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(12)
<223> OTHER INFORMATION: Xaa can be any naturally occurring amino acid

<400> SEQUENCE: 15

Pro Xaa Xaa Xaa Xaa Xaa Xaa Xaa Xaa Xaa Xaa Xaa Gly
1 5 10

<210> SEQ ID NO 16
<211> LENGTH: 14
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(13)
<223> OTHER INFORMATION: Xaa can be any naturally occurring amino acid

<400> SEQUENCE: 16

Pro Xaa Xaa Xaa Xaa Xaa Xaa Xaa Xaa Xaa Xaa Xaa Xaa Gly
1 5 10

<210> SEQ ID NO 17
<211> LENGTH: 15
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(14)
<223> OTHER INFORMATION: Xaa can be any naturally occurring amino acid

<400> SEQUENCE: 17

Pro Xaa Xaa Xaa Xaa Xaa Xaa Xaa Xaa Xaa Xaa Xaa Xaa Xaa Gly
1 5 10 15

<210> SEQ ID NO 18
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(15)
<223> OTHER INFORMATION: Xaa can be any naturally occurring amino acid

<400> SEQUENCE: 18

Pro Xaa Xaa Xaa Xaa Xaa Xaa Xaa Xaa Xaa Xaa Xaa Xaa Xaa Xaa Gly
1 5 10 15

<210> SEQ ID NO 19
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(16)
<223> OTHER INFORMATION: Xaa can be any naturally occurring amino acid

<400> SEQUENCE: 19

Pro Xaa Xaa Xaa Xaa Xaa Xaa Xaa Xaa Xaa Xaa Xaa Xaa Xaa Xaa Xaa
1 5 10 15

Gly

<210> SEQ ID NO 20
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (3)..(3)
<223> OTHER INFORMATION: a negatively or positively charged amino acid
<220> FEATURE:
<221> NAME/KEY: Xaa
<222> LOCATION: (4)..(4)
<223> OTHER INFORMATION: the other of a negatively or positively charged amino acid

<400> SEQUENCE: 20

Val Pro Xaa Xaa Gly
1 5

<210> SEQ ID NO 21
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (4)..(4)
<223> OTHER INFORMATION: any amino acid except proline

<400> SEQUENCE: 21

Val Pro Gly Xaa Gly
1 5

<210> SEQ ID NO 22
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: may repeat one or more times
<220> FEATURE:
<221> NAME/KEY: Xaa
<222> LOCATION: (3)..(3)
<223> OTHER INFORMATION: a negatively or positively charged amino
<220> FEATURE:
<221> NAME/KEY: Xaa
<222> LOCATION: (4)..(4)
<223> OTHER INFORMATION: the other of a negatively or positively charged amino
<220> FEATURE:
<221> NAME/KEY: misc_feature
<222> LOCATION: (6)..(10)
<223> OTHER INFORMATION: may repeat one or more times

<400> SEQUENCE: 22

Val Pro Xaa Xaa Gly Val Pro Gly Xaa Gly
1 5 10

<210> SEQ ID NO 23

<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: may repeat one or more times
<220> FEATURE:
<221> NAME/KEY: Xaa
<222> LOCATION: (4)..(4)
<223> OTHER INFORMATION: a negatively or positively charged amino acid
<220> FEATURE:
<221> NAME/KEY: misc_feature
<222> LOCATION: (6)..(10)
<223> OTHER INFORMATION: may repeat one or more times
<220> FEATURE:
<221> NAME/KEY: Xaa
<222> LOCATION: (8)..(8)
<223> OTHER INFORMATION: the other of a negatively or positively charged amino acid
<220> FEATURE:
<221> NAME/KEY: Xaa
<222> LOCATION: (9)..(9)
<223> OTHER INFORMATION: any amino acid except proline

<400> SEQUENCE: 23

Val Pro Gly Xaa Gly Val Pro Xaa Xaa Gly
1 5 10

<210> SEQ ID NO 24
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: may repeat one or more times
<220> FEATURE:
<221> NAME/KEY: Xaa
<222> LOCATION: (3)..(3)
<223> OTHER INFORMATION: a negatively or positively charged amino acid
<220> FEATURE:
<221> NAME/KEY: Xaa
<222> LOCATION: (4)..(4)
<223> OTHER INFORMATION: the other of a negatively or positively charged amino acid
<220> FEATURE:
<221> NAME/KEY: Xaa
<222> LOCATION: (9)..(9)
<223> OTHER INFORMATION: any amino acid except proline

<400> SEQUENCE: 24

Val Pro Xaa Xaa Gly Val Pro Gly Xaa Gly
1 5 10

<210> SEQ ID NO 25
<211> LENGTH: 11
<212> TYPE: PRT
<213> ORGANISM: Artificial sequence
<220> FEATURE:
<223> OTHER INFORMATION: Synthetic

<400> SEQUENCE: 25

Gly Leu Tyr Ala Ser Lys Leu Phe Ser Asn Leu
1 5 10

<210> SEQ ID NO 26
<211> LENGTH: 15
<212> TYPE: PRT

<213> ORGANISM: Artificial sequence
<220> FEATURE:
<223> OTHER INFORMATION: Synthetic

<400> SEQUENCE: 26

Gly Ser Ser Lys Ser Lys Pro Lys Asp Pro Ser Gln Arg Arg Arg
1               5                   10                  15

<210> SEQ ID NO 27
<211> LENGTH: 24
<212> TYPE: PRT
<213> ORGANISM: Artificial sequence
<220> FEATURE:
<223> OTHER INFORMATION: Synthetic

<400> SEQUENCE: 27

Gly Gly Cys Gly Gly Cys Gly Gly Cys Gly Gly Cys Gly Gly Cys Gly
1               5                   10                  15

Gly Cys Gly Gly Cys Gly Gly Cys
            20

<210> SEQ ID NO 28
<211> LENGTH: 15
<212> TYPE: PRT
<213> ORGANISM: Artificial sequence
<220> FEATURE:
<223> OTHER INFORMATION: Synthetic

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 3
<212> TYPE: PRT
<213> ORGANISM: Artificial sequence
<220> FEATURE:
<223> OTHER INFORMATION: Synthetic

<400> SEQUENCE: 29

Gly Gly Ser
1

<210> SEQ ID NO 30
<211> LENGTH: 1412
<212> TYPE: DNA
<213> ORGANISM: Artificial sequence
<220> FEATURE:
<223> OTHER INFORMATION: Synthetic

<400> SEQUENCE: 30
caatggtata tcttccgggc gctatcatgc catacctttt tataccatgg gcagcagcca 60
tcaccatcat caccacaaag accacaaatt ttggcgtacc cagccggtta aagattttga 120
tgaaaaagtt gttgaagaag gtccgatcga caaaccgaaa acaccggaag atattagcga 180
taaaccgctg ccgctgctga gcagctttga atggtgtagc attgatgtgg acaacaaaaa 240
acagctggaa gatgtttttg tgctgctgaa cgaaaactat gtggaagatc gtgatgcagg 300
ttttcgcttc aattatacca aagagttttt caactgggca ctgaaaagtc cgggttggaa 360
aaaagattgg catattggtg ttcgtgtgaa agaaacccag aaactggttg catttattag 420
cgcaattccg gttaccctgg gtgtgcgtgg taaacaggtt ccgagcgttg aaattaactt 480
tctgtgtgtt cataaacagc tgcgtagcaa acgtctgaca ccggttctga ttaaagaaat 540

```
cacccgtcgt gtgaacaaat gcgatatttg gcatgcactg tataccgcag gtattgttct    600

gcctgcaccg gttagcacct gtcgttatac ccatcgtccg ctgaactgga aaaaactgta    660

tgaagttgat ttcaccggtc tgccggatgg tcataccgaa gaagatatga ttgcagaaaa    720

tgcactgcct gcaaaaacca aaaccgcagg tctgcgtaaa ctgaaaaaag aggacatcga    780

tcaggtcttt gagctgttta aacgttatca gagccgcttt gaactgatcc agatttttac    840

caaagaagag ttcgagcaca actttattgg tgaagaaagc ctgccgctgg ataaacaggt    900

gatttttagc tatgttgttg aacagccgga tggcaaaatt accgattttt tcagctttta    960

tagcctgccg tttaccattc tgaacaacac caaatacaaa gacctgggca ttggctatct   1020

gtattattac gcaaccgatg ccgatttcca gtttaaagat cgttttgatc cgaaagcaac   1080

caaagccctg aaaacccgtc tgtgcgaact gatttatgat gcatgtattc tggccaaaaa   1140

cgccaacatg gatgttttta atgcactgac cagccaggat aataccctgt ttctggatga   1200

tctgaaattt ggtccgggtg atggttttct gaatttctac ctgtttaact atcgtgccaa   1260

accgattacc ggtggtctga atccggataa tagcaatgat attaaacgtc gcagcaatgt   1320

tggtgtggtt atgctgtgat aatgataatg atcttctgaa ttcccgtcat atccgctgag   1380

caataactag cataacccct tatacgttac at                                 1412
```

<210> SEQ ID NO 31
<211> LENGTH: 60
<212> TYPE: DNA
<213> ORGANISM: Artificial sequence
<220> FEATURE:
<223> OTHER INFORMATION: Synthetic

<400> SEQUENCE: 31

```
tatgggcctg tatgcgagca aactgtttag caacctgggc taatgatctc ctcaatgagc     60
```

<210> SEQ ID NO 32
<211> LENGTH: 62
<212> TYPE: DNA
<213> ORGANISM: Artificial sequence
<220> FEATURE:
<223> OTHER INFORMATION: Synthetic

<400> SEQUENCE: 32

```
acccggacat acgctcgttt gacaaatcgt tggacccgat tactagagga gttactcgag     60

ct                                                                    62
```

<210> SEQ ID NO 33
<211> LENGTH: 430
<212> TYPE: PRT
<213> ORGANISM: Artificial sequence
<220> FEATURE:
<223> OTHER INFORMATION: Synthetic

<400> SEQUENCE: 33

```
Met Gly Ser Ser His His His His His His Lys Asp His Lys Phe Trp
1               5                   10                  15

Arg Thr Gln Pro Val Lys Asp Phe Asp Glu Lys Val Val Glu Glu Gly
            20                  25                  30

Pro Ile Asp Lys Pro Lys Thr Pro Glu Asp Ile Ser Asp Lys Pro Leu
        35                  40                  45

Pro Leu Leu Ser Ser Phe Glu Trp Cys Ser Ile Asp Val Asp Asn Lys
    50                  55                  60
```

```
Lys Gln Leu Glu Asp Val Phe Val Leu Leu Asn Glu Asn Tyr Val Glu
65                  70                  75                  80

Asp Arg Asp Ala Gly Phe Arg Phe Asn Tyr Thr Lys Glu Phe Phe Asn
                85                  90                  95

Trp Ala Leu Lys Ser Pro Gly Trp Lys Lys Asp Trp His Ile Gly Val
            100                 105                 110

Arg Val Lys Glu Thr Gln Lys Leu Val Ala Phe Ile Ser Ala Ile Pro
        115                 120                 125

Val Thr Leu Gly Val Arg Gly Lys Gln Val Pro Ser Val Glu Ile Asn
    130                 135                 140

Phe Leu Cys Val His Lys Gln Leu Arg Ser Lys Arg Leu Thr Pro Val
145                 150                 155                 160

Leu Ile Lys Glu Ile Thr Arg Arg Val Asn Lys Cys Asp Ile Trp His
                165                 170                 175

Ala Leu Tyr Thr Ala Gly Ile Val Leu Pro Ala Pro Val Ser Thr Cys
            180                 185                 190

Arg Tyr Thr His Arg Pro Leu Asn Trp Lys Lys Leu Tyr Glu Val Asp
        195                 200                 205

Phe Thr Gly Leu Pro Asp Gly His Thr Glu Glu Asp Met Ile Ala Glu
    210                 215                 220

Asn Ala Leu Pro Ala Lys Thr Lys Thr Ala Gly Leu Arg Lys Leu Lys
225                 230                 235                 240

Lys Glu Asp Ile Asp Gln Val Phe Glu Leu Phe Lys Arg Tyr Gln Ser
                245                 250                 255

Arg Phe Glu Leu Ile Gln Ile Phe Thr Lys Glu Glu Phe Glu His Asn
            260                 265                 270

Phe Ile Gly Glu Glu Ser Leu Pro Leu Asp Lys Gln Val Ile Phe Ser
        275                 280                 285

Tyr Val Val Glu Gln Pro Asp Gly Lys Ile Thr Asp Phe Phe Ser Phe
    290                 295                 300

Tyr Ser Leu Pro Phe Thr Ile Leu Asn Asn Thr Lys Tyr Lys Asp Leu
305                 310                 315                 320

Gly Ile Gly Tyr Leu Tyr Tyr Tyr Ala Thr Asp Ala Asp Phe Gln Phe
                325                 330                 335

Lys Asp Arg Phe Asp Pro Lys Ala Thr Lys Ala Leu Lys Thr Arg Leu
            340                 345                 350

Cys Glu Leu Ile Tyr Asp Ala Cys Ile Leu Ala Lys Asn Ala Asn Met
        355                 360                 365

Asp Val Phe Asn Ala Leu Thr Ser Gln Asp Asn Thr Leu Phe Leu Asp
    370                 375                 380

Asp Leu Lys Phe Gly Pro Gly Asp Gly Phe Leu Asn Phe Tyr Leu Phe
385                 390                 395                 400

Asn Tyr Arg Ala Lys Pro Ile Thr Gly Gly Leu Asn Pro Asp Asn Ser
                405                 410                 415

Asn Asp Ile Lys Arg Arg Ser Asn Val Gly Val Val Met Leu
            420                 425                 430
```

<210> SEQ ID NO 34
<211> LENGTH: 614
<212> TYPE: PRT
<213> ORGANISM: Artificial sequence
<220> FEATURE:
<223> OTHER INFORMATION: Synthetic -continued

<400> SEQUENCE: 34

Met Gly Leu Tyr Ala Ser Lys Leu Phe Ser Asn Leu Gly Ala Gly Val
1 5 10 15

Pro Gly Ala Gly Val Pro Gly Val Gly Val Pro Gly Ala Gly Val Pro
20 25 30

Gly Ala Gly Val Pro Gly Ala Gly Val Pro Gly Ala Gly Val Pro Gly
35 40 45

Ala Gly Val Pro Gly Ala Gly Val Pro Gly Ala Gly Val Pro Gly Ala
50 55 60

Gly Val Pro Gly Ala Gly Val Pro Gly Val Gly Val Pro Gly Ala Gly
65 70 75 80

Val Pro Gly Ala Gly Val Pro Gly Ala Gly Val Pro Gly Ala Gly Val
85 90 95

Pro Gly Ala Gly Val Pro Gly Ala Gly Val Pro Gly Ala Gly Val Pro
100 105 110

Gly Ala Gly Val Pro Gly Ala Gly Val Pro Gly Val Gly Val Pro Gly
115 120 125

Ala Gly Val Pro Gly Ala Gly Val Pro Gly Ala Gly Val Pro Gly Ala
130 135 140

Gly Val Pro Gly Ala Gly Val Pro Gly Ala Gly Val Pro Gly Ala Gly
145 150 155 160

Val Pro Gly Ala Gly Val Pro Gly Ala Gly Val Pro Gly Val Gly Val
165 170 175

Pro Gly Ala Gly Val Pro Gly Ala Gly Val Pro Gly Ala Gly Val Pro
180 185 190

Gly Ala Gly Val Pro Gly Ala Gly Val Pro Gly Ala Gly Val Pro Gly
195 200 205

Ala Gly Val Pro Gly Ala Gly Val Pro Gly Ala Gly Val Pro Gly Val
210 215 220

Gly Val Pro Gly Ala Gly Val Pro Gly Ala Gly Val Pro Gly Ala Gly
225 230 235 240

Val Pro Gly Ala Gly Val Pro Gly Ala Gly Val Pro Gly Ala Gly Val
245 250 255

Pro Gly Ala Gly Val Pro Gly Ala Gly Val Pro Gly Ala Gly Val Pro
260 265 270

Gly Val Gly Val Pro Gly Ala Gly Val Pro Gly Ala Gly Val Pro Gly
275 280 285

Ala Gly Val Pro Gly Ala Gly Val Pro Gly Ala Gly Val Pro Gly Ala
290 295 300

Gly Val Pro Gly Ala Gly Val Pro Gly Ala Gly Val Pro Gly Ala Gly
305 310 315 320

Val Pro Gly Val Gly Val Pro Gly Ala Gly Val Pro Gly Ala Gly Val
325 330 335

Pro Gly Ala Gly Val Pro Gly Ala Gly Val Pro Gly Ala Gly Val Pro
340 345 350

Gly Ala Gly Val Pro Gly Ala Gly Val Pro Gly Ala Gly Val Pro Gly
355 360 365

Ala Gly Val Pro Gly Val Gly Val Pro Gly Ala Gly Val Pro Gly Ala
370 375 380

Gly Val Pro Gly Ala Gly Val Pro Gly Ala Gly Val Pro Gly Ala Gly
385 390 395 400

```
Val Pro Gly Ala Gly Val Pro Gly Ala Gly Val Pro Gly Ala Gly Val
                405                 410                 415

Pro Gly Ala Gly Val Pro Gly Val Gly Val Pro Gly Ala Gly Val Pro
            420                 425                 430

Gly Ala Gly Val Pro Gly Ala Gly Val Pro Gly Ala Gly Val Pro Gly
        435                 440                 445

Ala Gly Val Pro Gly Ala Gly Val Pro Gly Ala Gly Val Pro Gly Ala
    450                 455                 460

Gly Val Pro Gly Ala Gly Val Pro Gly Val Gly Val Pro Gly Ala Gly
465                 470                 475                 480

Val Pro Gly Ala Gly Val Pro Gly Ala Gly Val Pro Gly Ala Gly Val
                485                 490                 495

Pro Gly Ala Gly Val Pro Gly Ala Gly Val Pro Gly Ala Gly Val Pro
            500                 505                 510

Gly Ala Gly Val Pro Gly Ala Gly Val Pro Gly Val Gly Val Pro Gly
        515                 520                 525

Ala Gly Val Pro Gly Ala Gly Val Pro Gly Ala Gly Val Pro Gly Ala
    530                 535                 540

Gly Val Pro Gly Ala Gly Val Pro Gly Ala Gly Val Pro Gly Ala Gly
545                 550                 555                 560

Val Pro Gly Ala Gly Val Pro Gly Ala Gly Val Pro Gly Val Gly Val
                565                 570                 575

Pro Gly Ala Gly Val Pro Gly Ala Gly Val Pro Gly Ala Gly Val Pro
            580                 585                 590

Gly Ala Gly Val Pro Gly Ala Gly Val Pro Gly Ala Gly Val Pro Gly
        595                 600                 605

Ala Gly Val Pro Gly Tyr
    610


<210> SEQ ID NO 35
<211> LENGTH: 413
<212> TYPE: PRT
<213> ORGANISM: Artificial sequence
<220> FEATURE:
<223> OTHER INFORMATION: Synthetic

<400> SEQUENCE: 35

Met Gly Leu Tyr Ala Ser Lys Leu Phe Ser Asn Leu Gly Ala Gly Val
1               5                   10                  15

Pro Gly Ala Gly Val Pro Gly Val Gly Val Pro Gly Ala Gly Val Pro
            20                  25                  30

Gly Ala Gly Val Pro Gly Ala Gly Val Pro Gly Ala Gly Val Pro Gly
        35                  40                  45

Ala Gly Val Pro Gly Ala Gly Val Pro Gly Ala Gly Val Pro Gly Ala
    50                  55                  60

Gly Val Pro Gly Ala Gly Val Pro Gly Val Gly Val Pro Gly Ala Gly
65                  70                  75                  80

Val Pro Gly Ala Gly Val Pro Gly Ala Gly Val Pro Gly Ala Gly Val
                85                  90                  95

Pro Gly Ala Gly Val Pro Gly Ala Gly Val Pro Gly Ala Gly Val Pro
            100                 105                 110

Gly Ala Gly Val Pro Gly Ala Gly Val Pro Gly Val Gly Val Pro Gly
        115                 120                 125

Ala Gly Val Pro Gly Ala Gly Val Pro Gly Ala Gly Val Pro Gly Ala
    130                 135                 140
```

-continued

Gly Val Pro Gly Ala Gly Val Pro Gly Ala Gly Val Pro Gly Ala Gly
145 150 155 160

Val Pro Gly Ala Gly Val Pro Gly Ala Gly Val Pro Gly Val Gly Val
165 170 175

Pro Gly Ala Gly Val Pro Gly Ala Gly Val Pro Gly Ala Gly Val Pro
180 185 190

Gly Ala Gly Val Pro Gly Ala Gly Val Pro Gly Ala Gly Val Pro Gly
195 200 205

Ala Gly Val Pro Gly Ala Gly Val Pro Gly Ala Gly Val Pro Gly Val
210 215 220

Gly Val Pro Gly Ala Gly Val Pro Gly Ala Gly Val Pro Gly Ala Gly
225 230 235 240

Val Pro Gly Ala Gly Val Pro Gly Ala Gly Val Pro Gly Ala Gly Val
245 250 255

Pro Gly Ala Gly Val Pro Gly Ala Gly Val Pro Gly Ala Gly Val Pro
260 265 270

Gly Val Gly Val Pro Gly Ala Gly Val Pro Gly Ala Gly Val Pro Gly
275 280 285

Ala Gly Val Pro Gly Ala Gly Val Pro Gly Ala Gly Val Pro Gly Ala
290 295 300

Gly Val Pro Gly Ala Gly Val Pro Gly Ala Gly Val Pro Gly Ala Gly
305 310 315 320

Val Pro Gly Val Gly Val Pro Gly Ala Gly Val Pro Gly Ala Gly Val
325 330 335

Pro Gly Ala Gly Val Pro Gly Ala Gly Val Pro Gly Ala Gly Val Pro
340 345 350

Gly Ala Gly Val Pro Gly Ala Gly Val Pro Gly Ala Gly Val Pro Gly
355 360 365

Ala Gly Val Pro Gly Val Gly Val Pro Gly Ala Gly Val Pro Gly Ala
370 375 380

Gly Val Pro Gly Ala Gly Val Pro Gly Ala Gly Val Pro Gly Ala Gly
385 390 395 400

Val Pro Gly Ala Gly Val Pro Gly Ala Gly Val Pro Gly
405 410

<210> SEQ ID NO 36
<211> LENGTH: 213
<212> TYPE: PRT
<213> ORGANISM: Artificial sequence
<220> FEATURE:
<223> OTHER INFORMATION: Synthetic

<400> SEQUENCE: 36

Met Gly Leu Tyr Ala Ser Lys Leu Phe Ser Asn Leu Gly Ala Gly Val
1 5 10 15

Pro Gly Ala Gly Val Pro Gly Val Gly Val Pro Gly Ala Gly Val Pro
20 25 30

Gly Ala Gly Val Pro Gly Ala Gly Val Pro Gly Ala Gly Val Pro Gly
35 40 45

Ala Gly Val Pro Gly Ala Gly Val Pro Gly Ala Gly Val Pro Gly Ala
50 55 60

Gly Val Pro Gly Ala Gly Val Pro Gly Val Gly Val Pro Gly Ala Gly
65 70 75 80

Val Pro Gly Ala Gly Val Pro Gly Ala Gly Val Pro Gly Ala Gly Val
85 90 95

Pro Gly Ala Gly Val Pro Gly Ala Gly Val Pro Gly Ala Gly Val Pro
100 105 110

Gly Ala Gly Val Pro Gly Ala Gly Val Pro Gly Val Gly Val Pro Gly
115 120 125

Ala Gly Val Pro Gly Ala Gly Val Pro Gly Ala Gly Val Pro Gly Ala
130 135 140

Gly Val Pro Gly Ala Gly Val Pro Gly Ala Gly Val Pro Gly Ala Gly
145 150 155 160

Val Pro Gly Ala Gly Val Pro Gly Ala Gly Val Pro Gly Val Gly Val
165 170 175

Pro Gly Ala Gly Val Pro Gly Ala Gly Val Pro Gly Ala Gly Val Pro
180 185 190

Gly Ala Gly Val Pro Gly Ala Gly Val Pro Gly Ala Gly Val Pro Gly
195 200 205

Ala Gly Val Pro Gly
210

<210> SEQ ID NO 37
<211> LENGTH: 213
<212> TYPE: PRT
<213> ORGANISM: Artificial sequence
<220> FEATURE:
<223> OTHER INFORMATION: Synthetic

<400> SEQUENCE: 37

Met Gly Leu Tyr Ala Ser Lys Leu Phe Ser Asn Leu Gly Val Gly Val
1 5 10 15

Pro Gly Val Gly Val Pro Gly Val Gly Val Pro Gly Val Gly Val Pro
20 25 30

Gly Val Gly Val Pro Gly Val Gly Val Pro Gly Val Gly Val Pro Gly
35 40 45

Val Gly Val Pro Gly Val Gly Val Pro Gly Val Gly Val Pro Gly Val
50 55 60

Gly Val Pro Gly Val Gly Val Pro Gly Val Gly Val Pro Gly Val Gly
65 70 75 80

Val Pro Gly Val Gly Val Pro Gly Val Gly Val Pro Gly Val Gly Val
85 90 95

Pro Gly Val Gly Val Pro Gly Val Gly Val Pro Gly Val Gly Val Pro
100 105 110

Gly Val Gly Val Pro Gly Val Gly Val Pro Gly Val Gly Val Pro Gly
115 120 125

Val Gly Val Pro Gly Val Gly Val Pro Gly Val Gly Val Pro Gly Val
130 135 140

Gly Val Pro Gly Val Gly Val Pro Gly Val Gly Val Pro Gly Val Gly
145 150 155 160

Val Pro Gly Val Gly Val Pro Gly Val Gly Val Pro Gly Val Gly Val
165 170 175

Pro Gly Val Gly Val Pro Gly Val Gly Val Pro Gly Val Gly Val Pro
180 185 190

Gly Val Gly Val Pro Gly Val Gly Val Pro Gly Val Gly Val Pro Gly
195 200 205

Val Gly Val Pro Gly
210

RECOMBINANT PRODUCTION OF HYBRID LIPID-BIOPOLYMER MATERIALS THAT SELF-ASSEMBLE AND ENCAPSULATE AGENTS

CROSS-REFERENCE TO RELATED APPLICATIONS

This patent application is the U.S. national stage entry under 35 U.S.C. § 371, of International Application Number PCT/US2018/032785, filed May 15, 2018, which claims priority to U.S. Provisional Patent Application No. 62/506,593, filed May 15, 2017; U.S. Provisional Patent Application No. 62/534,442, filed Jul. 19, 2017; U.S. Provisional Patent Application No. 62/544,720, filed Aug. 11 , 2017; and U.S. Provisional Patent Application No. 62/545,313, filed Aug. 14, 2017, the entire contents of each of which are hereby incorporated by reference.

STATEMENT REGARDING FEDERALLY SPONSORED RESEARCH

This invention was made with government support under grant DMR1121107 awarded by the National Science Foundation. The government has certain rights in the invention.

SEQUENCE LISTING

The instant application includes a Sequence Listing which has been submitted electronically in ASCII format and is hereby incorporated by reference in its entirety. Said ASCII copy, created on Nov. 12, 2019, is named 028193-9239-US04_As_Filed_Sequence_Listing.txt and is 28,997 bytes in size.

FIELD

This disclosure relates to conjugates of lipids and polypeptides, such as fatty acid-modified elastin-like polypeptides, that are thermally responsive and can form micelles or vesicles. An agent may be encapsulated within the micelle or the vesicle.

INTRODUCTION

Recombinant biopolymers are used for a diverse array of applications including drug delivery, tissue engineering, and clinical diagnostics. Peptide polymers are particularly attractive candidates for biomedical applications because of their biocompatibility, biodegradability, and precisely specified, genetically encoded sequence. However, compared to their synthetic counterparts, recombinant peptide polymers are made up of a limited number of building blocks—the twenty standard amino acids—which severely restricts their potential design space. Nature itself has evolved numerous strategies to diversify the proteome through post-translational modifications (PTMs) such as lipidation, glycosylation, and phosphorylation. However, these PTMs have been largely unexplored in recombinantly produced polypeptides because the simplest and most well established recombinant expression protocols utilize prokaryotes, which evolutionarily lack complex PTM machinery. Despite their ubiquity in biology, there is still a need for the use of PTMs to synthesize hybrid biomaterials with properties suitable for applications such as drug-delivery.

SUMMARY

In an aspect, the disclosure relates to a composition including: a plurality of conjugates self-assembled into a micelle or a vesicle, wherein each conjugate includes a fatty acid conjugated to a N-terminal end of an unstructured polypeptide; and an agent encapsulated within the micelle or the vesicle.

In a further aspect, the disclosure relates to a method of delivering an agent to a subject, the method including: encapsulating the agent in a micelle or a vesicle as disclosed herein; and administering the micelle or the vesicle to the subject.

Another aspect of the disclosure provides a method of treating a disease in a subject in need thereof, the method including administering a composition as disclosed herein to the subject.

Another aspect of the disclosure provides a method of increasing the maximum tolerated dose of an agent, the method including: encapsulating the agent in a micelle or a vesicle, the micelle or the vesicle including a plurality of conjugates self-assembled into the micelle or vesicle, wherein each conjugate includes a fatty acid conjugated to a N-terminal end of an unstructured polypeptide; and administering the agent-encapsulated micelle or vesicle to a subject.

In some embodiments, the maximum tolerated dose ($IC_{50}$) of the agent is increased 0.5-fold to 20-fold compared to a non-encapsulated agent. In some embodiments, the fatty acid includes a substrate of N-myristoyltransferase (NMT). In some embodiments, the fatty acid includes myristic acid or an analog thereof.

In some embodiments, the agent includes a small molecule, a polynucleotide, a polypeptide, a carbohydrate, a lipid, a drug, an imaging agent, or a combination thereof. In some embodiments, the agent is hydrophobic. In some embodiments, the agent includes a hydrophobic small molecule. In some embodiments, the plurality of conjugates is self-assembled into a micelle, and wherein the agent is encapsulated within a hydrophobic core of the micelle. In some embodiments, the agent is hydrophilic. In some embodiments, the agent includes a hydrophilic small molecule. In some embodiments, the plurality of conjugates is self-assembled into an inverted micelle, wherein the agent is encapsulated within an aqueous core of the inverted micelle, or wherein the plurality of conjugates is self-assembled into a vesicle, wherein the agent is encapsulated within an aqueous core of the vesicle. In some embodiments, the plurality of conjugates is self-assembled into a vesicle, and wherein at least a portion of the agent is incorporated within a bilayer of the vesicle. In some embodiments, the agent includes Doxorubicin (DOX). In some embodiments, the agent includes Paclitaxel (PTX). In some embodiments, the agent includes a polypeptide. In some embodiments, the polypeptide is an antibody.

In some embodiments, the unstructured polypeptide includes a repeated unstructured polypeptide or a non-repeated unstructured polypeptide. In some embodiments, the unstructured polypeptide includes a PG motif. In some embodiments, the PG motif includes an amino acid sequence selected from PG, $P(X)_nG$ (SEQ ID NO:1), and $(U)_mP(X)_nG(Z)_p$ (SEQ ID NO:2), or a combination thereof, wherein m, n, and p are independently an integer from 1 to 15, and wherein U, X, and Z are independently any amino acid. In some embodiments, the unstructured polypeptide includes an amino acid sequence of $[GVGVP]_n$ (SEQ ID NO:3), wherein n is an integer from 1 to 200. In some embodiments, the unstructured polypeptide includes an amino acid sequence of $(VPGXG)_n$ (SEQ ID NO:4), wherein X is any amino acid except proline and n is an integer greater than or equal to 1. In some embodiments, the unstructured polypeptide includes an amino acid sequence of $(VPGXG)_n$ (SEQ ID NO:4), wherein X is any amino acid except proline and n is 40-120. In some embodiments, X is alanine, valine or a combination thereof. In some embodiments, the unstructured polypeptide includes at least one of the following: a non-repetitive polypeptide including a sequence of at least 60 amino acids, wherein at least about 10% of the amino acids are proline (P), wherein at least about 20% of the amino acids are glycine (G); a non-repetitive polypeptide including a sequence of at least 60 amino acids, wherein at least about 40% of the amino acids are selected from the group consisting of valine (V), alanine (A), leucine (L), lysine (K), threonine (T), isoleucine (1), tyrosine (Y), serine (S), and phenylalanine (F); and a non-repetitive polypeptide including a sequence of at least 60 amino acids, wherein the sequence does not contain three contiguous identical amino acids, wherein any 5-10 amino acid subsequence does not occur more than once in the non-repetitive polypeptide, and wherein when the non-repetitive polypeptide includes a subsequence starting and ending with proline (P), the subsequence further includes at least one glycine (G). In some embodiments, the unstructured polypeptide includes a zwitterionic polypeptide. In some embodiments, the zwitterionic polypeptide includes an amino acid sequence of $(VPX_1X_2G)_n$ (SEQ ID NO:5), wherein $X_1$ is a negatively or positively charged amino acid, $X_2$ is the other of a negatively or positively charged amino acid, and n is an integer greater than or equal to 1. In some embodiments, the micelle or the vesicle has a diameter of about 20 nm to about 200 nm.

In some embodiments, the unstructured polypeptide further includes an NMT recognition sequence. In some embodiments, the NMT recognition sequence includes a glycine at the N-terminus. In some embodiments, the NMT recognition sequence is derived from *S. cerevisiae* arf2 polypeptide. In some embodiments, the NMT is from *S. cerevisiae*. In some embodiments, the NMT includes an amino acid sequence consisting of residues 36-455 of NM_001182082.1 (*S. cerevisiae* NMTΔ36-455). In some embodiments, the conjugate further includes a linker.

The disclosure provides for other aspects and embodiments that will be apparent in light of the following detailed description and accompanying figures.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1A:
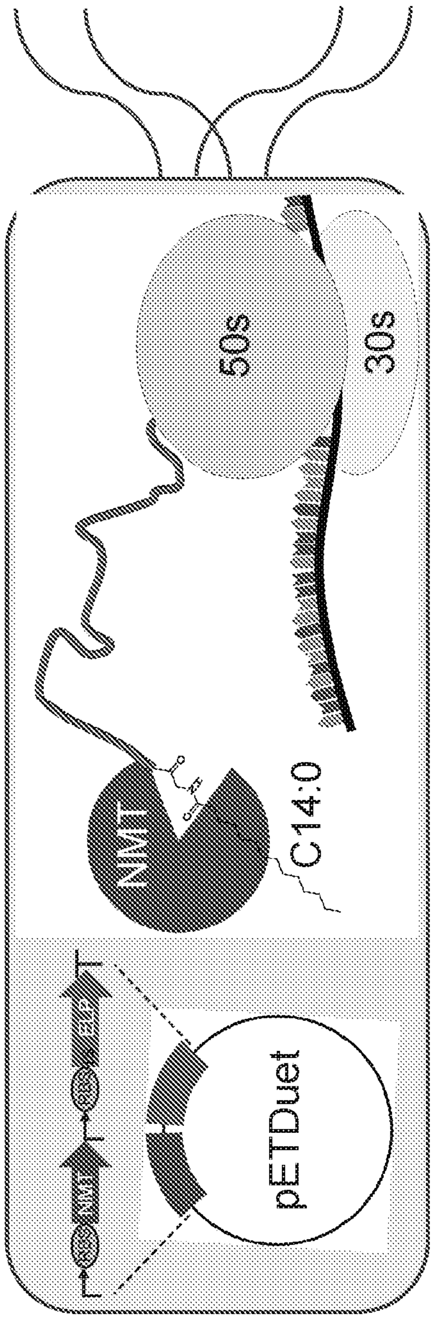
FIG. 1. A bicistronic vector transformed into *E. coli* is used to co-express two genes, (1) yeast NMT and (2) a recognition sequence fused to an elastin-like polypeptide (ELP) (A). Myristoylation of ELPs (M-ELP) creates an amphiphile that self-assembles into spherical or rod-like micelles (depending upon the ELP length) whose cores can be easily loaded with hydrophobic small molecules to form a stimulus-responsive drug carrier (B).
Figure 1B:
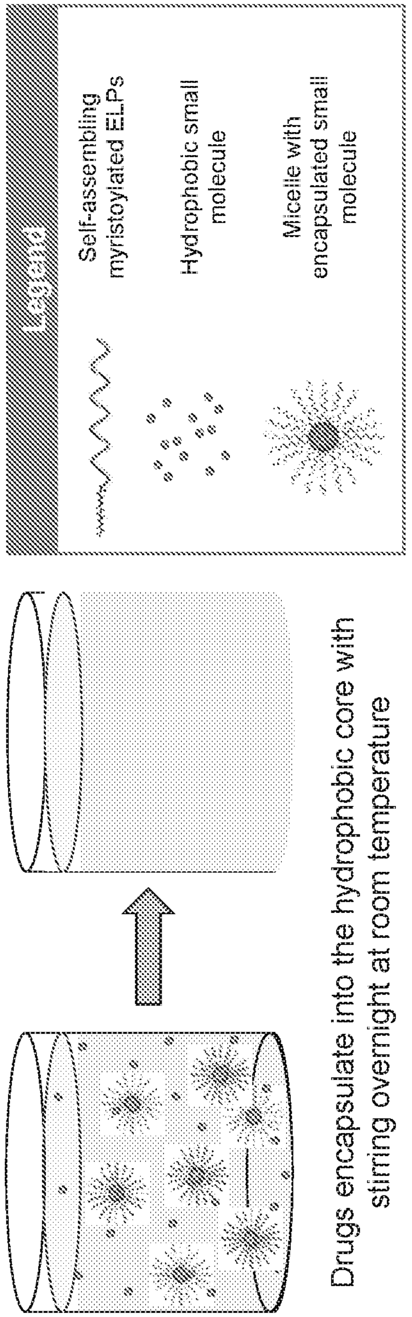

Described herein are conjugates that form micelles or vesicles. The conjugates include a fatty acid-modified polypeptide. The conjugates are thermally responsive and can exhibit temperature-triggered self-assembly into micelles or vesicles. The conjugates may be easily tailored and expressed recombinantly using a post-translational lipidation methodology, such that the synthesis of the conjugates may be easily regulated and amplified for commercial manufacturing. This is based in part on the results detailed herein, showing the successful and high yield, one-pot recombinant production of a highly tunable lipid-peptide polymer hybrid. This lipid-protein hybrid biomaterial self-assembles into nanoscale structures that can be used to encapsulate and deliver hydrophobic small molecule drugs.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, or diseased after treatment, or a combination thereof.

The term "expression vector" indicates a plasmid, a virus or another medium, known in the art, into which a nucleic acid sequence for encoding a desired protein can be inserted or introduced.

The term "host cell" is a cell that is susceptible to transformation, transfection, transduction, conjugation, and the like with a nucleic acid construct or expression vector.

Host cells can be derived from plants, bacteria, yeast, fungi, insects, animals, etc. In some embodiments, the host cell includes *Escherichia coli.*

"Imaging agent" is a substance capable of generating a detectable signal. "Imaging agent" and "reporter" and "reporter group" and "label" may be used interchangeably. A variety of imaging agents can be used, differing in the physical nature of signal transduction (e.g., fluorescence, electrochemical, nuclear magnetic resonance (NMR), PET, optical, ultrasound, radioactive, and electron paramagnetic resonance (EPR)) and in the chemical nature of the signal and imaging agent. In some embodiments, the signal from the imaging agent is a fluorescent signal. The imaging agent may comprise a fluorophore. Examples of fluorophores include, but are not limited to, acrylodan, badan, rhodamine, naphthalene, danzyl aziridine, 4-[N-[(2-iodoacetoxy)ethyl]-N-methylamino]-7-nitrobenz-2-oxa-1,3-diazole ester (IANBDE), 4-[N-[(2-iodoacetoxy)ethyl]-N-methylamino-7-nitrobenz-2-oxa-1,3-diazole (IANBDA), fluorescein, dipyrrometheneboron difluoride (BODIPY), 4-nitrobenzo[c][1,2,5]oxadiazole (NBD), Alexa fluorescent dyes, phycoerythrin (PE), carbocyanine, and derivatives thereof. Fluorescein derivatives may include, for example, 5-fluorescein, 6-carboxyfluorescein, 3'6-carboxyfluorescein, 5(6)-carboxyfluorescein, 6-hexachlorofluorescein, 6-tetrachlorofluorescein, fluorescein, fluorescein isothiocyanate (FITC), and isothiocyanate. In some embodiments, the imaging agent comprises the thiol-reactive acrylodan (6-acryloyl-2-dimethylaminonaphthalene). In other embodiments, the imaging agent comprises thiol-reactive badan (6-bromo-acetyl-2-dimethyl-amino-naphthalene). In some embodiments, the imaging agent includes quantum dots (i.e., fluorescent inorganic semiconductor nanocrystals). In some embodiments, the imaging agent includes paramagnetic metal chelates and nitroxyl spin labelled compounds. In some embodiments, the imaging agent includes a contrast reagent, such as, for example, a gadolinium based MRI contrast reagent. In some embodiments, the imaging agent comprises a radiolabel such as, for example, Tc-99m, P-32, deuterium, tritium, C-13, and N-15. In some embodiments, the imaging agent includes a small, hydrophobic molecule.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. Secondary structure includes, for example, beta sheet, alpha helix, and a combination thereof. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a polypeptide, conjugate, or target is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pretreated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described conjugates. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig: or non-human primate such as, for example, monkey, chimpanzee, gorilla, orangutan, and gibbon. The subject may be of any age or stage of development, such as, for example, an adult, an adolescent, or an infant.

"Treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Zwitterionic" or "zwitterion" refers to a molecule with net charge of zero, but including negative and positive charges on independent individual atoms within the molecule. The charged atoms are joined by one or more covalent bonds. A polypeptide may be zwitterionic.

2. Compositions Forming Micelles or Vesicles

Provided herein are compositions including a plurality of conjugates self-assembled into a micelle or a vesicle, and an agent encapsulated within the micelle or the vesicle. The compositions may be leveraged to package and deliver agents.

The vesicle comprises a bilayer separating a hydrophilic or aqueous internal compartment from a bulk hydrophilic phase. The micelle comprises a monolayer with a hydrophobic core and hydrophilic outer surface. In some embodiments, the micelle may be an inverted micelle comprising a hydrophilic core with a hydrophobic outer surface.

a. N-myristoyltransferase (NMT)

N-myristoyltransferase (NMT) is a protein that catalyzes the formation of a peptide bond between the carboxyl group of a fatty acid and the amine group of a polypeptide. In vivo, NMT covalently modifies polypeptides with myristic acid either cotranslationally or post-translationally, to covalently attach myristate to the N-terminal glycine of the polypeptide. Myristoylation of the polypeptide may be required for certain functions in vivo. As detailed herein, NMT can post-translationally modify a polypeptide with a fatty acid via a covalent amide bond in situ. In some embodiments, NMT recognize a N-terminal glycine for addition of the fatty acid. NMT may comprise NMT from *Saccharomyces cerevisiae*. In some embodiments, NMT comprises an amino acid sequence consisting of residues 38-455 of NM_001182082.1 (*S. cerevisiae* NMTΔ36-455).

b. Conjugate

The conjugate may include a fatty acid, an NMT recognition sequence, and an unstructured polypeptide. The conjugate may further include a linker. In some embodiments, the conjugate is amphiphilic. Amphiphiles include a hydrophilic portion as well as a lipophobic or hydrophobic portion.

i) Fatty Acid

The conjugates may include at least one fatty acid. Fatty acids include a carboxylic acid head and an aliphatic hydrocarbon chain tail. The hydrocarbon chain may be saturated or unsaturated. In some embodiments, the hydrocarbon chain comprises C2-C28. In some embodiments, the hydrocarbon chain comprises an even number of carbon atoms. In some embodiments, the hydrocarbon chain is branched. In some embodiments, the hydrocarbon chain is linear with no branches. The fatty acid may be any substrate of N-myristoyl transferase (NMT), including natural substrates and unnatural substrates. The fatty acid may be selected from, for example, myristic acid, and natural and unnatural analogues thereof. In some embodiments, the fatty acid comprises myristic acid.

ii) Unstructured Polypeptide

The conjugate includes an unstructured polypeptide. The unstructured polypeptide has minimal or no secondary structure as observed by CD, and has phase transition behavior. In some embodiments, the unstructured polypeptide comprises a repeated unstructured polypeptide, a non-repeated unstructured polypeptide, or a zwitterionic polypeptide, or a combination thereof. In some embodiments, the unstructured polypeptide is an exogenous protein that is not natively myristoylated.

(1) Transition Temperature Tt

The unstructured polypeptide has a phase transition behavior. "Phase transition" or "transition" may refer to the phase change or aggregation of the unstructured polypeptide, which occurs sharply and reversibly at a specific temperature called transition temperature (Tt). Below the transition temperature (Tt), for example, the unstructured polypeptides may be highly soluble. Upon heating above the transition temperature, for example, the unstructured polypeptides may hydrophobically collapse and aggregate, forming a separate, phase. Polypeptides having phase transition behavior may also be referred to as thermally responsive polypeptides.

The phase of the unstructured polypeptide may be described as, for example, soluble, a micelle, a vesicle, insoluble, or an aggregate. The aggregates or micelles or vesicles may be of a variety of sizes, depending on the phase or temperature. The aggregates or micelles or vesicles may be nanoscale, micron-sized, or macroscale. At the Tt, the unstructured polypeptide may change from soluble form to insoluble, or from insoluble form to a soluble form. In some embodiments, the unstructured polypeptide is soluble below the Tt. In some embodiments, the unstructured polypeptide is soluble above the Tt. In some embodiments, the unstructured polypeptide is insoluble below the Tt. In some embodiments, the unstructured polypeptide is insoluble above the Tt.

The Tt may be a LCST. The Tt may be a UCST. LCST is the temperature below which the unstructured polypeptide is miscible. UCST is the temperature above which the unstructured polypeptide is miscible. In some embodiments, the unstructured polypeptide has only UCST behavior. In some embodiments, the unstructured polypeptide has only LCST behavior. In some embodiments, the unstructured polypeptide has both UCST and LCST behavior.

The unstructured polypeptide can phase transition at a variety of temperatures and concentrations. The unstructured polypeptide may have a Tt from about 0° C. to about 100° C., from about 10° C. to about 50° C., or from about 20° C. to about 42° C. In some embodiments, the unstructured polypeptide has a Tt between room temperature (about 25° C.) and body temperature (about 37° C.). In some embodiments, the unstructured polypeptide has its Tt below body temperature or above body temperature at the concentration at which the conjugate is administered to a subject. The Tt can be adjusted by varying the amino acid sequence of the unstructured polypeptide, by varying the length of the unstructured polypeptide, or a combination thereof.

Phase transition may be reversible. Phase transition behavior may be used to form drug depots within a tissue of a subject for controlled (slow) release of a conjugate or agent. Phase transition behavior may also enable purification of the conjugate using inverse transition cycling, thereby eliminating the need for chromatography. "Inverse transition cycling" refers to a protein purification method for polypeptides having phase transition behavior, and the method may involve the use of the polypeptide's reversible phase transition behavior to cycle the solution through soluble and insoluble phases, thereby removing contaminants and eliminating the need for chromatography.

(2) Repeated Unstructured Polypeptide

The unstructured polypeptide may comprise a repeated unstructured polypeptide. The repeated unstructured polypeptide may comprise any polypeptide having minimal or no secondary structure as observed by CD, having phase transition behavior, and comprising a repeated amino acid sequence.

In some embodiments, the repeated unstructured polypeptide comprises an amino acid sequence that is rich in proline and glycine. In some embodiments, the repeated unstructured polypeptide comprises a PG motif. In some embodiments, the repeated unstructured polypeptide comprises a plurality of or repeated PG motifs. A PG motif comprises an amino acid sequence selected from PG, $P(X)_nG$ (SEQ ID NO:1), and $(U)_mP(X)_nG(Z)_p$ (SEQ ID NO:2), or a combination thereof, wherein m, n, and p are independently an integer from 1 to 15, and wherein U, X, and Z are independently any amino acid. $P(X)_nG$ (SEQ ID NO:1) may include PXG, PXXG (SEQ ID NO:6), PXXXG (SEQ ID NO:7), PXXXXG (SEQ ID NO:8), PXXXXXG (SEQ ID NO:9), PXXXXXXG (SEQ ID NO:10), PXXXXXXXG (SEQ ID NO:11), PXXXXXXXXG (SEQ ID NO:12), PXXXXXXXXXG (SEQ ID NO:13), PXXXXXXXXXXG (SEQ ID NO:14), PXXXXXXXXXXXG (SEQ ID NO:15), PXXXXXXXXXXXXG (SEQ ID NO:16), PXXXXXXXXXXXXXG (SEQ ID NO:17), PXXXXXXXXXXXXXXG (SEQ ID NO:18), and/or PXXXXXXXXXXXXXXXG (SEQ ID NO:19). The repeated unstructured polypeptide may further include additional amino acids at the C-terminal and/or N-terminal end of the PG motif. These amino acids surrounding the PG motif may also be part of the overall repeated motif. The amino acids that surround the PG motif may balance the overall hydrophobicity and/or charge so as to control the Tt of the repeated unstructured polypeptide.

In some embodiments, the repeated unstructured polypeptide comprises an amino acid sequence of $[GVGVP]_n$ (SEQ ID NO:3), wherein n is an integer from 1 to 200.

In some embodiments, the repeated unstructured polypeptide comprises one or more thermally responsive polypeptides. Thermally responsive polypeptides may include, for example, elastin-like polypeptides (ELP). 'ELP' refers to a polypeptide comprising the pentapeptide repeat sequence $(VPGXG)_n$ (SEQ ID NO:4), wherein X is any amino acid except proline and n is an integer greater than or equal to 1. The repeated unstructured polypeptide may comprise an amino acid sequence consisting of $(VPGXG)_n$ (SEQ ID NO:4). In some embodiments, X is not proline. In some embodiments, X is alanine, valine or a combination thereof. In some embodiments, X is 0% to 90% alanine, with the balance being valine. In some embodiments, X is 10% to 100% valine, with the balance being alanine. In some embodiments, n is 20, 30, 40, 50, 60, 70, 80, 90, 100, 110, 120, 130, 140, 150, 160, 170, 180, 190, 200, 210, 220, 230, 240, 250, 260, 270, 280, 290, or 300. In some embodiments, n may be less than 500, less than 400, less than 300, less than 200, or less than 100. In some embodiments, n may be from 1 to 500, from 1 to 400, from 1 to 300, from 1 to 200, or from 40 to 120. In some embodiments, n is 40, 60, 80, 120, or 180.

In other embodiments, the thermally responsive polypeptide comprises a resilin-like polypeptide (RLP). RLPs are derived from Rec1-resilin. Rec1-resilin is environmentally responsive and exhibits a dual phase transition behavior. The thermally responsive RLPs can have LCST and UCST (Li et. al, *Macromol. Rapid Commun.* 2015, 36, 90-95.)

Additional examples of suitable thermally responsive polypeptides are described in U.S. Patent Application Publication Nos. US2012/0121709, filed May 17, 2012, and US2015/0112022, filed Apr. 23, 2015, each of which is incorporated herein by reference.

(3) Non-Repeated Unstructured Polypeptide

The unstructured polypeptide may comprise a non-repetitive unstructured polypeptide. In some embodiments, the non-repeated unstructured polypeptide comprises a sequence of at least 60 amino acids, wherein at least about 10% of the amino acids are proline (P), and wherein at least about 20% of the amino acids are glycine (G). In some embodiments, the non-repeated unstructured polypeptide comprises a sequence wherein at least about 40% of the amino acids are selected from the group consisting of valine (V), alanine (A), leucine (L), lysine (K), threonine (T), isoleucine (I), tyrosine (Y), serine (S), and phenylalanine (F). In some embodiments, the non-repeated unstructured polypeptide comprises a sequence that does not contain three contiguous identical amino acids, wherein any 5-10 amino acid subsequence does not occur more than once in the non-repeated unstructured polypeptide, and wherein when the non-repeated unstructured polypeptide comprises a subsequence starting and ending with proline (P), the subsequence further comprises at least one glycine (G). In some embodiments, the non-repeated unstructured polypeptide comprises a sequence of at least 60 amino acids, wherein at least about 10% of the amino acids are proline (P), wherein at least about 20% of the amino acids are glycine (G), wherein at least about 40% of the amino acids are selected from the group consisting of valine (V), alanine (A), leucine (L), lysine (K), threonine (T), isoleucine (I), tyrosine (Y), serine (S), and phenylalanine (F), wherein the sequence does not contain three contiguous identical amino acids, wherein any 5-10 amino acid subsequence does not occur more than once in the non-repeated unstructured polypeptide, and wherein when the non-repeated unstructured polypeptide comprises a subsequence starting and ending with proline (P), the subsequence further comprises at least one glycine (G).

(4) Zwitterionic Polypeptide

The unstructured polypeptide may comprise a zwitterionic polypeptide (ZiPP). ZiPPs are overall neutral polypeptides that include both amino acids with negative charge and amino acids with positive charge. ZiPPs may comprise one or more charged motifs. The charged motif includes one or more positively charged amino acids and one or more negatively charged amino acids, wherein the positively charged amino acids and negatively charged amino acids are present in a ratio of 1:1. In some embodiments, the net charge of the motif is neutral. In some embodiments, the charged motif is a zwitterionic motif. The positively charged amino acids within one motif may be the same or different. The negatively charged amino acids within one motif may be the same or different. As used herein, the charge of an amino acid (positive and/or negative) refers to the charge of the amino acid side chain. A charged amino acid is positively and/or negatively charged at neutral pH, at physiological pH, or at the local pH within the protein fold, or a combination thereof. The charged motif may further include one or more uncharged amino acids. In some embodiments, the charged motif has an amino acid sequence of $VPX_1X_2G$ (SEQ ID NO:20), wherein $X_1$ is a negatively or positively charged amino acid, and wherein $X_2$ is the other of a negatively or positively charged amino acid.

In some embodiments, the zwitterionic polypeptide comprises a plurality of charged motifs. The plurality of charged motifs may be repeated. In some embodiments, zwitterionic polypeptide comprises the amino acid sequence of $(VPX_1X_2G)_n$ (SEQ ID NO:5), wherein $X_1$ is a negatively or positively charged amino acid, $X_2$ is the other of a negatively or positively charged amino acid, and n is an integer greater than or equal to 1. $X_1$ may be the same or different between adjacent motifs. $X_2$ may be the same or different between adjacent motifs. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a zwitterionic polypeptide comprises the amino acid sequence of $(VPX_1X_2G)_n$ (SEQ ID NO:5), wherein $X_1$ is a negatively or positively charged amino acid, $X_2$ is the other of a negatively or positively charged amino acid, and n is an integer greater than or equal to 1, may be referred to as a homopolymer.

In some embodiments, the zwitterionic polypeptide includes one or more uncharged motifs in addition to the one or more charged motifs. The uncharged motif includes uncharged amino acids. In some embodiments, the uncharged motif does not include any charged amino acids. In some embodiments, the uncharged motif has an amino acid sequence consisting of VPGXG (SEQ ID NO:21), wherein X is any amino acid except proline.

A plurality of uncharged motifs may be repeated in tandem. In some embodiments, the zwitterionic polypeptide comprises the amino acid sequence of $(VPGXG)_n$ (SEQ ID NO:4) in addition to the one or more charged motifs, wherein X is any amino acid except proline, and n is an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, zwitterionic polypeptides comprising an uncharged motif having an amino acid sequence consisting of $(VPGXG)_n$ (SEQ ID NO:4) in addition to the one or more charged motifs, wherein X is any amino acid except proline, and n is an integer greater than or equal to 1, are referred to as elastin-like polypeptides (ELP).

The motifs of the zwitterionic polypeptide can be arranged in any number of possible ways. Examples of possible arrangements and architectures include a homopolymer, a diblock polymer, and a multiblock polymer. A homopolymer is wherein each unit is a repeat of the pentapeptide sequence $VPX_1X_2G$ (SEQ ID NO:20), or charged motif. In a diblock architecture, one block of polymer is made with a repeating charged motif, while the other part includes a repeating uncharged motif. In a multiblock polymer, the charged motifs and uncharged motifs are placed at different sites to increase diversity of the polymer. The particular number, identity, and arrangement of motifs may be designed and varied. In some embodiments, one or more uncharged motifs are positioned between at least two adjacent charged motifs of the zwitterionic polypeptide. In some embodiments, the zwitterionic polypeptide includes a plurality of charged motifs repeated in tandem and a plurality of uncharged motifs repeated in tandem. In some embodiments, the plurality of charged motifs repeated in tandem are positioned C-terminal to the plurality of uncharged motifs repeated in tandem. In some embodiments, the plurality of charged motifs repeated in tandem are positioned N-terminal to the plurality of uncharged motifs repeated in tandem.

In some embodiments, the zwitterionic polypeptide comprises the amino acid sequence of $(VPX_1X_2G)_n(VPGXG)_m$ (SEQ ID NO:22), wherein $X_1$ is a negatively or positively charged amino acid, $X_2$ is the other of a negatively or positively charged amino acid, X is any amino acid except proline, and n and m are independently an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, m is an integer less than or equal to about 100, 200, 300, 400, or 500. In some embodiments, m is an integer greater than or equal to about 1, 10, 50, 100, 150, or 200. In some embodiments, m is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, m is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a zwitterionic polypeptide comprising the amino acid sequence of $(VPX_1X_2G)_n(VPGXG)_m$ (SEQ ID NO:22), wherein $X_1$ is a negatively or positively charged amino acid, $X_2$ is the other of a negatively or positively charged amino acid, X is any amino acid except proline, and n and m are independently an integer greater than or equal to 1, may be referred to as a diblock polymer.

In some embodiments, the zwitterionic polypeptide comprises the amino acid sequence of $(VPGXG)_m(VPX_1X_2G)_n$ (SEQ ID NO:23), wherein $X_1$ is a negatively or positively charged amino acid, $X_2$ is the other of a negatively or positively charged amino acid, X is any amino acid except proline, and n and m are independently an integer greater than or equal to 1. In some embodiments, n is an integer less than or equal to about 100, 200, 300, 400, or 500. In some embodiments, n is an integer greater than or equal to about 1, 10, 50, 100, 150, or 200. In some embodiments, n is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, n is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, m is an integer less than or equal to about 100, 200, 300, 400, or 500. In some embodiments, m is an integer greater than or equal to about 1, 10, 50, 100, 150, or 200. In some embodiments, m is an integer from about 10 to about 500, from about 10 to about 200, from about 10 to about 100, from about 10 to about 50, from about 1 to about 500, from about 1 to about 200, from about 1 to about 100, or from about 1 to about 50. In some embodiments, m is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500. In some embodiments, a zwitterionic polypeptide comprising the amino acid sequence of $(VPGXG)_m(VPX_1X_2G)_n$ (SEQ ID NO:23), wherein $X_1$ is a negatively or positively charged amino acid, $X_2$ is the other of a negatively or positively charged amino acid, X is any amino acid except proline, and n and m are independently an integer greater than or equal to 1, may be referred to as a diblock polymer.

In some embodiments, the zwitterionic polypeptide comprises the amino acid sequence of $\{(VPX_1X_2G)(VPGXG)\}_b$ (SEQ ID NO:24), wherein $X_1$ is a negatively or positively charged amino acid, $X_2$ is the other of a negatively or positively charged amino acid, X is any amino acid except proline, and b is an integer greater than or equal to 1. In some embodiments, b is an integer less than or equal to about 100, 200, or 300. In some embodiments, b is an integer greater than or equal to about 1, 10, 50, 100, 150, or 200. In some embodiments, b is an integer from about 10 to about 300, from about 10 to about 200, from about 10 to about 100, from about 10 to about 50, from about 1 to about 300, from about 1 to about 200, from about 1 to about 100, or from about 1 to about 50. In some embodiments, b is an integer equal to about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300. In some embodiments, a zwitterionic polypeptide comprising the amino acid sequence of $\{(VPX_1X_2G)(VPGXG)\}_b$ (SEQ ID NO:24), wherein $X_1$ is a negatively or positively charged amino acid, $X_2$ is the other of a negatively or positively charged amino acid, X is any amino acid except proline, and b is an integer greater than or equal to 1, may be referred to as a multiblock polymer.

In some embodiments, $X_1$ is a negatively charged amino acid, and $X_2$ is a positively charged amino acid. In some embodiments, $X_1$ is a positively charged amino acid, and $X_2$ is a negatively charged amino acid. In some embodiments, the negatively charged amino acid is independently selected from glutamatic acid and aspartic acid. In some embodiments, the positively charged amino acid is independently selected from lysine and arginine. In some embodiments, X is selected from arginine, histidine, lysine, aspartic acid, glutamic acid, serine, threonine, asparagine, glutamine, cysteine, selenocysteine, glycine, alanine, valine, leucine, isoleucine, methionine, phenylalanine, tyrosine, and tryptophan. In some embodiments, X is selected from glycine and valine.

iii) NMT Recognition Sequence

The unstructured polypeptide of the conjugate may include an NMT recognition sequence. An NMT recognition sequence is an amino acid sequence that NMT recognizes to catalyze the addition of a fatty acid to the polypeptide. The NMT recognition sequence may be at the N-terminal end of the unstructured polypeptide. In some embodiments, the NMT recognition sequence includes a N-terminal glycine. In some embodiments, the NMT recognition sequence comprises an amino acid sequence of GLYASKLFSNL (SEQ ID NO:25), which is the NMT recognition sequence from the natively myristoylated Arf2 protein from yeast. In some embodiments, the NMT recognition sequence comprises an amino acid sequence of GSSKSKPKDPSQRRR (SEQ ID NO:26), which is from the natively myristoylated Src protein from various mammalian species.

iv) Linker

The conjugate may further comprise a linker. The linker may be in between the NMT recognition sequence and the unstructured polypeptide, at the C-terminal end of the unstructured polypeptide, or a combination thereof. The linker may comprise a variety of amino acid sequences suitably known in the art. The linker may comprise, for example, an amino acid sequence selected from (GGC), ($[GGC]_8$) (SEQ ID NO:27), ($[G_4S]_3$) (SEQ ID NO:28), and ($[GGS]_n$ (SEQ ID NO:29) wherein n is an integer from 1 to 10).

c. Phase Transition of Conjugates

The conjugate may have a Tt that is different from the Tt of the unstructured polypeptide not attached to the conjugate, but that can be dependent on the Tt of the unstructured polypeptide. For example, the conjugate may have a Tt that is about 20° C. lower than the Tt of the unstructured polypeptide not attached to the conjugate. Generally, the above-description regarding the Tt of the unstructured polypeptide can also be applied to the conjugate. For the purposes of brevity, this description will not be repeated here.

The conjugates may self-assemble into micelles or vesicles below the Tt of the conjugates. The phase transition of the conjugates into micelles or vesicles can be based on the phase transition properties of the unstructured polypeptide. The phase transition of the conjugates into micelles or vesicles, and resolubilizing out of the micelle or vesicle form, may be triggered by the temperature. The phase transition may be reversible. Self-assembly or formation of the micelle or the vesicle may be driven by the addition of heat. Self-assembly or formation of the micelle or vesicle may be driven by the addition of salt.

The form and size of the micelle or vesicle may depend on the temperature, the sequence of the unstructured polypeptide, the sequence of the linker, or the fatty acid, or a combination thereof. The micelle or vesicle may be of a variety of sizes and shapes, such as spheres and rods, depending on the phase or temperature. The micelle or vesicle may be, for example, nanoscale, micron-sized, or macroscale. In some embodiments, the micelle or vesicle has a diameter of about 20-200 nm.

d. Agent

In some embodiments, the conjugate may encapsulate an agent upon self-assembling into a micelle or a vesicle. In some embodiments, the conjugate may release an agent upon resolubilizing out of the micelle or vesicle form. The agent may be loaded into the micelle or the vesicle by passive diffusion. In some embodiments, the agent is non-covalently associated with the micelle or vesicle. The agent may be a therapeutic. The agent may be a drug. In some embodiments, the agent is selected from a small molecule, nucleotide, polynucleotide, protein, polypeptide, lipid, carbohydrate, a drug, an imaging agent, and a combination thereof. The agent may be hydrophilic or hydrophobic. In some embodiments, the agent comprises a small molecule. In some embodiments, the agent comprises a protein. In some embodiments, the agent comprises a cancer therapeutic. In some embodiments, the agent comprises doxorubicin (DOX). In some embodiments, the agent comprises paclitaxel (PTX). In some embodiments, the agent comprises an antibody. In some embodiments, the agent is attached to a cysteine of the polypeptide of the conjugate. In some embodiments, the agent is hydrophobic.

In some embodiments, the conjugates detailed herein may forma drug delivery composition. The drug delivery composition may include a plurality of conjugates as detailed in herein self-assembled into a micelle or a vesicle, with an agent encapsulated within the micelle or the vesicle. One or more agents may be encapsulated within the micelle or vesicle. The core of the micelle may be hydrophobic or lipophilic, and the agent may be encapsulated within the hydrophobic or lipophilic core of the micelle. The core of the inverted micelle may be aqueous, and the agent may be encapsulated within the aqueous core of the inverted micelle. The core of the vesicle may be aqueous, and the agent may be encapsulated within the aqueous core of the vesicle. The agent may be hydrophobic, and at least a portion of the agent may be incorporated within the bilayer of the vesicle.

The micelles and vesicles provided from the conjugates disclosed herein may have advantageous drug loading capabilities. For example, the micelles or vesicles may have an agent (e.g., drug) loading efficiency of about 3% to about 5%. In addition, the micelles or vesicles may have an agent (e.g., drug) loading capacity of about 1% to about 3% (by weight percent of the micelle or vesicle).

e. Polynucleotides

Further provided are polynucleotides encoding the conjugates detailed herein. A vector may include the polynucleotide encoding the conjugates detailed herein. To obtain expression of a polypeptide, one may subclone the polynucleotide encoding the polypeptide into an expression vector that contains a promoter to direct transcription, a transcription/translation terminator, and if for a nucleic acid encoding a protein, a ribosome binding site for translational initiation. An example of a vector is pet24. Suitable bacterial promoters are well known in the art. Further provided is a host cell transformed or transfected with an expression vector comprising a polynucleotide encoding a conjugate as detailed herein. Bacterial expression systems for expressing the protein are available in, e.g., *E. coli, Bacillus* sp., and *Salmonella* (Paiva et al., *Gene* 1983, 22, 229-235; Mosbach et al., *Nature* 1983, 302, 543-545). Kits for such expression systems are commercially available. Eukaryotic expression systems for mammalian cells, yeast, and insect cells are well known in the art and are also commercially available. Retroviral expression systems can be used in the present invention.

The conjugate may be expressed recombinantly in a host cell according to one of skill in the art. The fatty acid may be included in or added to the culture for formation of the conjugate. The conjugate may be purified by any means known to one of skill in the art. For example, the conjugate may be purified using chromatography, such as liquid chromatography, size exclusion chromatography, or affinity chromatography, or a combination thereof. In some embodiments, the conjugate is purified without chromatography. In some embodiments, the conjugate is purified using inverse transition cycling.

f. Administration

A composition may comprise the conjugate. The conjugates as detailed herein can be formulated into a composition in accordance with standard techniques well known to those skilled in the pharmaceutical art. The composition may be prepared for administration to a subject. Such compositions comprising a conjugate can be administered in dosages and by techniques well known to those skilled in the medical arts taking into consideration such factors as the age, sex, weight, and condition of the particular subject, and the route of administration.

The conjugate can be administered prophylactically or therapeutically. In prophylactic administration, the conjugate can be administered in an amount sufficient to induce a response. In therapeutic applications, the conjugates are administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The conjugate can be administered by methods well known in the art as described in Donnelly et al. (*Ann. Rev. Immunol.* 1997, 15, 617-648); Feigner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The conjugate can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The conjugates can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the conjugate is administered intravenously, intraarterially, or intraperitoneally to the subject.

g. Methods i) Method of Preparing a Conjugate

The present disclosure is also directed to a method of preparing a conjugate as detailed herein. The method may include (a) transforming a bacteria with a recombinant expression vector comprising a first polynucleotide encoding a first polypeptide and a second polynucleotide encoding a second polypeptide, wherein the first polypeptide comprises an N-myristoyl transferase (NMT), and wherein the second polypeptide comprises an NMT recognition sequence and an unstructured polypeptide; and (b) culturing the transformed bacteria in the presence of a fatty acid to express the first and second polypeptides and add the fatty acid to the N-terminus of the NMT recognition sequence to form the conjugate. In some embodiments, the method further includes (c) isolating the conjugate. In some embodiments, the bacteria comprises *E. coli*. In some embodiments, the bacteria is cultured in media comprising myristic acid. The myristic acid may be present in a concentration of about 0 to 100 μM, or about 0 to about 200 μM. In some embodiments, the vector further comprises a single polynucleotide encoding a single antibiotic selection marker. In some embodiments, the bacteria is cultured in media comprising the antibiotic.

In some embodiments, the NMT comprises NMT from *S. cerevisiae*. In some embodiments, the NMT comprises an amino acid sequence consisting of residues 36-455 of NM_001182082.1 (*S. cerevisiae* NMTΔ36-455).

ii) Method of Delivering an Agent

The present disclosure is also directed to a method of delivering an agent to a subject. The method may include encapsulating the agent in a micelle or vesicle, the micelle or vesicle comprising a plurality of conjugates self-assembled into a micelle or vesicle as detailed herein, and administering the micelle or vesicle to the subject. In some embodiments, each conjugate comprises a fatty acid conjugated to the N-terminal end of an unstructured polypeptide.

iii) Method of Treating a Disease

The present disclosure is also directed to a method of treating a disease in a subject in need thereof. The method may include administering a composition as detailed herein to the subject.

iv) Method of Increasing the Maximum Tolerated Dose of an Agent

The present disclosure is also directed to a method of increasing the maximum tolerated dose of an agent. The method may include encapsulating the agent in a micelle or vesicle comprising a plurality of conjugates as detailed herein, and administering the agent-encapsulated micelle or agent-encapsulated vesicle to a subject. In some embodiments, each conjugate comprises a fatty acid conjugated to the N-terminal end of an unstructured polypeptide. In some embodiments, the maximum tolerated dose ($IC_{50}$) of the agent is increased 0.5-fold to 20-fold compared to a non-encapsulated agent.

3. Examples

Example 1

Materials and Methods

Materials

The pETDuet-1 vector and Amicon Ultra-15 centrifugal filters were purchased from EMD Millipore (Billerica, Mass.). Restriction enzymes, ligase, and corresponding buffers were purchased from New England Biolabs (Ipswich, Mass.). Chemically competent Eb5alpha and BL21(DE3) cells were purchased from EdgeBio (Gaithersburg, Md.). DNA extraction and purification kits were purchased from Qiagen (Valencia, Calif.). Components for 2× yeast tryptone medium (yeast extract and tryptone) were purchased from Amresco (Solon, Ohio). Isopropyl β-D-1-thiogalactopyranoside (IPTG) was purchased from Bioline USA (Boston, Mass.). Myristic acid, alpha-cyano-4-hydroxycinnamic acid, and trifluoroacetic acid (TFA) were purchased from Sigma-Aldrich (St. Louis, Mo.). SnakeSkin™ Dialysis Tubing featuring 3.5K nominal molecular weight cut off (MWCO), anhydrous dimethyl sulfoxide (DMSO), cell culture media, fetal bovine serum, and mass spectrometry grade trypsin were purchased from Thermo Fisher Scientific (Waltham, Mass.). High performance liquid chromatography-(HPLC) grade acetonitrile was purchased from VWR International (Radnor, Pa.) and was used as received without further purification. Water was obtained from a Milli-Q® system (Thermo Scientific, CA). The cell proliferation assay was purchased from Promega (Madison, Wis.), and the chemotherapeutics, doxorubicin-HCl (DOX-HCl) and paclitaxel (PTX), were purchased from Carbosynth Limited (Berkshire, UK).

Gene Synthesis

Figure 5:
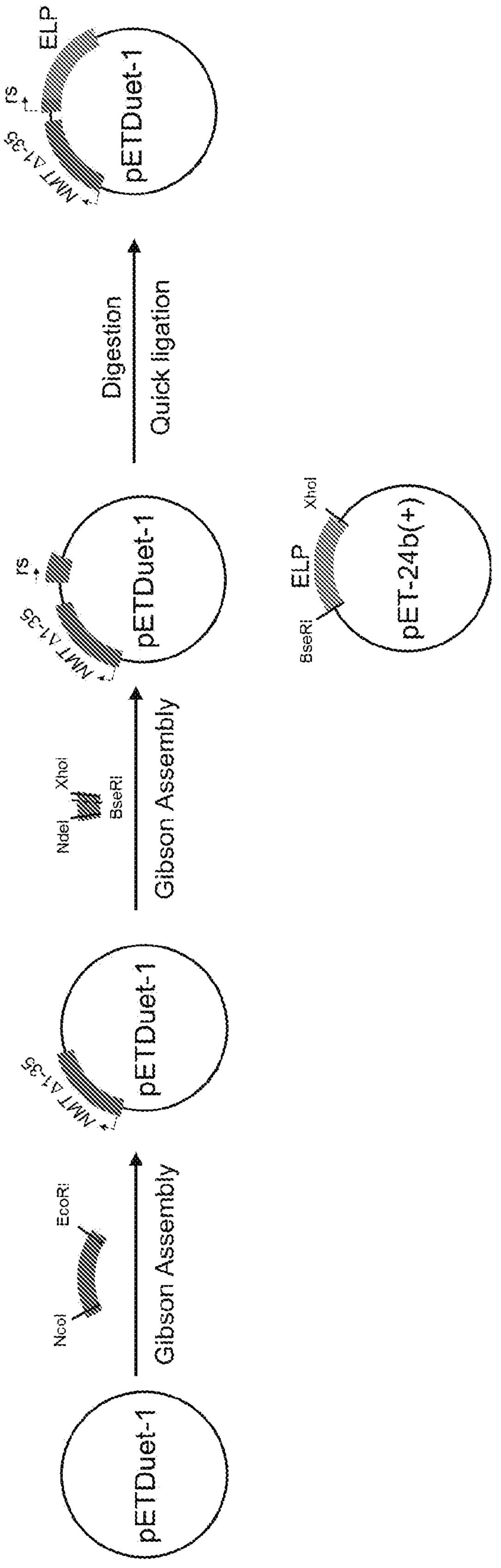
FIG. 5. Overview of genetic assembly of dual expression vector containing NMT and the recognition sequence fused to an ELP.

Construction of the Dual Expression Vector: To generate a single vector capable of expressing both the NMT and the recognition sequence-ELP fusion (FIG. 5), we purchased the bicistronic pETDuet-1 plasmid DNA, a dual expression system, from EMD Millipore. This vector contains an ampicillin resistance gene and two multiple cloning sites (MCS), each of which is preceded by its own T7 promoter, lac operator, and ribosomal binding site. The codon-optimized, double stranded genes were purchased from Integrated DNA Technologies that coded for residues 36 to 455 of the *S. cerevisiae* NMT enzyme (Swiss-Prot accession number P14743). This cDNA was then flanked on each end by a 40-80 bp segment that corresponded to the pETDuet-1 sequences upstream (which contains an MGSSHHHHHH leader) and downstream of the MCS 1 (shown in bold black in the gene sequence below) in addition to cleavage sites for NcoI and EcoR (underlined). After cutting and gel purifying pETDuet-1 DNA with NcoI and EcoRI-HF, the NMT gene was inserted into MCS 1 using the Gibson Assembly® Master Mix (New England Biolabs) according to the manufacturer's instructions. Ligated DNA (3 μL) was transformed into EB5alpha (25 μL) competent cells (EdgeBio) and spread onto agar plates containing 100 μg/mL ampicillin. Positive clones were identified with Sanger sequencing (Eton Biosciences) using the universal T7 Promoter primer.

(SEQ ID NO: 30)

5'-

CAATGGTATATCTTCCGGGCGCTATCATGCCATACCTTTTTATACCATGG

GCAGCAGCCATCACCATCATCACCACAAAGACCACAAATTTTGGCGTACC

CAGCCGGTTAAAGATTTTGATGAAAAAGTTGTTGAAGAAGGTCCGATCGA

CAAACCGAAAACACCGGAAGATATTAGCGATAAACCGCTGCCGCTGCTGA

GCAGCTTTGAATGGTGTAGCATTGATGTGGACAACAAAAAACAGCTGGAA

GATGTTTTTGTGCTGCTGAACGAAAACTATGTGGAAGATCGTGATGCAGG

TTTTCGCTTCAATTATACCAAAGAGTTTTTCAACTGGGCACTGAAAAGTC

CGGGTTGGAAAAAAGATTGGCATATTGGTGTTCGTGTGAAAGAAACCCAG

AAACTGGTTGCATTTATTAGCGCAATTCCGGTTACCCTGGGTGTGCGTGG

TAAACAGGTTCCGAGCGTTGAAATTAACTTTCTGTGTGTTCATAAACAGC

TGCGTAGCAAACGTCTGACACCGGTTCTGATTAAAGAAATCACCCGTCGT

GTGAACAAATGCGATATTTGGCATGCACTGTATACCGCAGGTATTGTTCT

GCCTGCACCGGTTAGCACCTGTCGTTATACCCATCGTCCGCTGAACTGGA

AAAAACTGTATGAAGTTGATTTCACCGGTCTGCCGGATGGTCATACCGAA

GAAGATATGATTGCAGAAAATGCACTGCCTGCAAAAACCAAAACCGCAGG

TCTGCGTAAACTGAAAAAAGAGGACATCGATCAGGTCTTTGAGCTGTTTA

AACGTTATCAGAGCCGCTTTGAACTGATCCAGATTTTTACCAAAGAAGAG

TTCGAGCACAACTTTATTGGTGAAGAAAGCCTGCCGCTGGATAAACAGGT

GATTTTTAGCTATGTTGTTGAACAGCCGGATGGCAAAATTACCGATTTTT

TCAGCTTTTATAGCCTGCCGTTTACCATTCTGAACAACACCAAATACAAA

GACCTGGGCATTGGCTATCTGTATTATTACGCAACCGATGCCGATTTCCA

GTTTAAAGATCGTTTTGATCCGAAAGCAACCAAAGCCCTGAAAACCCGTC

TGTGCGAACTGATTTATGATGCATGTATTCTGGCCAAAAACGCCAACATG

GATGTTTTTAATGCACTGACCAGCCAGGATAATACCCTGTTTCTGGATGA

TCTGAAATTTGGTCCGGGTGATGGTTTTCTGAATTTCTACCTGTTTAACT

ATCGTGCCAAACCGATTACCGGTGGTCTGAATCCGGATAATAGCAATGAT

ATTAAACGTCGCAGCAATGTTGGTGTGGTTATGCTGTGATAATGATAATG

ATCTTCTGAATTCCCGTCATATCCGCTGAGCAATAACTAGCATAACCCCT

TATACGTTACAT-3'.

This NMT(+) vector was then modified with cDNA corresponding to the 11-amino acid Arf2 recognition sequences (see below, double underlined). Forward and reverse strand oligonucleotides were purchased and designed to contain 5'-phosphorylated sticky end overhangs, corresponding to NdeI and XhoI (single underlined), as well as the recognition sequence for the enzyme, BseRI (bolded) C-terminal to the recognition sequence. The following oligonucleotides (Integrated DNA Technologies) were resuspended in water to 100 μM. 1 μL each of the forward and reverse strands were added to 50 μL of water containing 1×T4 DNA Ligase Buffer (NEB) and annealed by heating to 95° C., incubating for 5 min, and cooling back to room temperature. 5 μL of annealed DNA was ligated into MCS 2 of the NMT(+) pETDuet-1 vector that had been digested with NdeI and XhoI and purified. Importantly, this cDNA for the NMT recognition sequence was designed to contain a BseRI recognition sequence. BseRI is a type IIs enzyme and was inserted such that it would cut directly after the peptide substrate gene. This enables seamless cloning with our available in-house ELPs, most of which have been designed using the recursive directional ligation cloning system developed by McDaniel et al. (*Biomacromolecules* 2010, 11, 944-952). After Gibson Assembly (D. G. Gibson, et al. *Nat. Methods* 2009, 6, 343-345), these new ligated vectors were transformed into competent cells, and we identified positive clones with T7 Terminator sequencing. This NMT(+)/rs(+) plasmid could then be used to insert any in-house ELP by cutting both the vector and desired ELP with BseRI and XhoI, gel purifying the desired DNA fragments, and ligating the two pieces together.

To synthesize control plasmids, the cDNA encoding for the recognition sequence-ELP fusions was cut with NdeI and XhoI. The original, empty pETDuet-1 plasmid was also digested with NdeI and XhoI. After 1 h incubation, calf-intestinal phosphatase was added to the pET-Duet mixture to de-phosphorylate the 5' ends and prevent vector re-circularization. The digested DNA was run on a 1% agarose gel with 0.01% SybrSafe. The bands of interest were excised, dissolved, and purified with a QIAQuick purification kit. The DNA pieces were then ligated and transformed. Colonies were selected. Then, their plasmid DNA was purified and sent for Sanger sequencing (Eton Biosciences) using the T7 terminator promoter to confirm proper insertion of the ELP gene into pETDuet-1 without the NMT enzyme.

Oligonucleotides Used to Introduce Arf2 Recognition Sequence:

(SEQ ID NO: 31)

5'-TATGGGCCTGTATGCGAGCAACTGTTTAGCAACCTGGGCTAATGAT CTCCTCAATGAGC-3'

(SEQ ID NO: 32)

3'-ACCCGGACATACGCTCGTTTGACAAATCGTTGGACCCGATTACTAG AGGAGTTACTCGAGCT-5'.

Amino Acid Sequence of Proteins and Component MWs: The amino acid sequences of the proteins used in this study are reported below. N-terminal methionine is shown in parentheses and was removed co-translationally by methionine aminopeptidase before modification with the myristoyl group. $ELP_{90A,120}$ contain a single tryosine residue encoded at the C-terminus to assist with UV-Vis detection of the proteins. The MWs of all components used in these studies are listed in TABLE 2.

NMT(Δ35) (Accession number P14373)

(SEQ ID NO: 33)

(M)GSSHHHHHHKDHKFWRTQPVKDFDEKVVEEGPIDKPKTPEDISDKPL

PLLSSFEWCSIDVDNKKQLEDVFVLLNENYVEDRDAGFRFNYTKEFFNWA

LKSPGWKKDWHIGVRVKETQKLVAFISAIPVTLGVRGKQVPSVEINFLCV

HKQLRSKRLTPVLIKEITRRVNKCDIWHALYTAGIVLPAPVSTCRYTHRP

LNWKKLYEVDFTGLPDGHTEEDMIAENALPAKTKTAGLRKLKKEDIDQVF

ELFKRYQSRFELIQIFTKEEFEHNFIGEESLPLDKQVIFSYVVEQPDGKI

TDFFSFYSLPFTILNNTKYKDLGIGYLYYYATDADFQFKDRFDPKATKAL

KTRLCELIYDACILAKNANMDVFNALTSQDNTLFLDDLKFGPGDGFLNFY

LFNYRAKPITGGLNPDNSNDIKRRSNVGVVML $ELP_{90A,120}$

-continued (SEQ ID NO: 34)

```
(M)GLYASKLFSNLGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGY
```

$ELP_{90A,80}$ (SEQ ID NO: 35)

```
(M)GLYASKLFSNLGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPG
```

$ELP_{90A,40}$ (SEQ ID NO: 36)

```
(M)GLYASKLFSNLGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPGAGVPGAGVPGVGVPGAGVPGAGVPGAGVPGAGVPG
AGVPGAGVPGAGVPG
```

$ELP_{100V,40}$ (SEQ ID NO: 37)

```
(M)GLYASKLFSNLGVGVPGVGVPGVGVPGVGVPGVGVPGVGVPGVGVPG
VGVPGVGVPGVGVPGVGVPGVGVPGVGVPGVGVPGVGVPGVGVPGVGVPG
VGVPGVGVPGVGVPGVGVPGVGVPGVGVPGVGVPGVGVPGVGVPGVGVPG
VGVPGVGVPGVGVPGVGVPGVGVPGVGVPGVGVPGVGVPGVGVPGVGVPG
VGVPGVGVPGVGVPG
```

TABLE 2

| Materials used for recombinantly constructing lipid-polypeptide hybrids and their molecular weights. | | |
|---|---|---|
| Protein | N-terminal modification | Molecular weight (Da) |
| NMTp1(Δ35) | N/A | 49,799 |
| $ELP_{90A,120}$ | N/A | 47,541 |
| M-$ELP_{90A,120}$ | Myrisoyl | 47,752 |
| $ELP_{90A,80}$ | N/A | 32,008 |
| M-$ELP_{90A,80}$ | Myrisoyl | 32,219 |
| $ELP_{90A,40}$ | N/A | 16,802 |
| M-$ELP_{90A,40}$ | Myrisoyl | 17,013 |
| $ELP_{100V,40}$ | N/A | 17,649 |
| M-$ELP_{100V,40}$ | Myrisoyl | 17,859 |

Recombinant Expression

The pETDuet-1 vector harboring the NMTp1 enzyme in MCS 1 and an elastin-like polypeptide (ELP) fused to an N-terminal recognition sequence in MCS 2 was transformed into Ultra BL21 (DE3) competent *E. coli* cells. These cells were grown in 2XYT at 37° C. for approximately 6 h. The temperature was then reduced to 28° C. and 1 mL of exogenous myristic acid (100 mM in DMSO) was added to each 1 L culture. After 15 minutes, expression of the myristoylated polypeptide by T7 RNA polymerase was induced by the addition of 500 μL of 1 M isopropyl β-D-1-thiogalactopyranoside (IPTG).

Control samples were prepared by following a similar protocol with modified plasmids. To prove that the NMT is necessary for lipidation, we removed the NMT gene from the plasmid. To prove that the recognition sequence is necessary for successful myristoylation, we prepared a plasmid containing NMT and an ELP containing an N-terminal glycine but without Arf2 recognition sequence.

Protein Purification Protocols 18 h post-induction, the cells were harvested by centrifugation at 3500 rpm and 4° C. for 10 min. The bacterial pellet was re-suspended in deionized $H_2O$ to a volume of 40 mL. The cells were then lysed in an ice bath using sonication with sequential pulses of 10 s at 85 W followed by 40 s off for a total sonication period of 3 min. The lysed bacterial solution was transferred to polycarbonate centrifuge tubes and 10% w/v polyethylenimine (2 mL per every 1 L of expression culture) was added to pellet nucleic acids. Each tube was mixed to homogeneity after which the solution was centrifuged at 14,000 rpm and 4° C. for 10 min to separate the protein from insoluble cell debris. The clear supernatant layer was transferred to clean polycarbonate tubes and was then subjected to two rounds of "bakeout" and two rounds of inverse transition cycling (ITC)(D. E. Meyer, A. Chilkoti, Nat. Biotechnol 1999, 17, 1112-1115). For bakeout, the solution is incubated at 60° C. for 10 min and then on ice for 10 min, followed by a cold spin (14,000 rpm, 4° C. for 10 min). This step serves to denature and pellet unwanted proteins while the ELP, which is able to resolubilize when cooled, remains in the supernatant. For ITC, the phase-transition of the ELPs is triggered isothermally by the addition of NaCl. The polypeptide coacervates were then collected by a "hot spin" centrifugation step at 14,000 rpm and 35° C. for 10 min, after which the supernatant was discarded. The pellet was then re-suspended in 4 mL of deionized $H_2O$, and the tubes were placed in a rotator at 4° C. Once the gel-like pellet was fully re-solubilized, the mixture underwent a "cold spin" step, which involves centrifugation at 13,200 rpm and 4° C. for 10 min. The pellet from this step was discarded. The supernatant was transferred to a clean tube and was subjected to another round of ITC. For the second round of ITC, a 5 M NaCl aqueous solution was used to trigger the phase-transition isothermally. After the second "cold spin" cycle, the supernatant was collected and purified by preparative HPLC to ensure purity (>95%) for the self-assembly and in vitro studies. The details of the HPLC protocol are provided below.

Figure 6C:
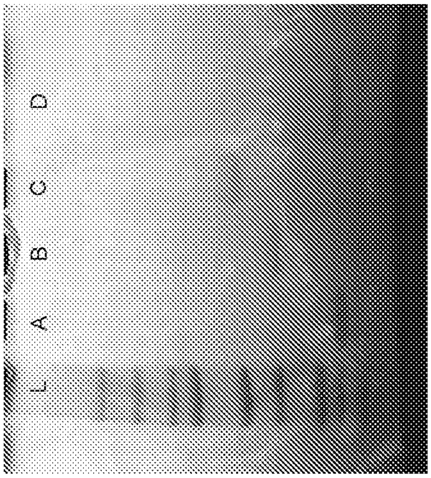
FIG. 6. SDS-PAGE of HPLC-purified ELP and M-ELPs. M-$ELP_{90A,120}$ and its control grown without NMT ($ELP_{90A,120}$) were purified by ITC and loaded for SDS-PAGE at low (A) and high (B) concentration: L: BioRad Kaleidoscope ladder, 1: cell lysate, 2: PEI supernatant 23, 3: ITC 1, 4: ITC 2, 5: ITC 3. The set of purified, myristoylated ELPs (C) were loaded as follows: A: M-$ELP_{90A,40}$, B: M-$ELP_{90A,80}$, C: M-$ELP_{90A,120}$, D: M-$ELP_{100V,40}$.

SDS-PAGE: Protein purity after ITC was verified with sodium dodecyl sulfate polyacrylamide gel electrophoresis (SDS-PAGE) on gels with a 4-20% Tris gradient (Bio-Rad) (FIG. 6). Proteins were added to Laemmli buffer containing 2-mercaptoethanol and heated at 95° C. for 5 minutes before applying them to the wells of the gel. The gel was run at 180 V for 48 min. Protein bands were compared to standard ladder (Precision Plus Protein Kaleidoscope, Bio-Rad) after negative staining with 0.5 M $CuCl_2$.

Reverse Phase HPLC: Analytical reverse phase HPLC (RP-HPLC) was performed on a Shimadzu instrument using a Phenomenex Jupiter® 5 μm C18 300 Å, LC Column 250×4.6 mm, solvent A: $H_2O$+0.1% TFA, solvent B: acetonitrile+0.1% TFA). A sample of the protein (50 μL, 30-100 μM) was injected into the HPLC system using the conditions outlined in TABLE 3. The absorbance at wavelengths between 190 and 800 nm was monitored using a photo-diode array detector. Representative chromatograms are shown for 230 nm. Small peaks visible before 5 min correspond to system peaks arising from differences between the sample buffer and the mobile phase. Fluorescence at 580 nm was also monitored for runs involving doxorubicin.

TABLE 3

Gradient program used for analytical HPLC analysis of each construct.

| Protein | N-terminal modification | Molecular weight (Da) |
|---|---|---|
| NMTp1(Δ35) | N/A | 49,799 |
| $ELP_{90A,120}$ | N/A | 47,541 |
| M-$ELP_{90A,120}$ | Myrisoyl | 47,752 |
| $ELP_{90A,80}$ | N/A | 32,008 |
| M-$ELP_{90A,80}$ | Myrisoyl | 32,219 |
| $ELP_{90A,40}$ | N/A | 16,802 |
| M-$ELP_{90A,40}$ | Myrisoyl | 17,013 |
| $ELP_{100V,40}$ | N/A | 17,649 |
| M-$ELP_{100V,40}$ | Myrisoyl | 17,859 |

The same gradient program was used for preparative RP-HPLC, which was performed on a Waters 600 HPLC system (Phenomenex Jupiter 10 μm C18 300 Å, LC Column 250×21.2 mm, solvent A: $H_2O$+0.1% TFA, solvent B: acetonitrile+0.1% TFA). A sample of the protein (0.5 mL, 5 mg/mL) was injected into the HPLC and assessed using the conditions outlined in TABLE 4. The Fractions corresponding to each peak were collected and analyzed using matrix-assisted laser desorption/ionization time-of-flight mass spectrometry (MALDI-TOF-MS) using an Applied Biosystems Voyager-DE™ PRO instrument according to the procedure detailed below.

TABLE 4

Gradient program used for preparative HPLC analysis of each construct.

| | Time (min) | Solvent B (%) |
|---|---|---|
| M-$ELP_{90A,120}$ | 0 | 30% |
| M-$ELP_{90A,80}$ | 5 | 30% |
| M-$ELP_{100V,40}$ | 25 | 90% |

TABLE 4-continued

Gradient program used for preparative HPLC analysis of each construct.

| | Time (min) | Solvent B (%) |
|---|---|---|
| M-$ELP_{90A,40}$ | 0 | 10% |
| | 5 | 10% |
| | 25 | 90% |

Size Exclusion Chromatography: Size exclusion chromatography on an LC10 Shimadzu instrument was used to separate the M-ELP carriers from free drug. Samples (80 μL, 20-300 μM) were loaded onto a Shodex OHPak KB-804 column and eluted in a mobile phase comprised of 30% $CH_3CN$ and 70% PBS.

Mass Spectrometry

Trypsin Digestion of Proteins: Protein samples were diluted to 50 μM in 50 mM ammonium bicarbonate. Mass spectrometry grade trypsin was added to protein at a ratio of 1:50 by mass. Samples were incubated, shaking, at 37° C. for 4-16 h prior to mass spectrometry.

MALDI-TOF-MS: Samples for MALDI-TOF-MS analysis (FIG. 7) were prepared by mixing 10 μL of each HPLC fraction with 10 μL of sinapinic acid (SA) matrix (a saturated solution was prepared by suspending 10 mg of SA in 700 μL $H_2O$+0.1% TFA and 300 μL acetonitrile+0.1% TFA). Afterward, 1.5 μL of this mixture was deposited onto a sample plate and dried in air at room temperature. All spectra with an acceptable signal-to-noise (S/N) ratio (>10) were calibrated against an aldolase standard (Sigma Aldrich, M, =39,211.28 Da). The following instrument parameters were optimized empirically to maximize the S/N ratio: accelerating voltage=25 kv; grid voltage=90%; guide wire=0.15%; extraction delay time=750 ns; acquisition range: 10,000-60,000 Da; low mass gate=5000 Da; number of laser shots=75/spectrum; laser intensity=3000; bin size=4 ns.

Figure 2B:
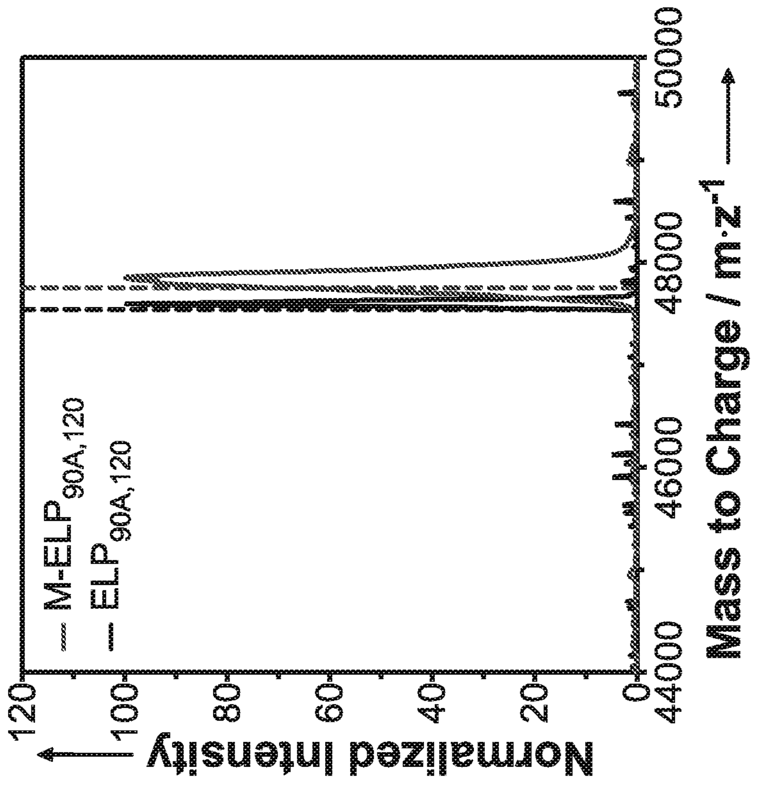
FIG. 2. Physical characterization of myristoylated ELPs and their LCST phase transition. A shift in RP-HPLC elution time between $ELP_{90A,120}$ grown with and without NMT (A) shows that the enzyme is necessary for myristoylation. MALDI-MS-TOF shows different experimental molecular weights (MWs) for M-$ELP_{90A,120}$ versus $ELP_{90A,120}$ (B), which is further supported by the 210 Da difference in the m/z of their N-terminal fragments after tryptic digestion (C), which corresponds to the MW of the myristoyl group. Myristoylation does not interfere with LCST phase behavior, but does suppress the $T_t$ (D) and reduce its concentration dependence (E). It also drives self-assembly into nanoparticles as seen with dynamic light scattering as an increase in the R of M-$ELP_{90A,120}$ compared to the $ELP_{90A,120}$ control (F).
Figure 2A:
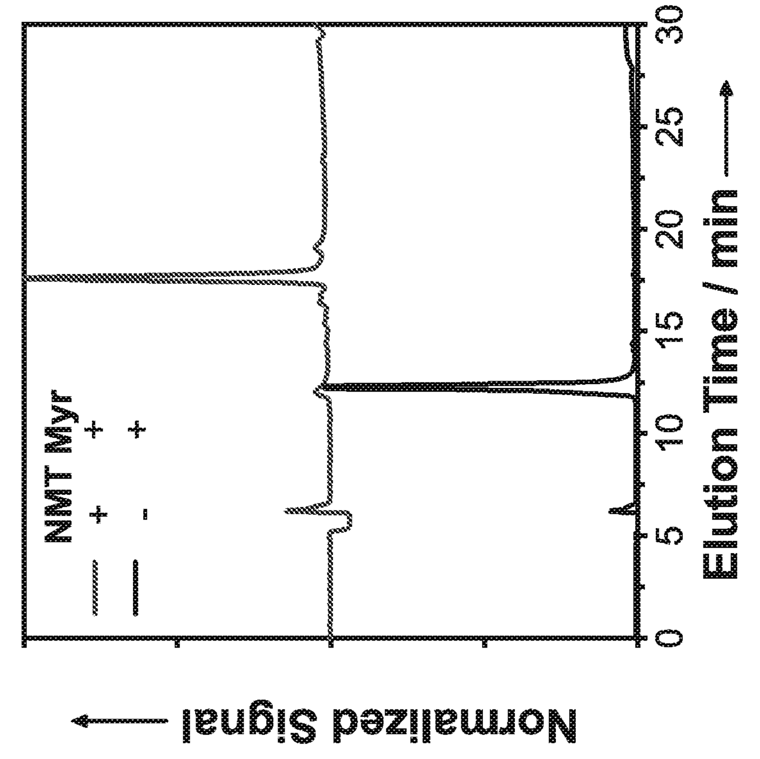
Figure 2D:
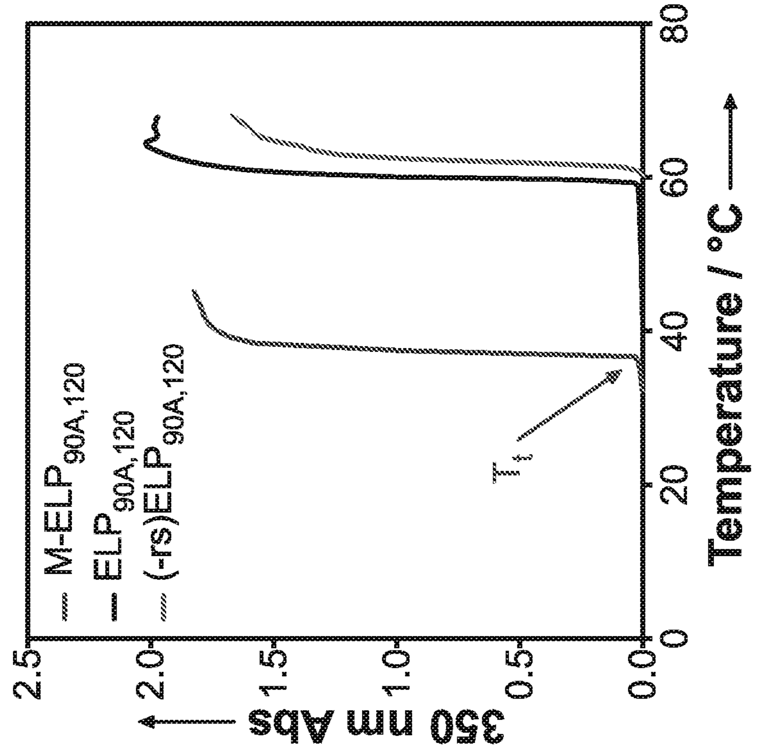
Figure 2C:
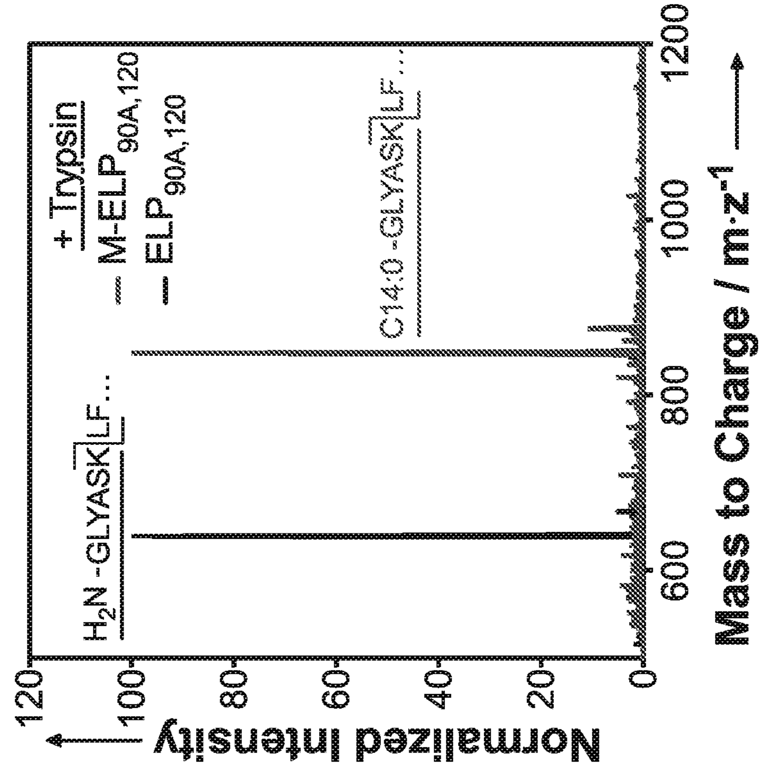

We used α-cyano-4-hydroxycinnamic acid as a matrix for analysis of the N-terminal peptide fragments (FIG. 2C). All spectra were calibrated against adrenocorticotropic hormone fragment 18-39 (Sigma Aldrich, $M_w$=2,464.1989). The following instrument parameters were optimized empirically to maximize the S/N ratio: accelerating voltage=20 kv; grid voltage=73.5%; guide wire=0.005%; extraction delay time=90 ns; acquisition range: 500-400 Da; low mass gate=500 Da; number of laser shots=40/spectrum; laser intensity=2000; bin size=0.5 ns. Where necessary, the spectra's baselines were corrected and noise removal and Gaussian smoothing were applied.

Quantification of Yield

2 L of cells expressing both NMT and $ELP_{A,120}$ were cultured and purified as previously described. After 2 rounds of bakeout (see above for details) and 2 rounds of ITC, the product was dialyzed into water and lyophilized. The total lyophilized protein was weighed and 1 mg was resuspended in 50 μL, injected, and analyzed by RP-HPLC as described in the section 4.2. The area of the peak eluting at 16 min in RP-HPLC (FIG. 8) was calculated as a percentage of total integrated peaks (threshold of 10% above corrected baseline), whose areas were quantified using the trapezoidal rule. Multiplying the value obtained from this calculation (74.5%) by the total protein purified from 2 L of cells (106.4 mg), we approximate that our yield of M-$ELP_{90A,120}$ is approximately 40.4 mg per 1 L of culture.

This same procedure was done for the other M-ELP constructs and for $ELP_{90A,120}$, grown without the NMT enzyme. The HPLC traces are shown (FIG. 9) and the AUC of the peak corresponding to the product was calculated as described above. The yield for each construct is presented in TABLE 5.

TABLE 5

Quantified yield for each construct.

| Construct | HPLC Peak % | Yield (mg/L) |
|---|---|---|
| M-$ELP_{90A,120}$ | 75.9 | 40.4 |
| $ELP_{90A,120}$ | 88.2 | 77.2 |
| M-$ELP_{90A,80}$ | 61.6 | 30.6 |
| M-$ELP_{90A,40}$ | 73.9 | 13.9 |
| M-$ELP_{100V,40}$ | 74.0 | 29.4 |

UV-Visible Spectroscopy

Figure 11:
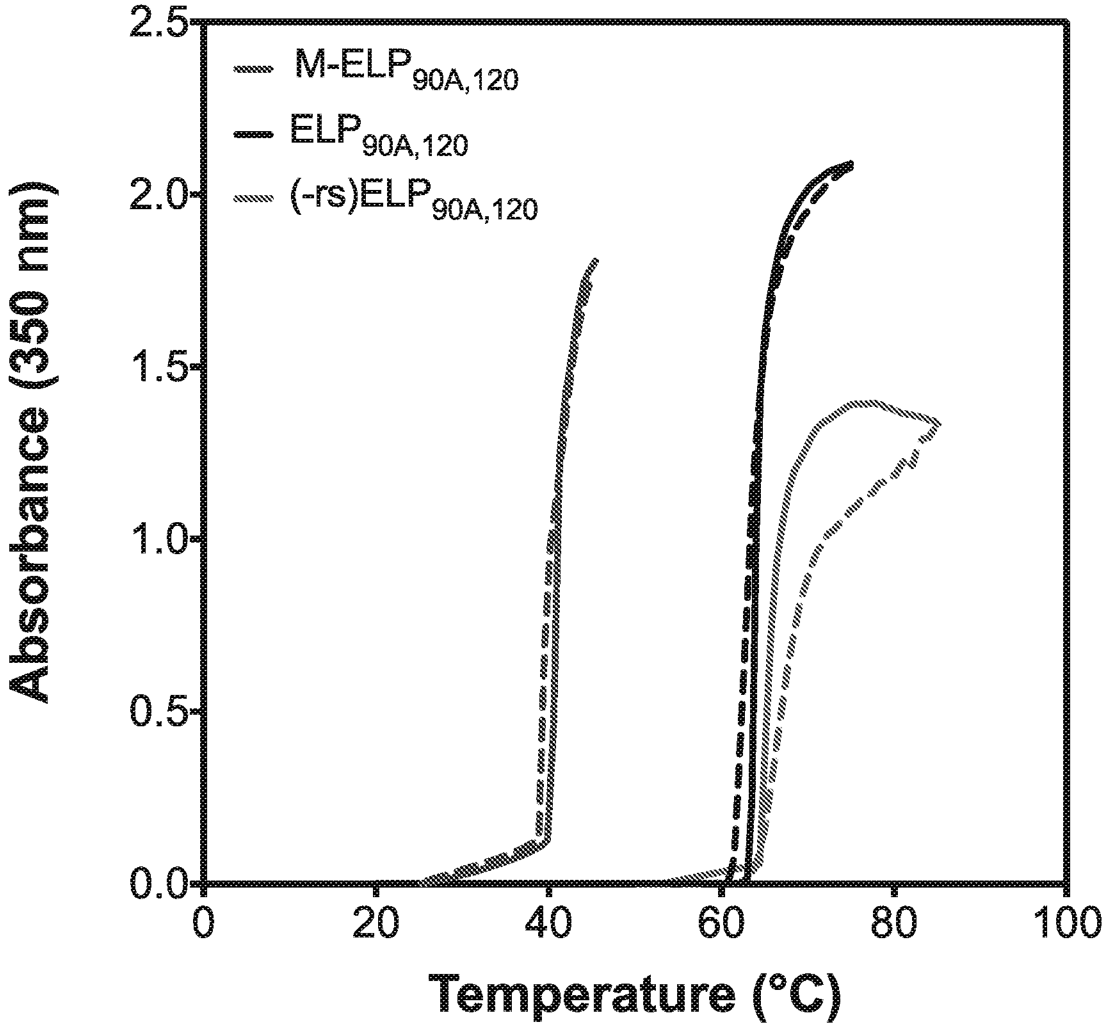
FIG. 11. Reversible phase behavior of M-$ELP_{90A,120}$ (blue) and controls grown without NMT (black) and without a recognition sequence (red). Solid lines indicate heating and dashed lines indicate cooling.
Figure 12A:
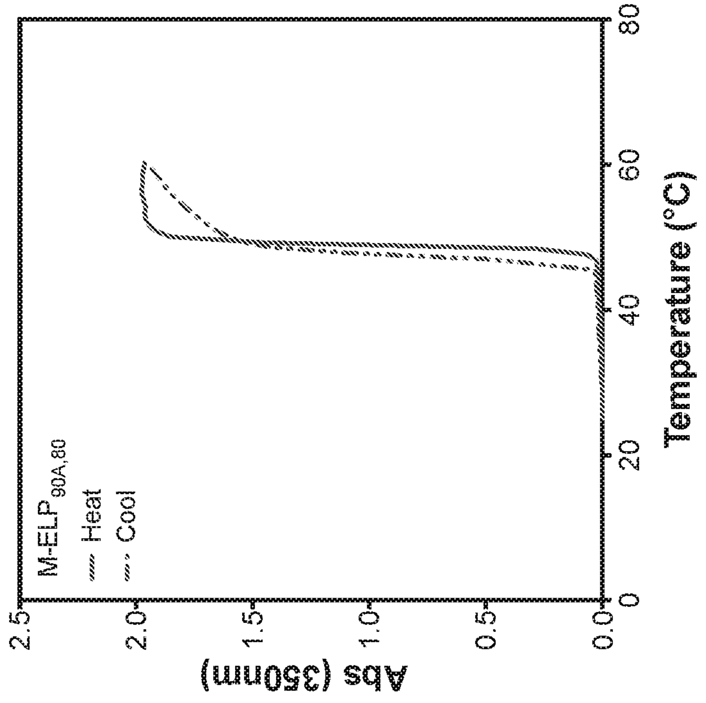
FIG. 12. The absorbance at 350 nm was measured as 50 μM samples of M-ELP were ramped up and down, demonstrating their soluble to insoluble phase LCST phase transition upon heating (solid lines) and the reversibility of the LCST behavior upon cooling (dashed lines); M-$ELP_{90A,120}$ (A), M-$ELP_{90A,40}$ (B), and M-$ELP_{100V,40}$ (C).
Figure 12B:
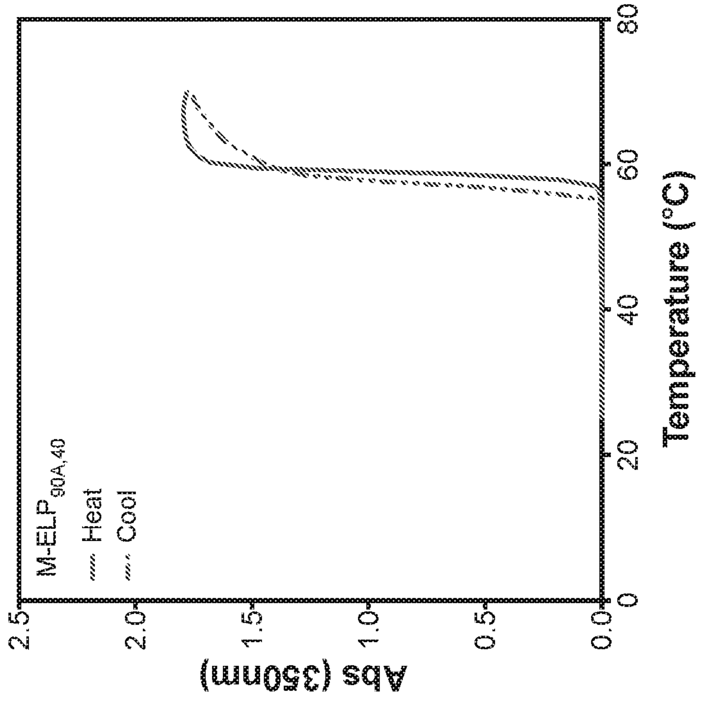
Figure 12C:
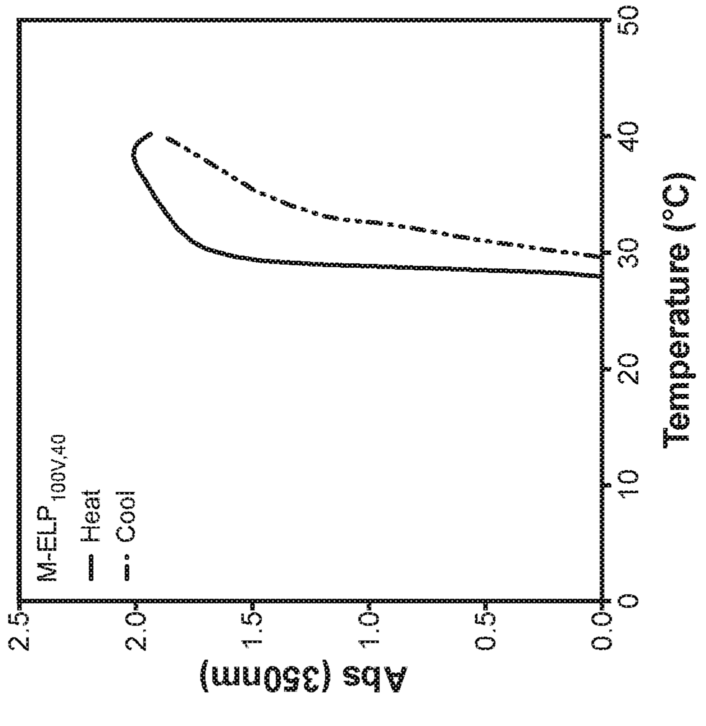

We investigated the temperature-triggered phase-transition of each construct by recording the optical density of the protein solution at 350 nm as the temperature is ramped up and down on a temperature-controlled UV-Vis spectrophotometer (Cary 300 Bio, Varian Instruments, Palo Alto, Calif.) (FIG. 10-FIG. 12). The transition temperature (T) is defined as the inflection point of the turbidity profile and was calculated as the maximum of the first derivative of $OD_{350}$ versus temperature, which was determined using Igor Pro software (FIG. 10). Turbidity profiles for each sample were measured in PBS at concentrations between 12.5 and 250 μM. For the non-myristoylated control sample, $ELP_{90A,40}$, the transition temperatures at these concentrations were well above 80° C. Consequently, their $OD_{3W}$ values were monitored in 1 M NaCl, which served to reduce the T into a temperature range that is experimentally accessible.

Light Scattering

Figure 13A:
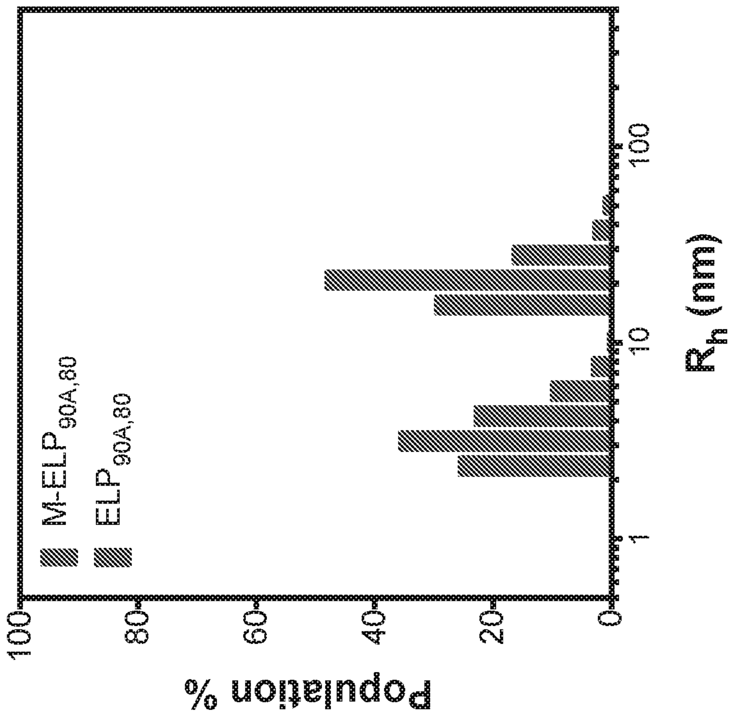
FIG. 13. Results of dynamic light scattering (DLS) fit to the autocorrelation function presented as size distribution histograms from the regularization fit for non-myristoylated samples (patterned bars) and myristoylated samples (solid filled bars); M-ELP$_{90A,80}$ (A), M-ELP$_{90A,40}$ (B), and M-ELP$_{100V,40}$ (C).
Figure 13B:
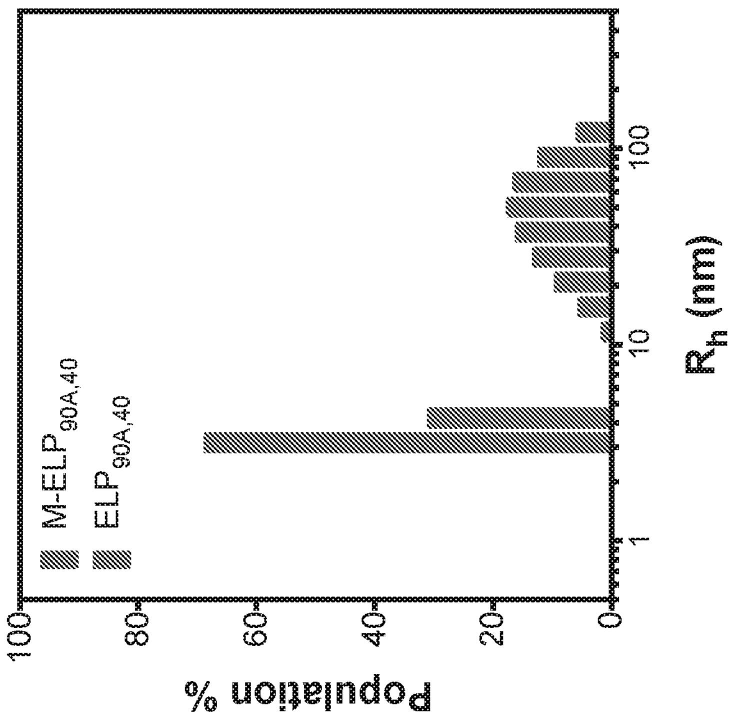
Figure 13C:
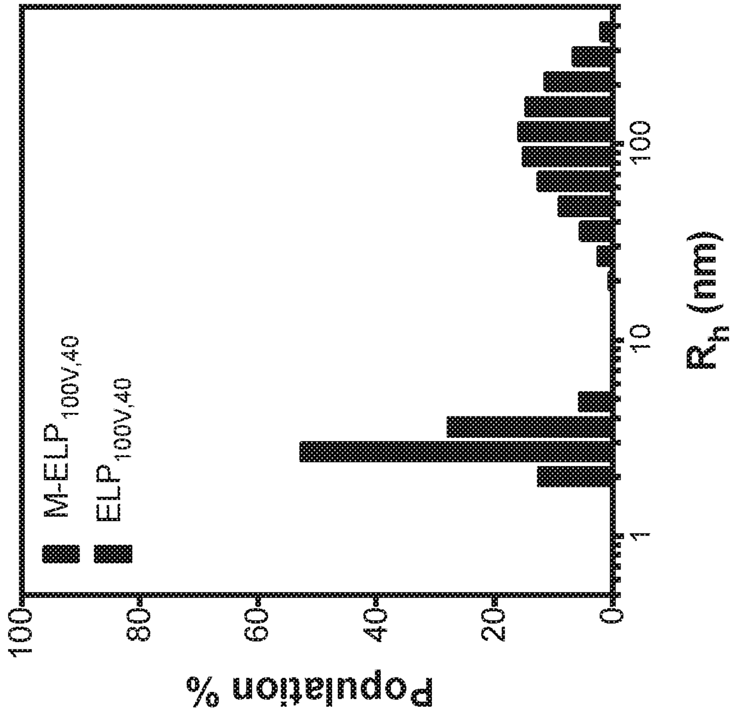

Characterization of myristoylated and non-myristoylated ELPs: Dynamic light scattering (DLS) studies were carried out to investigate the self-assembly of various myristoylated ELPs in aqueous solution. Prior to analysis, samples were prepared in PBS at a concentration of 50 μM, and filtered through a 0.22 μm polyvinylidene fluoride membrane (Durapore) directly into a quartz DLS cell. DLS experiments were conducted in a temperature-controlled DynaPro Microsampler (Wyatt Technologies). Measurements were obtained over a temperature range of 15 to 20° C. using 1° C. steps and at 25° C. 18 acquisitions of 5 s each were collected for every temperature point. Autocorrelation intensities at 15° C. were fitted using the regularization model and then depicted as a population size distribution histogram (FIG. 13) and intensity size distribution (FIG. 14) using Wyatt Dynamics software.

Static light scattering (SLS) studies were carried out to quantify the $R_g$, $R_h$, and $N_{agg}$ of myristoylated ELPs in aqueous solution. Samples were prepared in PBS at concentration ranging from 0.5-5 mg/mL and filtered through a 0.22 μm polyvinylidene fluoride membrane (Durapore) directly into a 10 mm, disposable borosilicate glass tube (Fisher Scientific). Experiments were performed using an ALV/CGS-3 goniometer system (Germany). For M-$ELP_{90A,120}$ and M-$ELP_{90A,80}$, as well as for M-$ELP_{90A,40}$ and M-$ELP_{100V,40}$ at early time points, measurements were obtained at 25° C. for angles between 30 and 150° C. and made at 5° C. increments with 3 runs of 10 s. Smaller angles (20-45° C.) were used to measure the 40-mer ELPs at later time points, after they had matured to their larger rod-like shape. Full Zimm plots were created by conducting SLS for each construct at different concentrations ranging from 25 μM to 100 μM. These Zimm plots were created using SLS data and ALVStat software after the refractive index increment (dn/dc) was calculated (FIG. 15). These plots provided the second virial coefficient and $R_g$ and from which shape factor was calculated (TABLE 1). Partial Zimm plots were used to calculate $N_{agg}$ at 1 mg/mL. Zimm plots for the constructs are shown in FIG. 16.

Figure 3A:
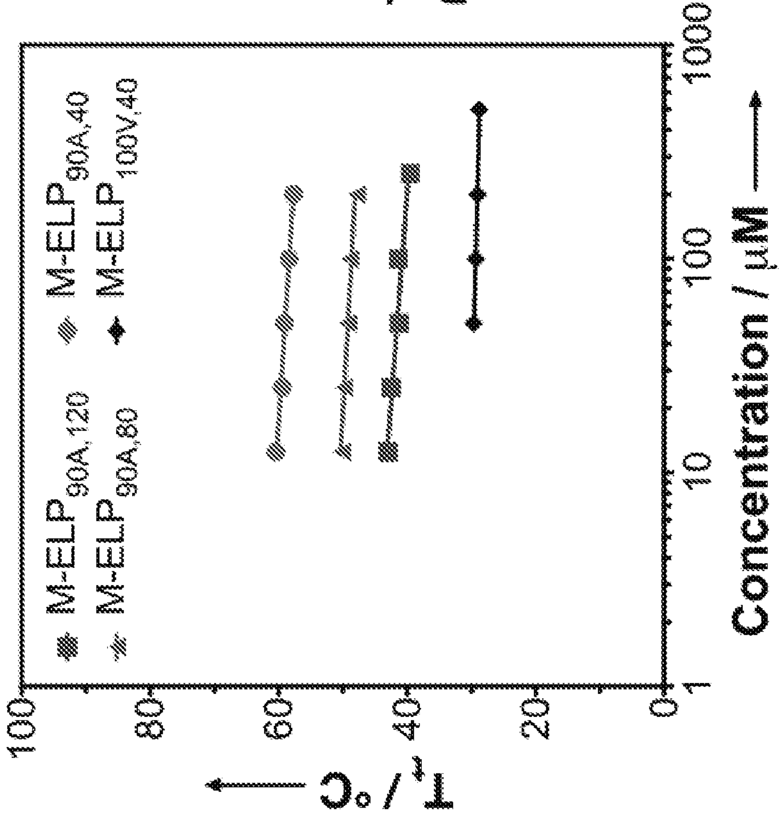
FIG. 3. By varying the length and composition of the ELP, M-ELPs can be synthesized that exhibit phase transition temperatures spanning a 30 degree C. range (A). The ELP affects the size and kinetic stability of the self-assembled particle as seen by the Rh as a function of time (B). Cryo-TEM of self-assembled myristoylated ELPs confirms the different size and shape of nanoparticles inferred from light scattering: spheres with a larger ELP (C) and rods with a shorter ELP (D).
Figure 3B:
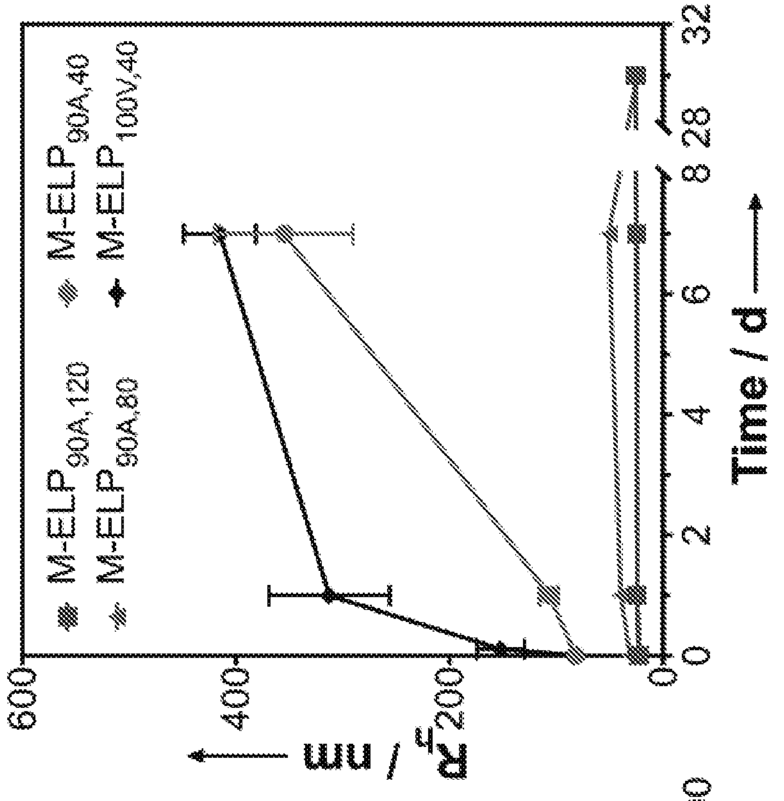

Kinetics Study: Initial DLS results (FIG. 3B) suggest that both M-ELP 40-mers take longer to reach equilibrium of their self-assembled state. Thus, we wanted to take more frequent light scattering measurements to track their changing size. Larger particles scatter more light, thus, we tracked intensity via DLS to monitor the size of the 40-mer M-ELPs' self-assembly.

Figure 17A:
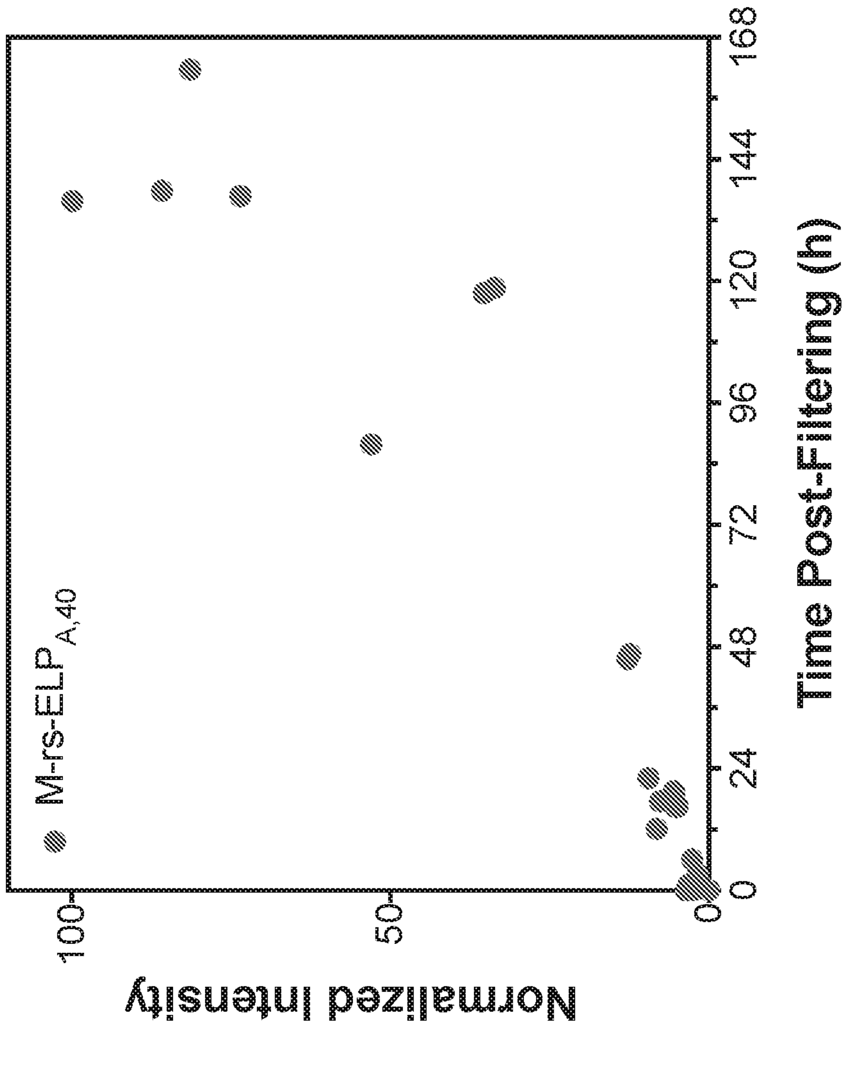
FIG. 17. Normalized change in intensity with time after filtering for myristoylated 40-mer ELPs, which shows less stable self-assembly behavior than the larger M-ELP$_{90A,120}$ and M-ELP$_{90A,80}$ constructs; M-rs-ELP$_{90A,40}$ (A), and M-rs-ELP$_{8,40}$ (B).
Figure 17B:
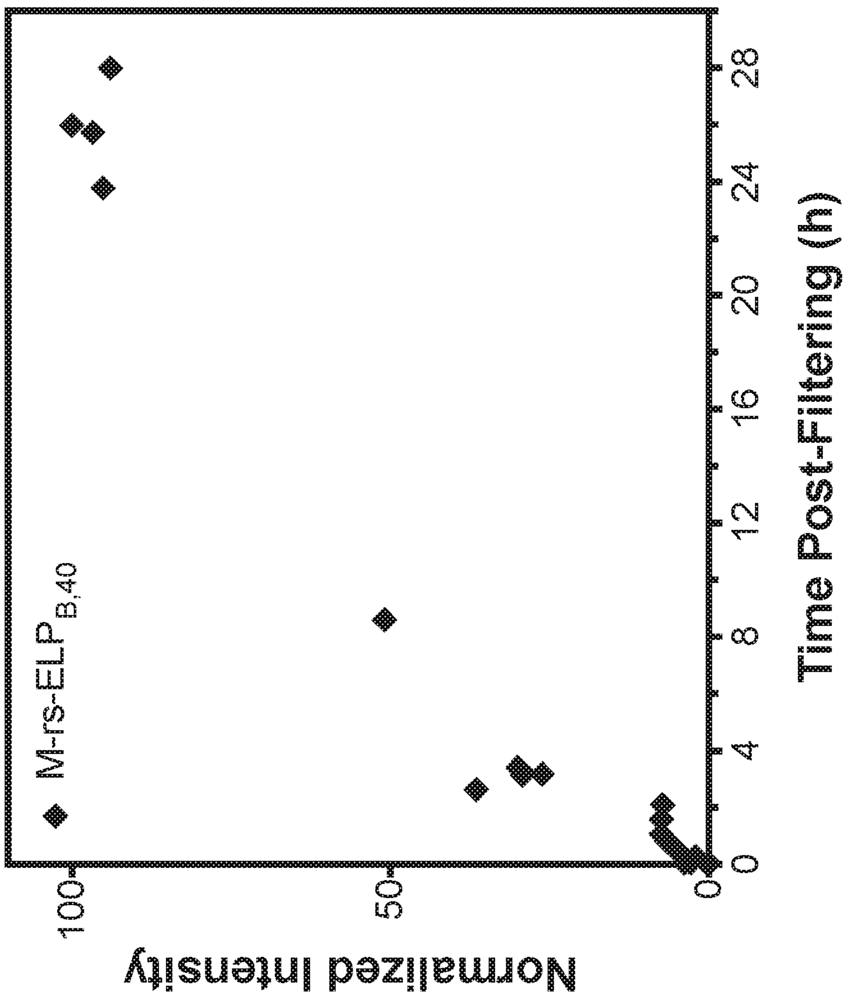

The 40-mer M-ELPs were prepared at 50 μM in PBS and filtered directly into the instrument's quartz cell. The instrument was pre-set to room temperature and, immediately after filtering, the sample was measured periodically over 24 h for both constructs and out to 1 week for M-$ELP_{90A,40}$. While M-$ELP_{90A,40}$ takes 144-168 h to reach equilibrium (FIG. 17A), M-$ELP_{100V,40}$ appears to do so more quickly, by 24 h after filtering (FIG. 17B).

Figure 18A:
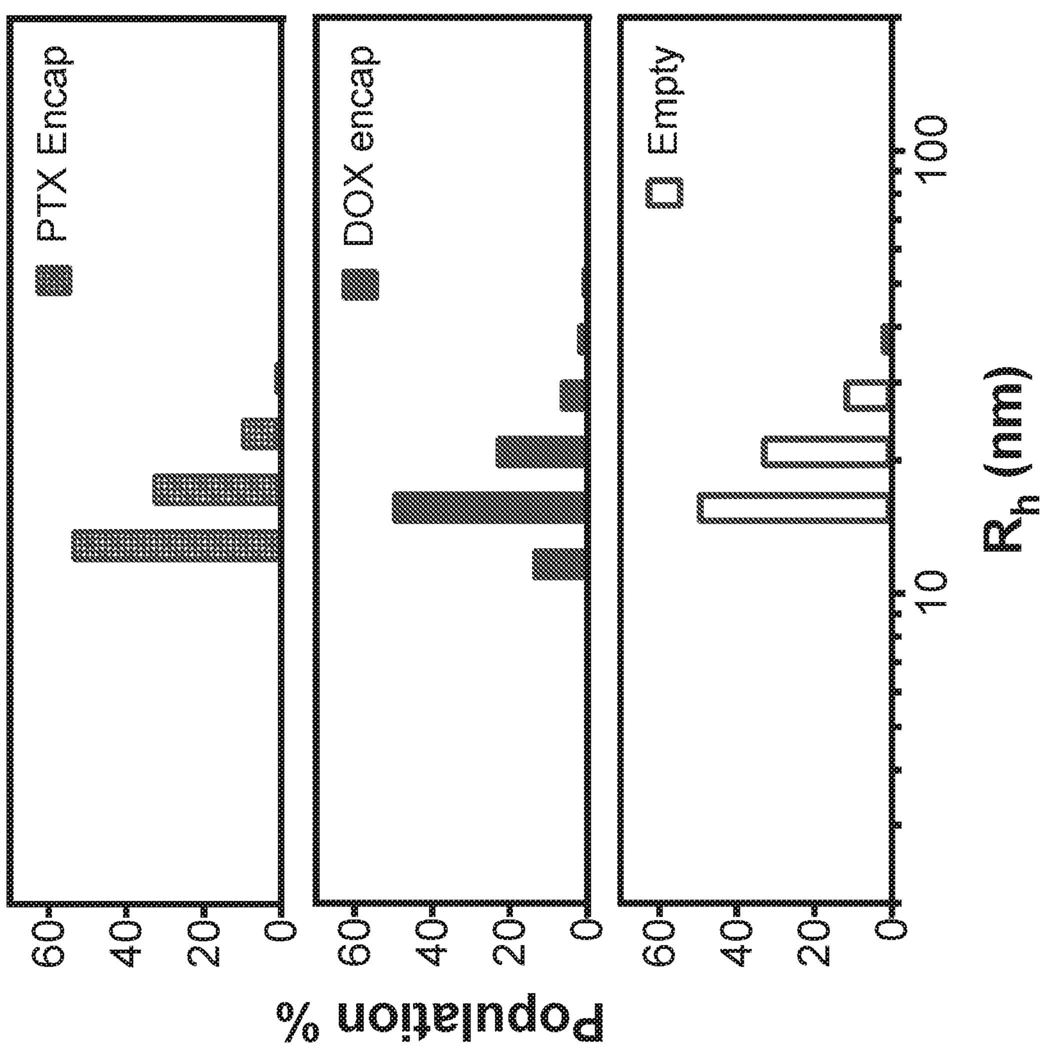
FIG. 18. $R_h$ population histograms generated from autocorrelation functions for M-ELP$_{90A,120}$ (blue, A) and M-ELP$_{90A,80}$ (green, B) both pre- (empty bars) and post-encapsulation with PTX (checkered bars) or DOX (solid bars). These histograms further demonstrate that hydrophobic drug loading has no significant effect on the micelles' size.
Figure 18B:
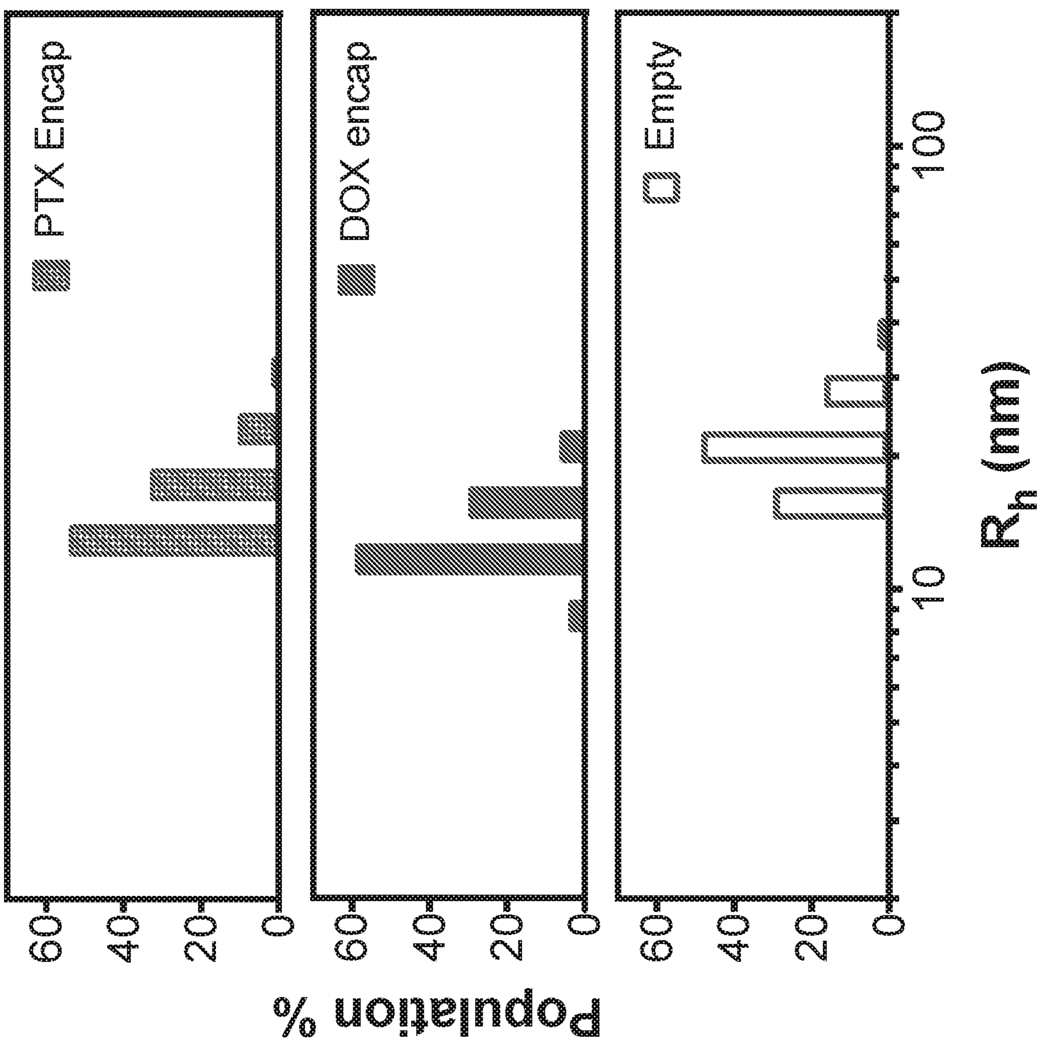

Comparing Particles Pre- and Post-Encapsulation: DLS measurements were performed prior to and after removing free drug from the encapsulated samples. This was done to ensure that the encapsulation process did not significantly alter the morphology of the particles, as shown by the population (FIG. 18) and intensity histogram plots (FIG. 19) generated from the autocorrelation functions.

Pyrene Assay 12 mM pyrene was prepared by dissolving it in ethanol and sonicating in a water bath until fully dissolved. 1.2 μL of this 12 mM pyrene was dissolved in 20 mL of PBS and sonicated again for 10 min. 1 mL of 100 μM M-ELP was prepared in this pyrene solution. 100 μL of the following serial dilutions were made: 100, 50, 25, 10, 5, 3, 1, 0.5, 0.25, 0.1, 0.05, 0.01, and 0.001. The fluorescence of these samples, along with a blank containing only pyrene, were measured using a Cary Elipse spectrophotometer reduced volume cuvette and scanned with the following parameters: 334 nm excitation, 360-380 nm emission).

Pyrene fluorescence has four characteristic peaks. For each concentration, the $I_1/I_3$ ratio was calculated by dividing intensity at 372 nm by that of the 383 nm. These ratios were plotted as a function of ELP concentration on a semi-tlog scale and two equations were fit. The intersection of these lines was calculated to quantify the critical aggregation concentration (CAC) (FIG. 20).

Cryo-TEM Imaging

Cryo-transmission electron microscopy (TEM) experiments were performed at Duke University's Shared Materials Instrumentation Facility and at Thermo Fisher Scientific (Formerly FEI). Lacey holey carbon grids (Ted Pella, Redding, Calif.) were glow discharged in a PELCO Easi-Glow Cleaning System (Ted Pella, Redding, Calif.). After filtering the samples, a 3 μL drop (1 mg/mL of each construct) at 25° C. (below the $T_t$ for M-ELP constructs) was deposited onto the grid, blotted for 3 s with an offset of −3 mm, and vitrified in liquid ethane using the Vitrobot Mark III (FEI, Eindhoven, Netherlands). The sample chamber was maintained at 100% relative humidity to prevent sample evaporation. Grids were transferred to a Gatan 626 cryoholder (Gatan, Pleasanton, Calif.) and imaged with an FEI Tecnai $G^2$ Twin TEM (FEI, Eindhoven, Netherlands), which was operated at 80 keV.

Drug Encapsulation

Processing and removing free drug: Lyophilized samples were prepared to a concentration of 50 μM in PBS and forced through a 0.22 μm filter into a glass vial. Doxorubicin (DOX) was made to 1 mg/mL in $H_2O$ and added drop-wise to each vial, under magnetic stirring at room temperature, to 10-fold molar excess. PTX was weighed and added directly to the vials to either 2- or 10-fold molar excess. We found that 2- and 10-fold excess of paclitaxel (PTX) encapsulated to similar efficiencies, as assessed with SEC-HPLC.

Figure 22:
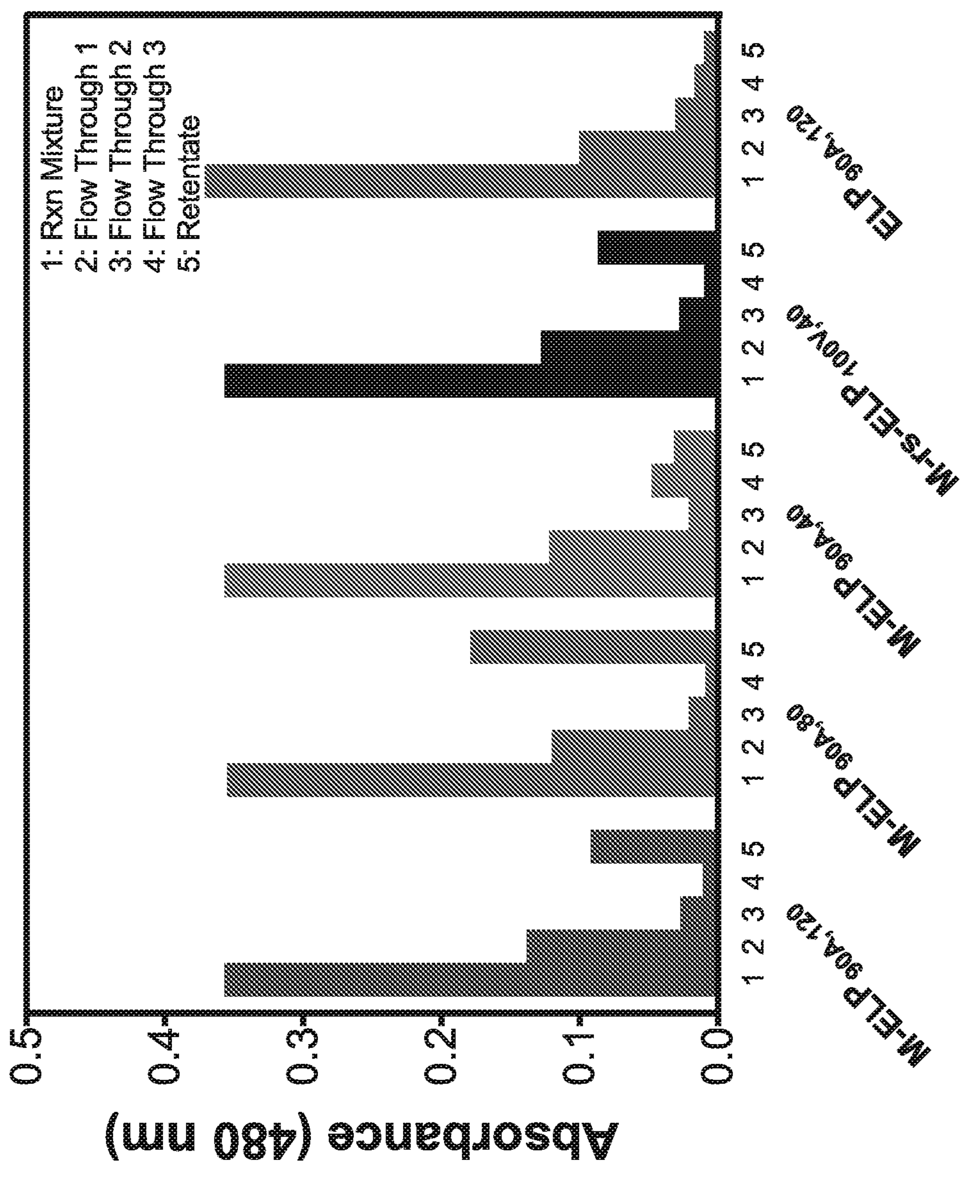
FIG. 22. Purification of free DOX from encapsulated DOX was performed using successive rounds of centrifugation through ultrafiltration centrifugal units with a 10 kDa cutoff while monitoring DOX's 480 nm absorbance. Successive flow through samples (bars 2-4), show a decline in DOX and the retentates show an accumulation of concentrated DOX for M-ELPs (bars labeled 5), but none in the non-myristoylated control (ELP$_{90A,120}$) (grey bar 5).
Figure 23:
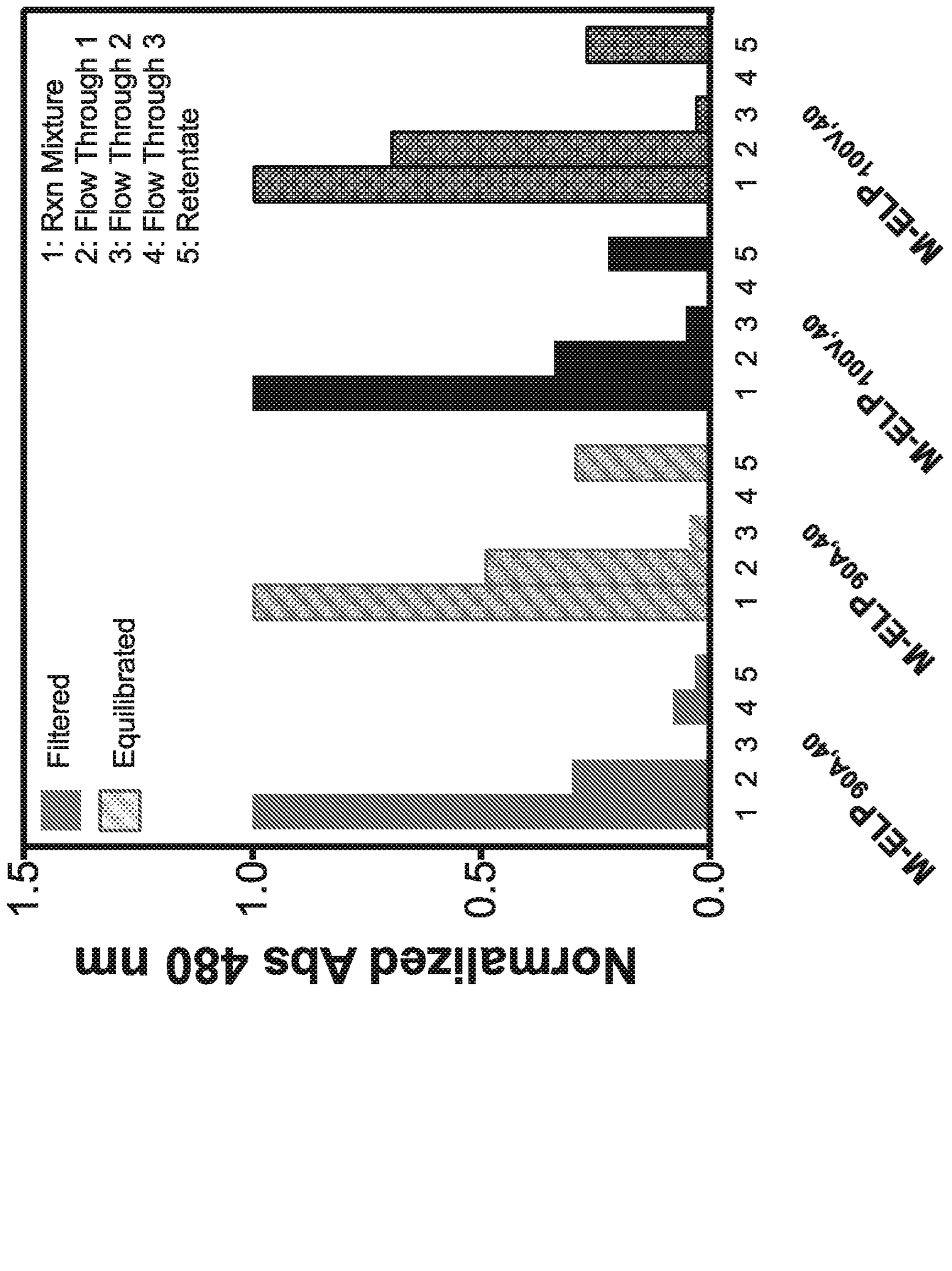
FIG. 23. Purification of free DOX from encapsulated DOX was performed on M-ELP 40-mers that were freshly filtered (solid bars) or equilibrated to their final shape for several weeks (checkered bars). The amount of DOX remaining in the retentate (bars labeled 5) is greater in the equilibrated samples than the freshly filtered ones. This difference is more pronounced in the M-ELP$_{90A,40}$ sample (red bars).
Figure 24:
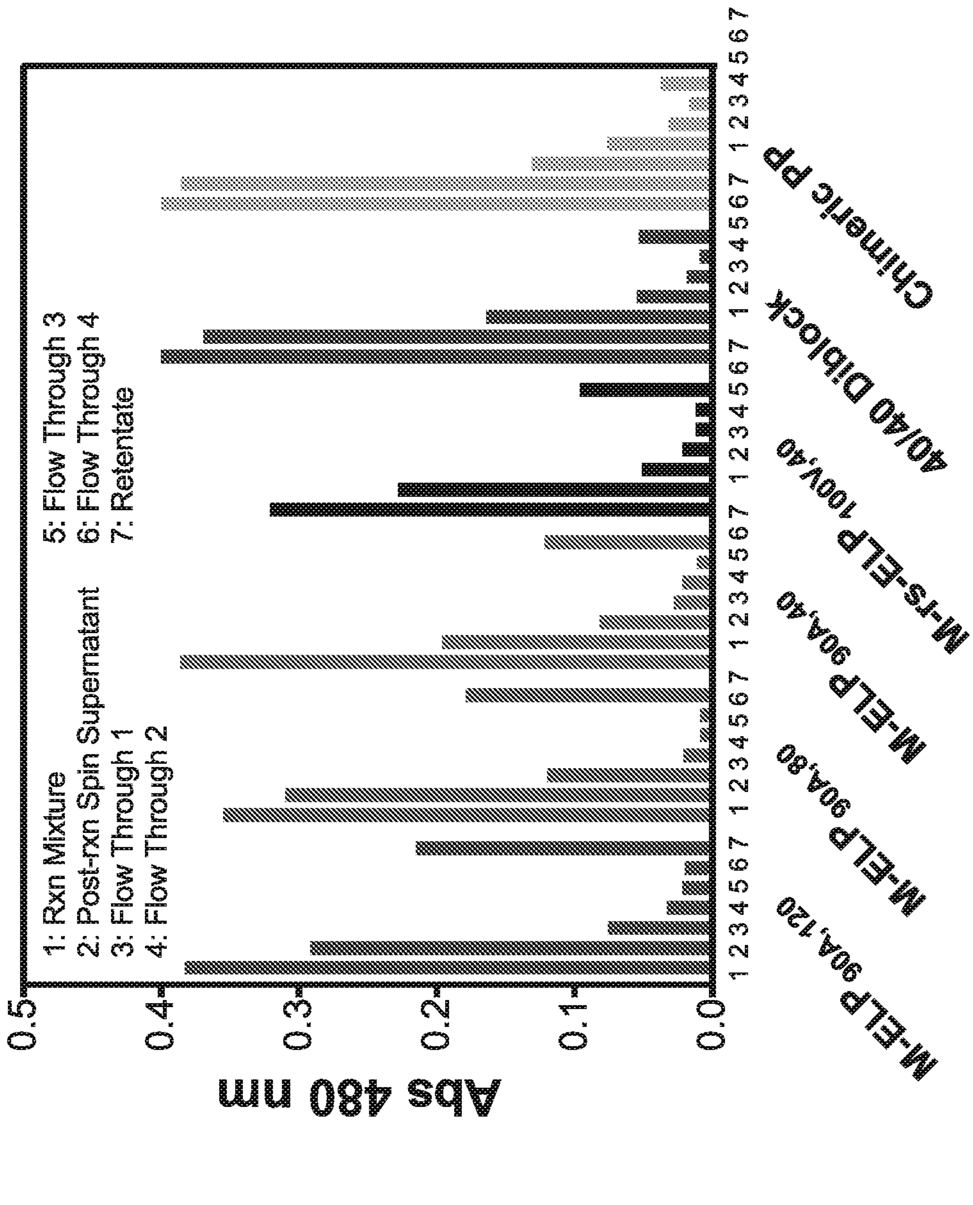
FIG. 24. Comparison showing the purification of free DOX from encapsulated DOX with M-ELPs versus other ELP-based nanoparticles (diblocks and chimeric PPs). The amount of DOX remaining in the retentate (bars labeled 7) is greater in the M-ELPs than either the diblock or chimeric PP sample.

The vials were left stirring at room temperature, protected from light, for 16 h. For removal of free DOX, which is poorly soluble in PBS, the samples were centrifuged at 13,200 rpm for 10 min. The supernatants were then applied to Amicon Ultra-15 centrifugal filter units with a 10 kDa cutoff. These were centrifuged for 30 minutes at 4,000×g in a centrifuge with swinging buckets. The flow through was removed and the retentate was re-diluted with PBS, making sure not to dilute to concentrations lower than 10 μM ELP (well above CAC values, FIG. 20) to ensure the nanoparticles remained assembled. This process was repeated until the 480 nm absorbance of the flow through, corresponding to DOX, was below 0.02 and remained unchanged between two successive runs (FIG. 22-FIG. 24).

Because their self-assembly takes longer to reach equilibrium, we also tested the loading of M-ELP 40-mer samples under two conditions: (1) encapsulating DOX immediately after filtering and (2) encapsulating DOX into 40-mers that had been left at room temperature to equilibrate for several weeks. The samples that had been left to equilibrate had superior loading to those that were freshly filtered, as evidenced by a higher concentration of DOX in the retentate (FIG. 23, bars labeled 5). This was especially apparent for M-$ELP_{90A,40}$, which required a greater length of time to reach a stable, self-assembled state. This difference was less pronounced for M-$ELP_{100V,40}$, which reaches its larger self-assembled state by 24 h (FIG. 17).

Figure 25A:
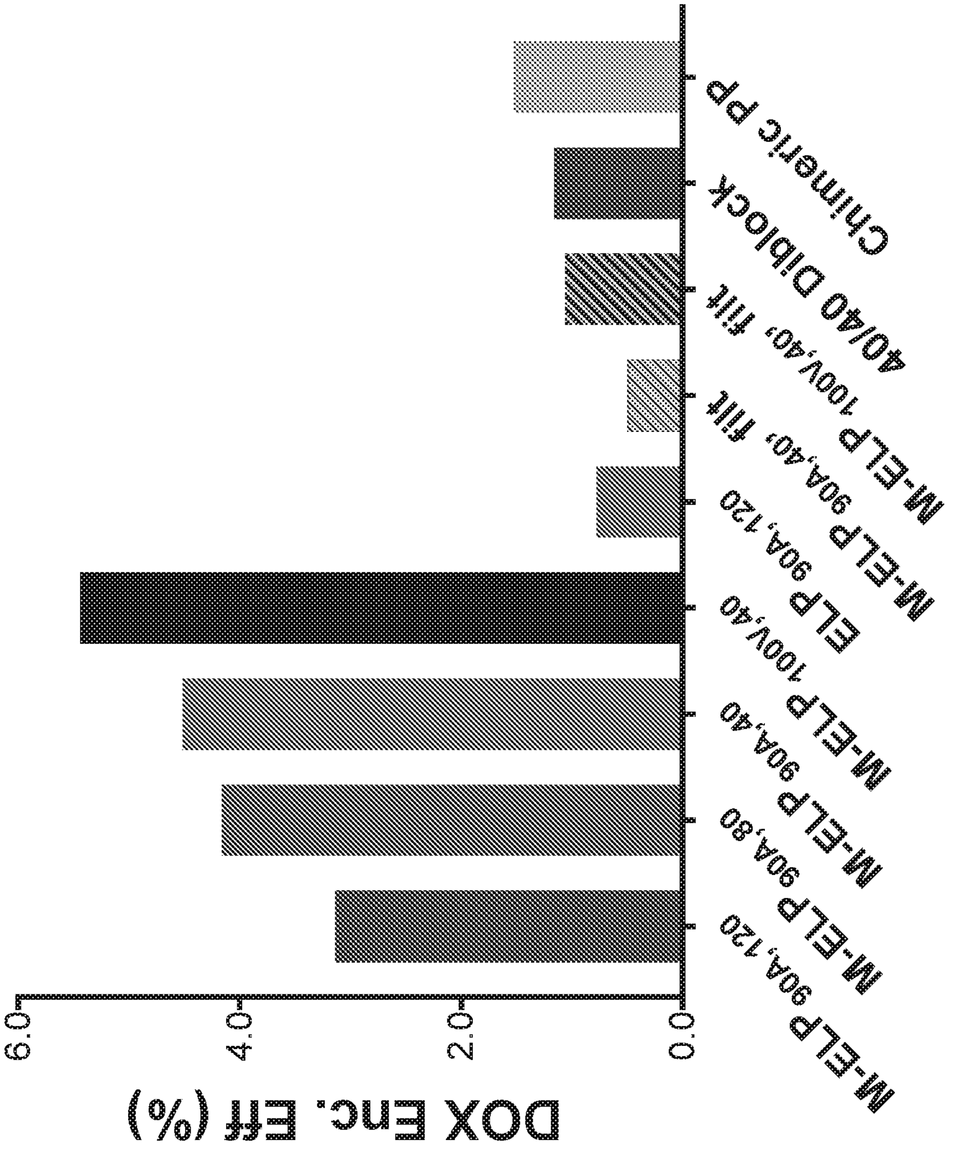
FIG. 25. Calculation of the encapsulation efficiency shows that M-ELPs are able to more efficiently trap DOX (A) and achieve a higher w % loading capacity (B) than other ELP-based nanoparticle systems (40/40 Diblock and Chimeric PP). Like the non-myristoylated control (grey bars) and the unequilibrated, freshly filtered 40-mer samples (patterned bars), encapsulation of DOX in these two other systems was significantly lower than M-ELPs.
Figure 25B:
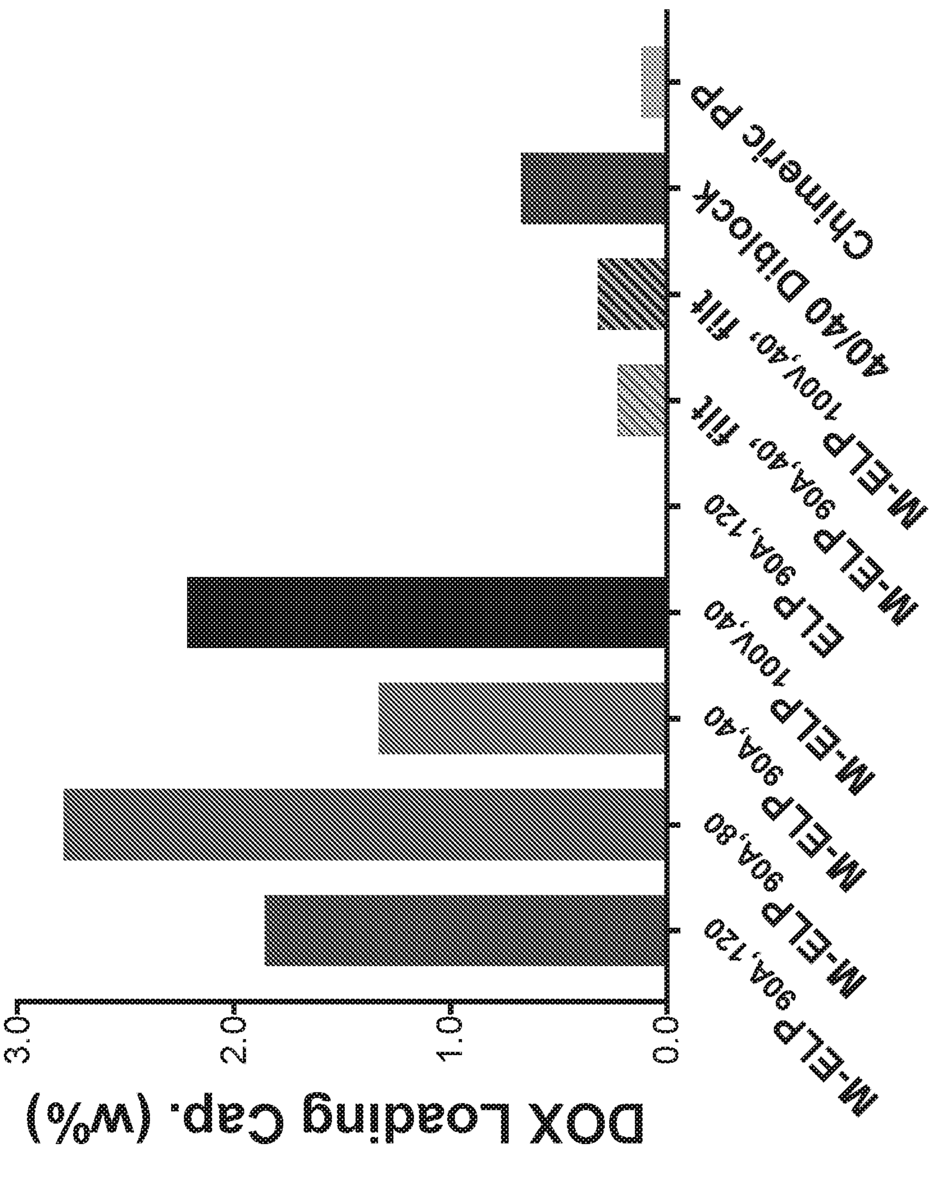

Our laboratory has previously reported on a number of self-assembling systems such as diblock ELPs and chimeric polypeptides (S. R. MacEwan, et al. *Biomacromolecules* 2017, 18, 599-609; J. R. McDaniel, et al. Nano. Let. 2014, 14, 6590-6598; W. Hassouneh, et al. *Macromolecules* 2015, 48, 4183-4195; W. Hassouneh, et al. *Biomacromolecules* 2012, 13, 1598-1605; E. Garanger, et al. *Macromolecules* 2015, 48, 6617-6627). We selected one prototypical example of each of these systems and processed them for DOX encapsulation as described above. 40/40 Diblock refers to a construct comprised of a 40-mer hydrophobic ELP block with 20% Trp and 80% Val in the guest residue position fused to a VPGSG 40-mer hydrophilic block. This diblock forms stable, spherical nanoparticles ($R_h$~30 nm) at room temperature (above 22° C.). We also tested a different system, more similar to the M-ELPs, an asymmetric chimeric polypeptide (labeled "chimeric PP"), which is comprised of 160 VPGAG repeats followed by a $(FG)_8$ trailer. This construct forms cylindrical micelles ($R_h$~30 nm). Neither of these systems were able to encapsulate DOX as effectively as the M-ELPs: they had 2-5 fold lower encapsulation efficiencies (FIG. 25A) and far lower drug loading capacity (FIG. 25B).

Figure 26:
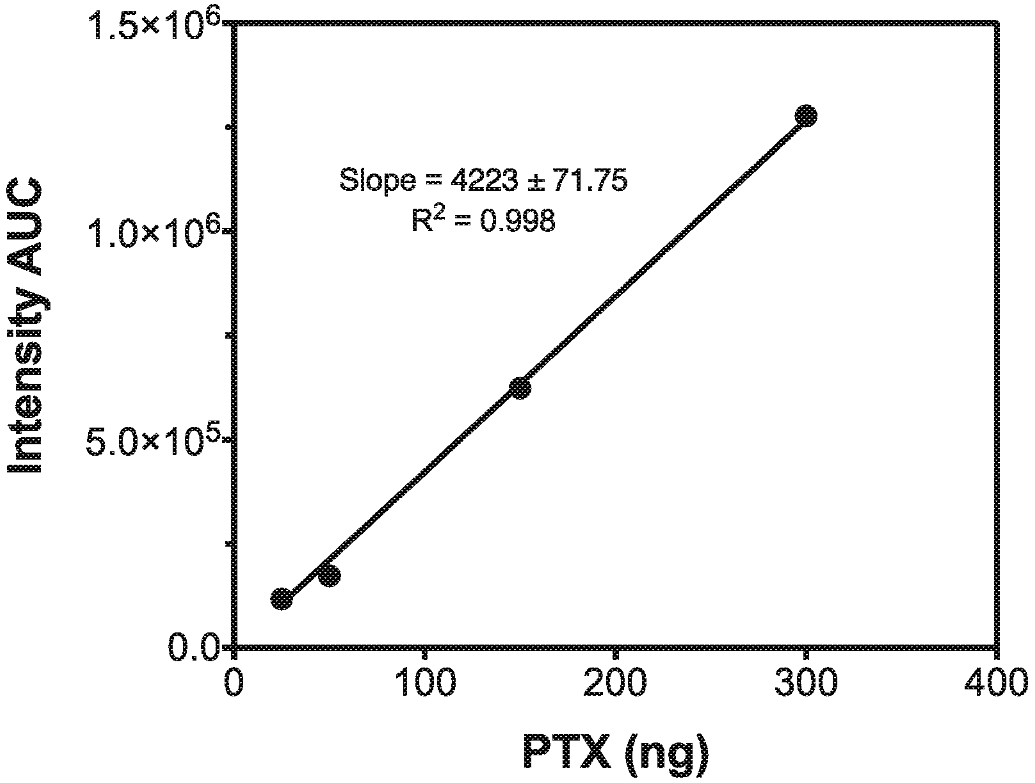
FIG. 26. Standard curve generated from the AUC of the free PTX peak on SEC. This curve was used to quantify the amount of encapsulated PTX in M-ELP samples.
Figure 27A:
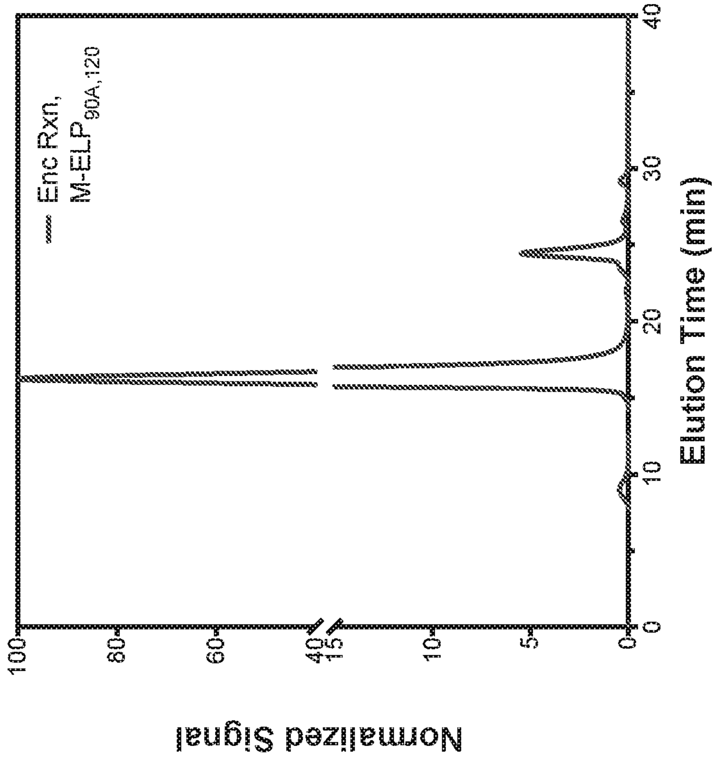
FIG. 27. SEC of encapsulation reactions and controls. After overnight PTX loading and centrifugation, M-ELP$_{90A,120}$ (A) and M-ELP$_{90A,80}$ (B) both show a peak at 24.5 min, corresponding to PTX (D), while non-myristoylated control (C) has no peak at 24.5 min.
Figure 27B:
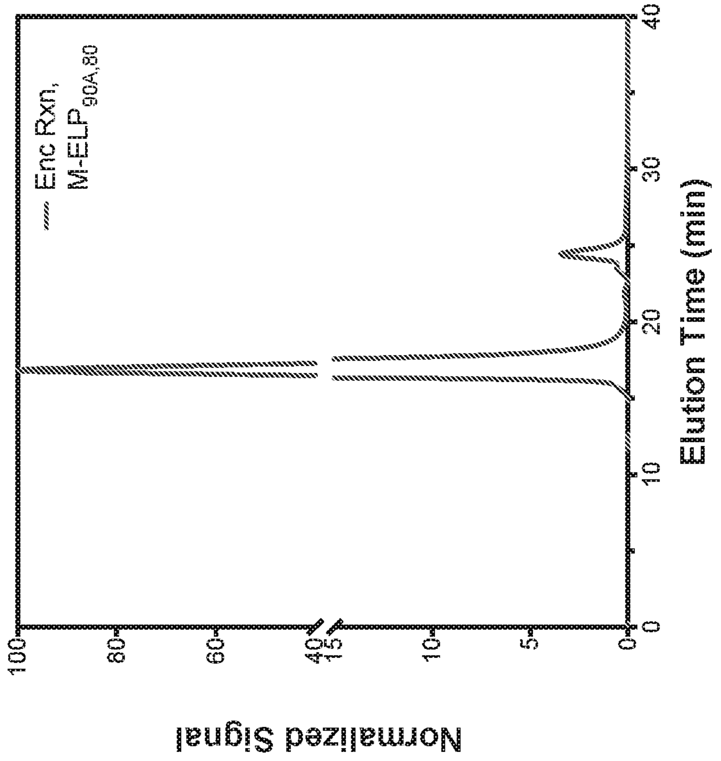
Figure 27D:
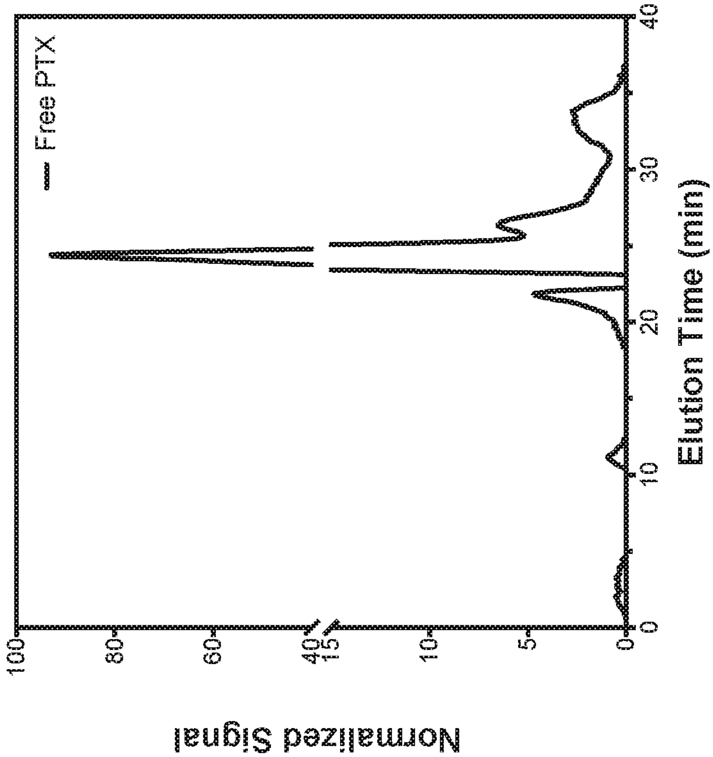
Figure 27C:
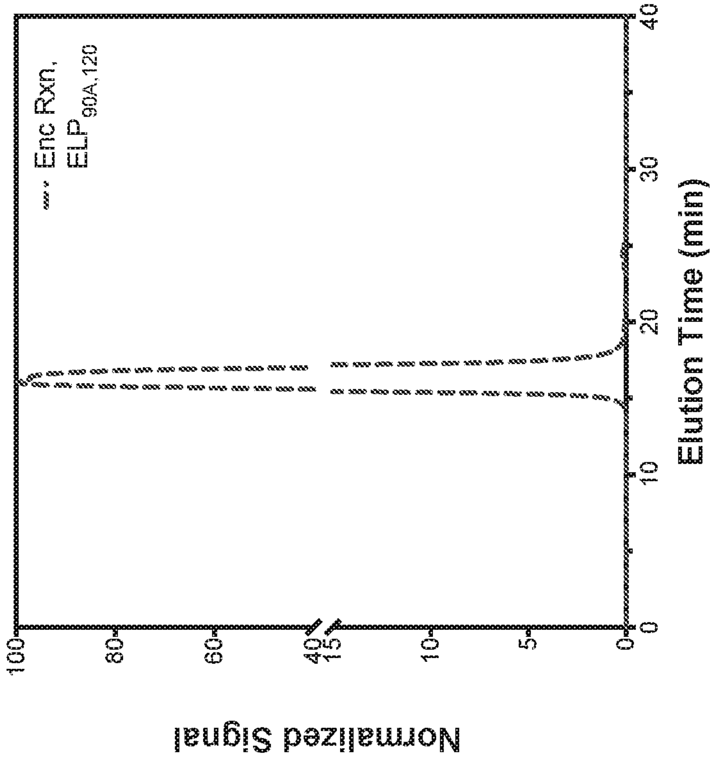

PTX encapsulated samples were spun at 13,200 rpm for 10 minutes. PTX is insoluble in PBS, thus, any unencapsulated drug will pellet upon centrifugation. After centrifugation, the supernatant (containing loaded drug) was removed and this step was repeated two more times. Because PTX lacks UV-vis signature or fluorescence, a standard curve was made using free PTX run on SEC with a mobile phase comprised of 30% $CH_3CN$ in PBS (FIG. 26). The loaded M-$ELP_{90A,120}$ and M-$ELP_{90A,80}$ micelles as well as $ELP_{90A,120}$ control were also run under the same conditions (FIG. 27). The micelles are disrupted in 30% $CH_3CN$ (see above), which enabled us to isolate and quantify the amount of loaded PTX for to in vitro cytotoxicity assays.

Calculation of Efficiency, Loading, and Drugs Per Particle:

Encapsulation Efficiency:

$$\frac{[\text{Drug Added}] - [\text{Unecapsulated Drug}]}{[\text{Drug Added}]} \times 100 =$$

$$\frac{[\text{Entrapped Drug}]}{[\text{Drug Added}]} \times 100 = \text{Efficiency}_{Encapsulation}(\%)$$

Example $$\frac{461\ \mu M \times 0.0002\ L}{1.72\ \mu\text{mol}} \times 100 = 5.3\%\ DOX \text{ encapsulation efficiency}$$

Loading Capacity:

$$\frac{\text{Mass of Entrapped Drug}}{\text{Mass of Carrier}} \times 100 = \text{Loading Capacity}(\%)$$

Example $$\frac{436\ \mu M\ DOX \times 580\ \mu g/\mu\text{mol}}{374\ \mu M(M - ELP) \times 32{,}219\ \mu g/\mu\text{mol}} \times 100 =$$

$$2.1\%\ DOX \text{ loading capacity in } M\text{-}ELP_{90A,80}$$

Drugs Per Particle:

$$\frac{[\text{Entrapped Drug}]}{[\text{Carrier}] \div N_{agg}} = \text{Drug molecules per particle}$$

Example $$\frac{431\ \mu M\ DOX}{374\ \mu M(M - ELP_{90A,80}) \div 48} = 55\ DOX \text{ per } M - ELP_{90A,80} \text{ particle}$$

In Vitro Cytotoxicity Assay

4T1 cells were cultured in high glucose DMEM (Sigma D6429) with 10% fetal bovine serum (FBS) in T-75 $cm^2$ flasks incubated at 37° C., 5% $CO_2$, and 95% relative humidity. Cells were passaged once they reached approximately 70% confluence at a 1:15 split ratio. For the cytotoxicity assay, cells were plated in 96-well tissue-culture treated Corning Costar plates at 10,000 cells per well in 100 μL. Cells were incubated for 24 h prior to performing the cytotoxicity assay.

Figure 28A:
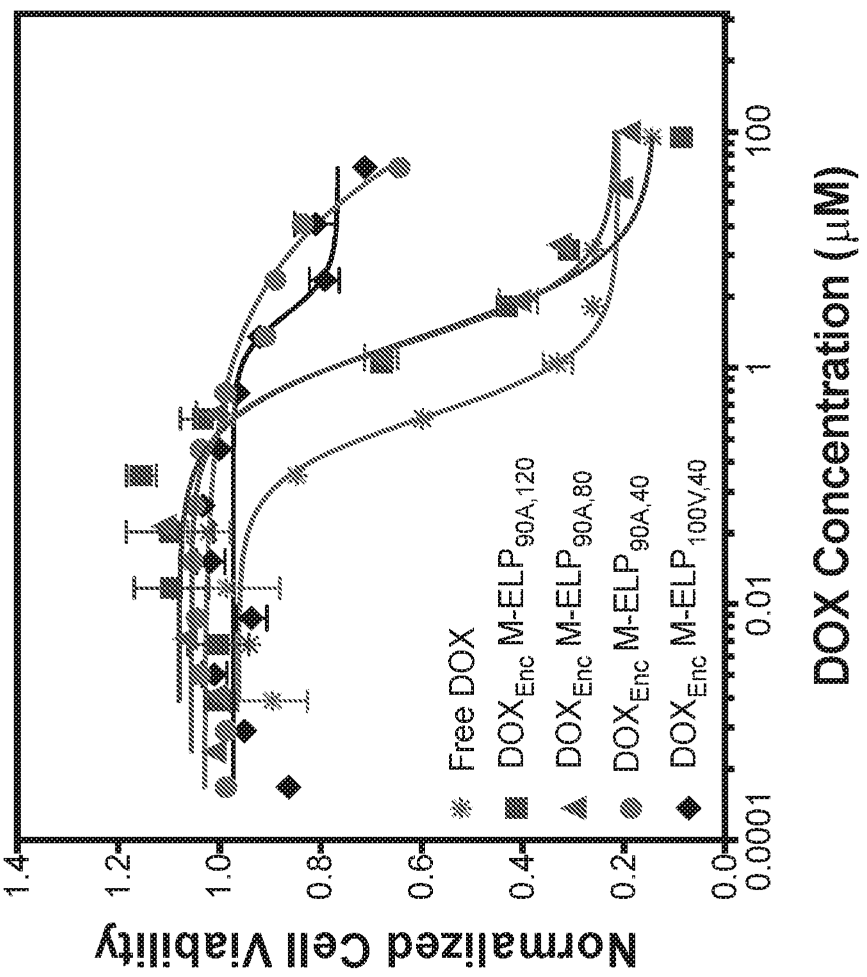
FIG. 28. DOX encapsulated in all four constructs show cytotoxicity towards 4T1 cells (A), although the spherical micelles (M-ELP$_{90A,120}$ and M-ELP$_{90A,80}$) are significantly more cytotoxic than the rod-shaped, micelles comprised of M-ELP 40-mers. None of the empty carriers were significantly cytotoxic (B).
Figure 28B:
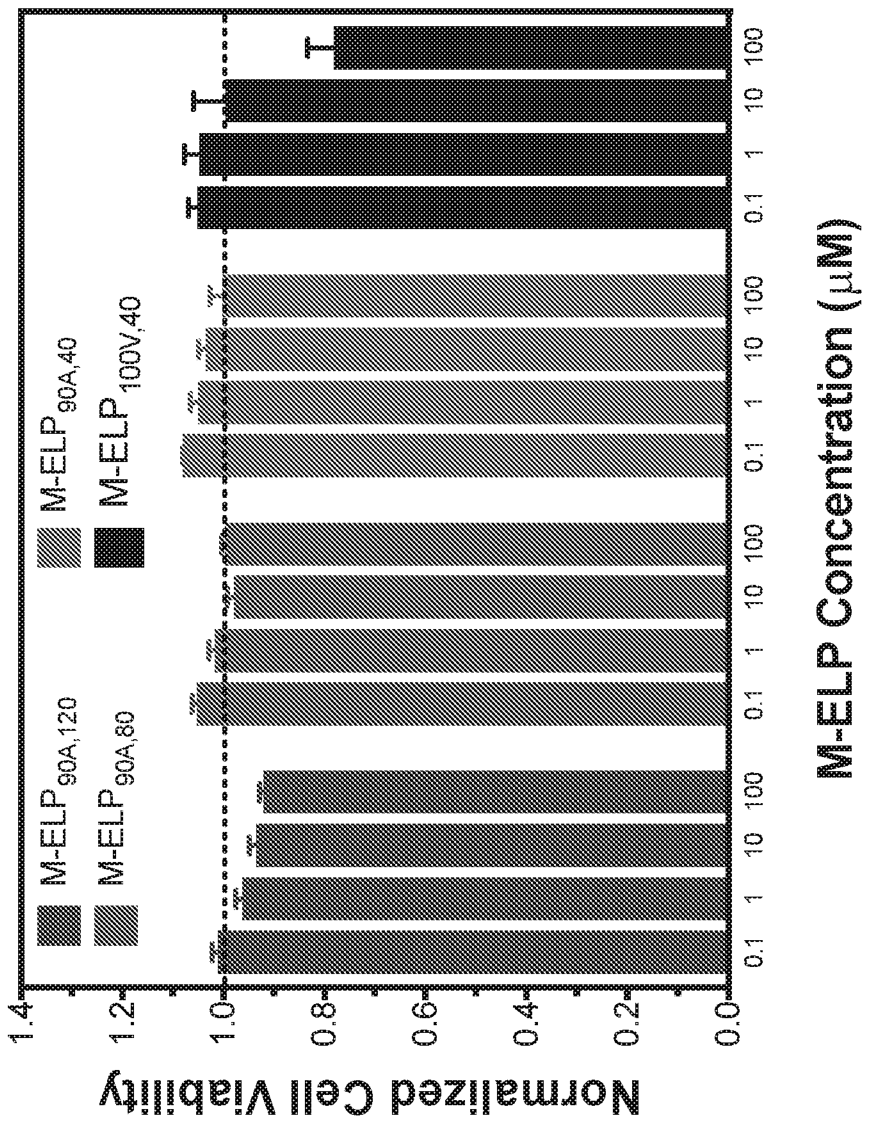

Encapsulated DOX was first concentrated using Amicon centrifugal filter units to at least 300 μM. This concentrated solution was used to prepare a stock solution of encapsulated DOX at 100 μM DOX concentration in cell culture media. The free DOX as well as DOX encapsulated in M-ELP$_{90A,120}$ and M-ELP$_{90A,80}$ were sterile filtered through 0.2 μm sodium acetate filters. The 40-mer M-ELP DOX encapsulations were not filtered, so as not to perturb their larger self-assembled structures. Eleven successive serial dilutions were made 1:3 in media. After the 24 h culture, media was removed from all wells using a multi-channel pipettor. 100 μL of the serial dilutions was added to the cells as well as 100 μL of media only. Each concentration was tested in triplicate. In addition, 100 μL of each drug dilution was added to an empty well (with no cells) as a control, to account for the absorbance of the drug. This same procedure was also done for empty M-ELPs, with no encapsulated drug. The treated 4T1 cells were incubated with the drug for 24 h. DOX encapsulated in spherical micelle carriers was much more cytotoxic than DOX encapsulated in the rod-shaped carriers (FIG. 28A). Empty M-ELP carriers were also tested; they demonstrated no significant cytotoxicity (FIG. 28B).

The cytotoxicity assay was performed with the CellTiter 96 Aqueous One cell proliferation assay, according to the manufacturer's instructions. Briefly, the reagent was mixed 1:1 with media and 40 μL of this solution was added to each well, including the cell-free drug only wells. The plates were returned to the 37° C. incubator for 4 h, after which the absorbance was read at 490 and 650 nm using a Wallac Victor3 plate reader. The 650 nm absorbance was subtracted from each 490 nm reading as was the drug-only absorbance for each corresponding concentration in cell-free wells. These values were plotted against the logarithm of drug concentration and a four-parameter logisitic curve was fit using GraphPad Prism 6.0, from which the $IC_{50}$ value was calculated.

Encapsulated PTX was concentrated using Amicon centrifugal filter units to at least 100 μM. Because of our finding that DOX encapsulated in rod-shaped micelles was less cytotoxic than that in spherical micelles, studies with PTX were only carried out with the M-ELP$_{90A,120}$ and M-ELP$_{90A,40}$ samples. Encapsulated and free PTX were made to 10 μM in media and sterile filtered through a 0.2 μm sodium acetate filter. Eleven successive serial dilutions were made 1:3 in media.

Figure 29:
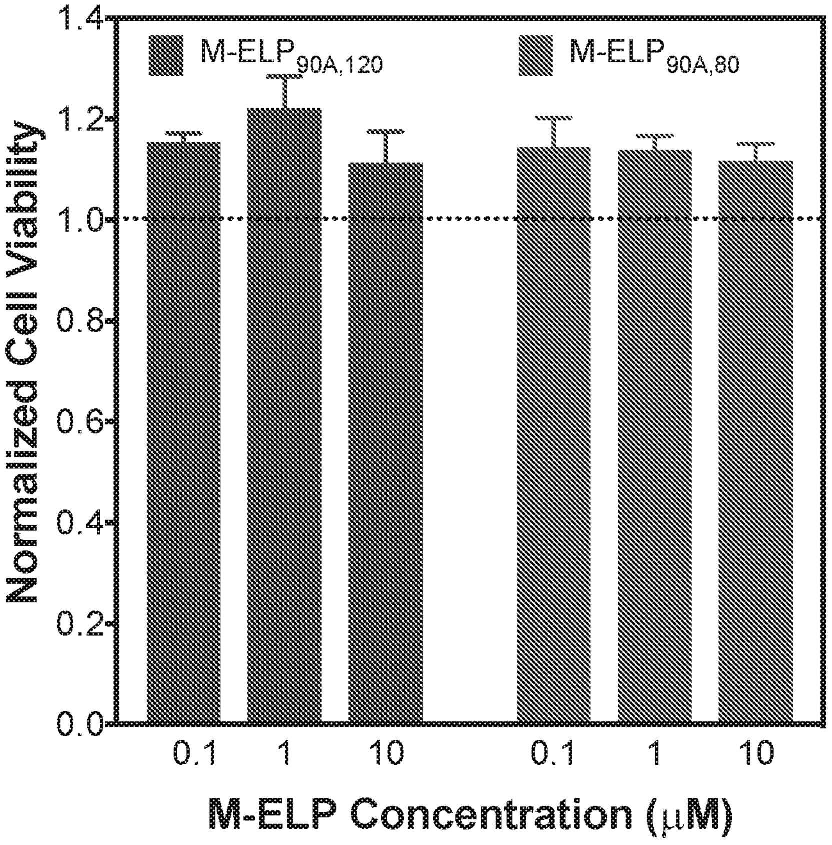
FIG. 29. Empty M-ELPs show no toxicity towards PC3-luc cells compared to PBS treated controls, whose cell viability is indicated by the dashed line.
Figure 30A:
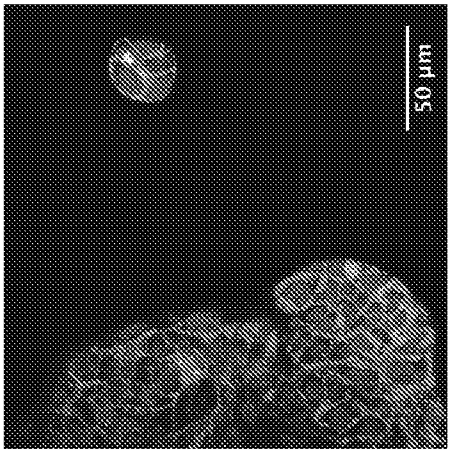
FIG. 30. 4T1 cells treated with free DOX (top row) or encapsulated DOX (bottom) and imaged after 30 min (A,F), 1 h (B,G), 3 h (C,H), 6 h (D,I), or 12 h (E,K). Nuclei are shown in blue, cell membranes in red, and DOX in green. The arrows show punctate fluorescence—evidence the encapsulated DOX, but not free DOX, is being taken up through the endosomal/lysosomal pathway.
Figure 30B:
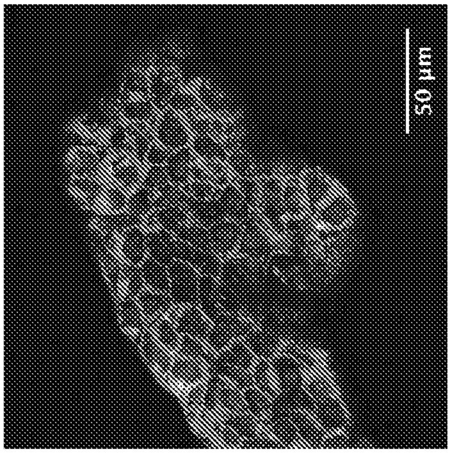
Figure 30C:
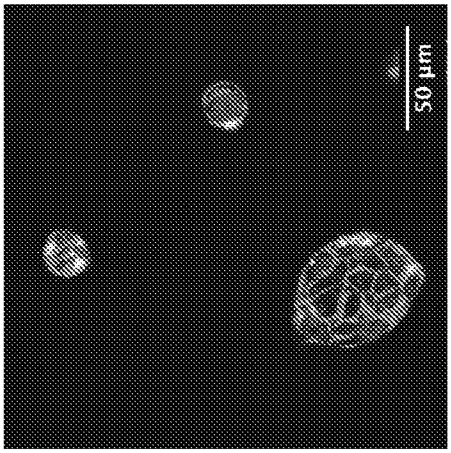
Figure 30E:
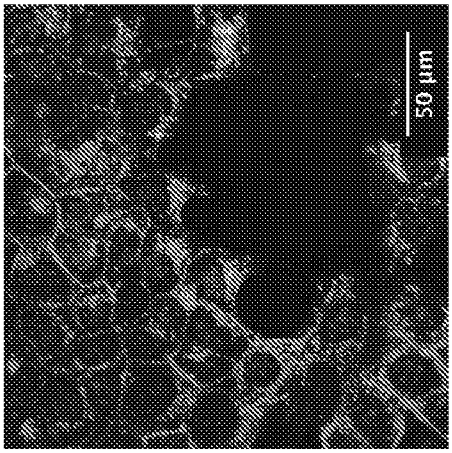
Figure 30D:
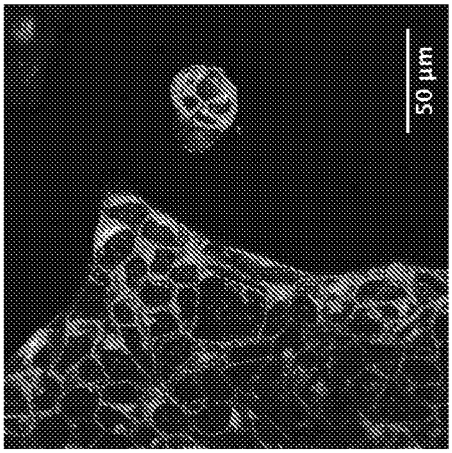
Figure 30H:
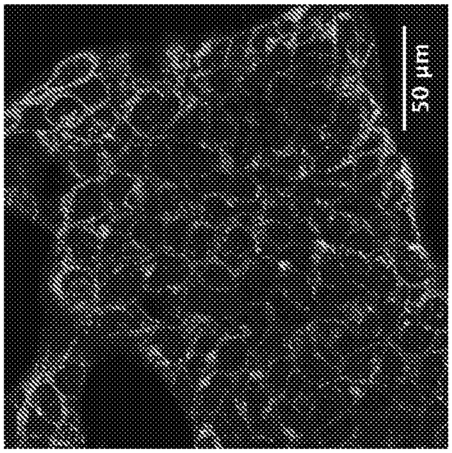
Figure 30G:
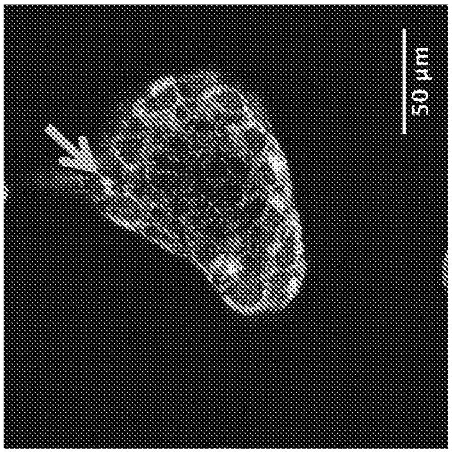
Figure 30F:
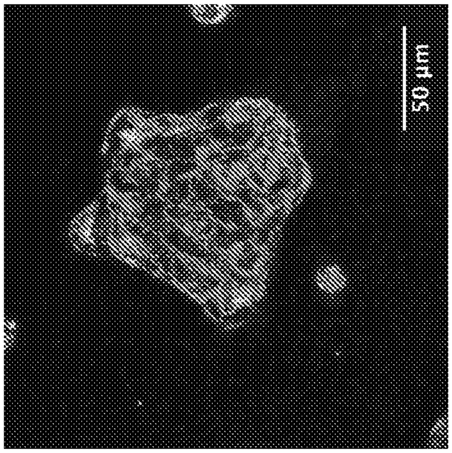
Figure 30I:
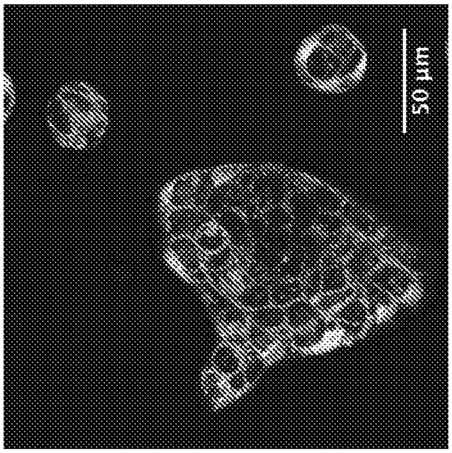
Figure 30J:
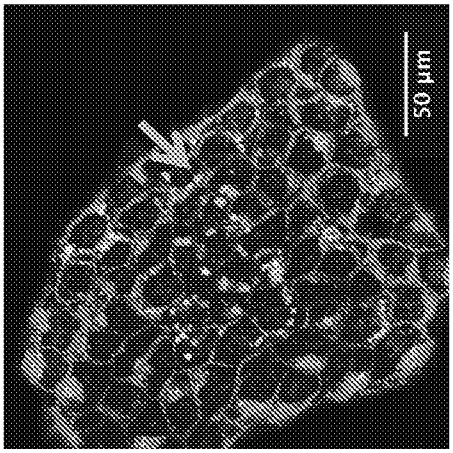

PC3-luc cells were cultured in F-12K media supplemented with 10% FBS in 75 $cm^2$ flasks. Cells were passaged once they reached confluence by splitting at a 1:5 ratio with fresh media. Cells were passaged at least once prior to conducting the cytotoxicity assay. For the assay, cells were plated in 96-well tissue-culture treated plates at 1500 cells per well in 100 μL of media and incubated for 24 h. After 24 h the media was removed and replaced with 100 μL of media containing PTX. The drug dilutions were performed in triplicate and one of each dilution was also added to cell-free wells as a control for the drug's absorbance. This same procedure was done for empty M-ELP$_{90A,120}$ and M-ELP$_{90A,80}$, with no encapsulated drug (FIG. 29). The plates were incubated with the drug for 72 h. The cytotoxicity assay and data analysis were performed in the same manner as described for the 4T1 cells.

In Vitro Drug Release Studies

Confocal imaging: 200 μL of 4T1 cells at 200,000 cells/mL were seeded onto 8-well Lab-Tek II chamber slides (Nunc®) at 24 h and 48 h prior to imaging. At pre-selected time points (12 h, 6 h, 3 h, 1 h, and 30 min) cells were treated with either free DOX or DOX encapsulated in M-ELP$_{90A,80}$ particles at the $IC_{75}$ concentration (as calculated from the cytotoxicity study detailed above). The study was designed so that all the time points' incubations would finish at the same time. At this point the cells were washed twice with 300 μL Hanks Balanced Salt Solution (HBSS) and then incubated for 10 min at 37° C. in HBSS with 5 μg/mL Alexa-594 labeled wheat germ agglutinin and 2 μM Hoechst 33342. This labeling solution was then removed, cells were washed with 300 μL HBSS twice more, and the cells were maintained in 300 μL fresh HBSS through the duration of the imaging process.

Each chamber (containing a different time point for either free or encapsulated DOX), was imaged on a Zeiss 710 inverted confocal microscope with heated stage. Preset laser and filter conditions were selected for the dyes (DOX, Hoechst 33342, and Alexa-594). Images were taken using the 40×1.30 Oil EC Plan Neofluar DIC or the 100×/1.4 oil Plan-Apochromat DIC objectives. Images were processed with ImageJ software.

Encapsulated drug stability: To measure the encapsulated drug's stability, we selected the encapsulated DOX M-ELP$_{90A,80}$ sample as a model system. We tested the stability of encapsulated DOX because our lab has extensive experience working with the drug and because its fluorescence makes it easier to detect and quantify. Free DOX and encapsulated DOX were both made to 400 μM and 250 μL was added with a syringe to small volume Slide-a-Lyzer dialysis cassettes with a 3,500 Da molecular weight cutoff. With this cutoff, any leeched drug should be able to pass through the membrane, while all encapsulated DOX, entrapped in the much larger nanoparticles, should remain in the retentate.

Figure 31:
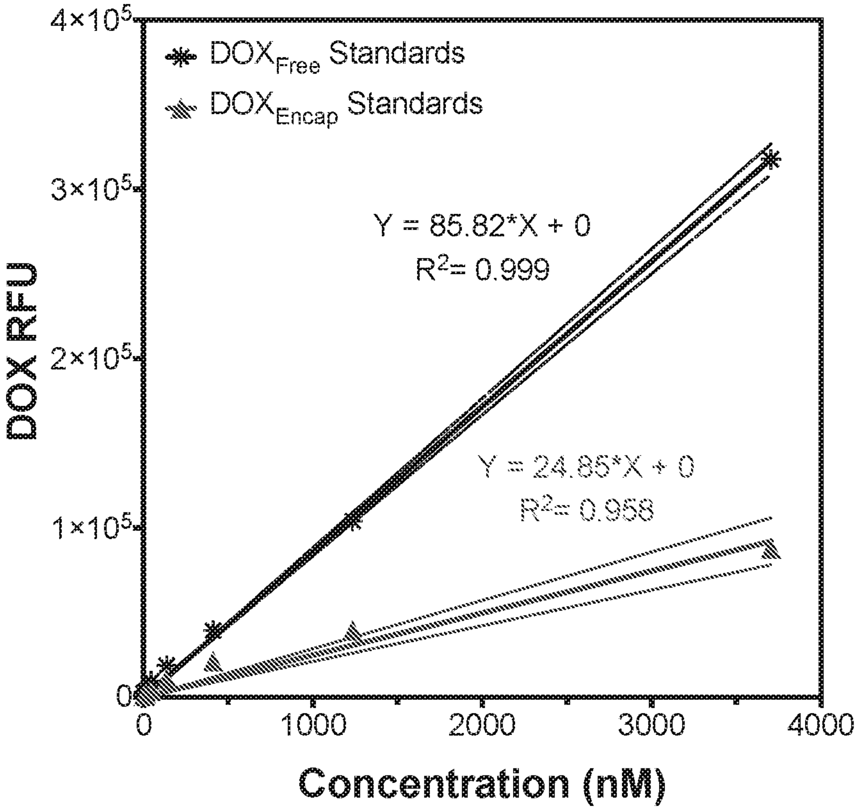
FIG. 31. Standard curves relating DOX$_{Free}$ and DOX$_{Enc}$ fluorescence to concentration shows the significant quenching that occurs when DOX is trapped within the hydrophobic cores of the lipidated ELP micelles.

The dialysis cassettes were placed into light protected Petri dishes containing 20 mL of PBS and incubated at 37° C. At various time points, 3 mL of the filtrate was removed and replaced with fresh PBS. The fluorescence of the starting sample, filtrate, and retentate were measured in duplicate with a Wallac 1420 Victor3 Plate Reader (Perkin Elmer). Relative fluorescing units were converted to DOX concentrations using a standard curve made using serial dilution of free and encapsulated DOX. These standard curves clearly demonstrate the quenching of DOX in the encapsulated samples (FIG. 31).

Figure 35:
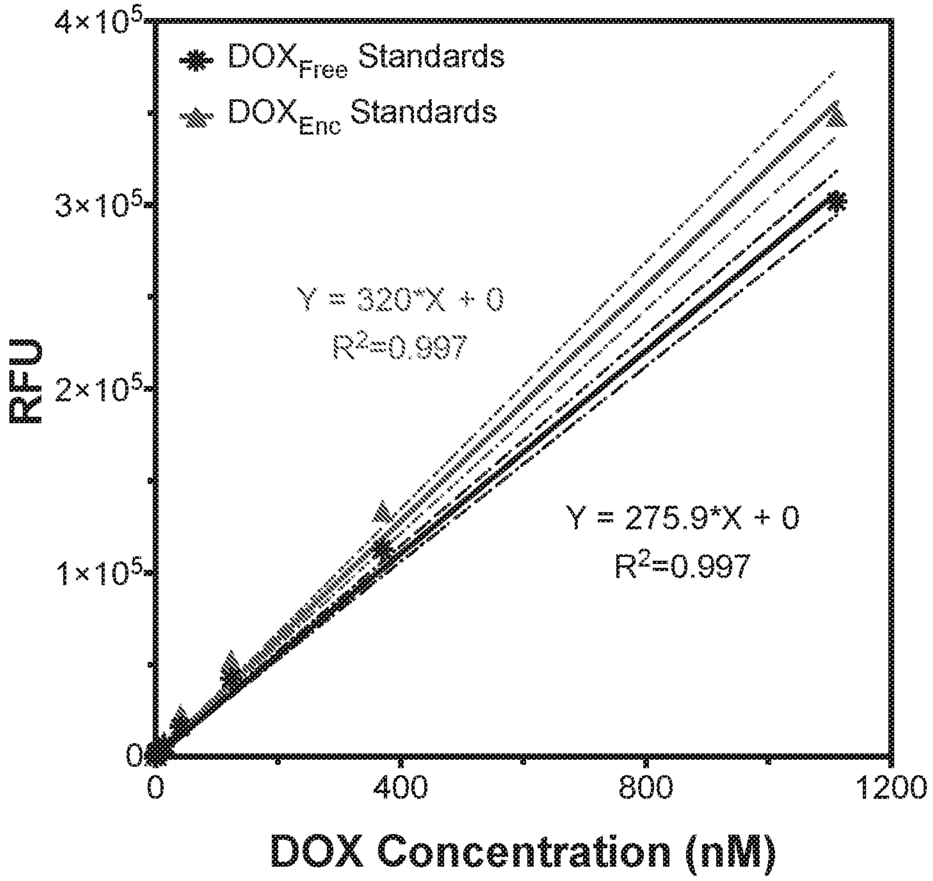
FIG. 35. Standard curves relating the fluorescence of $DOX_{Free}$ and $DOX_{Enc}$ to concentration after incubation in acidified isopropanol, which disassembles the lipid-ELP micelles. Standard curves are similar for $DOX_{Free}$ and $DOX_{Enc}$ and the linear regression was used to quantify DOX concentration in mouse plasma samples.

However, when $DOX_{Env}$ is released by incubation in acidified isopropanol prior to reading the fluorescence, the standard curves are nearly identical, showing that DOX fluorescence is restored upon release from the micelle cores (see below and FIG. 35).

Consequently, the $DOX_{Enc}$ sample filtrate was quantified using the $DOX_{Free}$ standard curve, while the starting sample and retentate were quantified using the encapsulated DOX standard curve. The cumulative DOX released was calculated and plotted as a function of dialysis time. This plot shows that there is a small amount of $DOX_{Enc}$ (~13%) that is leached from the micelles within the first 24 h, followed by slow and constant release with time over the course of the experiment (one week). In contrast, $DOX_{Free}$ is rapidly filtered out of the cassette and reaches equilibrium by 24 h. At the end of the one week study, the retentate from each sample was removed and measured. There was approximately 30-fold more DOX remaining in the retentate in the encapsulated form, 50% of the starting material, which is clearly demonstrated by a side-by-side image of both samples (FIG. 32C).

Release with pH: Because confocal microscopy showed punctate DOX fluorescence in 4T1 cells (FIG. 30), indicative of uptake through the endosomal/lysosomal pathway, we were curious about how DOX encapsulation would be affected at lower pH. The reported pH along the endocytic pathway ranges from pH 6.0-6.5 for early endosomes to pH 5.5 for late endosomes and pH 4.5 for lysosomes.

Figure 33A:
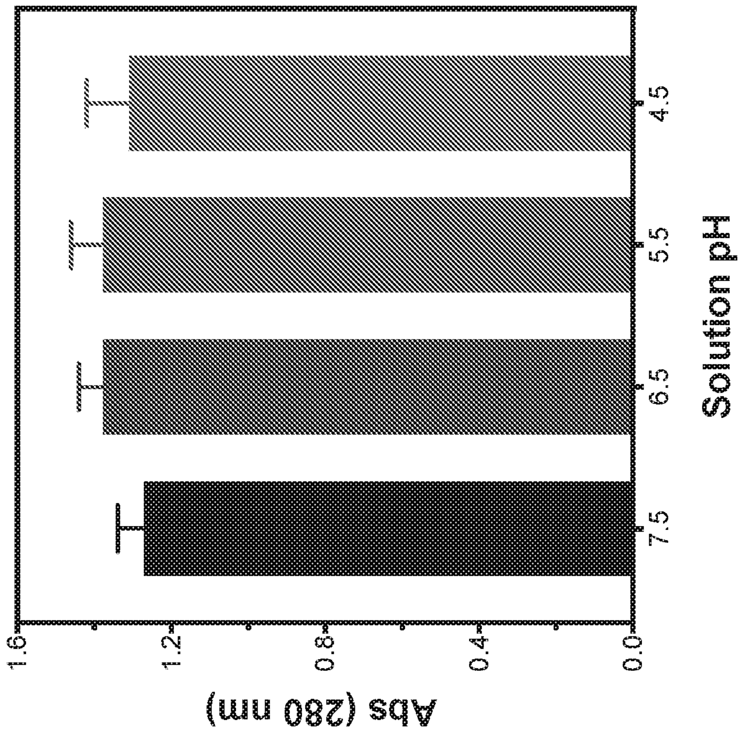
FIG. 33. The Abs$_{280}$ (A) and Abs$_{480}$ (B) of DOX encapsulated in M-ELP$_{90A,80}$ micelles and added to solutions with different pH were measured. There was no significant difference in protein or DOX concentration between the low pH groups and the control pH 7.5 group. The same procedure was done for free DOX at pH 4.5 and pH 7.5 (C). However, because free DOX has significantly greater fluorescence than encapsulated DOX due to quenching in the nanoparticle core, these free DOX samples were diluted 5-fold to ensure that the fluorescence would not saturate the detector of the NanoDrop 3300 Fluorospectrometer. Again, there was no statistically significant difference between the Abs$_{480}$, determined by an upaired t-test.
Figure 33B:
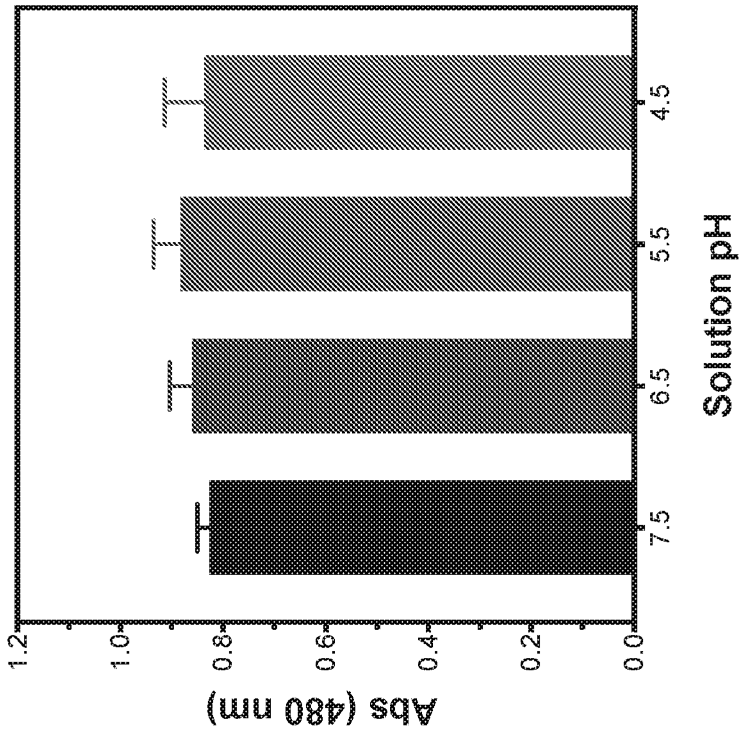
Figure 33C:
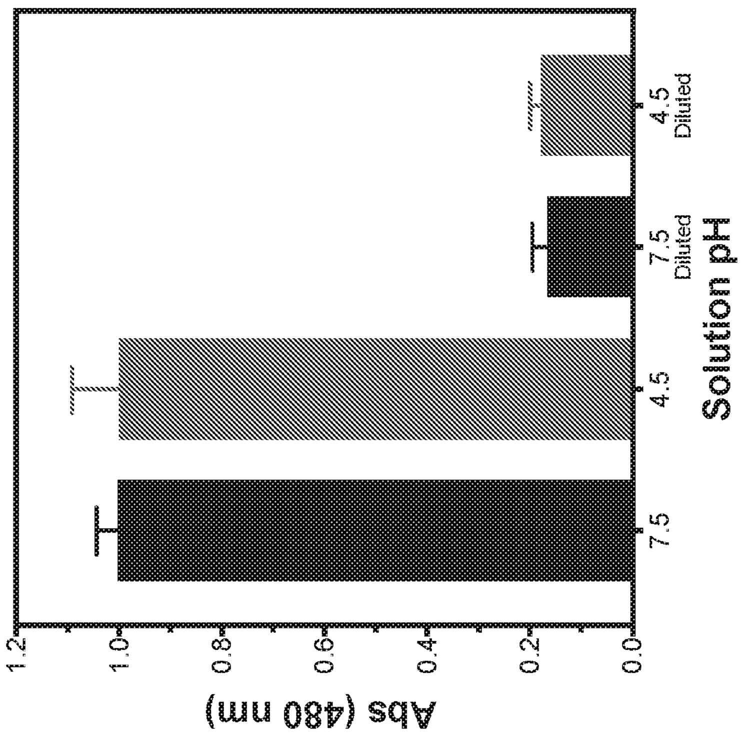
Figure 34A:
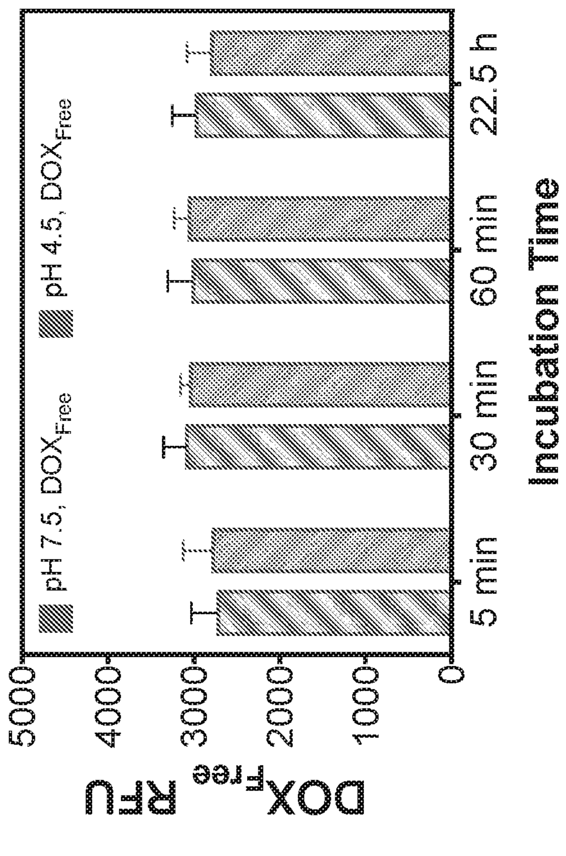
FIG. 34. There is no statistically significant difference between fluorescence of DOX$_{Free}$ at pH 7.5 versus at pH 4.5 (two-way ANOVA, no effect of time or pH) (A). In contrast, there was a significant effect of time, pH, and the interaction term for $DOX_{Enc}$ (B). This data shows that there is a trend of significantly increasing DOX release from M-$ELP_{90A,80}$ with decreasing pH and for increasing incubation times (C). This effect of increased DOX fluorescence with decreasing pH is especially pronounced at 24 h, shown by DOX's fluorescence spectrum with 22.5 h incubation in solution with varied pH (D).
Figure 34B:
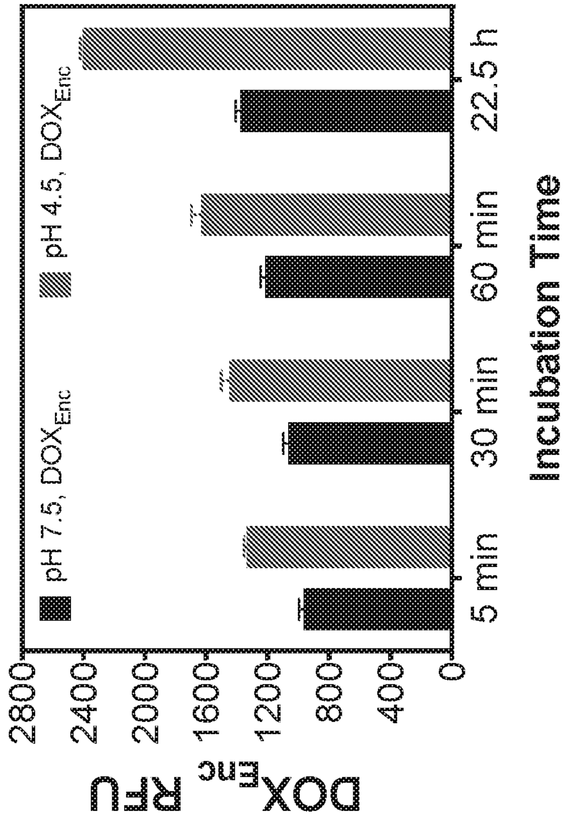
Figure 34C:
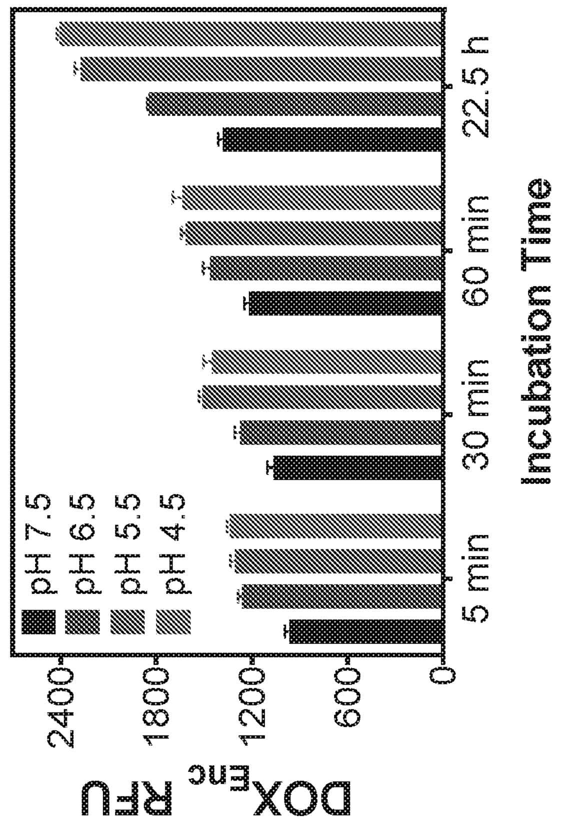
Figure 34D:
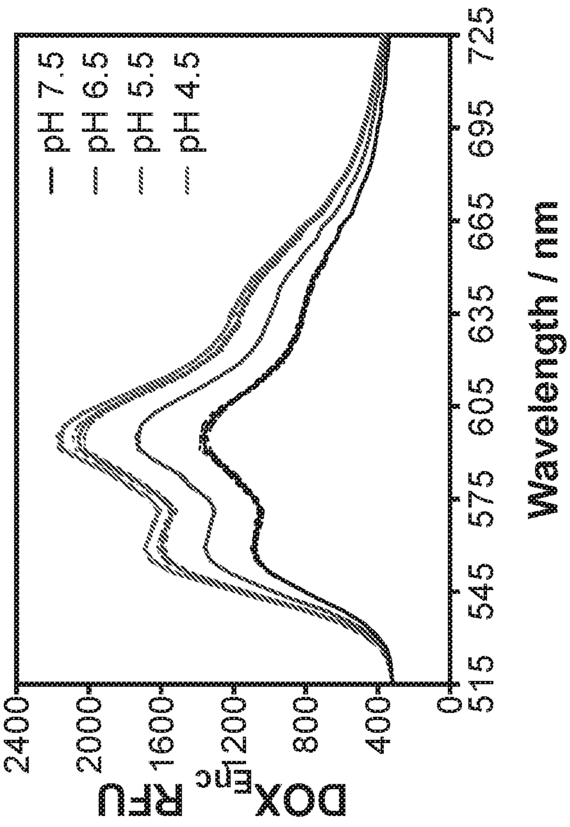

PBS at pH 7.5 was titrated with 2 M HCl to a pH of 6.5, 5.5 or 4.5. In triplicate, a concentrated volume of encapsulated DOX (975 μM) was then added to each solution with varying pH to a final concentration of approximately 100 μM. The 280 and 480 nm absorbances were measured. A one-way ANOVA followed by Dunnett's multiple comparison tests showed that there was no significant difference in protein absorbance ($Abs_{280}$) or DOX absorbance ($Abs_{480}$) between the experimental groups (pH 4.5, 5.5, and 6.5) and the control pH group (pH 7.5), as assessed by a one-way ANOVA. The same procedure was done for free DOX at pH 4.5 and pH 7.5. However, because free DOX has significantly greater fluorescence than encapsulated DOX due to quenching in the nanoparticle core, these free DOX samples were diluted 5-fold to ensure that the fluorescence would not saturate the detector of the NanoDrop 3300 Fluorospectrometer. Again, there was no statistically significant difference between the $Abs_M$, determined by an unpaired t-test. See FIG. 33.

At 5 min, 30 min, 1 h, and 24 h after the addition of DOX to the solutions at various pH, DOX fluorescence was measured using a NanoDrop 3300 Fluorospectrometer. Our experiments have shown that DOX's fluorescence is partially quenched after encapsulation in the lipid-ELP nanoparticles (FIG. 31). Thus, any increase in fluorescence can be attributed to DOX that has leached out or been released from the nanoparticle cores.

Figure 32A:
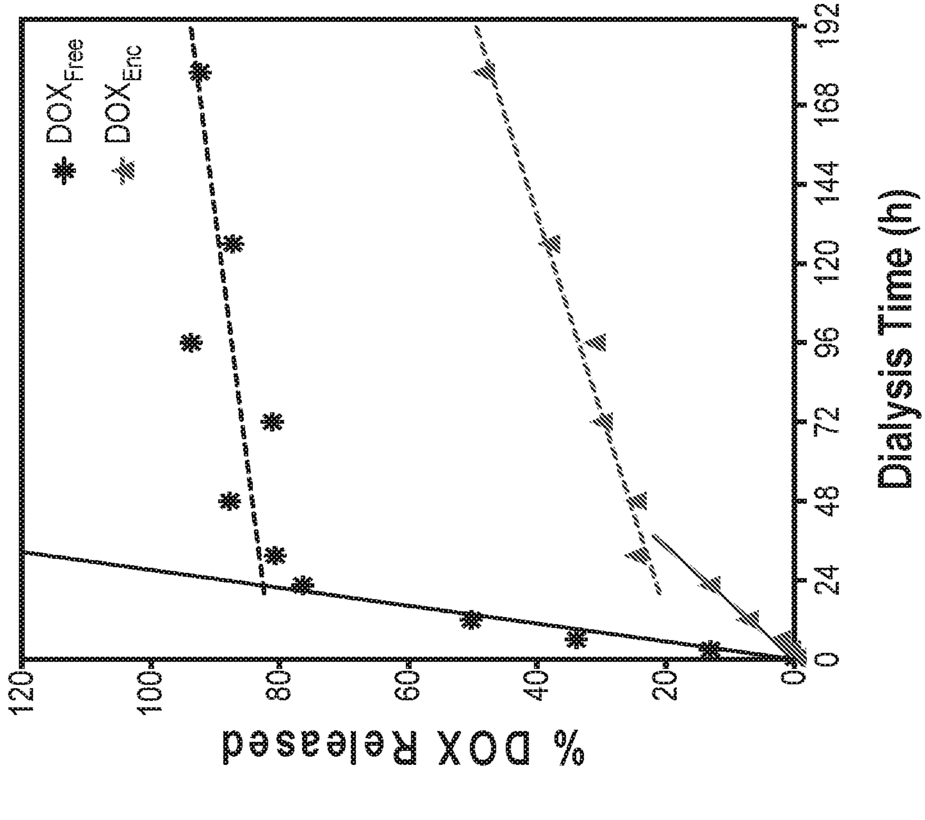
FIG. 32. In vitro DOX release study using dialysis against PBS shows the stability of the encapsulated DOX (A), where a significant portion (>50%) is kept encapsulated and in the retentate (b, filled bars) even after incubation for a week at 37° C. This is significantly different than DOX$_{Free}$, which is 99% filtered (B, patterned bars). The retentate after a week still has strong Abs$_{480}$ for DOX$_{Enc}$ which contrasts starkly to the retentate of DOX$_{Free}$ (C).
Figure 32B:
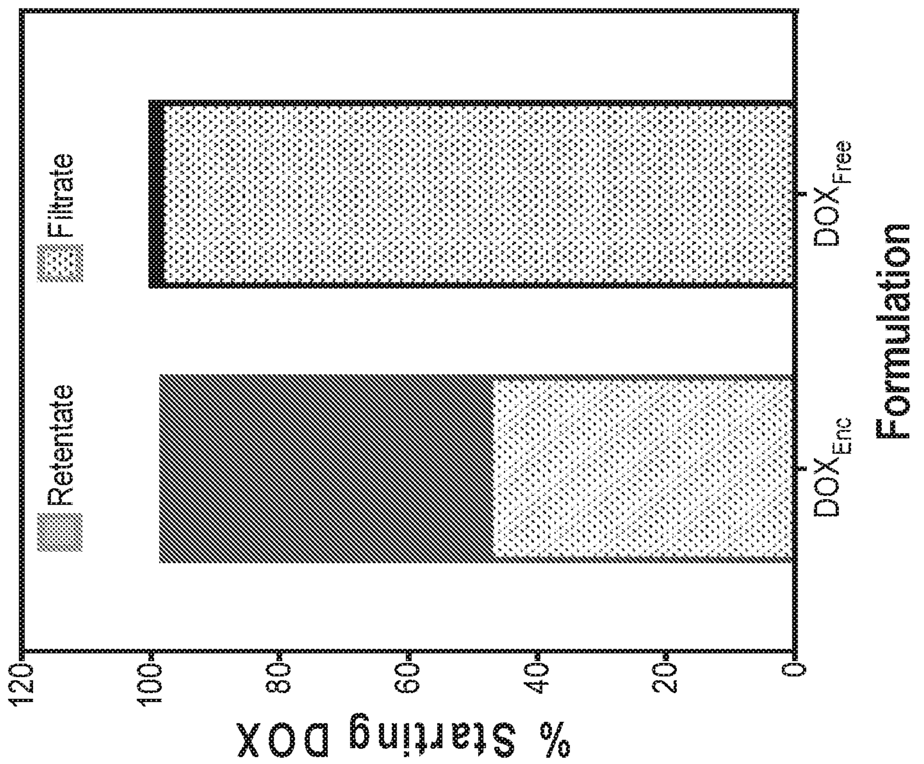
Figure 32C:
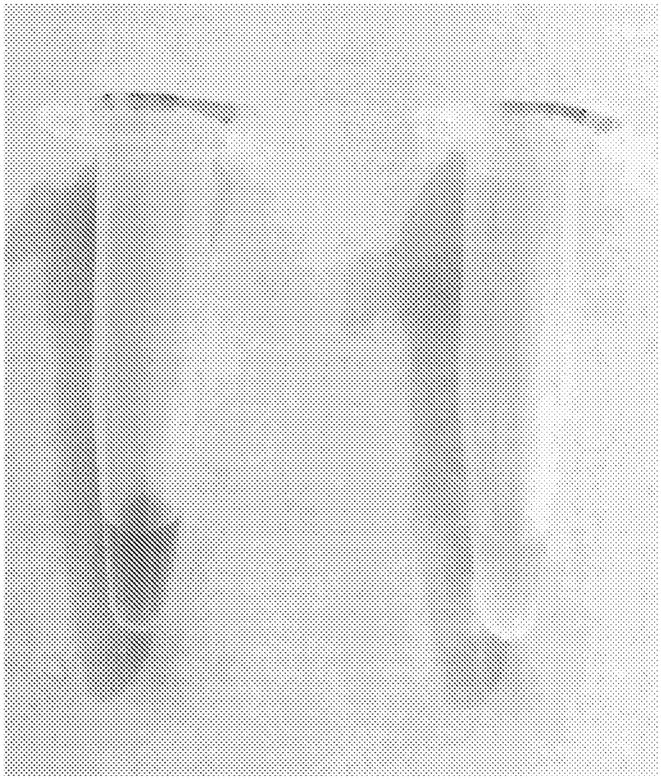

The results show that some DOX does leach out of the nanoparticles at pH 7.5, which corroborates the nanoparticle stability study (FIG. 32). However, this increase in fluorescence signal is much greater at lower pH (FIG. 34). There is a significant effect of time, pH, and an interaction between the two as analyzed by two-way ANOVA and Dunnett's multiple comparisons. After subtraction of baseline fluorescence and with a 24 h incubation, the difference in fluorescence between the pH 7.5 and pH 4.5 groups was 3.8-fold. This data explains how the encapsulated drugs are escaping nanoparticle entrapment and exerting their cytotoxic effects on cells in vitro. Because the most pronounced change occurs around pH 4.5-5.5, our hypothesis is that this release occurs as a result of charge loss in the corona at the densely packed C-termini.

In Vivo Pharmacokinetics

This study was conducted under protocol A192-16-08 using procedures approved by the Duke Institutional Animal Care and Use Committee (IACUC). Duke University's Division of Laboratory Animal Resources (DLAR) maintains compliance with Duke's Institutional Animal Care and Use Committee (IACUC) and its regulatory accreditation requirements. Duke's Animal Care and Use program is fully accredited by the Association for the Assessment and Accreditation of Laboratory Animal Care, International (AAALAC). Furthermore, the university is registered as a research facility with the US Department of Agriculture (USDA) in accordance with the Animal Welfare Ad and holds a Category I Assurance with the Public Health Service through the NIH's OLAW. All animal research at Duke University is conducted accordingly and upholds the standards put forth by these organizations.

To determine the in vivo consequence of encapsulation and, more specifically, to determine if encapsulation of a drug in our M-ELP system alters its pharmacokinetics, we injected BALB/C mice (Charles River Laboratories) IV via the tail vein with 5 mg/kg free DOX or encapsulated DOX (in M-$ELP_{90A,80}$). Free DOX and encapsulated DOX were prepared at 862 μM so that each mouse would be injected with a volume equal to 10×the body weight (in grams). At pre-determined time points (45 s, 10 m, 45 m, 1.5 h, 3 h, 6 h, 9 h, 12 h, and 22.5 h), 10 μL of blood was collected into 90 μL of 1000 U/mL heparin in PBS and kept on ice. Blood was centrifuged at 5,000×g for 10 minutes at 4° C. The plasma was then transferred to new tubes and stored at −80° C.

After all blood collections were completed, the plasma was thawed and 30 μL was added to a tube containing 270 μL acidified isopropanol (75 mM HCl, 10% $ddH_2O$, 90% isopropanol). Standards were also prepared in acidified isopropanol to range from 10 μM down to 0.1 nM using twelve, 3-fold serial dilutions. The standards and samples were then incubated overnight at 4° C. This step served to ensure full release of all encapsulated DOX. After overnight incubation, the samples and standards were spun for 5 min at 5,000×g and 4° C. Transferring the supernatants, duplicates of 125 μL were pipetted into a black, clear bottom 96-well plate. DOX fluorescence was quantified by reading the plate on a Wallac 1420 Victor3 Plate Reader (Perkin Elmer). Standard curves for free DOX and encapsulated DOX were very similar and were used to quantify the concentration of DOX in the blood at each time point.

Figure 4B:
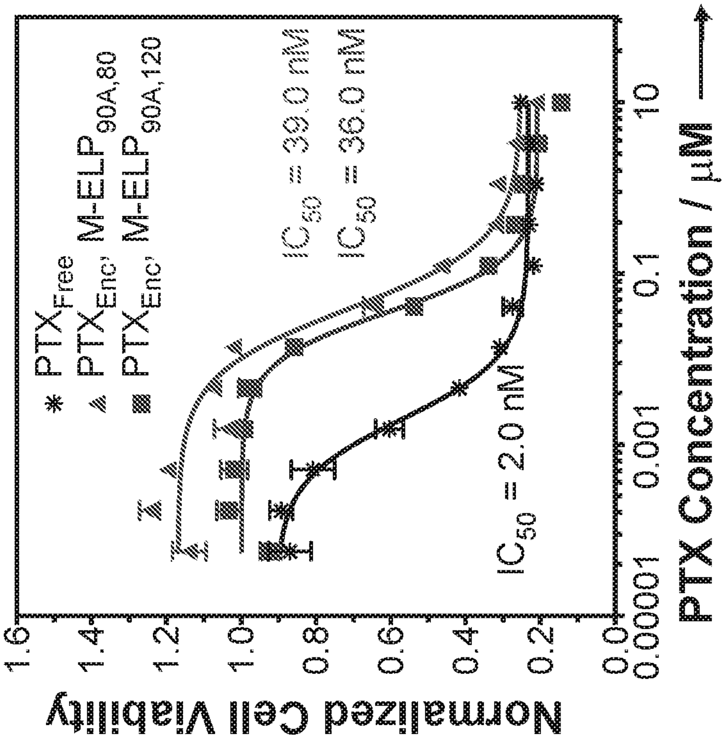
FIG. 4. DOX and PTX encapsulated in either M-$ELP_{90A,120}$ or M-$ELP_{90A,120}$ show in vitro cytotoxicity towards 4T1 (A) and PC3 (B) cells. Confocal fluorescence microscopy of 4T1 cells treated for 12 h with $DOX_{Free}$ (C) or $DOX_{Enc}$ (D) shows uptake of $DOX_{Enc}$, via the endosomal/lysosomal pathway, as indicated by punctate fluorescence (green arrow). Fluorescence is colored as: nucleus (blue), cell membrane (red), and DOX (green). $DOX_{Enc}$ has a longer plasma half-life (E) and greater distribution than $DOX_{Free}$, shown by the 5-fold lower plasma concentrations just 45 s post-injection (F).
Figure 4A:
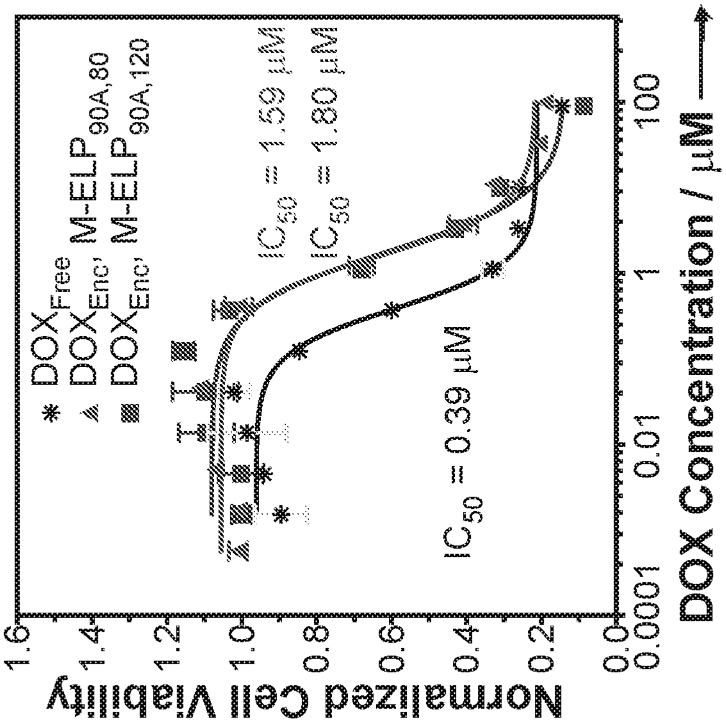
Figure 4C:
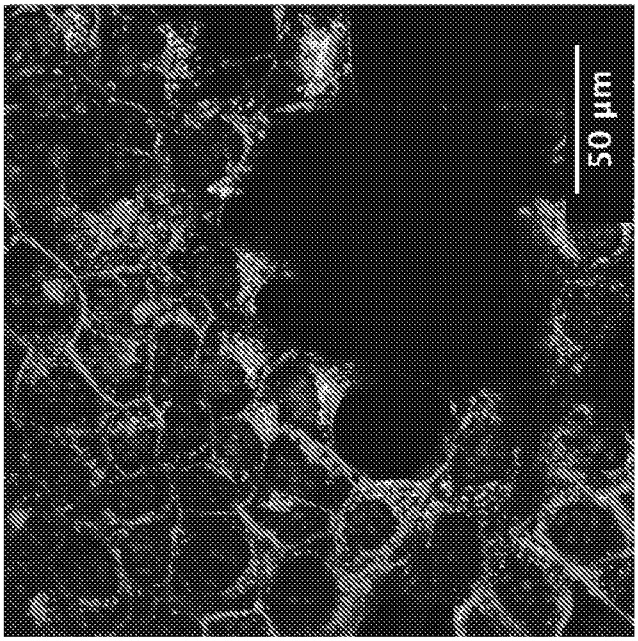
Figure 4D:
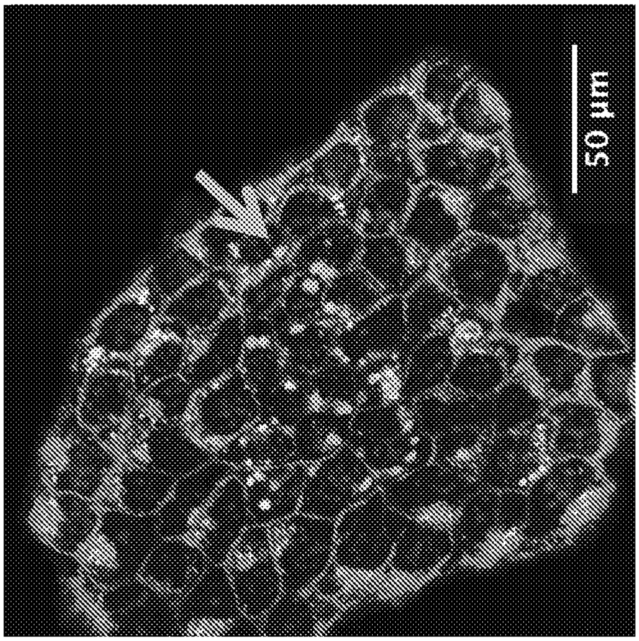
Figure 4E:
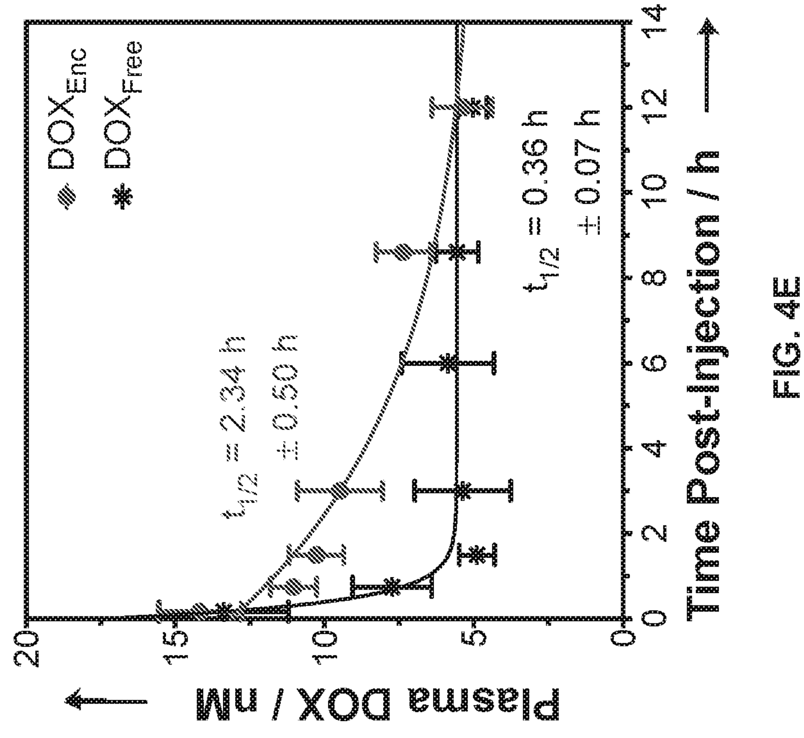
Figure 36:
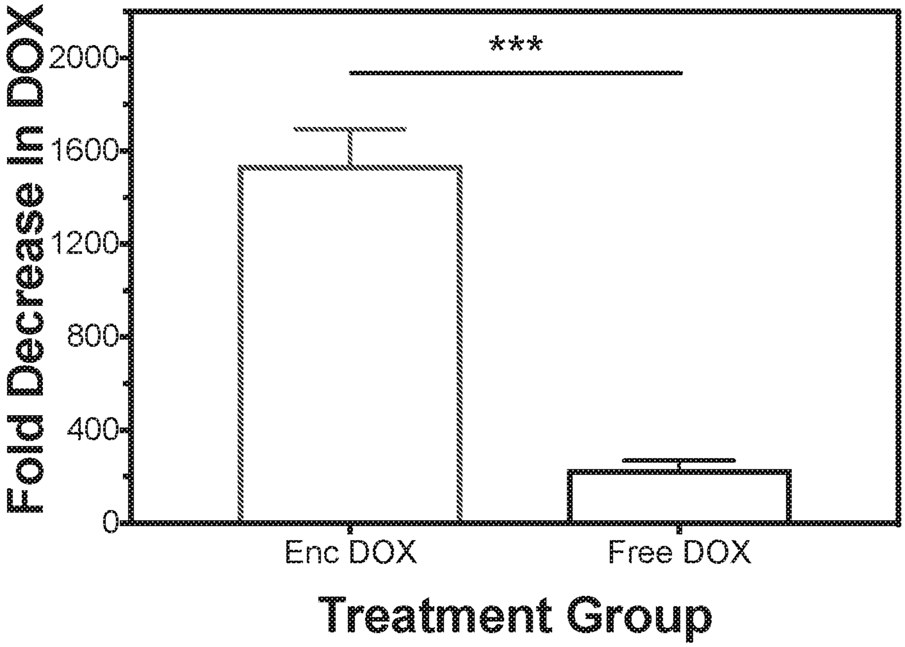
FIG. 36. Fold decrease in circulating DOX concentrations at t=45 s post-injection to the theoretically calculated t=0 concentration. The $DOX_{Enc}$ group has a much larger decrease in DOX at very early time points after injection, suggesting greater distribution and degree of uptake by tissues throughout the body.

The half-life for free and encapsulated DOX was calculated by fitting a one-phase exponential decay equation to data points in the elimination phase (t=10 min to 22.5 h) using Prism 7 software (FIG. 4E). The treatment groups received identical amounts of $DOX_{Free}$ as $DOX_{Enc}$, meaning the circulating concentration at t=0 should be the same. Using an approximation of mouse blood volume of 72 mL per kg, we estimated the DOX concentration at t=0 to be 105.1 μM in every mouse. By dividing this theoretical t=0 estimate of circulating DOX concentration by the measured concentration at t=45 s (which is in the distribution phase of the pharmacokinetic profile) we can quantify the fold-decrease in DOX by 45 s post-injection and gamer a sense of the drug's distribution throughout the body. $DOX_{Enc}$ had a 7-fold higher decrease in circulating DOX concentration at t=45 s compared to $DOX_{Free}$ (FIG. 36), which clearly indicates a difference in the drug's distribution and tissue uptake.

Example 2

The 11-amino acid Arf2 recognition sequence, GLYASK-LFSNL, was fused at the gene level to an ELP's N-terminus. For initial proof-of-concept studies, we selected a hydrophilic ELP, comprised of 120 repeats of VPGXG where X is 90% alanine and 10% valine ($ELP_{90A,120}$). The recognition sequence-ELP fusion was co-expressed with yeast NMT using a bicistronic expression vector (pETDuet-1) in BL21 (DE3) cells and myristic acid was added to the culture 10 min prior to induction of protein expression with isopropyl-β-D-thiogalactopyranoside. As a negative control, we expressed $ELP_{90A,120}$ from the pETDuet-1 plasmid without the NMT gene, and with supplemental myristic acid. Details of the cloning and expression protocols are detailed in Example 1.

Figure 6B:
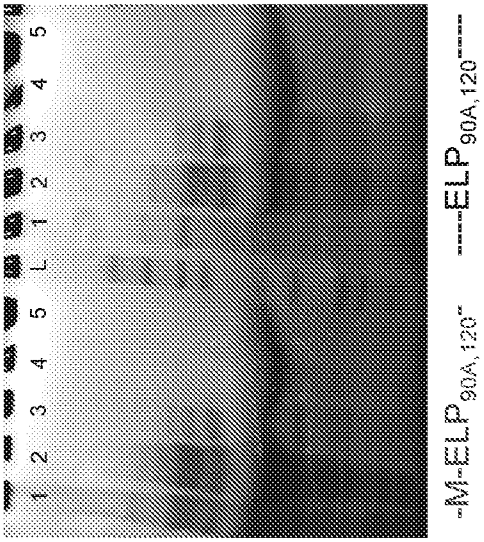
Figure 6A:
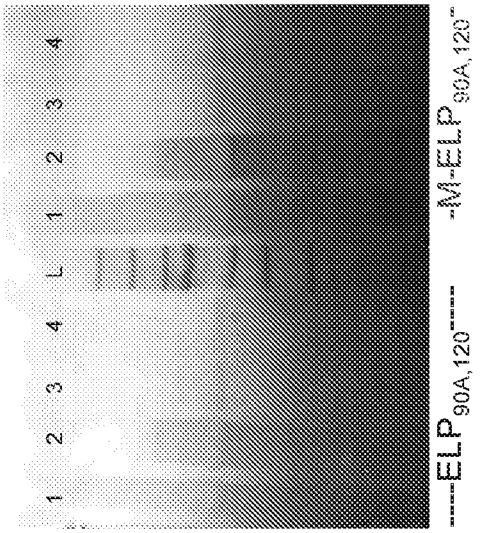
Figure 8:
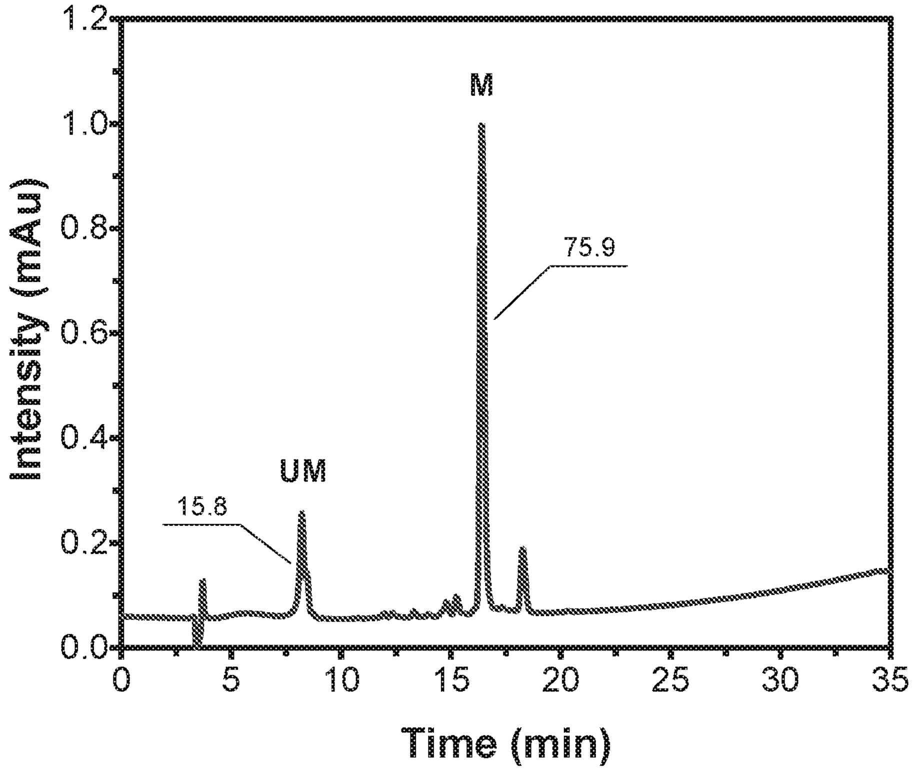
FIG. 8. M-$ELP_{90A,120}$ purified by ITC was run on HPLC, where UM indicates unmyristoylated and M indicates myristoylated ELP. Integrated peak areas were used to quantify total myristoylated product yield.
Figure 9B:
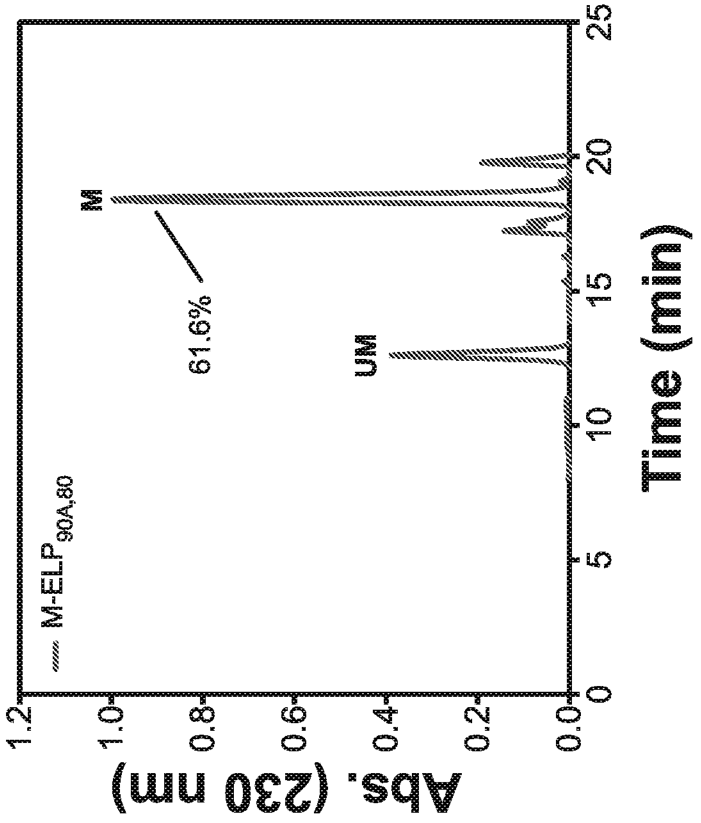
FIG. 9. $ELP_{90A,120}$ control (A) and M-ELPs (B-D) were purified by ITC and run on HPLC to quantify yield. UM indicates the unmyristoylated and M indicates the myristoylated product. Integrated peak areas were used to quantify total myristoylated product yield by multiplying the product fraction by the total lyophilized powder weight.
Figure 9A:
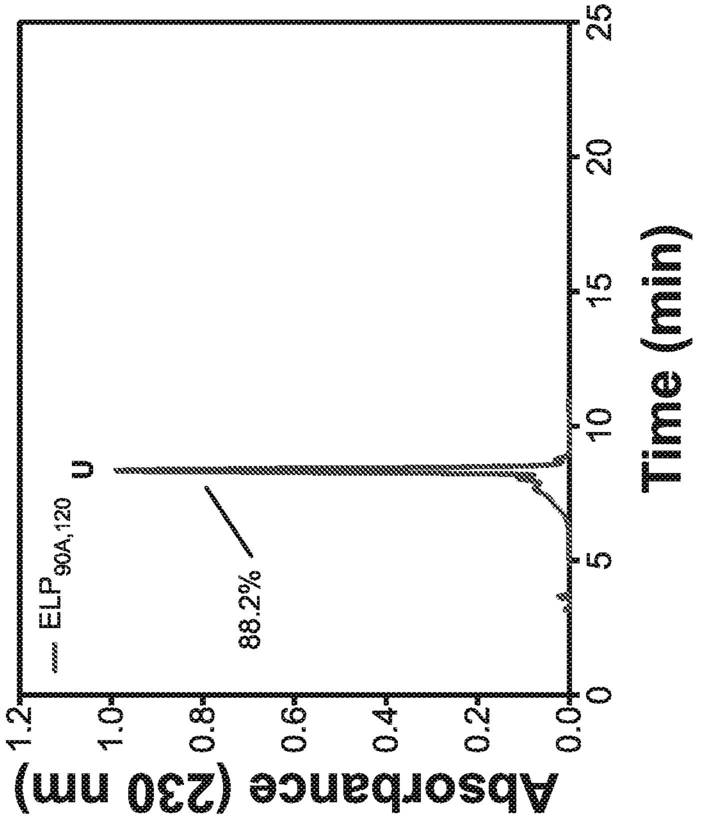
Figure 9D:
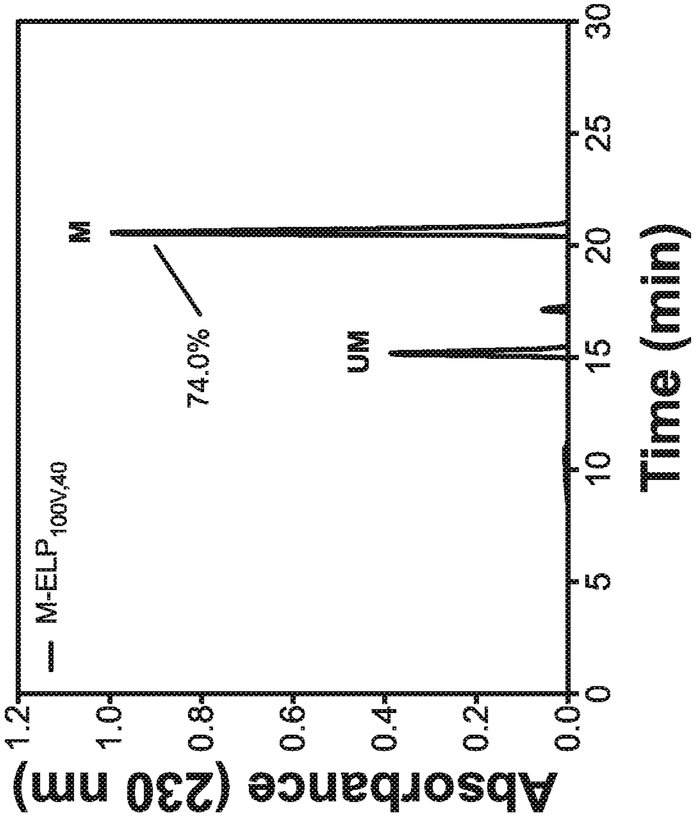
Figure 9C:
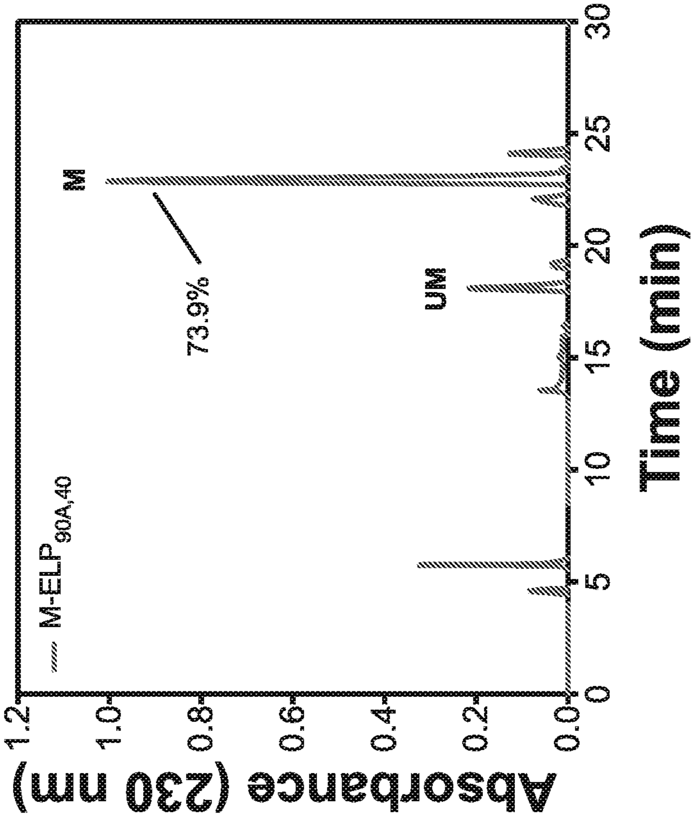
Figure 10A:
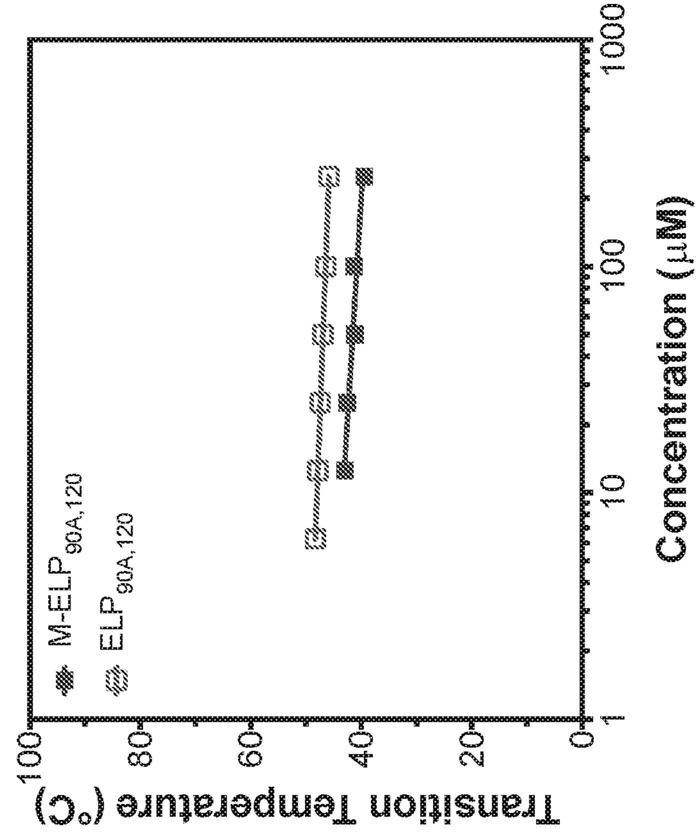
FIG. 10. Concentration dependence of the transition temperatures of myristoylated (colored, solid symbols) and unmyristoylated (grey, open symbols) constructs M-$ELP_{90A,120}$ (A), M-$ELP_{90A,80}$ (B), M-$ELP_{90A,40}$ (C), M-$ELP_{100V,40}$ (D).
Figure 10B:
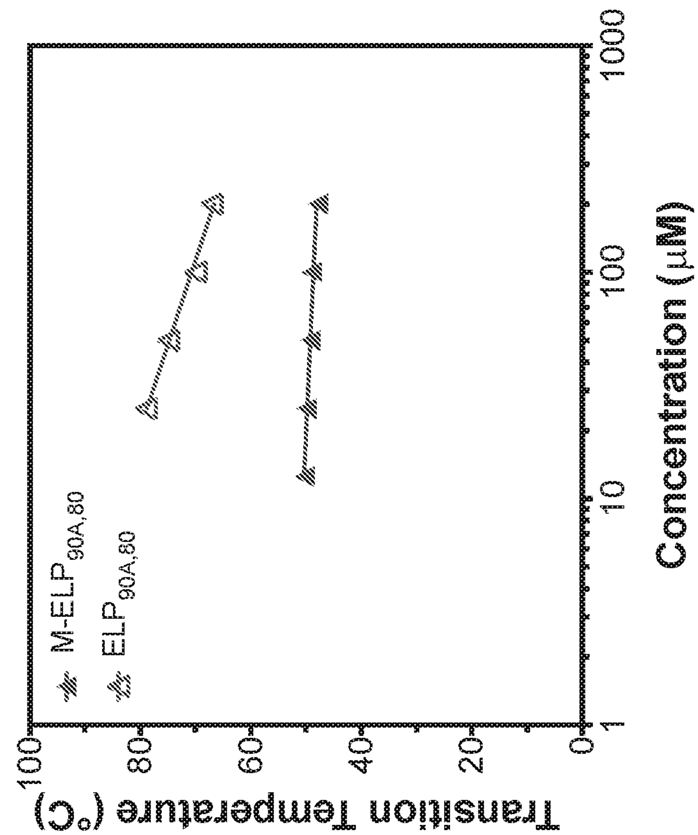
Figure 10D:
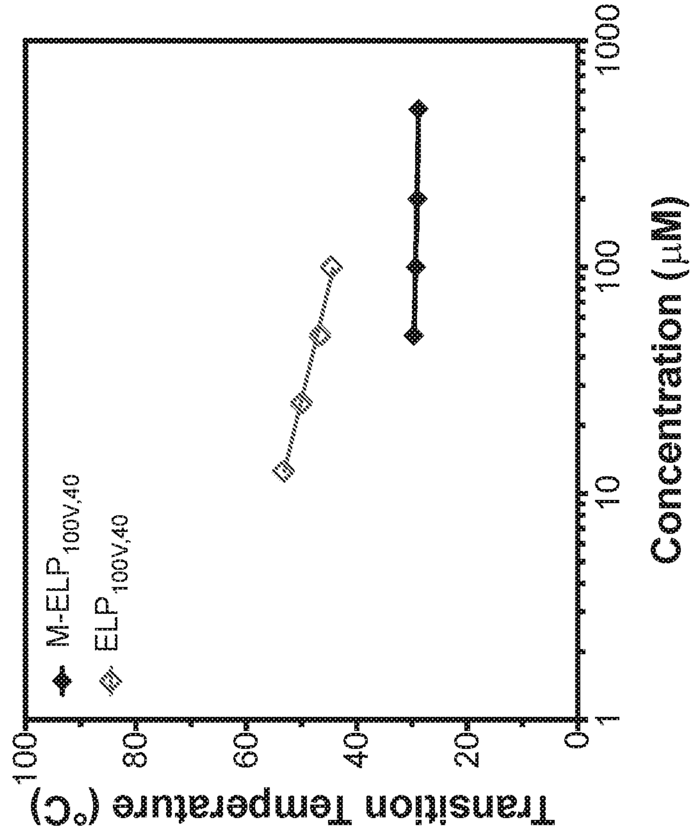
Figure 10C:
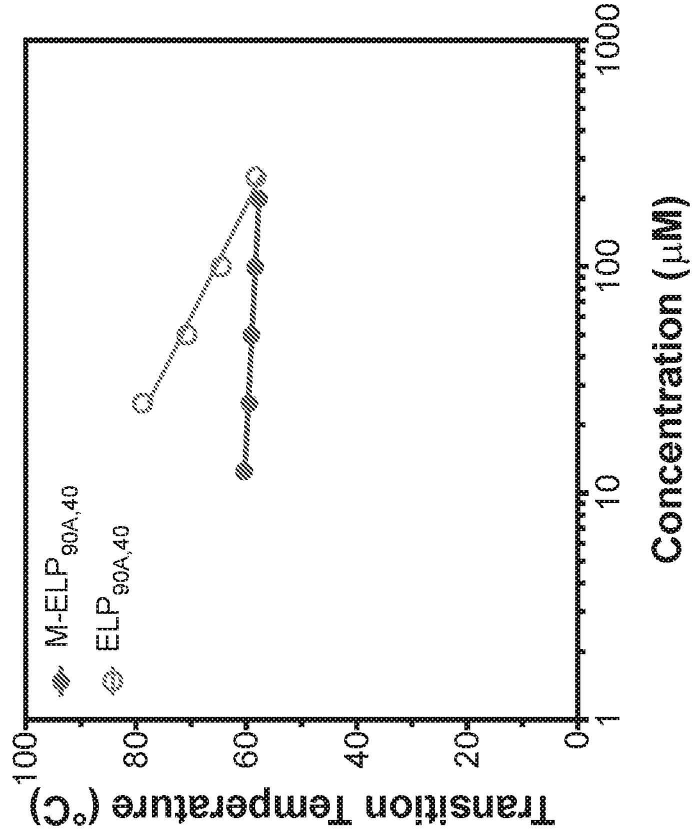

After expression, myristoylated ELP (M-$ELP_{90A,120}$) and control ($ELP_{90A,120}$) were purified using inverse transition cycling (ITC)(D. E. Meyer, A. Chilkoti, *Nat. Biotechnol.* 1999, 17, 1112-1115). Sodium dodecyl sulfate-polyacrylamide gel electrophoresis (SDS-PAGE) shows that the constructs could be efficiently purified with only a few rounds of ITC (FIG. 6A-FIG. 6B). We performed reversed-phase high-performance liquid chromatography (RP-HPLC) using a hydrophobic C18 stationary phase to further demonstrate the high degree of purity achieved with ITC and the extent of myristoylation. Addition of a hydrophobic myristoyl group is expected to increase the retention time of post-translationally modified ELPs. Co-expression of the target polypeptide with NMT is necessary for lipidation, as seen by the increase in the retention time of M-ELP$_{90A,120}$ to 17.6 min compared to the negative control (ELP$_{90A,120}$) grown in the absence of NMT, which elutes at 12.3 min (FIG. 2A). Quantification of purified product shows that M-ELP$_{90A,120}$ can be synthesized at high yield (>40 mg/L of culture), which is about half the yield of ELP$_{90A,120}$ (FIG. 8-FIG. 9, TABLE 5).

Successful myristoylation was further verified by matrix-assisted laser desorption ionization-time of flight-mass spectrometry (MALDI-TOF-MS). Experimentally observed mass-to-charge (m/z) ratios for both constructs (FIG. 2B) were in excellent agreement with the theoretical molecular weights (TABLE 2). MALDI-MS performed after digestion with trypsin confirmed myristoylation of the N-terminal glycine, as seen by a 210 Da shift between M-ELP$_{90A,120}$ (849.8 Da) and ELP$_{90A,120}$ (639.3 Da), which corresponds to the mass added from covalent addition of a myristoyl group (FIG. 2C).

Example 3

We next used UV-vis spectrophotometry to evaluate whether the lipid-ELP hybrid retained the LCST phase behavior of its parent ELP. The absorbance at 350 nm was monitored as the solution temperature was ramped up and then down at a rate of 1° C./min. M-ELP$_{90A,120}$, like its unmyristoylated controls, exhibited a reversible temperature-triggered LCST phase transition, forming a polypeptide-dense coacervate upon heating that resolubilizes upon cooling (FIG. 11). The transition temperature ($T_t$) is defined as the inflection point of absorbance versus temperature, calculated as the maximum of the curve's first derivative (FIG. 2D, arrow).

Figure 2E:
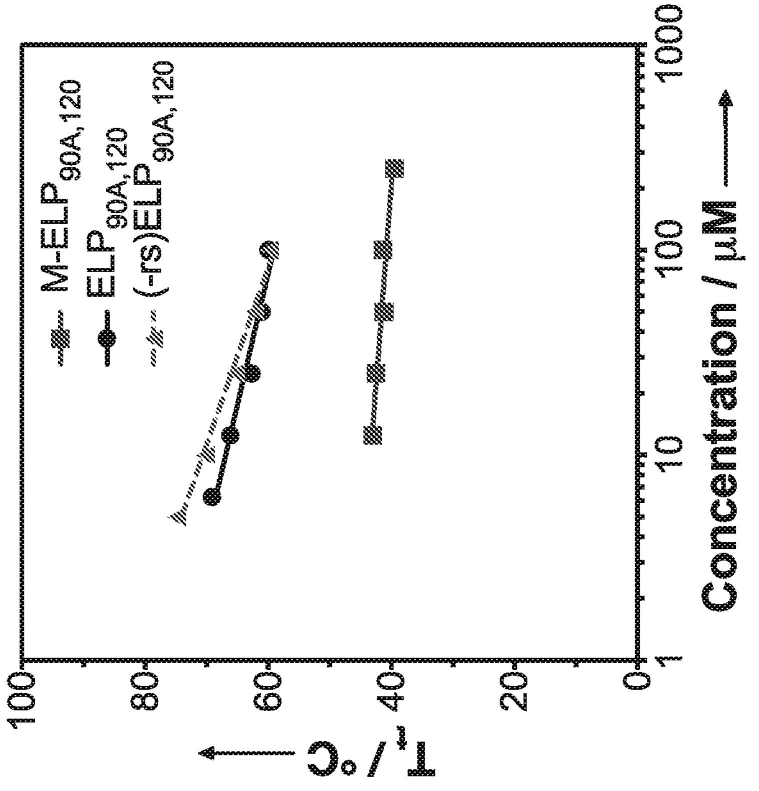

Lipidation of an ELP changes the LCST phase behavior in two ways: first, myristoylation suppresses the $T_t$ by ~20° C. (FIG. 2D), which can be attributed to the covalent attachment of myristic acid, which increases the polypeptide's overall hydrophobicity and also eliminates the N-terminal charge. We also showed that the addition of the recognition sequence has no appreciable impact on $T_t$ in the absence of myristoylation (ELP$_{90A,120}$ versus (–rs)-ELP$_{90A,120}$, FIG. 2D, FIG. 2E). Second, myristoylation reduces the inverse dependence of $T_t$ on concentration; when $T_t$ is plotted versus ELP concentration on a semi-log scale, the slope is nearly flat for M-ELP$_{90A,120}$, whereas the same plot for the parent ELP shows a sharper inverse log dependence of $T_t$ on concentration (FIG. 2E). This lack of concentration dependence is a hallmark of ELP self-assembly (J. R. McDaniel, et al. *Nano. Left.* 2014, 14, 6590-6598).

Figure 2F:
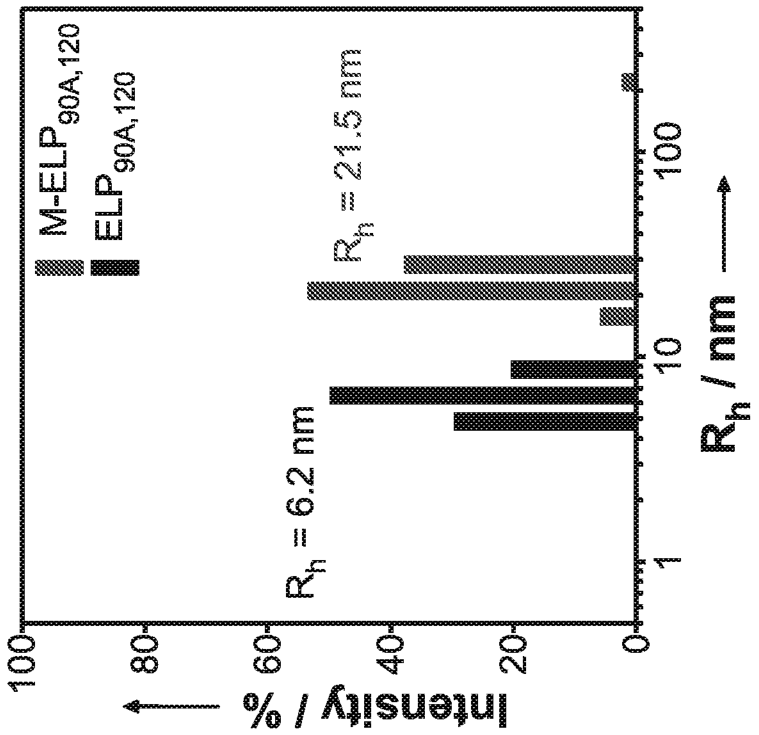

To characterize the self-assembly of M-ELP$_{90A,120}$ that is suggested by the turbidity measurements, we next performed light scattering on filtered samples in phosphate buffered saline (PBS) at 25° C., which is well below the $T_t$. Dynamic light scattering (DLS) of ELP$_{90A,120}$ and M-ELP$_{90A,120}$ confirms that myristoylation drives self-assembly into nanoparticles with a hydrodynamic radius ($R_h$) of ~22 nm (FIG. 2F). In contrast, ELP$_{90A,120}$ has an $R_h$ of 6.2 nm, a size that is consistent with soluble polymer chains in a Gaussian coil conformation.

Example 4

Figure 7A:
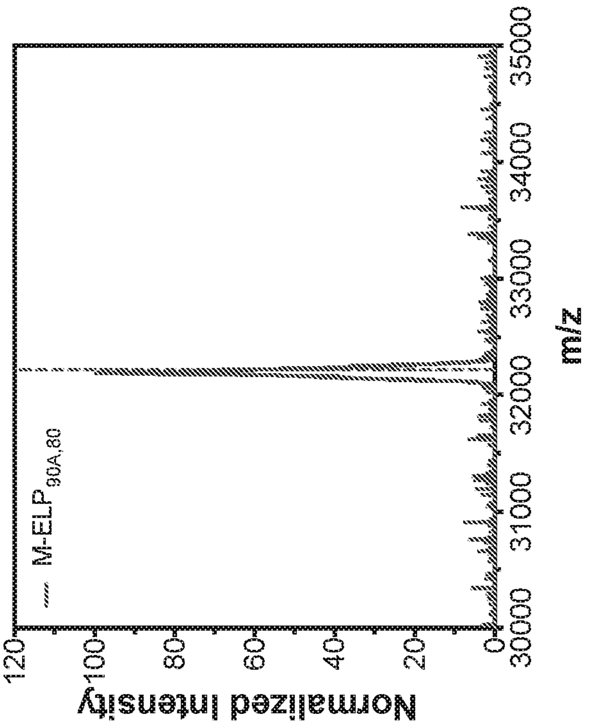
FIG. 7. MALDI-MS of myristoylated constructs—M-$ELP_{90A,80}$ (A), M-$ELP_{90A,40}$ (B), and M-$ELP_{100V,40}$ (C). Experimental mass is shown in a solid line and the calculated, theoretical mass is shown as a vertical, dashed line.
Figure 7B:
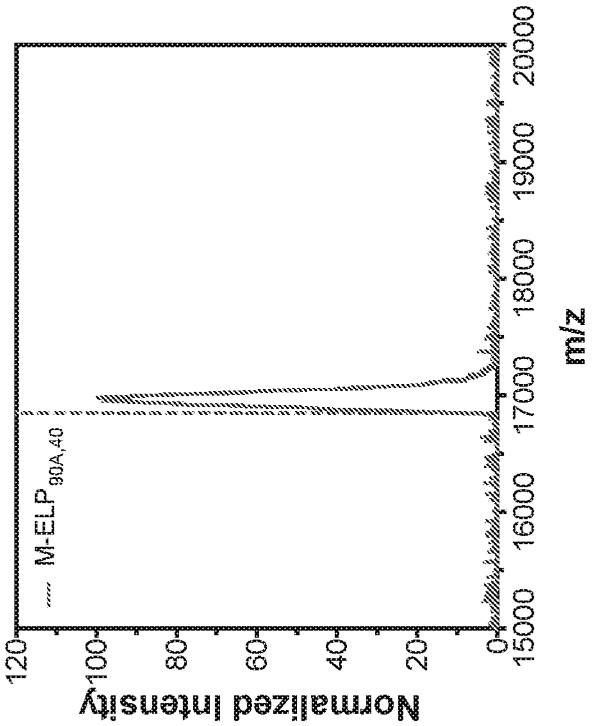
Figure 7C:
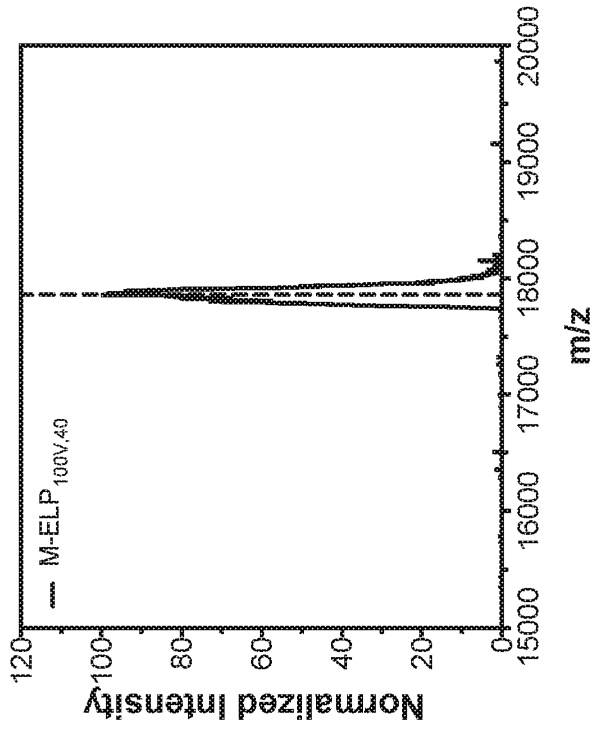

Having confirmed that we can successfully create self-assembling lipid-ELP biomaterials using a one-pot, recombinant method, we hypothesized that the length and hydrophilicity of the ELP could be used to control the morphology of the self-assembled constructs. We took advantage of our modular design, which allows the ELP domain to be precisely specified independently of the recognition sequence, and created three additional constructs to test this hypothesis. First, by keeping the composition constant, we systematically decreased the length of the ELP from 120 to 80 (M-ELP$_{90A,80}$) and 40 pentapeptide repeats (M-ELP$_{90A,40}$). We also synthesized a more hydrophobic construct with 40 repeats of VPGXG where X is 100% valine (M-ELP$_{100V,40}$) to explore the impact of ELP composition on myristoylation and subsequent self-assembly. This set of ELPs was expressed in the same manner as previously described. Detailed information on the sequence, expression, and characterization of these constructs can be found in Example 1. Their N-terminal myristoylation, size and purity were confirmed with SDS-PAGE (FIG. 6C) and MALDI-MS (FIG. 7). Characterization of their LCST phase behavior showed that their $T_t$'s spanned 28.8 to 60.4° C. at concentrations ranging from 12.5 to 500 μM, indicating that, even within this small set of ELPs, we are able to access a wide range of reversible LCST phase behavior (FIG. 3A and FIG. 12) that may be useful for various biomedical applications such as the formation of a controlled release depot for systemic therapy, intratumoral drug delivery, or as a scaffold for tissue regeneration.

Example 5

Figure 14B:
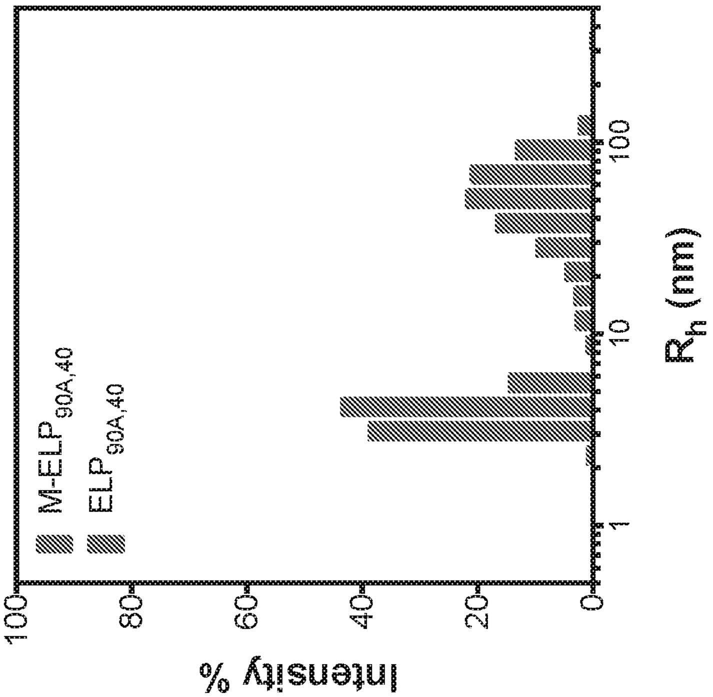
FIG. 14. Results of DLS fit to the autocorrelation function presented as intensity distribution histograms from the regularization fit. Non-myristoylated samples are represented by the empty/patterned bars and myristoylated samples are represented by solid filled bars; M-ELP$_{90A,80}$ (A), M-ELP$_{90A,40}$ (B), and M-ELP$_{100V,40}$ (C).
Figure 14A:
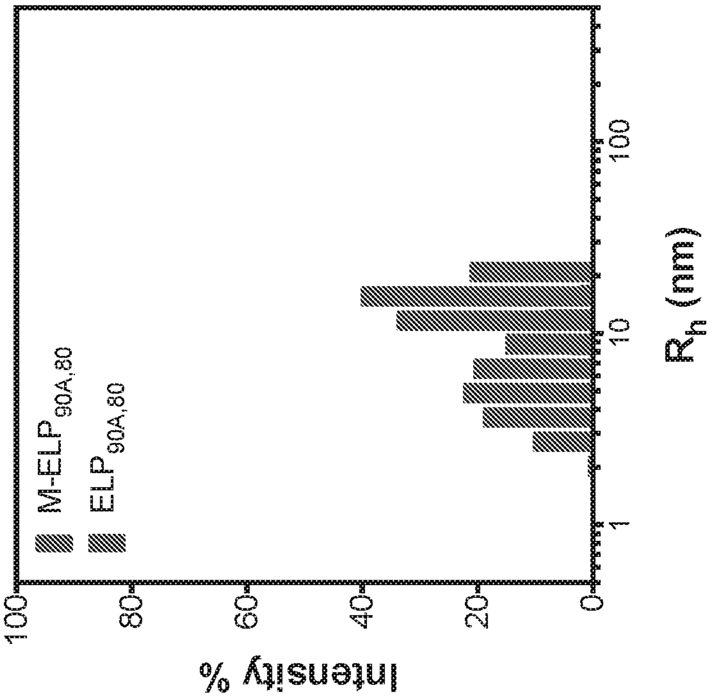
Figure 14C:
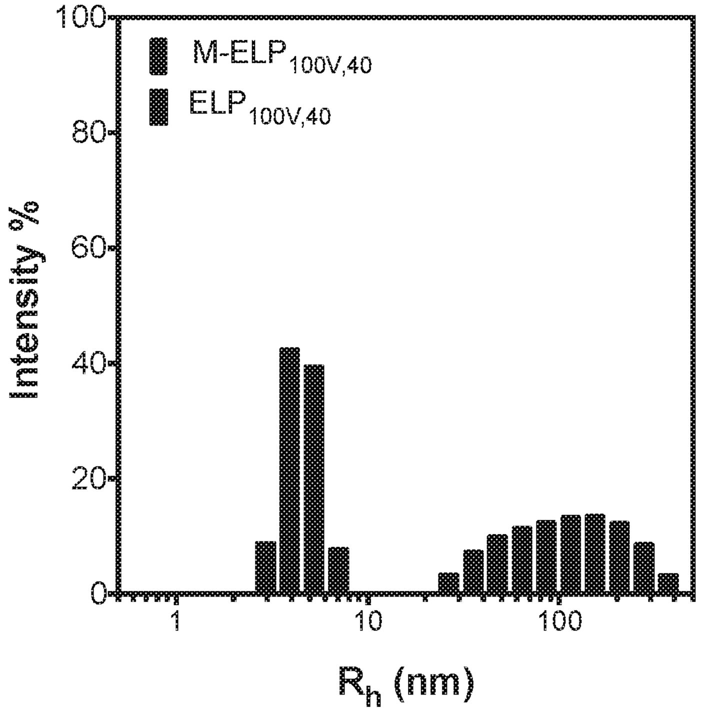
Figure 15A:
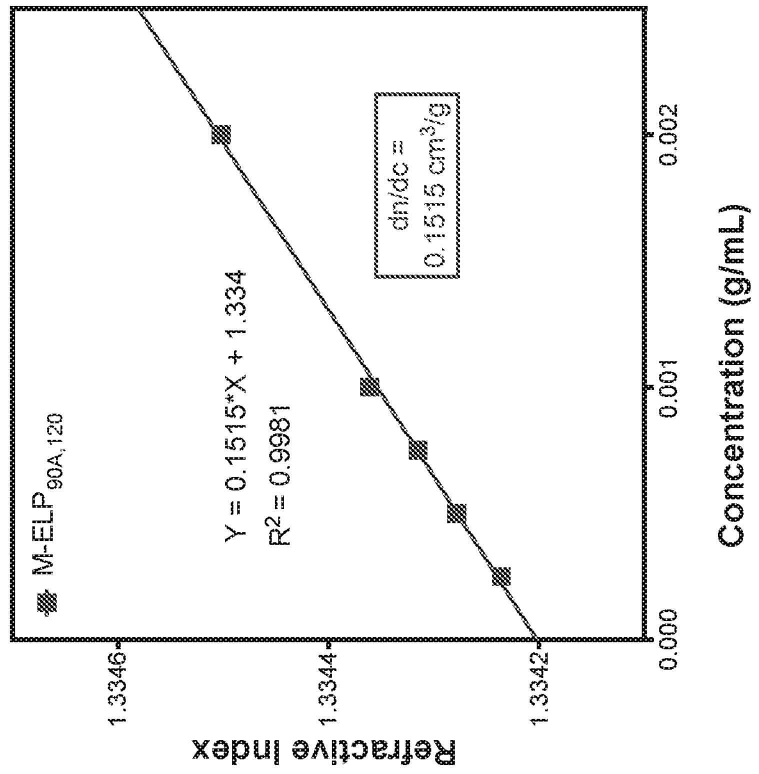
FIG. 15. The refractive indices of four to five different concentrations of M-ELP were measured and potted against concentration. Linear regression produces very small R2 values and the slope of this line is the dn/dc value used in ALVStat software for the calculation of Rg, particle MW, and the second virial coefficient (A2); M-ELP$_{90A,120}$ (A), M-ELP$_{90A,80}$ (B), M-ELP$_{90A,40}$ (C), and M-ELP$_{100V,40}$ (D).
Figure 15B:
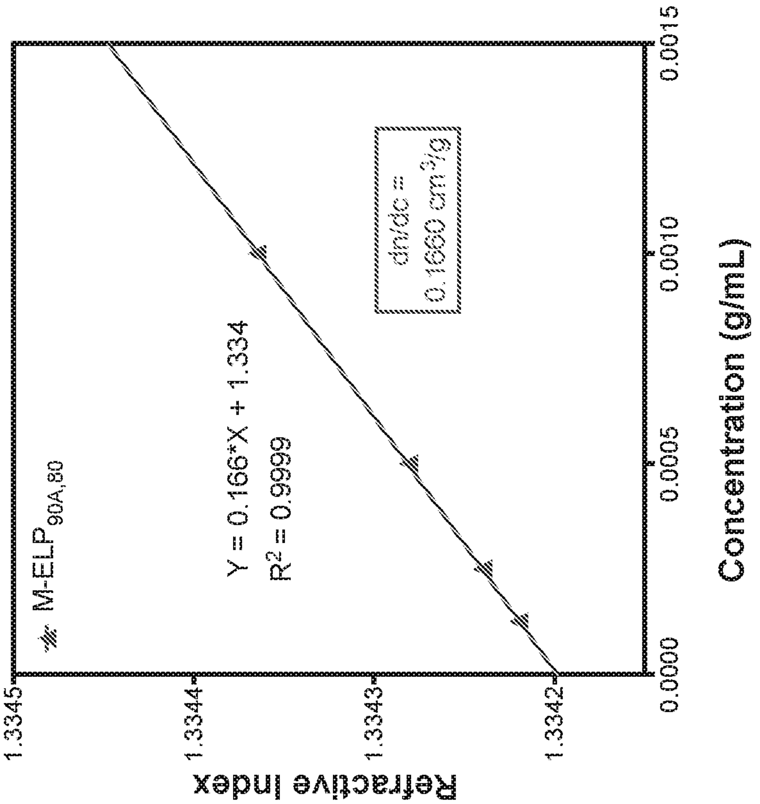
Figure 15C:
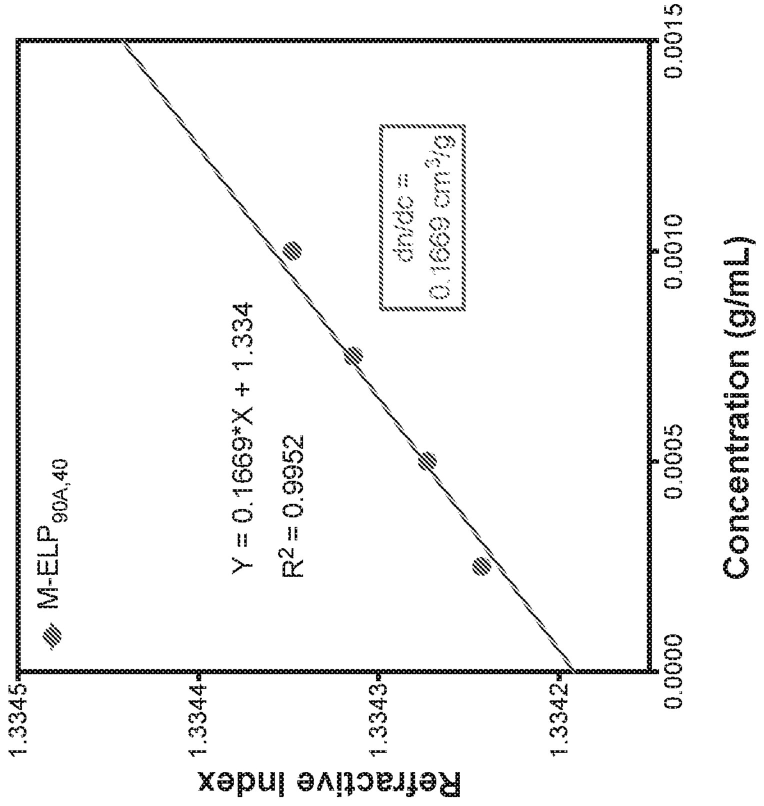
Figure 15D:
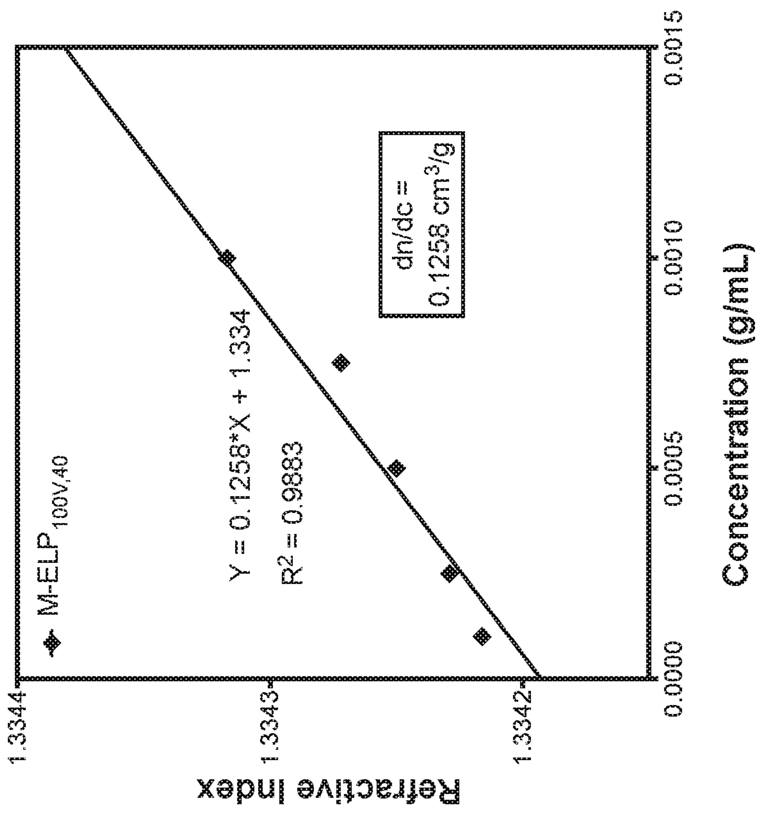
Figure 16A:
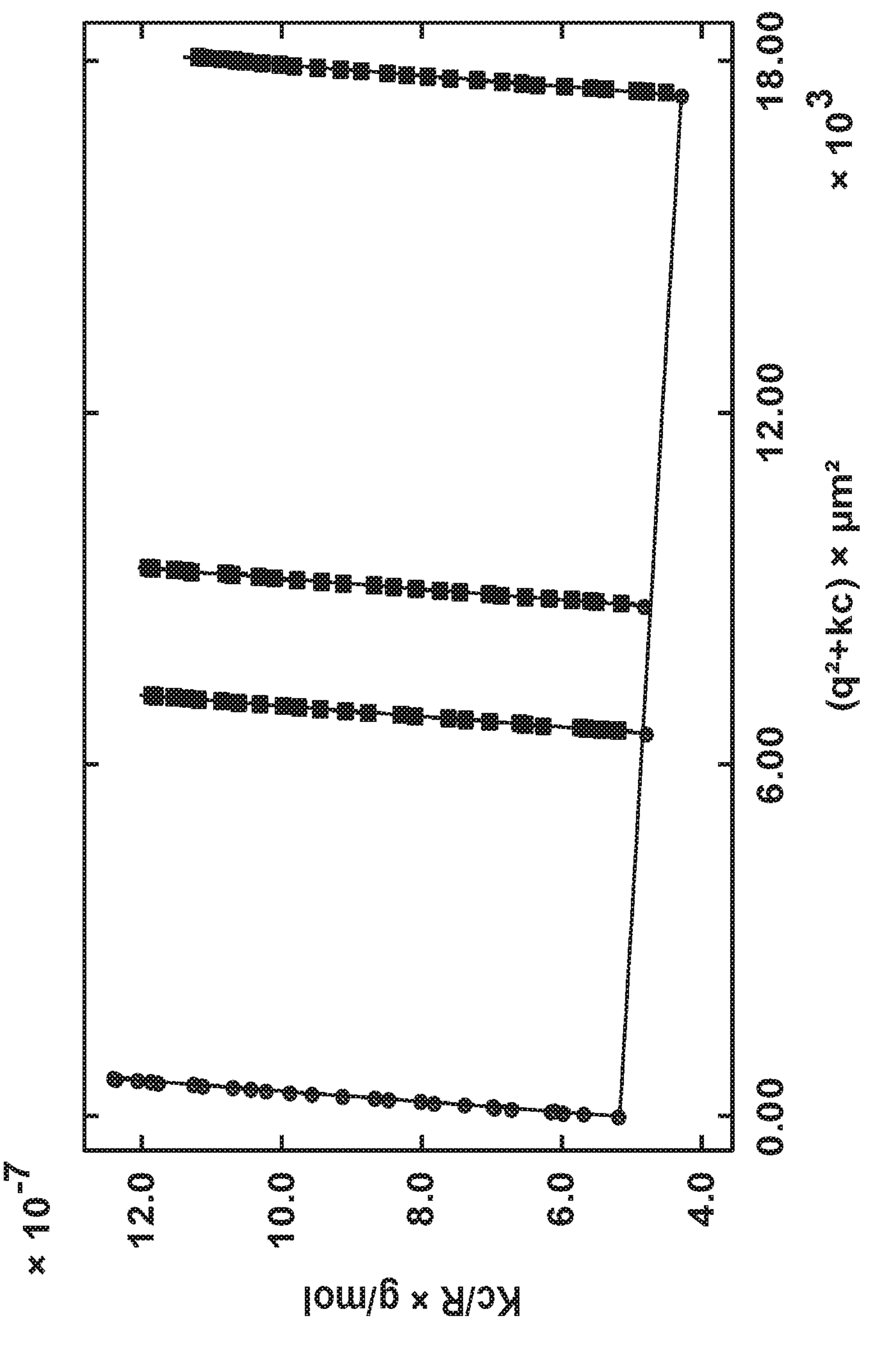
FIG. 16. Full Zimm plots made using SLS data acquired for M-ELP$_{90A,120}$ (A), M-ELP$_{90A,80}$ (B), M-ELP$_{90A,40}$ (C), and M-ELP$_{100V,40}$ (D) at concentrations ranging from 0.5-5 mg/mL.
Figure 16B:
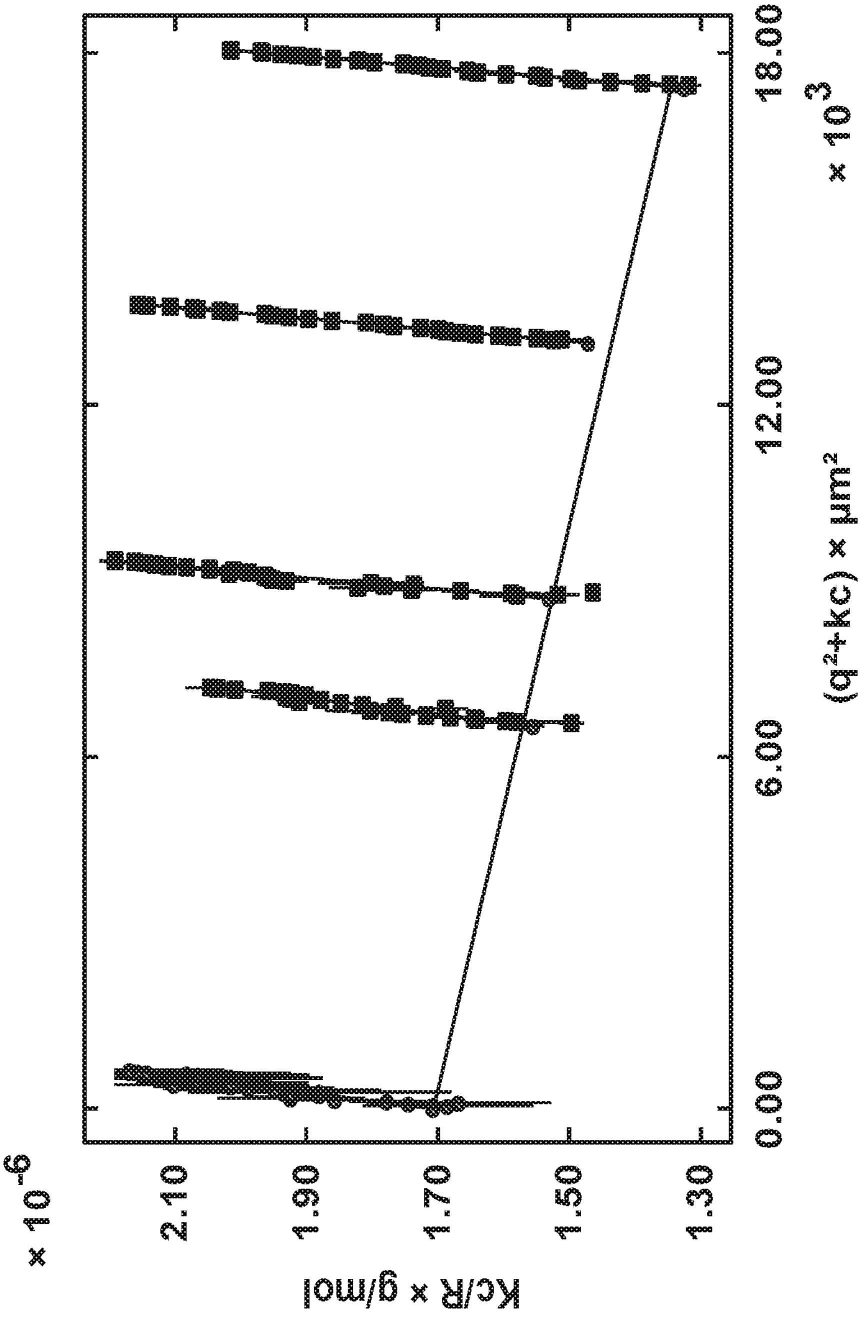
Figure 16C:
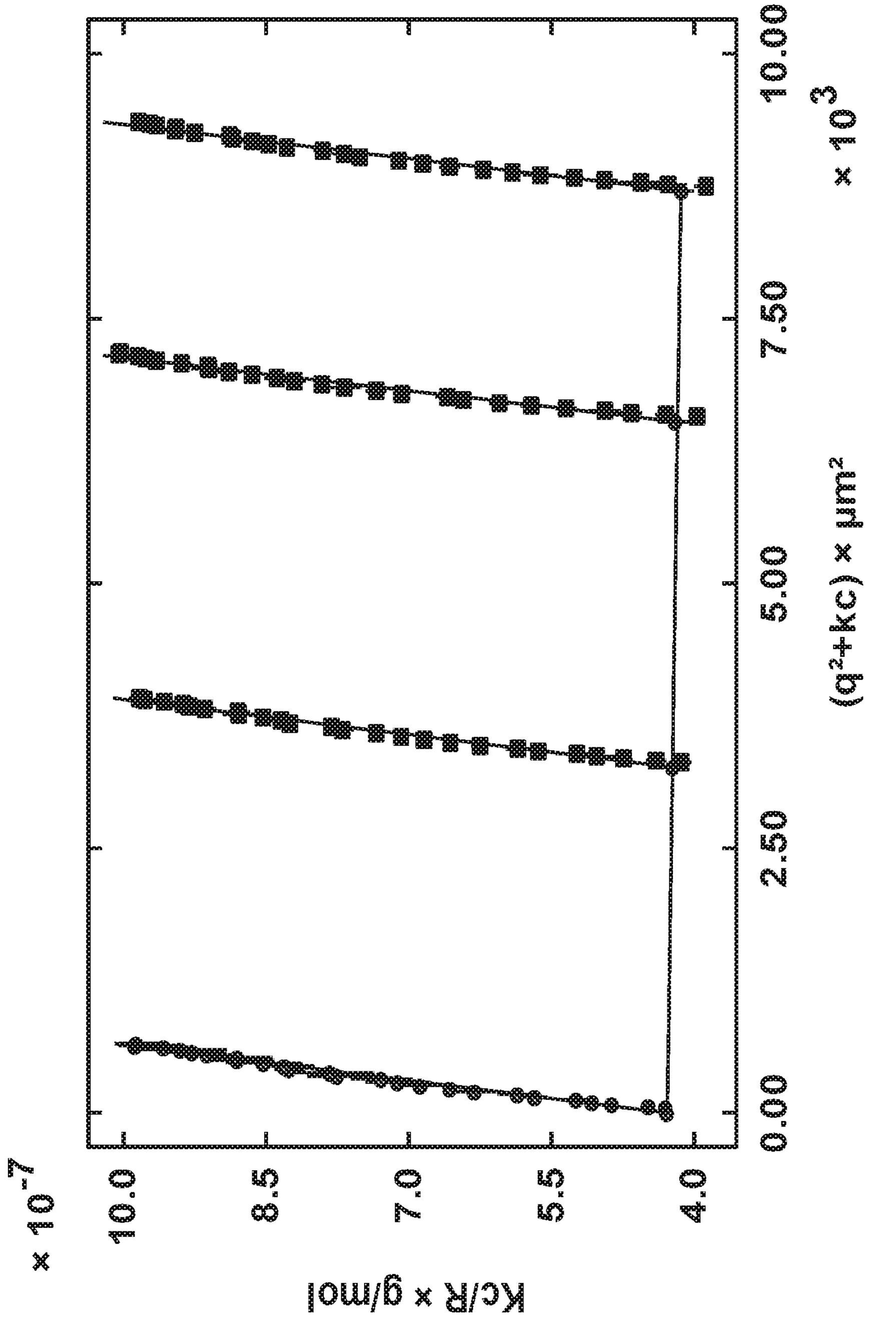
Figure 16D:
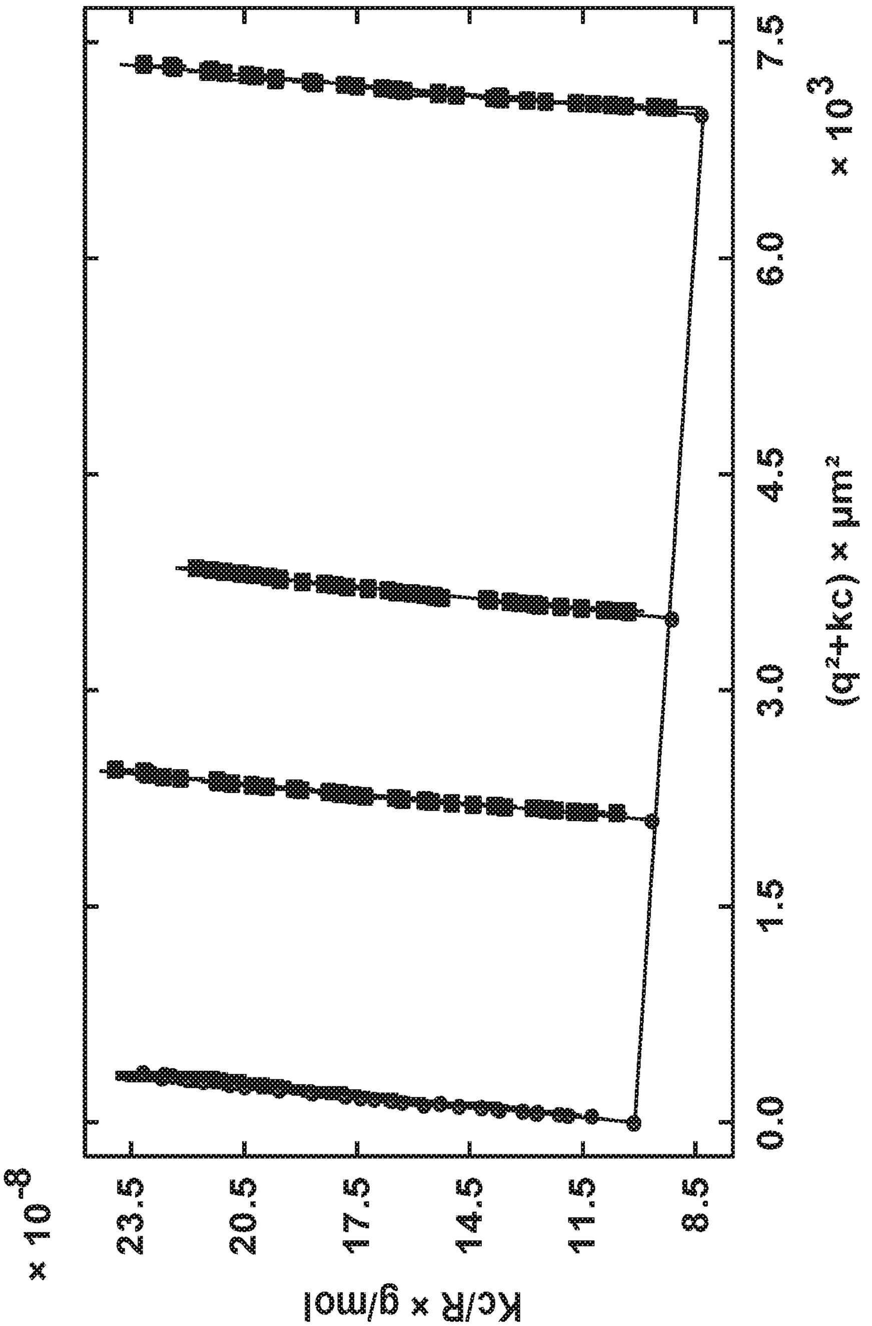

We next investigated the self-assembly of all four myristoylated constructs using DLS and static light scattering (SLS) as well as electron microscopy to determine whether the ELP length or composition impacts the nature of self-assembly. The critical aggregation concentration for all constructs, quantified by a pyrene assay, is in the low micromolar range (2-6 μM) (FIG. 20). After passing freshly reconstituted lyophilized sample through a 0.22 μm filter we observed that the size of the self-assembled nanoparticles is inversely related to ELP length (TABLE 1); as the number of ELP repeats increased from 40 to 120, the R of the self-assembled M-ELP nanoparticles decreased from 81.9±2.9 nm to 22.7±0.6 nm. In contrast, all non-myristoylated controls were unimers in solution, as seen by their small R, (FIG. 14).

TABLE 1

Size of the self-assembled nanoparticles.

| | M-ELP$_{90A,120}$ | M-ELP$_{90A,80}$ | M-ELP$_{90A,40}$ | M-ELP$_{100V,40}$ |
|---|---|---|---|---|
| Hydrodynamic Radius, Day 0[a] | 22.7 | 31.2 | 81.9 | 80.3 |
| $R_h$/nm | (±0.62) | (±1.03) | (±2.87) | (±1.29) |
| Shape Factor, ρ | 0.98 | 1.00 | 1.29 | 1.30 |

TABLE 1-continued

| Size of the self-assembled nanoparticles. | | | | |
|---|---|---|---|---|
| | M-ELP$_{90A,120}$ | M-ELP$_{90A,80}$ | M-ELP$_{90A,40}$ | M-ELP$_{100V,40}$ |
| $R_g/R_h$ | (±0.03) | (±0.07) | (±0.02) | (±0.13) |
| Second Virial Coefficient | $-9.23 \times 10^{-9}$ | $-5.58 \times 10^{-9}$ | $-2.30 \times 10^{-8}$ | $-5.10 \times 10^{9}$ |
| $A_2$/mol dm$^3$ g$^{-2}$ | (±25.2%) | (±18.0%) | (±33.9%) | (±13.2%) |
| Refractive Index Increment | 0.1515 | 0.1660 | 0.1669 | 0.1258 |
| dn/dc/cm$^3$ g$^{-1}$ | (±0.0038) | (±0.0010) | (±0.0067) | (±0.0069) |
| Aggregation Number, $N_{agg}$[a] | 29 | 48 | 137[b] | 201[b] |
| $MW_{particle}/M_{unimer}$ | (±1) | (±1) | (±1) | (±41) |

[a] These values were calculated using partial Zimm plots.

[b] After 7 days at room temperature, M-ELP$_{90A,40}$ and M-ELP$_{100V,40}$ grow in size (FIG. 3B) and have $N_{agg}$ values of 1075 and 6261, respectively, The 40-mers have a larger shape factor (p, defined as R/R) and a much larger aggregation number, $N_{agg}$, (defined as $MW_{agg}/MW_{unimer}$) (TABLE 1), indicating that they self-assemble into a non-spherical shape. The ELP's composition, although a very important determinant of phase behavior (FIG. 3A), does not significantly impact self-assembly, as M-ELP$_{90A,40}$ and M-ELP$_{100V,40}$ micelles have similar structural parameters. The second virial coefficient ($A_2$)—a global thermodynamic measure of protein-protein interaction—for all constructs was slightly negative, demonstrating an overall weak attractive interaction between the assembled particles in PBS. However, for all constructs and consistent with previous reports of ELP micelles, the magnitude of $A_2$ was very small and can safely be neglected in calculating $N_{agg}$.

Figure 3D:
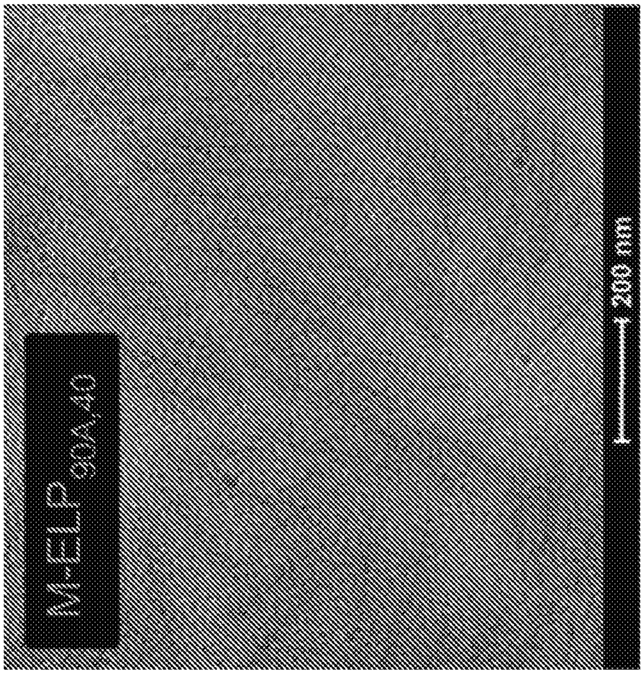
Figure 3C:
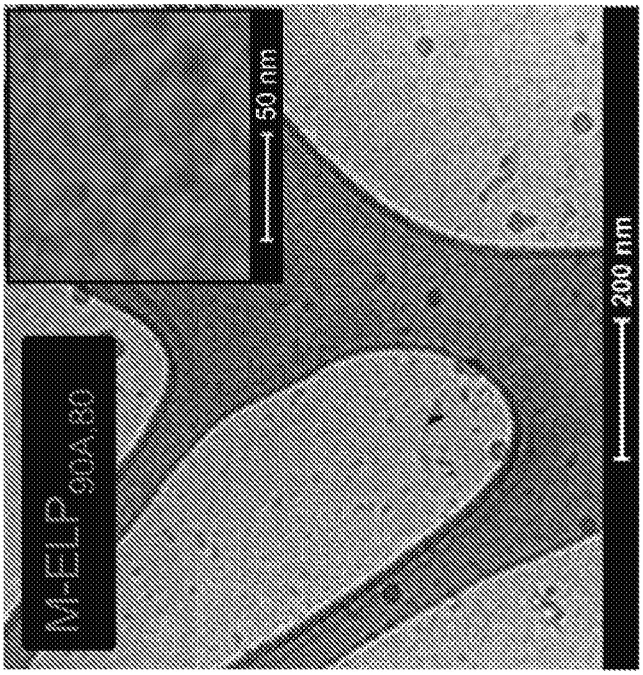
Figure 21A:
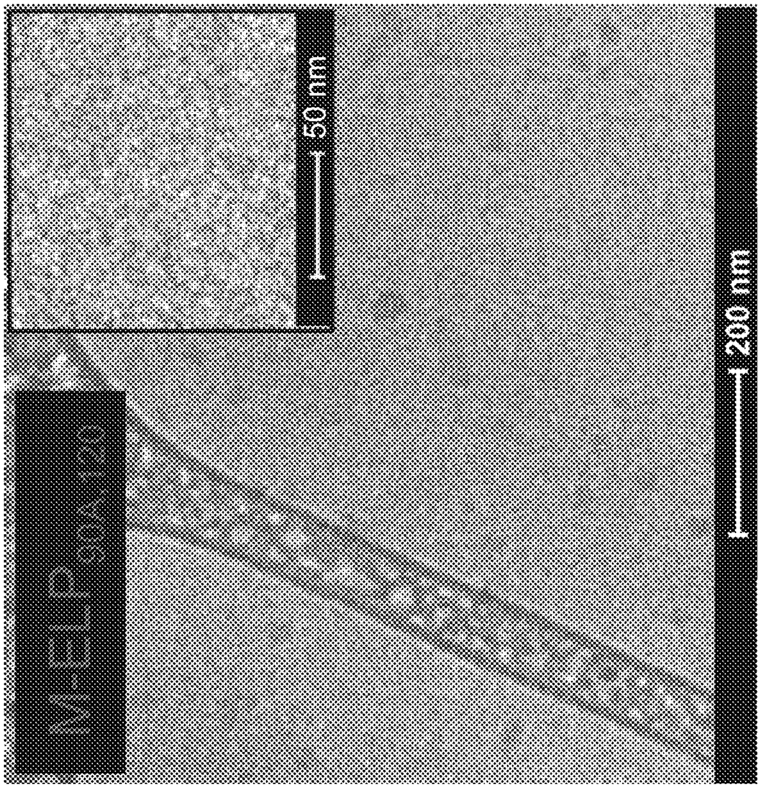
FIG. 21. Cryo-TEM images of M-ELP$_{90A,120}$ forming spherical micelles (A) and M-ELP$_{100V,40}$ forming rod-like micelles (B).
Figure 21B:
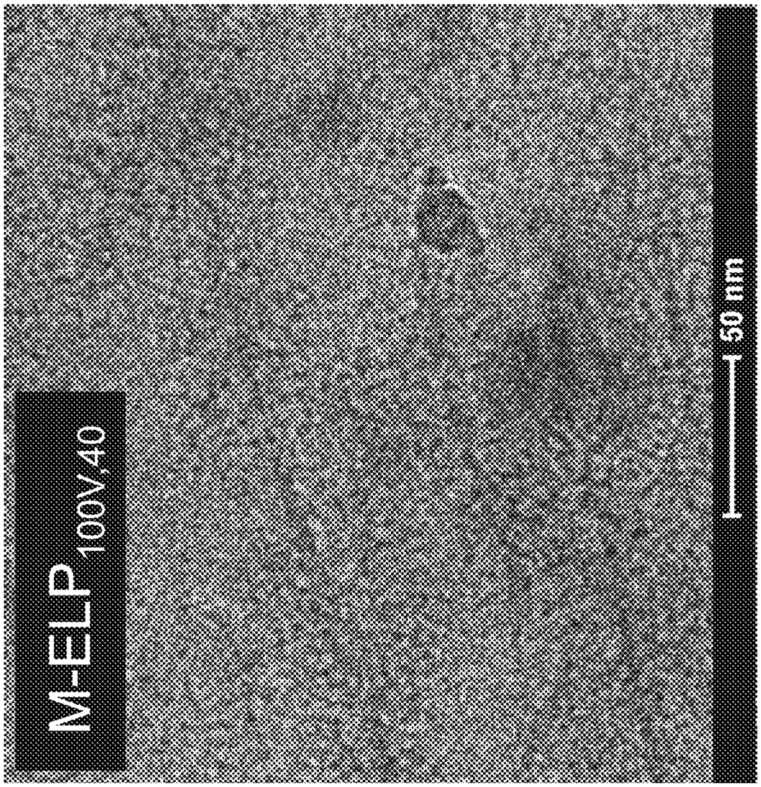

Interestingly, the length of the ELP also affects the kinetics of self-assembly. The larger ELPs with 80 and 120 pentapeptide repeats maintained their $R_h$ of ~25 nm, even when left for up to a month at room temperature (FIG. 3B), evidence that these are thermodynamically stable assemblies. In contrast the smaller 40-mer ELPs grow from an $R_h$ of ~80 nm at the time of initial preparation to ~400 nm after one week, indicating that the morphology of these constructs evolves overtime. To visualize these self-assembled structures, we next performed cryo-transmission electron microscopy (cryo-TEM). After resuspending lyophilized material in PBS and filtering the samples, cryo-TEM images show that the larger MW ELPs (M-ELP$_{90A,120}$ and M-ELP$_{90A,80}$) form spherical micelles (FIG. 3C, FIG. 21A) while the 40-mer ELPs assemble into rod-like micelles (FIG. 3D, FIG. 17B). These morphologies are consistent with the DLS and SLS results (TABLE 1).

Example 6

Figure 19A:
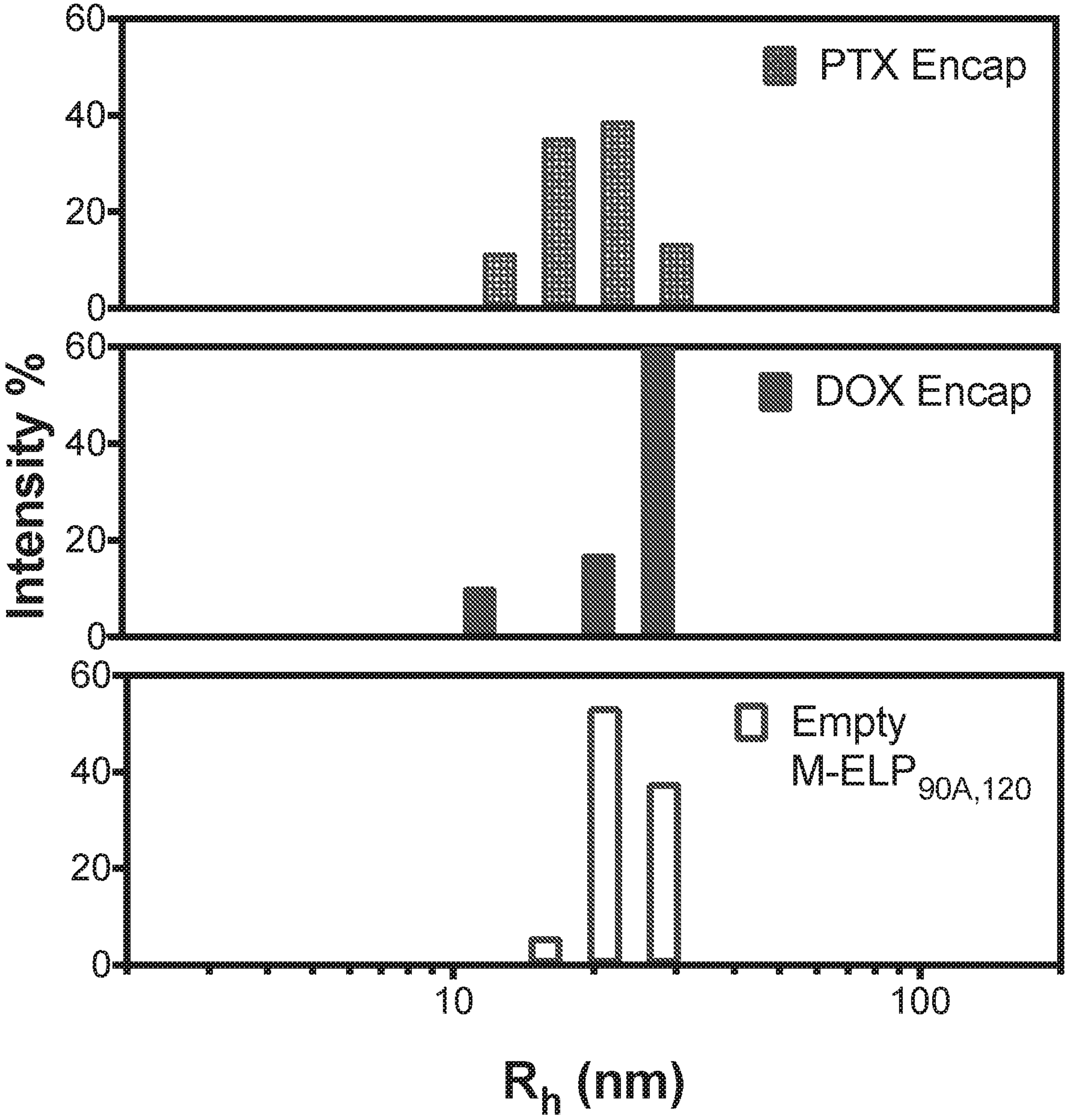
FIG. 19. $R_h$ percent intensity histograms generated from autocorrelation functions for M-ELP$_{90A,120}$ (blue, A) and M-ELP$_{90A,80}$ (green, B) both pre- (empty bars) and post-encapsulation with PTX (checkered bars) or DOX (solid bars). These histograms demonstrate that hydrophobic drug loading has no significant effect on the micelles' size.
Figure 19B:
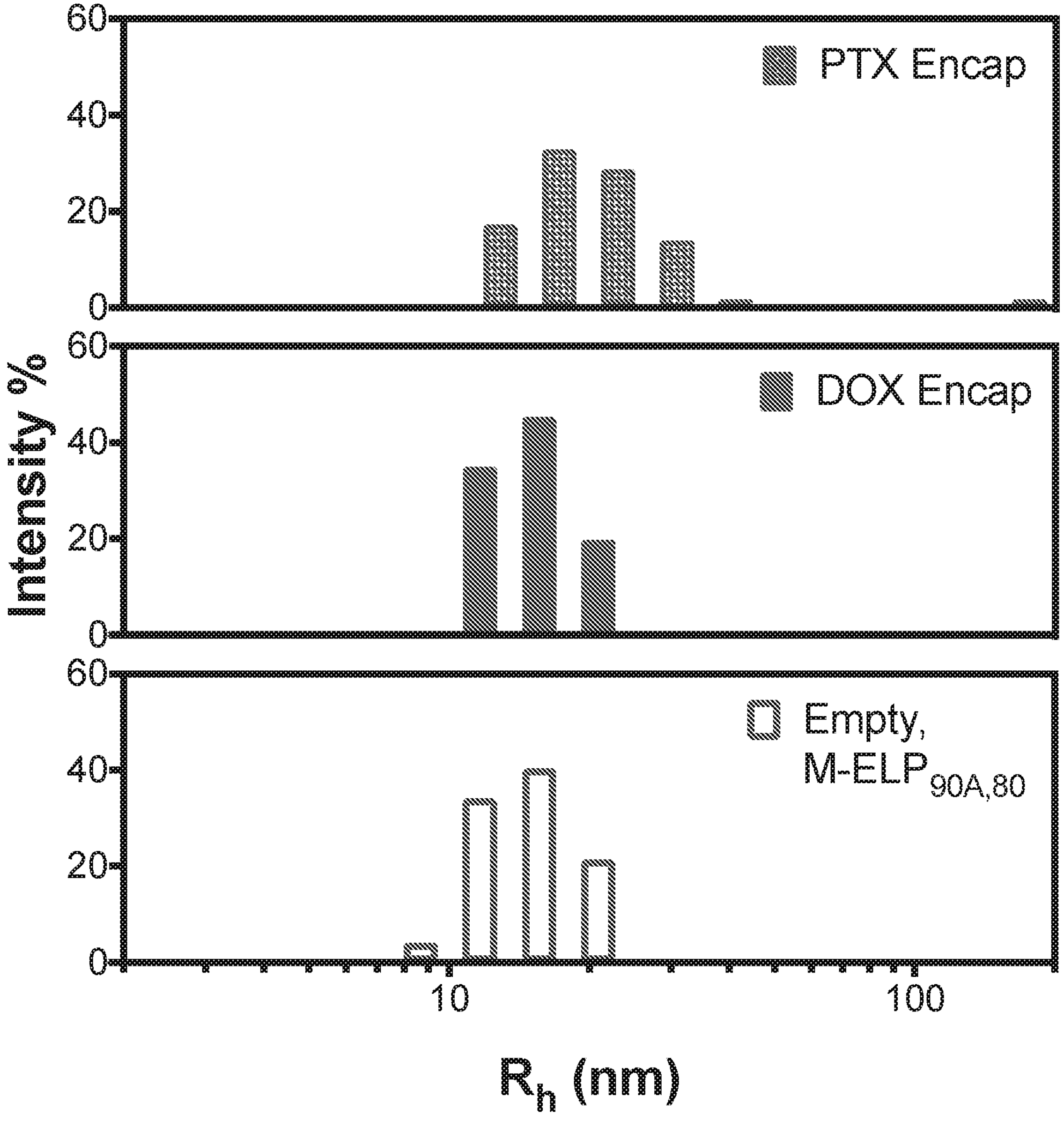
Figure 20A:
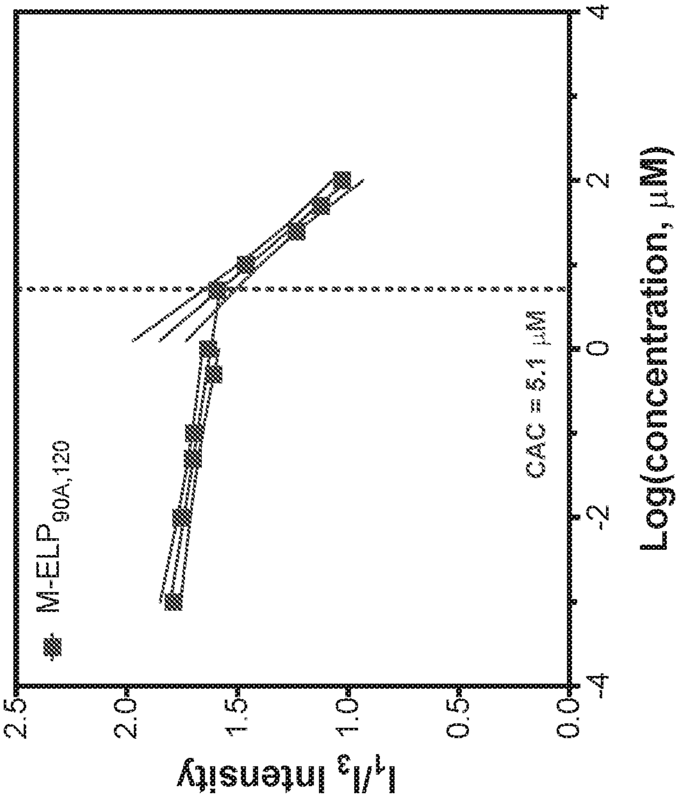
FIG. 20. Calculated peak 1 to peak 3 absorbance ratios for pyrene fluorescence are plotted against M-ELP concentrations, made in serial dilutions. Lines of fit are shown in solid lines and the calculated critical aggregation concentration (CAC) is shown as a dashed, vertical line for A), M-ELP$_{90A,120}$ (A), M-ELP$_{90A,80}$ (B), M-ELP$_{90A,40}$ (C), M-ELP$_{100V,40}$ (D).
Figure 20B:
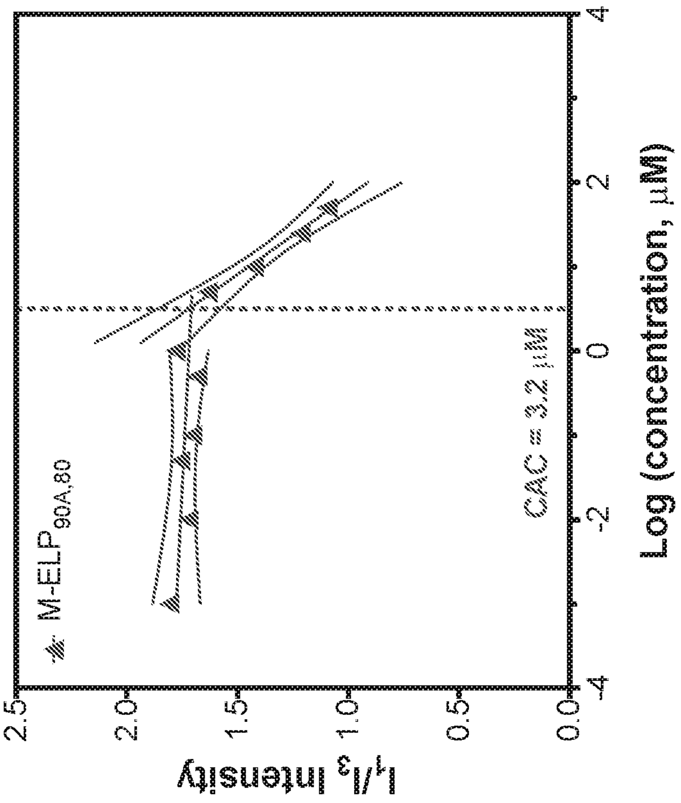
Figure 20C:
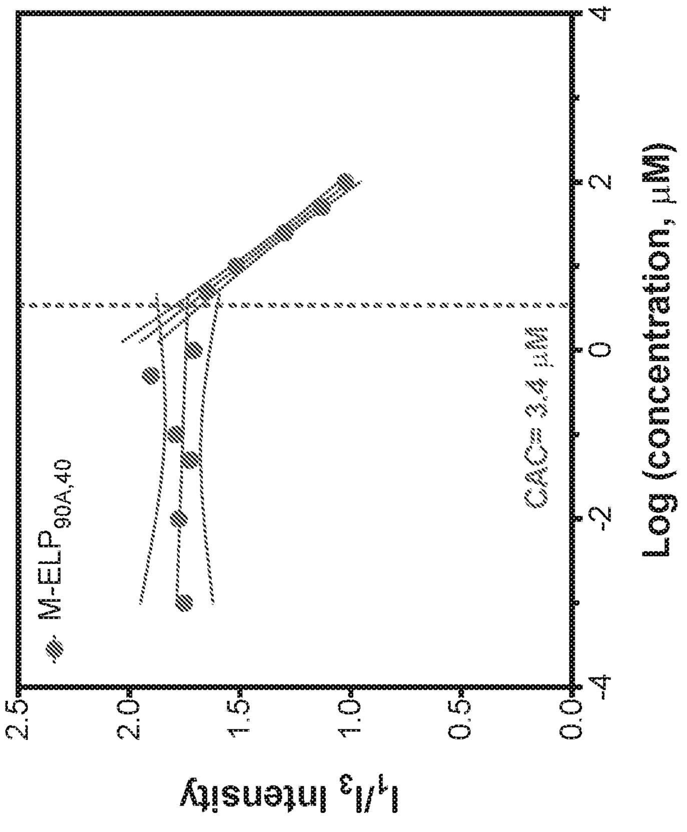
Figure 20D:
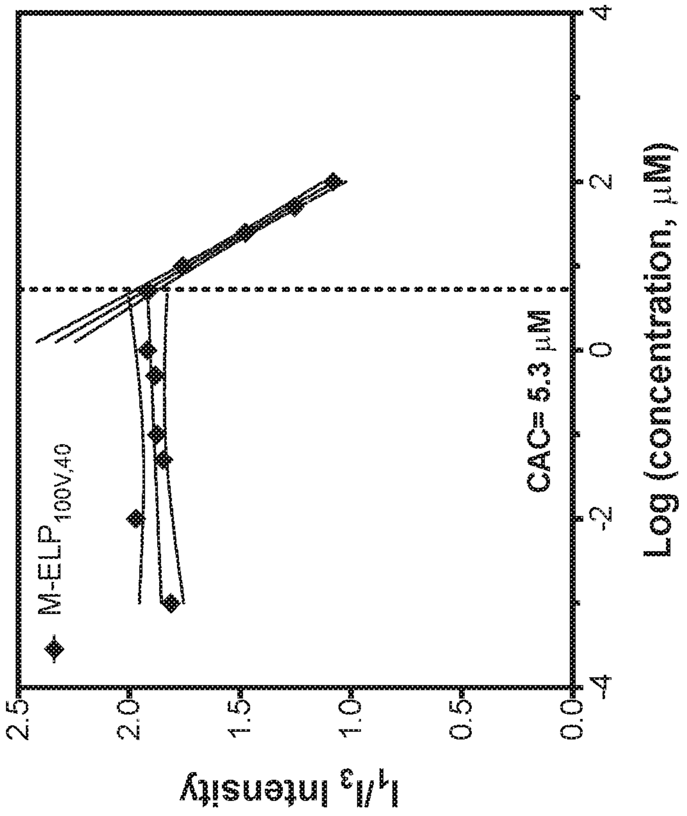

A number of amphiphilic ELPs with programmable self-assembly have been previously synthesized. However, these canonical protein-based assemblies are not capable of efficient physical encapsulation of hydrophobic compounds in their protein cores, due to the high water content of ELP coacervates (FIG. 24-FIG. 25). In contrast, we hypothesized that the fatty acid core of these hybrid micelles could be used to physically encapsulate hydrophobic small molecules. Because of their stability, we first selected M-ELP$_{90A,120}$ and M-ELP$_{90A,80}$ to encapsulate hydrophobic anti-cancer chemotherapeutics, DOX and PTX. M-ELPs were stirred overnight in a solution with excess DOX-HCl or PTX, and were then separated from free drug by ultrafiltration. The loading capacity of DOX and PTX is 1-3% and the encapsulation efficiency is 3-5%, although any unencapsulated drug could be easily recycled due to the gentle encapsulation process and simple purification scheme. The loading capacity of these nanoparticles is a reflection of the small and compact size of the hydrophobic, fatty acid core. Drug encapsulation did not significantly impact the size of the micelles (FIG. 19). An in vitro study of DOX encapsulated in M-ELP$_{90A,80}$ dialyzed against PBS showed that the formulation was remarkably stable, retaining 50% of the drug even after a week of incubation in PBS at 37° C., with only a small fraction (~13%) leaching out over the first 24 h (FIG. 32). For encapsulation protocols and characterization of drug-loaded micelles, see Example 1.

Next, the cytotoxicity of the encapsulated drugs was compared to their free drug counterparts by an in vitro cell proliferation assay that uses the reduction of tetrazolium by metabolically active cells to determine the number of viable cells (M. C. Alley, et al. *Cancer Res.* 1988, 48, 589-801). Encapsulated DOX ($DOX_{Enc}$) had a 50% inhibitory concentration ($IC_{50}$) that is 4-fold higher than free DOX ($DOX_{Free}$) in 4T1 cells (FIG. 4A), a murine model of mammary carcinoma. This loss in efficacy is an acceptable trade-off given the delivery benefits of nanoparticle formulations, as they enable higher maximal tolerated doses to be administered in vivo, have a longer circulating half-life, and accumulate to a greater extent in tumors than free drug. Furthermore, this $IC_b$ is almost identical to that of a nanoparticle formulation of DOX that uses chemical conjugation to cysteine-containing ELPs, which is a significantly more laborious and expensive process. DOX was also loaded into 40-mers that had been left at room temperature for 30 days. Interestingly, these rod-shaped carriers were much less cytotoxic (FIG. 28A). This is consistent with reports in the literature showing that the shape of nanocarriers can have a significant impact on cellular uptake. Empty carriers did not exhibit any cytotoxicity (FIG. 28B and FIG. 29).

PTX encapsulated into M-ELP$_{90A,80}$ and M-ELP$_{90A,120}$ had an $IC_{50}$ of ~40 nM-20-fold higher than free PTX–in PC3-luc cells (FIG. 4B), a human prostate cancer cell line.

This larger difference compared to free drug could be attributed to PTX's greater hydrophobicity than DOX. PTX has a reported octanol-water distribution coefficient (log $D_{pH\ 7.5}$) between 3.0 and 4.0, which may slow its diffusion out of the lipid-ELP nanoparticles relative to the less hydrophobic DOX, which has a log $D_{pH\ 7.5}$ of 2.4.

Example 7

Confocal fluorescence microscopy of 4T1 cells treated for 12 h with free or encapsulated DOX indicates that the $DOX_E$, is being taken up through the endosomal/lysosomal pathway, as indicated by punctate fluorescence throughout the cell (marked by a green arrow in FIG. 4D), which is less apparent in 4T1 cells treated with $DOX_{Free}$ (FIG. 4C, FIG. 30). Preliminary studies indicate that a greater amount of $DOX_{Enc}$ is released from the micelles as the pH is lowered from 7.5 to 4.5 (FIG. 34), the pH in late endosomes and lysosomes. We selected DOX for these studies because it is an ideal model drug due to its fluorescence and because of the extensive literature on its delivery with other carriers. We selected M-ELP$_{90A,80}$ because of its higher loading capacity.

Figure 4F:
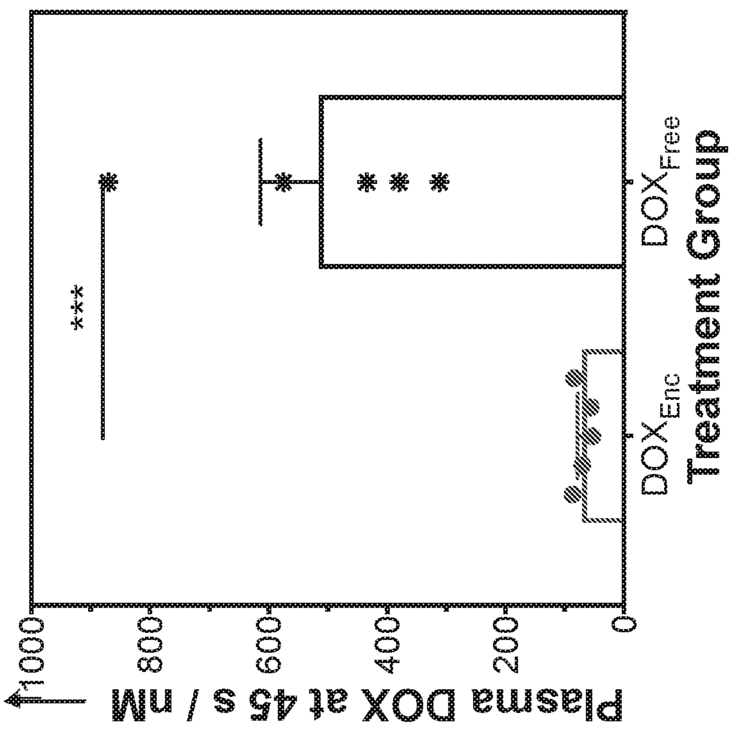

To further demonstrate the utility of encapsulating drugs in these hybrid materials, we conducted an in vivo pharmacokinetics (PK) study with DOX. Compared to free DOX, encapsulation in M-$ELP_{90A,80}$ increased the drug's elimination half-life ($t_{1/2}$) by 6.5-fold (FIG. 4E) and significantly altered its distribution, as seen by the 5-fold lower plasma concentrations than free DOX just 45 s after intravenous injection (FIG. 4F).

In summary, we have successfully shown that we can recombinantly produce a range of hybrid lipid-ELP materials with molecular precision and high yield. While post-expression chemical modification of ELPs has been demonstrated and solid-phase peptide synthesis (SPPS) has been used to make short lipidated ELPs (ELP length <20 residues), chemical synthesis of the size biomacromolecule shown here is not possible by SPPS. This recombinant, PTM methodology expands the size, complexity, and yield of lipidated peptide polymers, opening the door to a host of potential new materials and material properties not previously accessible. Furthermore, M-ELPs provide a biological complement to the exciting field of lipidated synthetic polymers and could be similarly used in combination with liposomes to create promising new drug carriers.

We have demonstrated the robustness and versatility of this system, where a range of ELP lengths and compositions can be used to make M-ELPs with tunable $T_t$ that self-assemble into nanoparticles with pre-programmable size, shape, and stability. These nanoparticles can be quickly and easily loaded with hydrophobic small molecules simply by preferential partitioning of the drug into the lipid core and this encapsulation method is effective at enhancing the drug's half-life.

This work has several notable features. First, while DOX was selected as a model drug for proof-of-principle studies, these methods could be applied to any hydrophobic small molecule and would be particularly useful for those that have no chemical handle for conjugation or that lose activity upon conjugation, such as camptothecin, Nutlin-3, and WP1066. Second, because the delivery vehicle is manufactured recombinantly, the nanoparticle corona could be functionalized for active targeted delivery by fusing a peptide or protein to the C-terminus of the ELP. Finally, recombinant myristoylation for drug delivery is not limited to ELPs. This methodology could be applied to other peptide polymers such as collagen and resilin-like polypeptides. In conclusion, this work lays the foundation for a novel class of biohybrid materials by recombinant lipidation of peptide polymers that can be used for diverse applications.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A composition comprising: a plurality of conjugates self-assembled into a micelle or a vesicle, wherein each conjugate comprises a fatty acid conjugated to a N-terminal end of an unstructured polypeptide; and an agent encapsulated within the micelle or the vesicle.

Clause 2. A method of delivering an agent to a subject, the method comprising: encapsulating the agent in the micelle or the vesicle of clause 1; and administering the micelle or the vesicle to the subject.

Clause 3. A method of treating a disease in a subject in need thereof, the method comprising administering the composition of clause 1 to the subject.

Clause 4. A method of increasing the maximum tolerated dose of an agent, the method comprising: encapsulating the agent in a micelle or a vesicle, the micelle or the vesicle comprising a plurality of conjugates self-assembled into the micelle or vesicle, wherein each conjugate comprises a fatty acid conjugated to a N-terminal end of an unstructured polypeptide; and administering the agent-encapsulated micelle or vesicle to a subject.

Clause 5. The method of any one of clauses 2-4, wherein the maximum tolerated dose (IC50) of the agent is increased 0.5-fold to 20-fold compared to a non-encapsulated agent.

Clause 6. The composition of clause 1 or the method of any one of clauses 2-5, wherein the fatty acid comprises a substrate of NMT.

Clause 7. The composition or method of any one of clauses 1-6, wherein the fatty acid comprises myristic acid or an analog thereof.

Clause 8. The composition or method of anyone of clauses 1-7, wherein the agent comprises a small molecule, a polynucleotide, a polypeptide, a carbohydrate, a lipid, a drug, an imaging agent, or a combination thereof.

Clause 9. The composition or method of clause 8, wherein the agent is hydrophobic.

Clause 10. The composition or method of clause 9, wherein the agent comprises a hydrophobic small molecule.

Clause 11. The composition or method of clause 9 or 10, wherein the plurality of conjugates is self-assembled into a micelle, and wherein the agent is encapsulated within a hydrophobic core of the micelle.

Clause 12. The composition or method of clause 8, wherein the agent is hydrophilic.

Clause 13. The composition or method of clause 12, wherein the agent comprises a hydrophilic small molecule.

Clause 14. The composition or method of clause 12 or 13, wherein the plurality of conjugates is self-assembled into an inverted micelle, wherein the agent is encapsulated within an aqueous core of the inverted micelle, or wherein the plurality of conjugates is self-assembled into a vesicle, wherein the agent is encapsulated within an aqueous core of the vesicle.

Clause 15. The composition or method of clause 8, wherein the plurality of conjugates is self-assembled into a vesicle, and wherein at least a portion of the agent is incorporated within a bilayer of the vesicle.

Clause 16. The composition or method of clause 8, wherein the agent comprises a small molecule comprising Doxorubicin.

Clause 17. The composition or method of clause 8, wherein the agent comprises a small molecule comprising Paclitaxel.

Clause 18. The composition or method of clause 8, wherein the agent comprises a polypeptide.

Clause 19. The composition or method of clause 18, wherein the polypeptide is an antibody.

Clause 20. The composition or the method of any one of clauses 1-19, wherein the unstructured polypeptide comprises a repeated unstructured polypeptide or a non-repeated unstructured polypeptide.

Clause 21. The composition or the method of any one of clauses 1-19, wherein the unstructured polypeptide comprises a PG motif.

Clause 22. The composition or the method of clause 21, wherein the PG motif comprises an amino acid sequence selected from PG, $P(X)_nG$ (SEQ ID NO:1), and $(U)_mP(X)_nG(Z)_p$ (SEQ ID NO:2), or a combination thereof, wherein m, n, and p are independently an integer from 1 to 15, and wherein U, X, and Z are independently any amino acid.

Clause 23. The composition or the method of any one of clauses 1-19, wherein the unstructured polypeptide comprises an amino acid sequence of $[GVGVP]_n$ (SEQ ID NO:3), wherein n is an integer from 1 to 200.

Clause 24. The composition or the method of any one of clauses 1-19, wherein the unstructured polypeptide comprises an amino acid sequence of $(VPGXG)_n$ (SEQ ID NO:4), wherein X is any amino acid except proline and n is an integer greater than or equal to 1.

Clause 25. The composition or the method of any one of clauses 1-19, wherein the unstructured polypeptide comprises at least one of the following: a non-repetitive polypeptide comprising a sequence of at least 60 amino acids, wherein at least about 10% of the amino acids are proline (P), wherein at least about 20% of the amino acids are glycine (G); a non-repetitive polypeptide comprising a sequence of at least 60 amino acids, wherein at least about 40% of the amino acids are selected from the group consisting of valine (V), alanine (A), leucine (L), lysine (K), threonine (T), isoleucine (1), tyrosine (Y), serine (S), and phenylalanine (F); and a non-repetitive polypeptide comprising a sequence of at least 60 amino acids, wherein the sequence does not contain three contiguous identical amino acids, wherein any 5-10 amino acid subsequence does not occur more than once in the non-repetitive polypeptide, and wherein when the non-repetitive polypeptide comprises a subsequence starting and ending with proline (P), the subsequence further comprises at least one glycine (G).

Clause 26. The composition or the method of anyone of clauses 1-19, wherein the unstructured polypeptide comprises a zwitterionic polypeptide.

Clause 27. The composition or the method of clause 26, wherein the zwitterionic polypeptide comprises an amino acid sequence of $(VPX_1X_2G)_n$ (SEQ ID NO:5), wherein $X_1$ is a negatively or positively charged amino acid, $X_2$ is the other of a negatively or positively charged amino acid, and n is an integer greater than or equal to 1.

Clause 28. The composition or the method of any one of clauses 1-27, wherein the micelle or the vesicle has a diameter of about 20 nm to about 200 nm.

Clause 29. The composition or the method of any one of clauses 1-28, wherein the unstructured polypeptide further comprises an NMT recognition sequence.

Clause 30. The composition or the method of clause 29, wherein the NMT recognition sequence comprises a glycine at the N-terminus.

Clause 31. The composition or the method of clause 29, wherein the NMT recognition sequence is derived from *S. cerevisiae* arf2 polypeptide.

Clause 32. The composition or the method of any one of clauses 1-31, wherein the NMT comprises NMT from *S. cerevisiae.*

Clause 33. The composition or the method of any one of clauses 1-31, wherein the NMT comprises an amino acid sequence consisting of residues 36-455 of NM_001182082.1 (*S. cerevisiae* NMTΔ36-455).

Clause 34. The composition or the method of any one of clauses 1-33, wherein the conjugate further comprises a linker.

Clause 35. The composition or method of any one of clauses 1-19, wherein the unstructured polypeptide comprises an amino acid sequence of $(VPGXG)_n$ (SEQ ID NO:4), wherein X is any amino acid except proline and n is 40 to 120.

Clause 36. The composition or method of clause 35, wherein X is alanine, valine, or a combination thereof.

| Sequences |
|---|
| $P(X)_nG$ (SEQ ID NO: 1) |
| $(U)_mP(X)_nG(Z)_p$ (SEQ ID NO: 2) |
| $[GVGVP]_n$ (SEQ ID NO: 3) |
| $(VPGXG)_n$ (SEQ ID NO: 4) |
| $(VPX_1X_2G)_n$ (SEQ ID NO: 5) |
| PXXG (SEQ ID NO: 6) |
| PXXXG (SEQ ID NO: 7) |
| PXXXXG (SEQ ID NO: 8), |
| PXXXXXG (SEQ ID NO: 9), |
| PXXXXXXG (SEQ ID NO: 10), |
| PXXXXXXXG (SEQ ID NO: 11), |
| PXXXXXXXXG (SEQ ID NO: 12), |

-continued

| Sequences |
|---|
| PXXXXXXXXXG (SEQ ID NO: 13), |
| PXXXXXXXXXXG (SEQ ID NO: 14), |
| PXXXXXXXXXXXG (SEQ ID NO: 15), |
| PXXXXXXXXXXXXG (SEQ ID NO: 16), |
| PXXXXXXXXXXXXXG (SEQ ID NO: 17), |
| PXXXXXXXXXXXXXXG (SEQ ID NO: 18), |
| PXXXXXXXXXXXXXXXG (SEQ ID NO: 19) |
| $VPX_1X_2G$ (SEQ ID NO: 20) |
| VPGXG (SEQ ID NO: 21) |
| $(VPX_1X_2G)_n(VPGXG)_m$ (SEQ ID NO: 22) |
| $(VPGXG)_m(VPX_1X_2G)_n$ (SEQ ID NO: 23) |
| $\{(VPX_1X_2G)(VPGXG)\}_b$ (SEQ ID NO: 24) |
| GLYASKLFSNL (SEQ ID NO: 25) |
| GSSKSKPKDPSQRRR (SEQ ID NO: 26) |
| $([GGC]_8)$ (SEQ ID NO: 27) |
| $([G4S]_3)$ (SEQ ID NO: 28) |
| $([GGS]_n$ (SEQ ID NO: 29) |

5'-
CAATGGTATATCTTCCGGGCGCTATCATGCCATACCTTTTTATACCATGGGCAGCAGC
CATCACCATCATCACCACAAAGACCACAAATTTTGGCGTACCCAGCCGGTTAAAGATTT
TGATGAAAAAGTTGTTGAAGAAGGTCCGATCGACAAACCGAAAACACCGGAAGATATTA
GCGATAAACCGCTGCCGCTGCTGAGCAGCTTTGAATGGTGTAGCATTGATGTGGACAA
CAAAAAACAGCTGGAAGATGTTTTTGTGCTGCTGAACGAAAACTATGTGGAAGATCGTG
ATGCAGGTTTTCGCTTCAATTATACCAAAGAGTTTTTCAACTGGGCACTGAAAAGTCCG
GGTTGGAAAAAAGATTGGCATATTGGTGTTCGTGTGAAAGAAACCCAGAAACTGGTTGC
ATTTATTAGCGCAATTCCGGTTACCCTGGGTGTGCGTGGTAAACAGGTTCCGAGCGTTG
AAATTAACTTTCTGTGTGTTCATAAACAGCTGCGTAGCAAACGTCTGACACCGGTTCTG
ATTAAAGAAATCACCCGTCGTGTGAACAAATGCGATATTTGGCATGCACTGTATACCGC
AGGTATTGTTCTGCCTGCACCGGTTAGCACCTGTCGTTATACCCATCGTCCGCTGAACT
GGAAAAAACTGTATGAAGTTGATTTCACCGGTCTGCCGGATGGTCATACCGAAGAAGAT
ATGATTGCAGAAAATGCACTGCCTGCAAAAACCAAAACCGCAGGTCTGCGTAAACTGAA
AAAAGAGGACATCGATCAGGTCTTTGAGCTGTTTAAACGTTATCAGAGCCGCTTTGAAC
TGATCCAGATTTTTACCAAAGAAGAGTTCGAGCACAACTTTATTGGTGAAGAAAGCCTG
CCGCTGGATAAACAGGTGATTTTTAGCTATGTTGTTGAACAGCCGGATGGCAAAATTAC
CGATTTTTTCAGCTTTTATAGCCTGCCGTTTACCATTCTGAACAACACCAAATACAAAGA
CCTGGGCATTGGCTATCTGTATTATTACGCAACCGATGCCGATTTCCAGTTTAAAGATC
GTTTTGATCCGAAAGCAACCAAAGCCCTGAAAACCCGTCTGTGCGAACTGATTTATGAT
GCATGTATTCTGGCCAAAAACGCCAACATGGATGTTTTTAATGCACTGACCAGCCAGGA
TAATACCCTGTTTCTGGATGATCTGAAATTTGGTCCGGGTGATGGTTTTCTGAATTTCTA
CCTGTTTAACTATCGTGCCAAACCGATTACCGGTGGTCTGAATCCGGATAATAGCAATG
ATATTAAACGTCGCAGCAATGTTGGTGTGGTTATGCTGTGATAATGATAATGATCTTCTG
AATTCCCGTCATATCCGCTGAGCAATAACTAGCATAACCCCTTATACGTTACAT-3'
(SEQ ID NO: 30)

5'-
TATGGGCCTGTATGCGAGCAAACTGTTTAGCAACCTGGGCTAATGATCTCCTCA
ATGAGC-3' (SEQ ID NO: 31)

3'-
ACCCGGACATACGCTCGTTTGACAAATCGTTGGACCCGATTACTAGAGGAGTTA
CTCGAGCT-5' (SEQ ID NO: 32).

(M)GSSHHHHHHKDHKFWRTQPVKDFDEKVVEEGPIDKPKTPEDISDKPLPLLSSFEWCSID
VDNKKQLEDVFVLLNENYVEDRDAGFRFNYTKEFFNWALKSPGWKKDWHIGVRVKETQKL
VAFISAIPVTLGVRGKQVPSVEINFLCVHKQLRSKRLTPVLIKEITRRVNKCDIWHALYTAGIVL
PAPVSTCRYTHRPLNWKKLYEVDFTGLPDGHTEEDMIAENALPAKTKTAGLRKLKKEDIDQ
VFELFKRYQSRFELIQIFTKEEFEHNFIGEESLPLDKQVIFSYVVEQPDGKITDFFSFYSLPFTI
LNNTKYKDLGIGYLYYYATDADFQFKDRFDPKATKALKTRLCELIYDACILAKNANMDVFNAL
TSQDNTLFLDDLKFGPGDGFLNFYLFNYRAKPITGGLNPDNSNDIKRRSNVGVVML (SEQ
ID NO: 33)

-continued

Sequences (M)GLYASKLESNLGAGVPGAGVPGVGVPGAGVPGAGVPGAGVPGAGVPGAGVPGAGVP
GAGVPGAGVPGAGVPGVGVPGAGVPGAGVPGAGVPGAGVPGAGVPGAGVPGAGVPGA
GVPGAGVPGVGVPGAGVPGAGVPGAGVPGAGVPGAGVPGAGVPGAGVPGAGVPGAGV
PGVGVPGAGVPGAGVPGAGVPGAGVPGAGVPGAGVPGAGVPGAGVPGAGVPGVGVPG
AGVPGAGVPGAGVPGAGVPGAGVPGAGVPGAGVPGAGVPGAGVPGVGVPGAGVPGAG
VPGAGVPGAGVPGAGVPGAGVPGAGVPGAGVPGAGVPGVGVPGAGVPGAGVPGAGVP
GAGVPGAGVPGAGVPGAGVPGAGVPGAGVPGVGVPGAGVPGAGVPGAGVPGAGVPGA
GVPGAGVPGAGVPGAGVPGAGVPGVGVPGAGVPGAGVPGAGVPGAGVPGAGVPGAGV
PGAGVPGAGVPGAGVPGVGVPGAGVPGAGVPGAGVPGAGVPGAGVPGAGVPGAGVPG
AGVPGAGVPGVGVPGAGVPGAGVPGAGVPGAGVPGAGVPGAGVPGAGVPGAGVPGAG
VPGVGVPGAGVPGAGVPGAGVPGAGVPGAGVPGAGVPGAGVPGY (SEQ ID NO: 34)

(M)GLYASKLESNLGAGVPGAGVPGVGVPGAGVPGAGVPGAGVPGAGVPGAGVPGAGVP
GAGVPGAGVPGAGVPGVGVPGAGVPGAGVPGAGVPGAGVPGAGVPGAGVPGAGVPGA
GVPGAGVPGVGVPGAGVPGAGVPGAGVPGAGVPGAGVPGAGVPGAGVPGAGVPGAGV
PGVGVPGAGVPGAGVPGAGVPGAGVPGAGVPGAGVPGAGVPGAGVPGAGVPGVGVPG
AGVPGAGVPGAGVPGAGVPGAGVPGAGVPGAGVPGAGVPGAGVPGVGVPGAGVPGAG
VPGAGVPGAGVPGAGVPGAGVPGAGVPGAGVPGAGVPGVGVPGAGVPGAGVPGAGVP
GAGVPGAGVPGAGVPGAGVPGAGVPGAGVPGVGVPGAGVPGAGVPGAGVPGAGVPGA
GVPGAGVPGAGVPG (SEQ ID NO: 35)

(M)GLYASKLESNLGAGVPGAGVPGVGVPGAGVPGAGVPGAGVPGAGVPGAGVPGAGVP
GAGVPGAGVPGAGVPGVGVPGAGVPGAGVPGAGVPGAGVPGAGVPGAGVPGAGVPGA
GVPGAGVPGVGVPGAGVPGAGVPGAGVPGAGVPGAGVPGAGVPGAGVPGAGVPGAGV
PGVGVPGAGVPGAGVPGAGVPGAGVPGAGVPGAGVPGAGVPGAGVPG (SEQ ID NO: 36)

(M)GLYASKLFSNLGVGVPGVGVPGVGVPGVGVPGVGVPGVGVPGVGVPGVGVPGVGVP
GVGVPGVGVPGVGVPGVGVPGVGVPGVGVPGVGVPGVGVPGVGVPGVGVPGVGVPGV
GVPGVGVPGVGVPGVGVPGVGVPGVGVPGVGVPGVGVPGVGVPGVGVPGVGVPGVGV
PGVGVPGVGVPGVGVPGVGVPGVGVPGVGVPGVGVPGVGVPG (SEQ ID NO: 37)

The invention claimed is:

1. A composition comprising:

a plurality of conjugates self-assembled into a micelle or a vesicle, wherein each conjugate comprises a fatty acid conjugated to a N-terminal end of an unstructured polypeptide, wherein the fatty acid comprises a substrate of N-myristoyltransferase (NMT), and the unstructured polypeptide comprises an NMT recognition sequence and an amino acid sequence of $(VPGXG)_n$ (SEQ ID NO:4), wherein X is any amino acid except proline and n is an integer greater than or equal to 1; and an agent encapsulated within the micelle or the vesicle, wherein the micelle includes a monolayer and the vesicle includes a bilayer, and wherein each conjugate is present in the monolayer or the bilayer.

2. The composition of claim 1, wherein the NMT is from *S. cerevisiae.*

3. The composition of claim 1, wherein the fatty acid comprises myristic acid or an analog thereof.

4. The composition of claim 1, wherein the agent comprises a small molecule, a polynucleotide, a polypeptide, a carbohydrate, a lipid, a drug, an imaging agent, or a combination thereof.

5. The composition of claim 4, wherein the agent is hydrophobic.

6. The composition of claim 5, wherein the plurality of conjugates is self-assembled into a micelle, and wherein the agent is encapsulated within a hydrophobic core of the micelle.

7. The composition of claim 4, wherein the agent is hydrophilic.

8. The composition of claim 7, wherein the plurality of conjugates is self-assembled into an inverted micelle, wherein the agent is encapsulated within an aqueous core of the inverted micelle, or wherein the plurality of conjugates is self-assembled into a vesicle, wherein the agent is encapsulated within an aqueous core of the vesicle.

9. The composition of claim 4, wherein the plurality of conjugates is self-assembled into a vesicle, and wherein at least a portion of the agent is incorporated within a bilayer of the vesicle.

10. The composition of claim 4, wherein the agent comprises Doxorubicin.

11. The composition of claim 4, wherein the agent comprises Paclitaxel.

12. The composition of claim 1, wherein the unstructured polypeptide comprises a repeated unstructured polypeptide or a non-repeated unstructured polypeptide.

13. The composition of claim 1, wherein n is from 40 to 120.

14. The composition of claim 13, wherein X is alanine, valine, or a combination thereof.

15. The composition of claim 1, wherein the unstructured polypeptide comprises a PG motif.

16. The composition of claim 15, wherein the PG motif comprises an amino acid sequence selected from PG, $P(X)_nG$ (SEQ ID NO:1), and $(U)_mP(X)_nG(Z)_p$ (SEQ ID NO:2), or a combination thereof, wherein m, n, and p are independently an integer from 1 to 15, and wherein U, X, and Z are independently any amino acid.

17. The composition of claim 1, wherein the unstructured polypeptide comprises an amino acid sequence of $[GVGVP]_n$ (SEQ ID NO:3), wherein n is an integer from 1 to 200.

18. The composition of claim 1, wherein the unstructured polypeptide comprises at least one of the following:

(i) a non-repetitive polypeptide comprising a sequence of at least 60 amino acids, wherein at least about 10% of the amino acids are proline (P), wherein at least about 20% of the amino acids are glycine (G);

(ii) a non-repetitive polypeptide comprising a sequence of at least 60 amino acids, wherein at least about 40% of the amino acids are selected from the group consisting of valine (V), alanine (A), leucine (L), lysine (K), threonine (T), isoleucine (I), tyrosine (Y), serine (S), and phenylalanine (F); and (iii) a non-repetitive polypeptide comprising a sequence of at least 60 amino acids, wherein the sequence does not contain three contiguous identical amino acids, wherein any 5-10 amino acid subsequence does not occur more than once in the non-repetitive polypeptide, and wherein when the non-repetitive polypeptide comprises a subsequence starting and ending with proline (P), the subsequence further comprises at least one glycine (G).

19. The composition of claim 1, wherein the unstructured polypeptide comprises a zwitterionic polypeptide.

20. The composition of claim 19, wherein the zwitterionic polypeptide comprises an amino acid sequence of $(VPX_1X_2G)_n$ (SEQ ID NO:5), wherein $X_1$ is a negatively or positively charged amino acid, $X_2$ is the other of a negatively or positively charged amino acid, and n is an integer greater than or equal to 1.

21. The composition of claim 1, wherein the micelle or the vesicle has a diameter of about 20 nm to about 200 nm.

22. The composition of claim 1, wherein the NMT recognition sequence comprises a glycine at the N-terminus.

23. The composition of claim 1, wherein the NMT recognition sequence is derived from *S. cerevisiae* arf2 polypeptide.

24. The composition of claim 1, wherein the conjugate further comprises a linker.

25. A method of delivering an agent to a subject, the method comprising:

encapsulating the agent in the micelle or vesicle of claim 1; and administering the micelle or the vesicle to the subject.

26. A method of treating a disease in a subject in need thereof, the method comprising administering the composition of claim 1 to the subject, wherein the disease is cancer.

27. The method of claim 25, wherein a maximum tolerated dose ($IC_{50}$) of the agent is increased 0.5-fold to 20-fold compared to a non-encapsulated agent.

28. The composition of claim 1, wherein the NMT recognition sequence comprises an amino acid sequence of GLYASKLFSNL (SEQ ID NO:25) or GSSKSKPKDPSQRRR (SEQ ID NO:26).

* * * * *